(12) United States Patent
Culler et al.

(10) Patent No.: US 10,941,454 B2
(45) Date of Patent: Mar. 9, 2021

(54) VINYLISOMERASE-DEHYDRATASES, ALKENOL DEHYDRATASES, LINALOOL DEHYDRATASES AND CROTYL ALCOHOL DEHYDRATASES AND METHODS FOR MAKING AND USING THEM

(71) Applicants: GENOMATICA, INC., San Diego, CA (US); BRASKEM S.A., Camaçari (BR)

(72) Inventors: Stephanie J. Culler, San Diego, CA (US); Robert J. Haselbeck, San Diego, CA (US); Harish Nagarajan, San Diego, CA (US); Iuri Estrada Gouvea, Camaçari (BR); Daniel Johannes Koch, Camaçari (BR); Mateus Schreiner Garcez Lopes, Camaçari (BR); Lucas Pedersen Parizzi, Camaçari (BR)

(73) Assignees: GENOMATICA, INC., San Diego, CA (US); BRASKEM S.A., Camaçari (BR)

( * ) Notice: Subject to any disclaimer, the term of this patent is extended or adjusted under 35 U.S.C. 154(b) by 0 days.

(21) Appl. No.: 15/578,488

(22) PCT Filed: May 26, 2016

(86) PCT No.: PCT/US2016/034488
§ 371 (c)(1),
(2) Date: Nov. 30, 2017

(87) PCT Pub. No.: WO2016/196233
PCT Pub. Date: Dec. 8, 2016

(65) Prior Publication Data
US 2019/0010479 A1    Jan. 10, 2019

Related U.S. Application Data

(60) Provisional application No. 62/168,787, filed on May 30, 2015, provisional application No. 62/236,662, filed on Oct. 2, 2015, provisional application No. 62/314,531, filed on Mar. 29, 2016.

(51) Int. Cl.
| | |
|---|---|
| *C12N 9/88* | (2006.01) |
| *C12N 9/90* | (2006.01) |
| *C07K 16/40* | (2006.01) |
| *C08F 36/06* | (2006.01) |
| *C12N 15/82* | (2006.01) |
| *C12P 5/02* | (2006.01) |
| *C12P 7/16* | (2006.01) |

(52) U.S. Cl.
CPC ...... *C12Y 402/01127* (2013.01); *C07K 16/40* (2013.01); *C08F 36/06* (2013.01); *C12N 9/88* (2013.01); *C12N 9/90* (2013.01); *C12N 15/8243* (2013.01); *C12P 5/026* (2013.01); *C12P 7/16* (2013.01); *C12Y 402/01* (2013.01); *C12Y 504/04004* (2013.01); *C07K 2319/02* (2013.01); *C07K 2319/034* (2013.01)

(58) Field of Classification Search
None
See application file for complete search history.

(56) References Cited

U.S. PATENT DOCUMENTS

| | | | | |
|---|---|---|---|---|
| 8,703,455 | B2 * | 4/2014 | Marliere | C12P 5/007 435/167 |
| 8,916,358 | B2 * | 12/2014 | Swartz | C12N 9/50 435/41 |
| 9,422,578 | B2 * | 8/2016 | Pearlman | C12P 5/02 |
| 9,518,273 | B2 * | 12/2016 | Garcez Lopes | C12N 15/52 |
| 9,862,973 | B2 * | 1/2018 | Botes | C12N 9/1029 |
| 2014/0017273 | A1 | 1/2014 | Sleep et al. | |
| 2014/0065686 | A1 | 3/2014 | Marliere | |

FOREIGN PATENT DOCUMENTS

| | | |
|---|---|---|
| WO | 2013090915 A1 | 6/2013 |
| WO | 2014184345 A1 | 11/2014 |

OTHER PUBLICATIONS

Liang P.H. et al. Structure, mechanism and function of prenyltransferases. Eur J Biochem. Jul. 2002;269(14):3339-54. Review. (Year: 2002).*
Hill M.A. et al. Functional analysis of conserved histidines in ADP-glucose pyrophosphorylase from *Escherichia coli*. Biochem Biophys Res Commun. Mar. 17, 1998;244(2):573-7. (Year: 1998).*
Sprinks, Supplementary European Search Report for EP 16804082 dated Feb. 11, 2019.
Copenheaver, International Search Report for PCT/US2016/034488, dated Oct. 26, 2016.

(Continued)

*Primary Examiner* — Cynthia E Collins
(74) *Attorney, Agent, or Firm* — Greer, Burns & Crain, Ltd.; Gregory P. Einhorn

(57) ABSTRACT

In alternative embodiments, provided are non-natural or genetically engineered vinylisomerase-dehydratase enzymes, including alkenol dehydratases, linalool dehydratases and crotyl alcohol dehydratases. In alternative embodiments, provided are non-natural or genetically engineered polypeptides having an activity comprising, for example, a vinylisomerase-dehydratase, an alkenol dehydratase, a linalool dehydratase and/or a crotyl alcohol dehydratase activity, or a combination thereof. In alternative embodiments, also provided are non-natural or genetically engineered nucleic acids (polynucleotides) encoding polypeptides described herein, expression or cloning vehicles comprising or having contained therein nucleic acids as described herein, and non-natural or genetically engineered cells comprising or having contained therein nucleic acids as described herein. In alternative embodiments, also provided are methods for making various organic compounds, including methyl vinyl carbinol and butadiene.

18 Claims, 19 Drawing Sheets
Specification includes a Sequence Listing.

(56) References Cited

OTHER PUBLICATIONS

Petasch et al., "The oxygen-independent metabolism of cyclic monoterpenes in Castellaniella defragans 65Phen" BMC Microbiology, 2014, v 14, p. 1-13.

Brodkorb et al., "Linalool dehydratase-isomerase, a bifunctional enzyme in the anaerobic degradation of monoterpenes" The Journal of Biological Chemistry, v 285, n 40, p. 30436-30442.

Luddeke et al., "Physiology of deletion mutants in the anaerobic beta-myrcene degradation pathway in Castellaniella defragrans" BMC Microbiology, Sep. 4, 2012, v 12, p. 1-11.

Jia, First Office Action for Chinese Patent Application No. 201680042415.2, dated Oct. 9, 2019.

* cited by examiner

FIG. 3A

| pG | sample | PTS | BD, uM | % wt |
|---|---|---|---|---|
| 6839 | 1 | wt | 10 | 104% |
| 6839 | 12 | wt | 9.8 | 102% |
| 6839 | 11 | wt | 9.4 | 98% |
| 6839 | 22 | wt | 9.2 | 96% |
| 7211 | 2 | LamB | 9.1 | 95% |
| 7211 | 21 | LamB | 9.1 | 95% |
| 7212 | 20 | MalE | 8.9 | 93% |
| 7212 | 3 | MalE | 8.5 | 89% |
| 7310 | 5 | FhuD | 7 | 73% |
| 7310 | 18 | FhuD | 6.7 | 70% |
| 7269 | 19 | PelB | 4.3 | 45% |
| 7269 | 4 | PelB | 3.7 | 39% |
| 7312 | 7 | dsbA | 3.3 | 34% |
| 7312 | 16 | dsbA | 2.8 | 29% |
| 7314 | 8 | YcdO | 2.2 | 23% |
| 7313 | 10 | MalE | 2 | 21% |
| 7315 | 9 | MdoD | 1.8 | 19% |
| 7315 | 14 | MdoD | 1.8 | 19% |
| 7311 | 6 | TorA | 1.5 | 16% |
| 7311 | 17 | TorA | 1.3 | 14% |
| 7313 | 13 | MalE | 0.4 | 4% |
| 7314 | 15 | YcdO | 0.4 | 4% |

FIG. 3B

| Signal Sequence | Pathway |
|---|---|
| DsbA | SRP |
| DsbAss | SRP |
| SfmCss | SRP |
| TolBss | SRP |
| TorTss | SRP |
| LamBss | Sec |
| MalEss | Sec |
| MglBss | Sec |
| OmpAss | Sec |
| PelBss | Sec |
| PhoAss | Sec |
| MalE | Sec |
| OmpA | Sec |
| TorA | TAT |
| DsbA | SRP |
| FhuD | TAT + SEC |
| YcdO | TAT + SEC |
| MdoD | TAT + SEC |

FIG. 4

Alignment 2753 (SEQ ID NO: 2) and 9819 (SEQ ID NO: 12)

| Score | Expect | Method | Identities | Positives | Gaps |
|---|---|---|---|---|---|
| 767 bits(1980) | 0.0 | Compositional matrix adjust. | 375/398(94%) | 378/398(94%) | 1/398(0%) |

```
2753        MRFTLKTTAIVSA-AALLAGFGPPPRA AELPFGRLATTEDYFAQQAKQAVTPDVMAQLAY    59
            MRFTLKT AI SA AALL G G P   A A LP GRLA TEDYFAQQAKQAVTPDVMAQLAY
9819        MRFTLKTPAIASAVAALLVGLGQPAHA APLPLGRLAPTEDYFAQQAKQAVTPDVMAQLAY    60

Query  60   MNYIDFISPFYSRGCSFEAWELKHTPQRVIKYSIAFYAYGLASVALIDPKLRALAGHDLD   119
            MNYIDFISPFYSRGCSFEAWELKHTPQRVIKYSIAFYAYGLASVALIDP LRALAGHDLD
Sbjct  61   MNYIDFISPFYSRGCSFEAWELKHTPQRVIKYSIAFYAYGLASVALIDPNLRALAGHDLD   120

Query 120   IAVSKMKCKRVWGDWEEDGFGTDPIEKENIMYKGHLNLMYGLYQLVTGSRRYEAEHAHLT   179
            IAVSKMKCKRVWGDWEEDGFG  DPIEKENIMYKGHLNLMYGLYQLVTGSRRYEAEHAHLT
Sbjct 121   IAVSKMKCKRVWGDWEEDGFGDDPIEKENIMYKGHLNLMYGLYQLVTGSRRYEAEHAHLT   180

Query 180   RIIHDEIAANPFAGIVCEPDNYFVQCNSVAYLSLWVYDRLHGTDYRAATRAWLDFIQKDL   239
            RIIHDEI ANPFAGIVCEPDNYFVQCNSVAYLSLWVYDRLHGTDYRAATRAWLDFIQKDL
Sbjct 181   RIIHDEIGANPFAGIVCEPDNYFVQCNSVAYLSLWVYDRLHGTDYRAATRAWLDFIQKDL   240

Query 240   IDPERGAFYLSYHPESGAVKPWISAYTTAWTLAMVHGMDPAFSERYYPRFKQTFVEVYDE   299
            IDPERGAFYLSYHPESGAVKPWISAYTTAWTLAMVHGMDPAFSERYYP FK+TFVEVYD
Sbjct 241   IDPERGAFYLSYHPESGAVKPWISAYTTAWTLAMVHGMDPAFSERYYPAFKKTFVEVYDG   300

Query 300   GRKARVRETAGTDDADGGVGLASAFTLLLAREMGDQQLFDQLLNHLEPPAKPSIVSASLR   359
            GRKARVRETAGT DADGGVGLASAFTLLLAREMGDQ LFDQLLNHLEPPA+PSIVSASLR
Sbjct 301   GRKARVRETAGTADADGGVGLASAFTLLLAREMGDQ LFDQLLNHLEPPAQPSIVSASLR   360

Query 360   YEHPGSLLFDELLFLAKVHAGFGALLRMPPPAAKLAGK                        397
            YEHPGSLLFDELLFLAKVHAGFGALL+MPPPAAK GK
Sbjct 361   YEHPGSLLFDELLFLAKVHAGFGALLQMPPPAAKSGGK                        398
```

FIG. 5

Alignment 9819A (SEQ ID NO: 12) and 9819C (SEQ ID NO: 22)

| Score | Expect | Method | Identities | Positives | Gaps |
|---|---|---|---|---|---|
| 805 bits(2078) | 0.0 | Compositional matrix adjust. | 387/398(97%) | 392/398(98%) | 0/398(0%) |

```
9819   MRFTLKTPAIASAVAALIVGLGQPAHAAPLPLGRLAPTEDYFAQQAKQAVTPDVMAQLAY     60
       MRFTLKTPAIASAVAALL GLGQPAHAAPLPLGRLAPTEDYFAQQAKQAVTPDVMAQLAY
9819C  MRFTLKTPAIASAVAALLIGLGQPAHAAPLPLGRLAPTEDYFAQQAKQAVTPDVMAQLAY     60

Query  61   MNYIDFISPFYSRGCSFEAWELKHTPQRVIKYSIAFYAYGLASVALIDPNLRALAGHDLD   120
            MNYIDFISPF+SR  CSFEAWELKHTPQRVIKYSIAFYAYGLASVALIDPNLRALAGHDLD
Sbjct  61   MNYIDFISPFFSRSCSFEAWELKHTPQRVIKYSIAFYAYGLASVALIDPNLRALAGHDLD   120

Query  121  IAVSKMKCKRVWGDWEEDGFGDDPIEKENIMYKGHLNLMYGLYQLVTGSRRYEAEHAHLT   180
            IAVSKMKCKRVW D EEDGFGDDPIEKENIMYKGHLNLMYGLYQLVTGSR+YEAEHAHLT
Sbjct  121  IAVSKMKCKRVWMDWEEDGFGDDPIEKENIMYKGHLNLMYGLYQLVTGSRKYEAEHAHLT   180

Query  181  RIIHDEIGANPFAGIVCEPDNYFVQCNSVAYLSLMVYDRLHGTDYRAATRAWLDFIQKDL   240
            R+IHDEIGANPFAGI  CEP+NYFVQCNSVAYLSLMVYDRLHGTDYRAATRAWLDFIQKDL
Sbjct  181  RLIHDEIGANPFAGIFCEPNNYFVQCNSVAYLSLMVYDRLHGTDYRAATRAWLDFIQKDL   240

Query  241  IDPERGAFYLSYHPESGAVKPWISAYTTAWTLAMVHGMDPAFSERYYPAFKKTFVEVYDG   300
            IDPERGAFYLSYHPESGAVKPWISAYTTAWTLAMVHGMDPAFSERYYPAFKKTFVEVYDG
Sbjct  241  IDPERGAFYLSYHPESGAVKPWISAYTTAWTLAMVHGMDPAFSERYYPAFKKTFVEVYDG   300

Query  301  GRKARVRETAGTADADGGVGLASAFTLLLAREMGDQTLFDQLLNHLEPPAQPSIVSASLR   360
            GRKARVRETAGTADADGGVGLASA  TLLLAREMGDQTLFDQLLNHLEPPAQPSIVSASLR
Sbjct  301  GRKARVRETAGTADADGGVGLASASTLLLAREMGDQTLFDQLLNHLEPPAQPSIVSASLR   360

Query  361  YEHPGSLLFEDELLFLAKVHAGEGALLQMPPPAAKSGGK   398
            YEHP SL FDELLFLAKVHAGEGALLQMPPPAAKSGGK
Sbjct  361  YEHPSSLFFDELLFLAKVHAGEGALLQMPPPAAKSGGK   398
```

A-B could be N-heterocyclic carbenes or inorganic compounds (e.g., S chelotrophic reactions)

FIG. 11

>cds_9819 vs cds_2753
Alignment of 2 sequences: cds_9819 (SEQ ID NO:12), cds_2753 (SEQ ID NO:2)
signal peptides underlined Identities = 375/398 (94%),
Positives = 378/398 (94%), Gaps = 1/398 (0%)

```
cds_9819    1 MRFTLKTPAIASAVAALLVGLGQPAHAAPLPLGRLAPTEDYFAQQAKQAVTPDVMAQLAY  60
              MRFTLKT AI SA AALL G G P  AA LP GRLA TEDYFAQQAKQAVTPDVMAQLAY
cds_2753    1 MRFTLKTTAIVSA-AALLAGFGPPPRAAELPPGRLATTEDYFAQQAKQAVTPDVMAQLAY  59 cds_9819   61 MNYIDFISPFYSRGCSFEAWELKHTPQRVIKYSIAFYAYGLASVALIDPNLRALAGHDLD 120
              MNYIDFISPFYSRGCSFEAWELKHTPQRVIKYSIAFYAYGLASVALIDP LRALAGHDLD
cds_2753   60 MNYIDFISPFYSRGCSFEAWELKHTPQRVIKYSIAFYAYGLASVALIDPKLRALAGHDLD 119 cds_9819  121 IAVSKMKCKRVWGDWEEDGFGDDPIEKENIMYKGHLNLMYGLYQLVTGSRRYEAEHAHLT 180
              IAVSKMKCKRVWGDWEEDGFG DPIEKENIMYKGHLNLMYGLYQLVTGSRRYEAEHAHLT
cds_2753  120 IAVSKMKCKRVWGDWEEDGFGTDPIEKENIMYKGHLNLMYGLYQLVTGSRRYEAEHAHLT 179 cds_9819  181 RIIHDEIGANPFAGIVCEPDNYFVQCNSVAYLSLWVYDRLHGTDYRAATRAWLDFIQKDL 240
              RIIHDEI ANPFAGIVCEPDNYFVQCNSVAYLSLWVYDRLHGTDYRAATRAWLDFIQKDL
cds_2753  180 RIIHDEIAANPFAGIVCEPDNYFVQCNSVAYLSLWVYDRLHGTDYRAATRAWLDFIQKDL 239 cds_9819  241 IDPERGAFYLSYHPESGAVKPWISAYTTAWTLAMVHGMDPAFSERYYPAFKKTFVEVYDG 300
              IDPERGAFYLSYHPESGAVKPWISAYTTAWTLAMVHGMDPAFSERYYP FK+TFVEVYD
cds_2753  240 IDPERGAFYLSYHPESGAVKPWISAYTTAWTLAMVHGMDPAFSERYYPRFKQTFVEVYDE 299 cds_9819  301 GRKARVRETAGTADADGGVGLASAFTILLAREMGDQTLFDQLLNHLEPPACPSIVSASLR 360
              GRKARVRETAGT DADGGVGLASAFTILLAREMGDQ LFDQLLNHLEPPA+PSIVSASLR
cds_2753  300 GRKARVRETAGTDDADGGVGLASAFTILLAREMGDQQLFDQLLNHLEPPAKPSIVSASLR 359 cds_9819  361 YEHPGSLLFDELLFLAKVHAGFGALLQMPPPAAKSGGK 398
              YEHPGSLLFDELLFLAKVHAGFGALL+MPPPAAK GK
cds_2753  360 YEHPGSLLFDELLFLAKVHAGFGALLRMPPPAAKLAGK 397
```

FIG. 12

>cds_9873 vs cds_2753
Alignment of 2 sequences: cds_9873 (SEQ ID NO:43), cds_2753 (SEQ ID NO:2)
<u>signal peptide underlined</u>

```
Identities = 303/402 (75%),
Positives = 338/402 (84%), Gaps = 7/402 (1%)

cds_9873     1  MIKPHRRSAARLSLIIAATL--GFGSSASAEDLFPGRLATTADYFAQREKHTVTPDVMAH   58
                  R +    +++ AA L GFG    A +L PGRLATT DYFAQ+ K  VTPDVMA
cds_2753     1  ----MRFTLKTTAIVSAAALLAGFGPPPRAAELPPGRLATTEDYFAQQAKCAVTPDVMAQ   56 cds_9873    59  LAFMNYTDFISPFYSRGCAFDAWDIKKTPQRIIKYSLAFYSYGLASVALTDPKLRPLAAH  118
                LA+MNY DFISPFYSRGC+F+AW++K TPQR+IKYS+AFY+YGLASVAL DPKLR LA H
cds_2753    57  LAYMNYIDFISPFYSRGCSFEAWELKHTPQRVIKYSIAFYAYGLASVALIDPKLRALAGH  116 cds_9873   119  AIDVATSKMKCKRVWEDWEEDGFGSDPIEKQNIMYKGHLNLMYGLYQLVSGNRQYEAEHK  178
                 +D+A SKMKCKRVW DWEEDGFG+DPIEK+NIMYKGHLNLMYGLYQLV+G R+YEAEH
cds_2753   117  DLDIAVSKMKCKRVWGDWEEDGFGTDPIEKENIMYKGHLNLMYGLYQLVTGSRRYEAEHA  176 cds_9873   179  HLTKIIHDEIKANPFAGALCEPDNYFVQCNSVAYLSLWVYDRLHGTSYKAATEPWLKFLK  238
                HLT+IIHDEI ANPFAG +CEPDNYFVQCNSVAYLSLWVYDRLHGT Y+AAT  WL F++
cds_2753   177  HLTRIIHDEIAANPFAGIVCEPDNYFVQCNSVAYLSLWVYDRLHGTDYRAATRAWLDFIQ  236 cds_9873   239  KDLIDPKTGAFYLSFHPESGTVKPWLSAYTTAWTLAMVHGMDPAFSERYYPAFKKTFVEV  298
                KDLIDP+ GAFYLS+HPESG VKPW+SAYTTAWTLAMVHGMDPAFSERYYP FK+TFVEV
cds_2753   237  KDLIDPERGAFYLSYHPESGAVKPWISAYTTAWTLAMVHGMDPAFSERYYPRFKQTFVEV  296 cds_9873   299  YDGGRKARVRETTNTPDADGGVGAASAFTLLLAREMGDQTLFDQLLNHLEPPAKPKITSA  358
                YD GRKARVRET  T DADGGVG ASAFTLLLAREMGDQ LFDQLLNHLEPPAKP I SA
cds_2753   297  YDEGRKARVRETAGTDDADGGVGLASAFTLLLAREMGDQQLFDQLLNHLEPPAKPSIVSA  356 cds_9873   359  ILNYEAPSNLLFDELLFLSKVHVGFGELLKATPPPARADSQK  400
                 L YE P +LLFDELLFL+KVH GFG LL+   PP A+   +
cds_2753   357  SLRYEHPGSLLFDELLFLAKVHAGFGALLRMPPPAAKLAGK-  397
```

FIG. 13

>cds_9874 vs cds_2753
Alignment of 2 sequences: cds_9874 (SEQ ID NO:37), cds_2753 (SEQ ID NO:2)
<u>signal peptide underlined</u>

```
Identities = 395/397 (99%),
Positives = 397/397 (100%), Gaps = 0/397 (0%)

cds_9874      1 MRFTLKTTAIVSAAALLAGFGPPPRAAELPPGRLATTEDYFAQQAKQAVTPDVMAQLAYM  60
                MRFTLKTTAIVSAAALLAGFGPPPRAAELPPGRLATTEDYFAQQAKQAVTPDVMAQLAYM
cds_2753      1 MRFTLKTTAIVSAAALLAGFGPPPRAAELPPGRLATTEDYFAQQAKQAVTPDVMAQLAYM  60 cds_9874     61 NYIDFISPFYSRGCSFEAWELKHTPQRVIKYSIAFYAYGLASVALIDPKLRALAGHDLDI 120
                NYIDFISPFYSRGCSFEAWELKHTPQRVIKYSIAFYAYGLASVALIDPKLRALAGHDLDI
cds_2753     61 NYIDFISPFYSRGCSFEAWELKHTPQRVIKYSIAFYAYGLASVALIDPKLRALAGHDLDI 120 cds_9874    121 AVSKMKCKRVWGDWEEDGFGTDPIEKENIMYKGHLNLMYGLYQLVTGSRRYEAEHAHLTR 180
                AVSKMKCKRVWGDWEEDGFGTDPIEKENIMYKGHLNLMYGLYQLVTGSRRYEAEHAHLTR
cds_2753    121 AVSKMKCKRVWGDWEEDGFGTDPIEKENIMYKGHLNLMYGLYQLVTGSRRYEAEHAHLTR 180 cds_9874    181 IIHDEIAANPFAGIVCEPDNYFVQCNSVAYLSLWVYDRLHGTDYRAATRAWLDFIQKDLI 240
                IIHDEIAANPFAGIVCEPDNYFVQCNSVAYLSLWVYDRLHGTDYRAATRAWLDFIQKDLI
cds_2753    181 IIHDEIAANPFAGIVCEPDNYFVQCNSVAYLSLWVYDRLHGTDYRAATRAWLDFIQKDLI 240 cds_9874    241 DPERGAFYLSYHPESGAVKPWISAYTTAWTLAMVHGMDPAFSERYYPRFKQTFVELYDEG 300
                DPERGAFYLSYHPESGAVKPWISAYTTAWTLAMVHGMDPAFSERYYPRFKQTFVE+YDEG
cds_2753    241 DPERGAFYLSYHPESGAVKPWISAYTTAWTLAMVHGMDPAFSERYYPRFKQTFVEVYDEG 300 cds_9874    301 RKARVRETAGTDDADGGVGLASAFTLLLAREMGDQQLFDQLLNHLEPPAKPSIVSASLRY 360
                RKARVRETAGTDDADGGVGLASAFTLLLAREMGDQQLFDQLLNHLEPPAKPSIVSASLRY
cds_2753    301 RKARVRETAGTDDADGGVGLASAFTLLLAREMGDQQLFDQLLNHLEPPAKPSIVSASLRY 360 cds_9874    361 EHPGSLLFDELLFLAKVHAGFGALLQMPPPAAKLAGK 397
                EHPGSLLFDELLFLAKVHAGFGALL+MPPPAAKLAGK
cds_2753    361 EHPGSLLFDELLFLAKVHAGFGALLRMPPPAAKLAGK 397
```

FIG. 14

\>cds_9875 vs cds_2753

Alignment of 2 sequences: cds_9875, (SEQ ID NO:49), cds_2753 (SEQ ID NO:2)
<u>signal peptide underlined</u>

```
Identities = 316/402 (78%),
Positives = 348/402 (86%), Gaps = 6/402 (1%)

cds_9875     1 MKNIQKTAAALPAILAAVLA-FSAPAHSADLPPGRLASTEEYFAQREKQAVTPDVMAHLA  59
               M+   K  A + A  AA+LA F  P  +A+LPPGRLA+TE+YFAQ+ KQAVTPDVMA LA
cds_2753     1 MRFTLKTTAIVSA--AALLAGFGPPPRAAELPPGRLATTEDYFAQQAKQAVTPDVMAQLA  58 cds_9875    60 YMNYTDFVSPFYSRGCAFDAWAIKKTPQRIIKYSLAFYAYGLASVALTDPQLRPLAGHAI 119
               YMNY DF+SPFYSRGC+F+AW  +K TPQR+IKYS+AFYAYGLASVAL DP+LR LAGH +
cds_2753    59 YMNYIDFISPFYSRGCSFEAWELKHTPQRVIKYSIAFYAYGLASVALIDPKLRALAGHDL 118 cds_9875   120 DIATAKMKCKQVWGDWEEDGFGEDPIEKENIMYKGHLNLMYGLYQLVTGNRRYEKEHARL 179
               DIA +KMKCK+VWGDWEEDGFG DPIEKENIMYKGHLNLMYGLYQLVTG+RRYE EHA L
cds_2753   119 DIAVSKMKCKRVWGDWEEDGFGTDPIEKENIMYKGHLNLMYGLYQLVTGSRRYEAEHAHL 178 cds_9875   180 TRIIHDEIKANPYAGIVCEPDNYFVQCNSVAYLSLWVHDRLHGTDYRAATAEWLKFIEHD 239
               TRIIHDEI ANP+AGIVCEPDNYFVQCNSVAYLSLWV+DRLHGTDYRAAT  WL FI+ D
cds_2753   179 TRIIHDEIAANPFAGIVCEPDNYFVQCNSVAYLSLWVYDRLHGTDYRAATRAWLDFIQKD 238 cds_9875   240 LIDPKHGAFHLSYHPESHAVKPWVSAYTTAWTLAMVHGMDPAFAERYYPRFKETFVEVYD 299
               LIDP+ GAF+LSYHPES AVKPW+SAYTTAWTLAMVHGMDPAF+ERYYPRFK+TFVEVYD
cds_2753   239 LIDPERGAFYLSYHPESGAVKPWISAYTTAWTLAMVHGMDPAFSERYYPRFKQTFVEVYD 298 cds_9875   300 DGRKARVRETTGTTDADGGVGAASAFTLLLAREMGDRQLFDQLLNHLEPPARPRITSGIL 359
               +GRKARVRET GT DADGGVG ASAFTLLLAREMGD+QLFDQLLNHLEPPA+P I S  L
cds_2753   299 EGRKARVRETAGTDDADGGVGLASAFTLLLAREMGDQQLFDQLLNHLEPPAKPSIVSASL 358 cds_9875   360 EYAAPSNLLFDELLFLAKVHVGFGQLLQAGSAPPPPGPARGK 401
                Y   P +LLFDELLFLAKVH GFG LL+    PPP   GK
cds_2753   359 RYEHPGSLLFDELLFLAKVHAGFGALLR---MPPPAAKLAGK 397
```

FIG. 15

>cds_9894 vs cds_2753
Alignment of 2 sequences: cds_9894, (SEQ ID NO:55), cds_2753 (SEQ ID NO:2)
<u>signal peptide underlined</u>

```
Identities = 312/398 (78%),
Positives = 347/398 (87%), Gaps = 3/398 (0%)

cds_9894      1  MKNIARAAALAAAIIATMPGPGTPAHAAELLPGRLASTEAYFAQRERQAVTPDVMAHLAY   60
                 M+   + A+ +A  A + G G P  AAEL PGRLA+TE YFAQ+ +QAVTPDVMA LAY
cds_2753      1  MRFTLKPTAIVSA-AALLAGFGPPPRAAELPPGRLATTEDYFAQQAKQAVTPDVMAQLAY   59 cds_9894     61  MNYTDFVSPFYSRGCAFDAWTIKKTPQRIIKYSLAFYAYGLASVALIDPQLRPLAGHALD  120
                 MNY DF+SPFYSRGC+F+AW +K TPQR+IKYS+AFYAYGLASVALIDP+LR LAGH LD
cds_2753     60  MNYIDFISPFYSRGCSFEAWELKHTPQRVIKYSIAFYAYGLASVALIDPKLRALAGHDLD  119 cds_9894    121  IATAKMKCKQVWGDWEEDGFGDDPIEKENIMYKGHLNLMYGLHQLVTGNRRYEKEHARLT  180
                 IA +KMKCK+VWGDWEEDGFG DPIEKENIMYKGHLNLMYGL+QLVTG+RRYE EHA LT
cds_2753    120  IAVSKMKCKRVWGDWEEDGFGTDPIEKENIMYKGHLNLMYGLYQLVTGSRRYEAEHAHLT  179 cds_9894    181  QIIRDEIAANPYAGIVCEPDNYFVQCNSVAYLSLWVYDRLHGTNHRAATAAWLKFIEDDL  240
                 +II DEIAANP+AGIVCEPDNYFVQCNSVAYLSLWVYDRLHGT++RAAT AWL FI+ DL
cds_2753    180  RIIHDEIAANPFAGIVCEPDNYFVQCNSVAYLSLWVYDRLHGTDYRAATRAWLDFIQKDL  239 cds_9894    241  IDPKHGVFHLSYHPESGAVKPWVSAYTTAWTLAMVHGMDPAFAERYYPRFKETFVEVYDD  300
                 IDP+ G F+LSYHPESGAVKPW+SAYTTAWTLAMVHGMDPAF+ERYYPRFK+TFVEVYD+
cds_2753    240  IDPERGAFYLSYHPESGAVKPWISAYTTAWTLAMVHGMDPAFSERYYPRFKQTFVEVYDE  299 cds_9894    301  GRKARVRETTGTTDADGGVGAASAFTLLLAREMGDQQLFDQLLNHLEPPARPKITSGILD  360
                 GRKARVRET GT DADGGVG ASAFTLLLAREMGDQQLFDQLLNHLEPPA+P I S  L
cds_2753    300  GRKARVRETAGTDDADGGVGLASAFTLLLAREMGDQQLFDQLLNHLEPPAKPSIVSASLR  359 cds_9894    361  YEAPSNLLFDELLFLAKVHVGFGQLLQARPDPAR--GQ  396
                 YE P +LLFDELLFLAKVH GFG LL+   P  A+  G+
cds_2753    360  YEHPGSLLFDELLFLAKVHAGFGALLRMPPPAAKLAGK  397
```

FIG. 16

>cds_9895 vs cds_2753
Alignment of 2 sequences: cds_9895, (SEQ ID NO:61), cds_2753 (SEQ ID NO:2)
<u>signal peptide underlined</u>

```
Identities = 267/400 (66%),
Positives = 317/400 (79%), Gaps = 9/400 (2%)

cds_9895      1 MTQWLSTPCL--AAILSAIFIVVPKFGLTETLLPGRLATTKAYFSQQRNQKLTPDMDAQL   58
                M  L T  +  AA L A F   P+     L PGRLATT+ YF+QQ  Q +TPD+ AQL
cds_2753      1 MRFTLKTTAIVSAAALLAGFGPPPR---AAELPPGRLATTEDYFAQQAKQAVTPDVMAQL   57
alternative
cds_9895      1 MTQWLSTPCL--AAILSAIFIVVPKFGLTETLLPGRLATTKAYFSQQRNQKLTPDMDAQL   58
cds_2753      1 MRFTLKTTAIVSAAALLAGFGPPPR--AAE LPPGRLATTEDYFAQQAKQAVTPDVMAQL   57 cds_9895     59 AYMSYTDFISPFYSRGCAFEAWELKQAPQRIIKYSLAWYSYGLASVAVIDPSLHRYAGHN  118
                AYM+Y DFISPFYSRGC+FEAWELK  PQR+IKYS+A+Y+YGLASVA+IDP L   AGH+
cds_2753     58 AYMNYIDFISPFYSRGCSFEAWELKHTPQRVIKYSIAFYAYGLASVALIDPKLRALAGHD  117 cds_9895    119 IDIAIAKMKCRQVWGDWEEDGFGSNPIAHQNIMYKGHLNLMYGLYQLLTGNTQYEEEFID  178
                +DIA++KMKC++VWGDWEEDGFG++PI   +NIMYKGHLNLMYGLYQL+TG+ +YE E
cds_2753    118 LDIAVSKMKCKRVWGDWEEDGFGTDPIEKENIMYKGHLNLMYGLYQLVTGSRRYEAEHAH  177 cds_9895    179 LSNIIYSEIKENPYAGIACEPDNYFPQCNSVAYLSLWVYDRLYHTDYKAVTKPWLDFLQK  238
                L+ II+ EI  NP+AGI CEPDNYF QCNSVAYLSLWVYDRL+ TDY+A T+ WLDF+QK
cds_2753    178 LTRIIHDEIAANPFAGIVCEPDNYFVQCNSVAYLSLWVYDRLHGTDYRAATRAWLDFIQK  237 cds_9895    239 KLIDPETGTFHVAYHPTSHAVKPWVSAYTTAWALTMIHGLNPEFAKKYYPNFKQTFVEVF  298
                 LIDPE G F+++YHP S AVKPW+SAYTTAW L M+HG++P F+++YYP FKQTFVEV+
cds_2753    238 DLIDPERGAFYLSYHPESGAVKPWISAYTTAWTLAMVHGMDPAFSERYYPRFKQTFVEVY  297 cds_9895    299 DNGTKARVRETAHTTDVDGGVGAASIFTLVLAREMNDQELFDQLLNYLEPPAKPVIYSGI  358
                D G KARVRETA T D DGGVG AS FTL+LAREM DQ+LFDQLLN+LEPPAKP I S
cds_2753    298 DEGRKARVRETAGTDDADGGVGLASAFTLLLAREMGDQQLFDQLLNHLEPPAKPSIVSAS  357 cds_9895    359 LRYENPTSLLFDELLFVAKVHVGFGELINLKPVETD----  394
                LRYE+P SLLFDELLF+AKVH GFG L+ + P
cds_2753    358 LRYEHPGSLLFDELLFLAKVHAGFGALLRMPPPAAKLAGK  397
```

FIG. 17

| | | | Substrate | | |
|---|---|---|---|---|---|
| SEQ ID NO | GNM number | Source | CrOH | MVC | Prenol |
| SEQ ID NO:2 | 2753 | Castellaniella defragrans 65Phen | + | ++ | ** |
| SEQ ID NO:12 | 9819 | Castellaniella defragrans 62Car | + | ++ | ** |
| SEQ ID NO:37 | 9874 | Metagenomics on Activated sludge from Padre Dam enriched on Myrcene | NT | NT | NT |
| SEQ ID NO:43 | 9873 | Metagenomics on Activated sludge from Camp Pendleton enriched on Myrcene (Secondary Enrichment) | + | ++ | NT |
| SEQ ID NO:49 | 9875 | Metagenomics on Activated sludge from Camp Pendleton enriched on Myrcene (Primary Enrichment) | + | ++ | NT |
| SEQ ID NO:55 | 9894 | Metagenomics on activated sludge (Camp Pendleton) | NT | NT | NT |
| SEQ ID NO:61 | 9895 | Metagenomics on activated sludge (Camp Pendleton) | ND | + | ** |
| SEQ ID NO:64 | 9819T | Genetically engineered variant of 9819 | ++ | ++ | ** |
| SEQ ID NO:10 | 2753N | Known genetically engineered variant of 2753 | ++ | ++ | ** |

++ = >1 ppm 1,3-butadiene
+ = <1 ppm 1,3-butadiene
** = >1ppm isoprene
* = <1 ppm isoprene
NT = Not Tested
ND = Not detectable
5 mM of each substrate was used

FIG. 18A

| | Pairwise % ID for full length protein amino acid sequence | | | | | | | | | | | | | | |
|---|---|---|---|---|---|---|---|---|---|---|---|---|---|---|---|
| | cds_2753 | cds_9819 | cds_9819T | cds_9873 | cds_9874 | cds_9875 | cds_9894 | cds_9895 | cds_10038 | cds_10039 | cds_10058 | cds_10092 | cds_10093 | cds_10094 | cds_10097 |
| cds_2753 | 100 | 94 | 94 | 76 | 99.5 | 78 | 78 | 66 | 99 | 66 | 70 | 72 | 70 | 77 | 71 |
| cds_9819 | 94 | 100 | 98 | 76 | 94 | 78 | 78 | 65 | 95 | 66 | 70 | 71 | 70 | 77 | 70 |
| cds_9819T | 94 | 98 | 100 | 79 | 94 | 79 | 80 | 68 | | | | | | | |
| cds_9873 | 76 | 76 | 79 | 100 | 76 | 79 | 79 | 65 | 76 | 65 | 72 | 73 | 72 | 78 | 73 |
| cds_9874 | 99.5 | 94 | 94 | 76 | 100 | 78 | 78 | 66 | 98 | 66 | 70 | 72 | 70 | 77 | 70 |
| cds_9875 | 78 | 78 | 79 | 79 | 78 | 100 | 89 | 65 | 78 | 65 | 77 | 77 | 77 | 97 | 78 |
| cds_9894 | 78 | 78 | 80 | 79 | 78 | 89 | 100 | 67 | 78 | 67 | 76 | 77 | 76 | 89 | 78 |
| cds_9895 | 66 | 65 | 68 | 65 | 66 | 65 | 67 | 100 | 66 | 99.7 | 64 | 63 | 63 | 65 | 65 |
| cds_10038 | 99 | 95 | | 76 | 98 | 78 | 78 | 66 | 100 | 66 | 71 | 72 | 71 | 77 | 71 |
| cds_10039 | 66 | 66 | | 65 | 66 | 65 | 67 | 99.7 | 66 | 100 | 64 | 63 | 63 | 66 | 65 |
| cds_10058 | 70 | 70 | | 72 | 70 | 77 | 76 | 64 | 71 | 64 | 100 | 86 | 99.5 | 77 | 88 |
| cds_10092 | 72 | 71 | | 73 | 72 | 77 | 77 | 63 | 72 | 63 | 86 | 100 | 87 | 77 | 85 |
| cds_10093 | 70 | 70 | | 72 | 70 | 77 | 76 | 63 | 71 | 63 | 99.5 | 87 | 100 | 77 | 88 |
| cds_10094 | 77 | 77 | | 78 | 77 | 97 | 89 | 65 | 77 | 66 | 77 | 77 | 77 | 100 | 78 |
| cds_10097 | 71 | 70 | | 73 | 70 | 78 | 78 | 65 | 71 | 65 | 88 | 85 | 88 | 78 | 100 |

FIG. 18B

| | Pairwise %ID for mature protein amino acid sequence | | | | | | | | | | | | | | | |
|---|---|---|---|---|---|---|---|---|---|---|---|---|---|---|---|---|
| | cds_2753 | cds_9819 | cds_9819T | cds_9873 | cds_9874 | cds_9875 | cds_9894 | cds_9895 | cds_10038 | cds_10039 | cds_10058 | cds_10092 | cds_10093 | cds_10094 | cds_10097 |
| cds_2753 | 100 | 96 | 94 | 80 | 99.5 | 82 | 81 | 70 | 99.7 | 70 | 73 | 74 | 73 | 81 | 74 |
| cds_9819 | 96 | 100 | 98 | 80 | 96 | 81 | 81 | 69 | 96 | 69 | 72 | 74 | 72 | 81 | 74 |
| cds_9819T | 94 | 98 | 100 | 79 | 94 | 79 | 80 | 68 | | | | | | | |
| cds_9873 | 80 | 80 | 79 | 100 | 80 | 82 | 80 | 68 | 80 | 68 | 75 | 75 | 75 | 82 | 77 |
| cds_9874 | 99.5 | 96 | 94 | 80 | 100 | 82 | 81 | 69 | 99 | 70 | 73 | 74 | 73 | 81 | 74 |
| cds_9875 | 82 | 81 | 79 | 82 | 82 | 100 | 92 | 69 | 80 | 69 | 75 | 75 | 75 | 82 | 82 |
| cds_9894 | 81 | 81 | 80 | 80 | 81 | 92 | 100 | 70 | 82 | 69 | 81 | 80 | 81 | 97 | 81 |
| cds_9895 | 70 | 69 | 68 | 68 | 69 | 69 | 70 | 100 | 70 | 99.7 | 67 | 67 | 67 | 70 | 68 |
| cds_10038 | 99.7 | 96 | | 80 | 99 | 82 | 81 | 70 | 100 | 70 | 73 | 75 | 73 | 81 | 74 |
| cds_10039 | 70 | 69 | | 68 | 70 | 69 | 70 | 99.7 | 70 | 100 | 67 | 67 | 67 | 70 | 68 |
| cds_10058 | 73 | 72 | | 75 | 73 | 81 | 79 | 67 | 73 | 67 | 100 | 89 | 99.5 | 81 | 90 |
| cds_10092 | 74 | 74 | | 75 | 74 | 80 | 80 | 67 | 75 | 67 | 89 | 100 | 89 | 81 | 88 |
| cds_10093 | 73 | 72 | | 75 | 73 | 81 | 79 | 67 | 73 | 67 | 99.5 | 89 | 100 | 81 | 90 |
| cds_10094 | 81 | 81 | | 82 | 81 | 97 | 92 | 70 | 81 | 70 | 81 | 81 | 81 | 100 | 81 |
| cds_10097 | 74 | 74 | | 77 | 74 | 82 | 81 | 68 | 74 | 68 | 90 | 88 | 90 | 81 | 100 |

SEQUENCE LISTING

```
<160> NUMBER OF SEQ ID NOS: 114

<210> SEQ ID NO 1
<211> LENGTH: 1194
<212> TYPE: DNA
<213> ORGANISM: C. defragrans
<220> FEATURE:
<221> NAME/KEY: misc_feature
<222> LOCATION: (1)..(1194)
<223> OTHER INFORMATION: C. defragrans 65Phen, Native Nucleic acid
      sequence encoding wild type (WT) linalool dehydratase polypeptide
      SEQ ID NO:2; including  signal peptide encoding sequence

<400> SEQUENCE: 1
atgcggttca cattgaagac gacggcgatt gtgtcggccg ccgccctgct ggccggtttc      60
gggccgccgc cccgcgcggc ggaactgccg ccggggcggc tcgccaccac cgaggactat     120
ttcgcgcagc aggcgaagca ggccgtcacc cccgacgtga tggcccagct ggcctacatg     180
aactacatcg atttcatctc gcccttctac agccggggct gctccttcga ggcctgggag     240
ctcaagcaca cgccgcagcg ggtcatcaag tattcgatcg ccttctatgc gtatggcctg     300
gccagcgtgg cgctcatcga cccgaagctg cgtgcgctcg ccggccatga cctggacatc     360
gcggtctcca agatgaagtg caagcgggtc tggggcgact gggaggaaga cgggttcggc     420
accgacccga tcgagaaaga gaacatcatg tacaagggcc acctgaacct gatgtacggc     480
ctctatcagc tggtgaccgg cagccgccgg tacgaagccg agcatgccca cctcacccgc     540
atcatccatg acgagatcgc ggccaacccc tttgccggca tcgtctgcga gccggacaat     600
tattttgtcc agtgcaattc ggtcgcctac ctgagcctgt gggtctatga ccggctgcat     660
ggcaccgact accgggcggc caccagggcc tggctggatt tcatccagaa ggacctgatc     720
gatcccgagc ggggcgcctt ctacctgtcc tatcaccccg agtccggcgc ggtgaagccg     780
tggatctcgg cgtatacgac agcctggacg ctcgccatgg tgcacggcat ggaccccgcc     840
ttttccgagc gctactaccc ccggttcaag cagaccttcg tcgaggtcta cgacgagggc     900
cgcaaggccc gggtgcgcga cacggccggc acggacgacg cggatggcgg ggtgggcctg     960
gcttcggcgt tcaccctgct gctggcccgc gagatgggcg accagcagct cttcgaccaa    1020
ttgctgaatc acctggagcc gccggccaag ccgagcatcg tctcggcctc gctgcggtac    1080
gagcatcccg gcagcctgct gttcgacgag ctgctgttcc tcgccaaggt gcatgccggc    1140
tttggcgccc tgcttcggat gccgcctccg gcggccaagc tcgcagggaa ataa          1194

<210> SEQ ID NO 2
<211> LENGTH: 397
<212> TYPE: PRT
<213> ORGANISM: C. defragrans
<220> FEATURE:
<221> NAME/KEY: misc_feature
<222> LOCATION: (1)..(397)
<223> OTHER INFORMATION: C. defragrans 65Phen, Native full-length wild
``` type linalool dehydratase polypeptide

<400> SEQUENCE: 2

```
Met Arg Phe Thr Leu Lys Thr Thr Ala Ile Val Ser Ala Ala Ala Leu
1               5                   10                  15

Leu Ala Gly Phe Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
                35                  40                  45

Val Thr Pro Asp Val Met Ala Gln Leu Ala Tyr Met Asn Tyr Ile Asp
    50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
                115                 120                 125

Arg Val Trp Gly Asp Trp Glu Glu Asp Gly Phe Gly Thr Asp Pro Ile
130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
                180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr Asp Tyr
210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
                260                 265                 270

Met Val His Gly Met Asp Pro Ala Phe Ser Glu Arg Tyr Tyr Pro Arg
            275                 280                 285

Phe Lys Gln Thr Phe Val Glu Val Tyr Asp Glu Gly Arg Lys Ala Arg
            290                 295                 300

Val Arg Glu Thr Ala Gly Thr Asp Asp Ala Asp Gly Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Ala Lys Pro Ser
                340                 345                 350

Ile Val Ser Ala Ser Leu Arg Tyr Glu His Pro Gly Ser Leu Leu Phe
            355                 360                 365

Asp Glu Leu Leu Phe Leu Ala Lys Val His Ala Gly Phe Gly Ala Leu
            370                 375                 380

Leu Arg Met Pro Pro Pro Ala Ala Lys Leu Ala Gly Lys
385                 390                 395
```

<210> SEQ ID NO 3
<211> LENGTH: 1194
<212> TYPE: DNA
<213> ORGANISM: C. defragrans
<220> FEATURE:
<221> NAME/KEY: misc_feature
<222> LOCATION: (1)..(1194)
<223> OTHER INFORMATION: C. defragrans 65Phen, Codon-optimized Nucleic acid encoding SEQ ID NO:2

<400> SEQUENCE: 3

```
atgcggttca cattgaaaac gacggcaatt gttagcgctg ctgctttgtt ggccggtttc      60
ggtccaccac cacgtgcagc agaattgcca ccaggtcgtc tcgccaccac cgaggactat     120
ttcgcgcagc aggcgaagca ggccgtcacc cccgacgtga tggcccagct ggcctacatg     180
aactacatcg atttcatctc gcccttctac agccggggct gctcccttcga ggcctgggag    240
ctcaagcaca cgccgcagcg ggtcatcaag tattcgatcg ccttctatgc gtatggcctg     300
gccagcgtgg cgctcatcga cccgaagctg cgtgcgctcg ccggccatga cctggacatc     360
gcggtctcca agatgaagtg caagcgggtc tggggcgact gggaggaaga cgggttcggc     420
accgacccga tcgagaaaga gaacatcatg tacaagggcc acctgaacct gatgtacggc     480
ctctatcagc tggtgaccgg cagccgccgg tacgaagccg agcatgccca cctcacccgc     540
atcatccatg acgagatcgc ggccaacccc tttgccggca tcgtctgcgc gccggacaat    600
tatttttgtcc agtgcaattc ggtcgcctac ctgagcctgt gggtctatga ccggctgcat    660
ggcaccgact accgggcggc caccagggcc tggctggatt tcatccagaa ggacctgatc    720
gatcccgagc ggggcgcctt ctacctgtcc tatcaccccg agtccggcgc ggtgaagccg    780
tggatctcgg cgtatacgac agcctggacg ctcgccatgg tgcacggcat ggaccccgcc    840
ttttccgagc gctactaccc ccggttcaag cagaccttcg tcgaggtcta tgatgaaggt    900
cgtaaagcac gtgttcgtga acggcaggt acggatgatg cagatggtgg tgttggtttg    960
gcttcggcgt tcaccctgct gctggcccgc gagatgggcg accagcagct cttcgaccaa  1020
ttgctgaatc acctggagcc gccggccaag ccgagcatcg tctcggcctc gctgcggtac  1080
gagcatcccg gcagcctgct gttcgacgag ctgctgttcc tcgccaaggt gcatgccggc  1140
tttggcgccc tgcttcggat gccgcctccg gcggccaagc tcgcagggaa ataa         1194
```

<210> SEQ ID NO 4
<211> LENGTH: 1194
<212> TYPE: DNA
<213> ORGANISM: C. defragrans
<220> FEATURE:
<221> NAME/KEY: misc_feature
<222> LOCATION: (1)..(1194)
<223> OTHER INFORMATION: C. defragrans 65Phen, Codon-optimized Nucleic acid encoding SEQ ID NO:2

<400> SEQUENCE: 4

```
atgcgcttta cgttgaaaac caccgccatc gtgtccgctg cggcgttgct ggcaggtttc      60
ggtccgccac cgcgtgcggc agaattacca cctggccgcc tggcaacgac cgaagattac    120
tttgcgcagc aagcaaaaca agccgttacc ccggacgtca tggcgcagct ggcatatatg    180
aactatatcg atttcatttc tccgttctat agccgcggtt gctcctttga ggcgtgggaa    240
ctgaagcata ctccgcagcg tgtgatcaag tatagcattg cgttctacgc gtacggtctg    300
gcgagcgtcg cgctgattga cccgaagttg agagccctgg caggccacga tttggacatc    360
gctgtttcca aaatgaaatg taaacgcgtt tggggcgact gggaggagga cggtttcggt    420
```

```
accgatccga tcgagaaaga aaacatcatg tacaagggcc acctgaacct gatgtatggt    480
ctgtaccaac tggtcaccgg ctctcgtcgc tatgaagccg agcacgcgca tcttacccgc    540
atcattcatg atgaaattgc ggcgaacccg ttcgcgggta tcgtgtgtga gccggacaat    600
tactttgttc agtgcaatag cgttgcctac ctgagcctgt gggtctatga ccgtctgcac    660
ggcacggact atcgtgcggc gacgcgtgct tggctggact tcattcagaa agatttgatt    720
gatccggagc gtgcgccctt ttacctgagc taccatccgg agagcggtgc agtgaagccg    780
tggatcagcg cttacaccac cgcttggact ctggccatgg ttcacggtat ggacccggcg    840
tttagcgagc gttactaccc cgcgcttcaag caaacgtttg tcgaggtgta cgacgagggt    900
cgtaaggcac gtgtgcgtga accgcgggt accgacgacg cggatggtgg cgtgggtctg    960
gcaagcgcct tcacgctgct gctggcacgc gagatgggtg atcagcaatt gttcgatcag   1020
ctgttgaatc atctcgaacc gccagcgaag ccgtcgattg tgagcgcctc cctgcgttat   1080
gaacacccgg gtagcctgct gtttgatgaa ctgctgtttc tggcgaaagt acacgcgggc   1140
ttcggcgcac tgctgcgtat gccgcctccg gcagctaaac tggcgggtaa ataa          1194
```

<210> SEQ ID NO 5
<211> LENGTH: 1116
<212> TYPE: DNA
<213> ORGANISM: C. defragrans
<220> FEATURE:
<221> NAME/KEY: misc_feature
<222> LOCATION: (1)..(1116)
<223> OTHER INFORMATION: C. defragrans 65Phen, Codon Optimized Nucleic
      acid encoding SEQ ID NO:6

<400> SEQUENCE: 5

```
gcagaattac cacctggccg cctggcaacg accgaagatt actttgcgca gcaagcaaaa     60
caagccgtta ccccggacgt catggcgcag ctggcatata tgaactatat cgatttcatt    120
tctccgttct atagccgcgg ttgctccttt gaggcgtggg aactgaagca tactccgcag    180
cgtgtgatca agtatagcat tgcgttctac gcgtacggtc tggcgagcgt cgcgctgatt    240
gacccgaagt tgagagccct ggcaggccac gatttggaca tcgctgtttc caaaatgaaa    300
tgtaaacgcg tttgggcga ctgggaggag acggtttcg gtaccgatcc gatcgagaaa     360
gaaaacatca tgtacaaggg ccacctgaac ctgatgtatg gtctgtacca actggtcacc    420
ggctctcgtc gctatgaagc cgagcacgcg catcttaccc gcatcattca tgatgaaatt    480
gcggcgaacc cgttcgcggg tatcgtgtgt gagccggaca attactttgt tcagtgcaat    540
agcgttgcct acctgagcct gtgggtctat gaccgtctgc acggcacgga ctatcgtgcg    600
gcgacgcgtg cttggctgga cttcattcag aaagatttga ttgatccgga gcgtggcgcc    660
ttttacctga gctaccatcc ggagagcggt gcagtgaagc cgtggatcag cgcttacacc    720
accgcttgga ctctggccat ggttcacggt atgacccgg cgtttagcga gcgttactac    780
ccgcgcttca gcaaacgttt gtcgaggtg tacgacgagg tcgtaaggc acgtgtgcgt    840 gaaccgcgcgg gtaccgacga cgcggatggt ggcgtgggtc tggcaagcgc cttcacgctg    900
ctgctggcac gcgagatggg tgatcagcaa ttgttcgatc agctgttgaa tcatctcgaa    960
ccgccagcga agccgtcgat tgtgagcgcc tccctgcgtt atgaacaccc gggtagcctg   1020
ctgtttgatg aactgctgtt tctggcgaaa gtacacgcgg gcttcggcgc actgctgcgt   1080
atgccgcctc cggcagctaa actggcgggt aaataa                              1116
```

```
<210> SEQ ID NO 6
<211> LENGTH: 371
<212> TYPE: PRT
<213> ORGANISM: C. defragrans
<220> FEATURE:
<221> NAME/KEY: misc_feature
<222> LOCATION: (1)..(371)
<223> OTHER INFORMATION: C. defragrans 65Phen, Mature (processed) form
      of SEQ ID NO:2 wild type linalool dehydratase

<400> SEQUENCE: 6

Ala Glu Leu Pro Pro Gly Arg Leu Ala Thr Thr Glu Asp Tyr Phe Ala
1               5                   10                  15

Gln Gln Ala Lys Gln Ala Val Thr Pro Asp Val Met Ala Gln Leu Ala
            20                  25                  30

Tyr Met Asn Tyr Ile Asp Phe Ile Ser Pro Phe Tyr Ser Arg Gly Cys
        35                  40                  45

Ser Phe Glu Ala Trp Glu Leu Lys His Thr Pro Gln Arg Val Ile Lys
    50                  55                  60

Tyr Ser Ile Ala Phe Tyr Ala Tyr Gly Leu Ala Ser Val Ala Leu Ile
65                  70                  75                  80

Asp Pro Lys Leu Arg Ala Leu Ala Gly His Asp Leu Asp Ile Ala Val
                85                  90                  95

Ser Lys Met Lys Cys Lys Arg Val Trp Gly Asp Trp Glu Glu Asp Gly
            100                 105                 110

Phe Gly Thr Asp Pro Ile Glu Lys Glu Asn Ile Met Tyr Lys Gly His
        115                 120                 125

Leu Asn Leu Met Tyr Gly Leu Tyr Gln Leu Val Thr Gly Ser Arg Arg
    130                 135                 140

Tyr Glu Ala Glu His Ala His Leu Thr Arg Ile Ile His Asp Glu Ile
145                 150                 155                 160

Ala Ala Asn Pro Phe Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Asp Tyr Arg Ala Ala Thr Arg Ala Trp Leu Asp Phe
        195                 200                 205

Ile Gln Lys Asp Leu Ile Asp Pro Glu Arg Gly Ala Phe Tyr Leu Ser
    210                 215                 220

Tyr His Pro Glu Ser Gly Ala Val Lys Pro Trp Ile Ser Ala Tyr Thr
225                 230                 235                 240

Thr Ala Trp Thr Leu Ala Met Val His Gly Met Asp Pro Ala Phe Ser
                245                 250                 255

Glu Arg Tyr Tyr Pro Arg Phe Lys Gln Thr Phe Val Glu Val Tyr Asp
            260                 265                 270

Glu Gly Arg Lys Ala Arg Val Arg Glu Thr Ala Gly Thr Asp Asp Ala
        275                 280                 285

Asp Gly Gly Val Gly Leu Ala Ser Ala Phe Thr Leu Leu Leu Ala Arg
    290                 295                 300

Glu Met Gly Asp Gln Gln Leu Phe Asp Gln Leu Leu Asn His Leu Glu
305                 310                 315                 320

Pro Pro Ala Lys Pro Ser Ile Val Ser Ala Ser Leu Arg Tyr Glu His
                325                 330                 335

Pro Gly Ser Leu Leu Phe Asp Glu Leu Leu Phe Leu Ala Lys Val His
            340                 345                 350

Ala Gly Phe Gly Ala Leu Leu Arg Met Pro Pro Pro Ala Ala Lys Leu
```

```
                      355                 360                 365

Ala Gly Lys
    370

<210> SEQ ID NO 7
<211> LENGTH: 78
<212> TYPE: DNA
<213> ORGANISM: C. defragrans
<220> FEATURE:
<221> NAME/KEY: misc_feature
<222> LOCATION: (1)..(78)
<223> OTHER INFORMATION: C. defragrans 65Phen, Native Nucleic acid
      encoding signal sequence SEQ ID NO:8

<400> SEQUENCE: 7
atgcggttca cattgaagac gacggcgatt gtgtcggccg ccgccctgct ggccggtttc      60
gggccgccgc cccgcgcg                                                   78

<210> SEQ ID NO 8
<211> LENGTH: 26
<212> TYPE: PRT
<213> ORGANISM: C. defragrans
<220> FEATURE:
<221> NAME/KEY: misc_feature
<222> LOCATION: (1)..(26)
<223> OTHER INFORMATION: C. defragrans 65Phen, Signal sequence peptide
      from SEQ ID NO:2

<400> SEQUENCE: 8

Met Arg Phe Thr Leu Lys Thr Thr Ala Ile Val Ser Ala Ala Ala Leu
1               5                   10                  15

Leu Ala Gly Phe Gly Pro Pro Pro Arg Ala
            20                  25

<210> SEQ ID NO 9
<211> LENGTH: 1194
<212> TYPE: DNA
<213> ORGANISM: C. defragrans
<220> FEATURE:
<221> NAME/KEY: misc_feature
<222> LOCATION: (1)..(1194)
<223> OTHER INFORMATION: C. defragrans 65Phen, Nucleic acid encoding SEQ
      ID NO:10; differs from SEQ ID NO:4 by having 12 codon
      substitutions

<400> SEQUENCE: 9
atgcgcttta cgttgaaaac caccgccatc gtgtccgctg cggcgttgct gattggtctg      60
ggtccgccac gcgtgcggc agaactgcct cctggtcgtc tggcaaccac cgaagattat     120
tttgcacagc aggcaaaaca ggcagttaca ccggatgtta tggcacagct ggcatatatg     180
aactatatcg attttatcag cccgtttttt agccgcagct gtagctttga agcatgggaa     240
ctgaaacata caccgcagcg tgtttatcaaa tatagcattg ccttttatgc atatggtctg     300
gcaagcgttg cactgattga tccgaaactg cgtgcactgg caggtcatga tctggatatt     360
gcagttagca aaatgaaatg caaacgcgtg tggatggatt gggaagaaga tggttttggc     420
accgatccga ttgaaaaaga aaacatcatg tataaaggcc atctgaacct gatgtatggt     480
ctgtatcagc tggttaccgg tagccgtaaa tatgaagcag aacatgcaca tctgacccgt     540
ctgattcatg atgaaattgc agcaaatccg tttgccggta ttttttgtga accgaacaac     600 tatttttgtgc agtgtaatag cgttgcatat ctgagcctgt gggttatga tcgtctgcat     660 ggtacagatt atcgtgcagc aacccgtgca tggctggatt ttattcagaa agatctgatc     720
```

```
gatccggaac gtggtgcatt ttatctgagc tatcatccgg aaagcggtgc agttaaaccg    780
tggattagcg catataccac cgcatggacc ctggcaatgg ttcatggtat ggatccggca    840
tttagcgaac gttattatcc gcgttttaaa cagaccttcg tggaagttta tgatgaaggt    900
cgtaaagcac gtgttcgtga accgcaggc accgatgatg cagatggtgg tgttggtctg    960
gccagtgcaa gcaccctgct gctggcacgt gaaatgggtg atcagcagct gtttgatcaa   1020
ctgctgaatc atctggaacc gcctgcaaaa ccgagcattg tgagcgcaag cctgcgttat   1080
gaacatccga gcagcctgtt ttttgatgag ctgctgtttc tggcaaaagt tcatgcaggt   1140
tttggtgcac tgctgcgtat gcctccgcca gcagccaaac tggcaggcaa ataa         1194
```

<210> SEQ ID NO 10
<211> LENGTH: 397
<212> TYPE: PRT
<213> ORGANISM: C. defragrans
<220> FEATURE:
<221> NAME/KEY: misc_feature
<222> LOCATION: (1)..(397)
<223> OTHER INFORMATION: C. defragrans 65Phen, Full-length polypeptide
       variant of SEQ ID NO:2; having 12 substitutions

<400> SEQUENCE: 10

Met Arg Phe Thr Leu Lys Thr Thr Ala Ile Val Ser Ala Ala Ala Leu
1               5                   10                  15

Leu Ile Gly Leu Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
            35                  40                  45

Val Thr Pro Asp Val Met Ala Gln Leu Ala Tyr Met Asn Tyr Ile Asp
        50                  55                  60

Phe Ile Ser Pro Phe Phe Ser Arg Ser Cys Ser Phe Glu Ala Trp Glu
65                  70                  75                  80

Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
        115                 120                 125

Arg Val Trp Met Asp Trp Glu Glu Asp Gly Phe Gly Thr Asp Pro Ile
    130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Lys Tyr Glu Ala Glu His Ala
                165                 170                 175

His Leu Thr Arg Leu Ile His Asp Glu Ile Ala Ala Asn Pro Phe Ala
            180                 185                 190

Gly Ile Phe Cys Glu Pro Asn Asn Tyr Phe Val Gln Cys Asn Ser Val
        195                 200                 205

Ala Tyr Leu Ser Leu Trp Val Tyr Asp Arg Leu His Gly Thr Asp Tyr
    210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

```
Met Val His Gly Met Asp Pro Ala Phe Ser Glu Arg Tyr Tyr Pro Arg
        275                 280                 285

Phe Lys Gln Thr Phe Val Glu Val Tyr Asp Glu Gly Arg Lys Ala Arg
        290                 295                 300

Val Arg Glu Thr Ala Gly Thr Asp Asp Ala Asp Gly Gly Val Gly Leu
305                 310                 315                 320

Ala Ser Ala Ser Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
                340                 345                 350

Ile Val Ser Ala Ser Leu Arg Tyr Glu His Pro Ser Ser Leu Phe Phe
                355                 360                 365

Asp Glu Leu Leu Phe Leu Ala Lys Val His Ala Gly Phe Gly Ala Leu
        370                 375                 380

Leu Arg Met Pro Pro Pro Ala Ala Lys Leu Ala Gly Lys
385                 390                 395
```

<210> SEQ ID NO 11
<211> LENGTH: 1197
<212> TYPE: DNA
<213> ORGANISM: Castellaniella defragrans
<220> FEATURE:
<221> NAME/KEY: misc_feature
<222> LOCATION: (1)..(1197)
<223> OTHER INFORMATION: Castellaniella defragrans 62Car, Native Nucleic
      acid encoding SEQ ID NO:12; including signal peptide

<400> SEQUENCE: 11

```
atgcgattca cattgaagac gccggcgatc gcgtcggccg tcgctgccct gctggtcggt      60
cttggacagc cggcgcatgc ggcgccgctg ccgctgggc gccttgcccc gaccgaggac      120
tacttcgccc agcaggcgaa gcaggccgtc accccgacg tgatggccca gctggcctac      180
atgaactata tcgatttcat ctcgcctttc tacagccggg ggtgttcctt cgaggcctgg      240
gaactcaagc acacaccgca gcgggtcatc aagtattcga tcgctttcta tgcgtatggc      300
ctggccagcg tggcgctcat cgatccgaat ctgcgcgcgc tcgccggcca tgacctggac      360
atcgcggtct ccaagatgaa atgcaagcgg gtctggggcg actgggagga agacgggttc      420
ggcgacgatc cgatcgagaa agagaacatc atgtacaagg ccacctgaa cctgatgtac      480 ggcctctatc agctggtgac cggcagccgc cggtacgaag ccgagcatgc gcacctcacc      540
cgcatcatcc acgacgagat cggcgccaac ccctttgccg gcatcgtctg tgagccggat      600
aattatttcg tccaatgcaa ctcggtcgcc tacctgagcc tgtgggtcta tgaccgcctg      660
catggcaccg attatcgggc ggcgaccccg gcctggctgg acttcatcca gaaagacctg      720
atcgaccccg agcggggcgc cttctacctg tcctatcatc cggagtccgg cgcggtgaag      780
ccgtggatct cggcgtatac gaccgcctgg acgctcgcca tggtgcatgg catggatccc      840
gccttttccg agcgctacta ccccgcgttc aagaaaacct tcgtcgaggt ctacgacggg      900
ggccgcaagg cccgggtgcg agagacggcc ggcacggccg acgcggatgg cggggtgggc      960
ctggcgtcgg catttaccct gctgctggcc cgcgagatgg gcgaccagac gctcttcgac     1020
cagctgctga atcacctgga accgccggcc cagcccagca tcgtctcggc ctcattgcgt     1080
tacgagcatc ccggcagcct gttgttcgac gaactgctgt tcctggccaa ggtgcatgcc     1140
ggctttggcg ccctgctcca gatgccgcct ccggcggcga aatccgggggg gaaatga      1197
```

<210> SEQ ID NO 12
<211> LENGTH: 398
<212> TYPE: PRT
<213> ORGANISM: Castellaniella defragrans
<220> FEATURE:
<221> NAME/KEY: misc_feature
<222> LOCATION: (1)..(398)
<223> OTHER INFORMATION: Full-length wild type LinD from C. defragrans 62Car, with signal peptide

<400> SEQUENCE: 12

```
Met Arg Phe Thr Leu Lys Thr Pro Ala Ile Ala Ser Ala Val Ala Ala
1               5                   10                  15

Leu Leu Val Gly Leu Gly Gln Pro Ala His Ala Pro Leu Pro Leu
            20                  25                  30

Gly Arg Leu Ala Pro Thr Glu Asp Tyr Phe Ala Gln Gln Ala Lys Gln
            35                  40                  45

Ala Val Thr Pro Asp Val Met Ala Gln Leu Ala Tyr Met Asn Tyr Ile
    50                  55                  60

Asp Phe Ile Ser Pro Phe Tyr Ser Arg Gly Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Asn Leu Arg
            100                 105                 110

Ala Leu Ala Gly His Asp Leu Asp Ile Ala Val Ser Lys Met Lys Cys
            115                 120                 125

Lys Arg Val Trp Gly Asp Trp Glu Glu Asp Gly Phe Gly Asp Asp Pro
130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Ser Arg Arg Tyr Glu Ala Glu His
                165                 170                 175

Ala His Leu Thr Arg Ile Ile His Asp Glu Ile Gly Ala Asn Pro Phe
            180                 185                 190

Ala Gly Ile Val Cys Glu Pro Asp Asn Tyr Phe Val Gln Cys Asn Ser
            195                 200                 205

Val Ala Tyr Leu Ser Leu Trp Val Tyr Asp Arg Leu His Gly Thr Asp
210                 215                 220

Tyr Arg Ala Ala Thr Arg Ala Trp Leu Asp Phe Ile Gln Lys Asp Leu
225                 230                 235                 240

Ile Asp Pro Glu Arg Gly Ala Phe Tyr Leu Ser Tyr His Pro Glu Ser
                245                 250                 255

Gly Ala Val Lys Pro Trp Ile Ser Ala Tyr Thr Thr Ala Trp Thr Leu
            260                 265                 270

Ala Met Val His Gly Met Asp Pro Ala Phe Ser Glu Arg Tyr Tyr Pro
        275                 280                 285

Ala Phe Lys Lys Thr Phe Val Glu Val Tyr Asp Gly Gly Arg Lys Ala
    290                 295                 300

Arg Val Arg Glu Thr Ala Gly Thr Ala Asp Ala Asp Gly Gly Val Gly
305                 310                 315                 320

Leu Ala Ser Ala Phe Thr Leu Leu Leu Ala Arg Glu Met Gly Asp Gln
                325                 330                 335

Thr Leu Phe Asp Gln Leu Leu Asn His Leu Glu Pro Pro Ala Gln Pro
            340                 345                 350

Ser Ile Val Ser Ala Ser Leu Arg Tyr Glu His Pro Gly Ser Leu Leu
```

```
                   355                 360                 365
    Phe Asp Glu Leu Leu Phe Leu Ala Lys Val His Ala Gly Phe Gly Ala
        370                 375                 380

Leu Leu Gln Met Pro Pro Pro Ala Ala Lys Ser Gly Gly Lys
    385                 390                 395
```

<210> SEQ ID NO 13
<211> LENGTH: 1197
<212> TYPE: DNA
<213> ORGANISM: Castellaniella defragrans
<220> FEATURE:
<221> NAME/KEY: misc_feature
<222> LOCATION: (1)..(1197)
<223> OTHER INFORMATION: 1st codon optimized Nucleic acid encoding full
      length SEQ ID NO:12; designated GNM 9819A

<400> SEQUENCE: 13

```
atgcgcttta ccctgaaaac accggcaatt gcaagcgcag ttgcagcact gctggttggt      60
ctgggtcagc ctgcacatgc agcaccgctg ccgctgggtc gtctggcacc gaccgaagat     120
tattttgcac agcaggcaaa acaggcagtt acaccggatg ttatggcaca gctggcatat     180
atgaactata tcgattttat cagcccgttc tatagccgtg ttgtagctt tgaagcatgg      240 gaactgaaac atacaccgca gcgtgttatc aaatatagca ttgccttttta tgcatatggt    300 ctggcaagcg ttgcactgat tgatccgaat ctgcgtgcac tggcaggtca tgatctggat    360
attgcagtta gcaaaatgaa atgcaaacgt gtttggggtg attgggaaga ggatggtttt    420
ggtgatgatc cgattgagaa agaaaacatc atgtataaag ccatctgaa cctgatgtat    480 ggtctgtatc agctggttac cggtagccgt cgttatgaag cagaacatgc acatctgacc    540
cgtattattc atgatgaaat tggtgcaaat ccgtttgccg gtattgtttg tgaaccggat    600
aactattttg tgcagtgtaa tagcgttgca tatctgagcc tgtgggttta tgatcgtctg    660
catggcaccg attatcgtgc agcaacccgt gcatggctgg attttattca gaaagatctg    720
atcgatccgg aacgtggtgc atttttatctg agctatcatc cggaaagcgg tgcagttaaa    780
ccgtggatta cgcatatac caccgcatgg accctggcaa tggttcatgg tatggatccg    840
gcatttagcg aacgttatta tcctgcattc aaaaaaaacct ttgtcgaggt gtatgatggt    900
ggtcgtaaag cacgtgttcg tgaaaccgca ggcaccgcag atgcagatgg tggtgtgggt    960
ctggccagtg catttaccct gctgctggca cgtgaaatgg gtgatcagac cctgtttgat    1020
cagctgctga atcatctgga accgcctgca cagccgagca ttgttagcgc aagcctgcgt    1080
tatgaacatc cgggtagcct gctgttcgat gaactgctgt ttctggcaaa agttcatgca    1140
ggttttggcg cactgctgca gatgcctccg cctgcagcaa aaagcggtgg taaataa     1197
```

<210> SEQ ID NO 14
<211> LENGTH: 1197
<212> TYPE: DNA
<213> ORGANISM: Castellaniella defragrans
<220> FEATURE:
<221> NAME/KEY: misc_feature
<222> LOCATION: (1)..(1197)
<223> OTHER INFORMATION: 2nd codon optimized Nucleic acid encoding full-
      length SEQ ID NO:12; designated GNM 9819B

<400> SEQUENCE: 14

```
atgcgcttta ctctgaaaac ccctgctatc gcttccgccg ttgctgcact gttggttggt      60
ctgggtcagc cagcgcacgc ggcaccgctg ccgttaggcc gcttggcacc gaccgaagat    120
tactttgccc aacaggcgaa acaagccgtc accccggatg ttatggccca gctggcgtac    180
```

```
atgaattaca tcgacttcat tagcccgttt tacagccgtg gttgcagctt cgaggcgtgg    240
gagttgaaac acacgccgca gcgtgtcatc aagtatagca ttgcgttcta tgcgtacggc    300
ctggcaagcg tcgcactgat cgacccgaat ctgcgtgctc tggcgggtca tgacctggat    360
atcgcggtca gcaagatgaa atgtaagcgc gtgtggggtg attgggaaga agatggcttt    420
ggtgatgacc cgattgagaa agaaaacatt atgtataagg gccacctgaa cctcatgtac    480
ggtctgtatc aactggtgac cggtagccgt cgctatgaag cggagcatgc ccacttgacc    540
cgtattatcc acgacgaaat cggtgcaaac ccgttcgcgg gtattgtgtg cgagccggac    600
aattactttg tgcagtgtaa ctctgtcgcg tacctgagcc tgtgggtata tgatcgtctg    660
catggcaccg actaccgtgc agcgacgcgt gcctggctgg atttcatcca gaaagatctg    720
attgacccgg agcgcggtgc gttttacctg agctatcacc ctgagtccgg tgccgtgaaa    780
ccgtggatta gcgcgtacac tacggcgtgg accctggcga tggtgcatgg catggatccg    840
gcgttcagcg agcgttatta cccggcgttc aaaaagacct tgttgaagt ttacgacggt    900 ggccgcaagg cacgtgtccg tgaaacggca ggcacggcag atgccgacgg tggcgttggt    960
ctggcgtctg ctttcacccct gctgcttgcg cgcgagatgg gtgaccaaac gctgtttgac    1020
caattgctga atcacctgga gccgccagca caaccgtcca tcgtgagcgc tagcctgcgt    1080
tatgagcacc cgggtagcct gctgttcgac gaactgctgt tcttggccaa ggttcatgcc    1140
ggctttggcg cgctgctgca gatgccgcca ccggcagcta aatcgggtgg caagtaa     1197
```

<210> SEQ ID NO 15
<211> LENGTH: 1116
<212> TYPE: DNA
<213> ORGANISM: Castellaniella defragrans
<220> FEATURE:
<221> NAME/KEY: misc_feature
<222> LOCATION: (1)..(1116)
<223> OTHER INFORMATION: Native Nucleic acid encoding SEQ ID NO:16;
      Processed (mature) form of SEQ ID NO:11 Nucleic acid, GNM 9819

<400> SEQUENCE: 15

```
gcgccgctgc cgctgggggcg ccttgccccg accgaggact acttcgccca gcaggcgaag     60
caggccgtca cccccgacgt gatggcccag ctggcctaca tgaactatat cgatttcatc    120
tcgcctttct acagccgggg gtgttccttc gaggcctggg aactcaagca cacaccgcag    180
cgggtcatca agtattcgat cgcttttctat gcgtatggcc tggccagcgt ggcgctcatc    240
gatccgaatc tgcgcgcgct cgccggccat gacctggaca tcgcggtctc caagatgaaa    300
tgcaagcggg tctggggcga ctgggaggaa gacgggttcg gcgacgatcc gatcgagaaa    360
gagaacatca tgtacaaggg ccacctgaac ctgatgtacg gcctctatca gctggtgacc    420
ggcagccgcc ggtacgaagc cgagcatgcg cacctcaccc gcatcatcca cgacgagatc    480
ggcgccaacc cctttgccgg catcgtctgt gagccggata attatttcgt ccaatgcaac    540
tcggtcgcct acctgagcct gtgggtctat gaccgcctgc atggcaccga ttatcgggcg    600
gcgacccggg cctggctgga cttcatccag aaagacctga tcgaccccga gcggggcgcc    660
ttctacctgt cctatcatcc ggagtccggc gcggtgaagc cgtggatctc ggcgtatacg    720
accgcctgga cgctcgccat ggtgcatggc atggatcccg ccttttccga gcgctactac    780
cccgcgttca gaaaaacctt cgtcgaggtc tacgacgggg ccgcaaggc ccgggtgcga    840 gagacggccg gcacggccga cgcggatggc ggggtgggcc tggcgtcggc atttaccctg    900
ctgctggccc gcgagatggg cgaccagacg ctcttcgacc agctgctgaa tcacctggaa    960
```

```
ccgccggccc agcccagcat cgtctcggcc tcattgcgtt acgagcatcc cggcagcctg   1020
ttgttcgacg aactgctgtt cctggccaag gtgcatgccg gctttggcgc cctgctccag   1080
atgccgcctc cggcggcgaa atccggggg aaatga                              1116
```

<210> SEQ ID NO 16
<211> LENGTH: 371
<212> TYPE: PRT
<213> ORGANISM: Castellaniella defragrans
<220> FEATURE:
<221> NAME/KEY: misc_feature
<222> LOCATION: (1)..(371)
<223> OTHER INFORMATION: Mature form of LinD polypeptide SEQ ID NO:12
      (GNM 9819)

<400> SEQUENCE: 16

```
Ala Pro Leu Pro Leu Gly Arg Leu Ala Pro Thr Glu Asp Tyr Phe Ala
1               5                   10                  15

Gln Gln Ala Lys Gln Ala Val Thr Pro Asp Val Met Ala Gln Leu Ala
            20                  25                  30

Tyr Met Asn Tyr Ile Asp Phe Ile Ser Pro Phe Tyr Ser Arg Gly Cys
        35                  40                  45

Ser Phe Glu Ala Trp Glu Leu Lys His Thr Pro Gln Arg Val Ile Lys
    50                  55                  60

Tyr Ser Ile Ala Phe Tyr Ala Tyr Gly Leu Ala Ser Val Ala Leu Ile
65                  70                  75                  80

Asp Pro Asn Leu Arg Ala Leu Ala Gly His Asp Leu Asp Ile Ala Val
                85                  90                  95

Ser Lys Met Lys Cys Lys Arg Val Trp Gly Asp Trp Glu Glu Asp Gly
            100                 105                 110

Phe Gly Asp Asp Pro Ile Glu Lys Glu Asn Ile Met Tyr Lys Gly His
        115                 120                 125

Leu Asn Leu Met Tyr Gly Leu Tyr Gln Leu Val Thr Gly Ser Arg Arg
    130                 135                 140

Tyr Glu Ala Glu His Ala His Leu Thr Arg Ile Ile His Asp Glu Ile
145                 150                 155                 160

Gly Ala Asn Pro Phe Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Asp Tyr Arg Ala Ala Thr Arg Ala Trp Leu Asp Phe
        195                 200                 205

Ile Gln Lys Asp Leu Ile Asp Pro Glu Arg Gly Ala Phe Tyr Leu Ser
    210                 215                 220

Tyr His Pro Glu Ser Gly Ala Val Lys Pro Trp Ile Ser Ala Tyr Thr
225                 230                 235                 240

Thr Ala Trp Thr Leu Ala Met Val His Gly Met Asp Pro Ala Phe Ser
                245                 250                 255

Glu Arg Tyr Tyr Pro Ala Phe Lys Lys Thr Phe Val Glu Val Tyr Asp
            260                 265                 270

Gly Gly Arg Lys Ala Arg Val Arg Glu Thr Ala Gly Thr Ala Asp Ala
        275                 280                 285

Asp Gly Gly Val Gly Leu Ala Ser Ala Phe Leu Leu Leu Ala Arg
    290                 295                 300

Glu Met Gly Asp Gln Thr Leu Phe Asp Gln Leu Leu Asn His Leu Glu
305                 310                 315                 320
```

```
Pro Pro Ala Gln Pro Ser Ile Val Ser Ala Ser Leu Arg Tyr Glu His
            325                 330                 335

Pro Gly Ser Leu Leu Phe Asp Glu Leu Leu Phe Leu Ala Lys Val His
            340                 345                 350

Ala Gly Phe Gly Ala Leu Leu Gln Met Pro Pro Ala Ala Lys Ser
            355                 360                 365

Gly Gly Lys
    370

<210> SEQ ID NO 17
<211> LENGTH: 1116
<212> TYPE: DNA
<213> ORGANISM: Castellaniella defragrans
<220> FEATURE:
<221> NAME/KEY: misc_feature
<222> LOCATION: (1)..(1116)
<223> OTHER INFORMATION: Codon optimized Nucleic acid encoding SEQ ID
      NO:16 (shortened from SEQ ID NO:13 GNM 9819A)

<400> SEQUENCE: 17
gcaccgctgc cgctgggtcg tctggcaccg accgaagatt attttgcaca gcaggcaaaa      60
caggcagtta caccggatgt tatggcacag ctggcatata tgaactatat cgattttatc    120
agcccgttct atagccgtgg ttgtagcttt gaagcatggg aactgaaaca tacaccgcag    180
cgtgttatca aatatagcat tgcctttttat gcatatggtc tggcaagcgt tgcactgatt    240
gatccgaatc tgcgtgcact ggcaggtcat gatctggata ttgcagttag caaaatgaaa    300
tgcaaacgtg tttgggggtga ttgggaagag atggttttg gtgatgatcc gattgagaaa    360
gaaaacatca tgtataaagg ccatctgaac ctgatgtatg gtctgtatca gctggttacc    420
ggtagccgtc gttatgaagc agaacatgca catctgaccc gtattattca tgatgaaatt    480
ggtgcaaatc cgtttgccgg tattgtttgt gaaccggata ctatttttgt gcagtgtaat    540
agcgttgcat atctgagcct gtgggtttat gatcgtctgc atggcaccga ttatcgtgca    600
gcaacccgtg catggctgga ttttattcag aaagatctga tcgatccgga acgtggtgca    660 tttttatctga gctatcatcc ggaaagcggt gcagttaaac cgtggattag cgcatatacc    720
accgcatgga ccctggcaat ggttcatggt atggatccgg catttagcga acgttattat    780
cctgcattca aaaaaacctt tgtcgaggtg tatgatggtg tcgtaaagc acgtgttcgt    840 gaaaccgcag gcaccgcaga tgcagatggt ggtgtgggtc tggccagtgc atttacccctg    900 ctgctggcac gtgaaatggg tgatcagacc ctgtttgatc agctgctgaa tcatctggaa    960
ccgcctgcac agccgagcat tgttagcgca agcctgcgtt atgaacatcc gggtagcctg   1020
ctgttcgatg aactgctgtt tctggcaaaa gttcatgcag gttttggcgc actgctgcag   1080
atgcctccgc ctgcagcaaa aagcggtggt aaataa                              1116

<210> SEQ ID NO 18
<211> LENGTH: 1116
<212> TYPE: DNA
<213> ORGANISM: Castellaniella defragrans
<220> FEATURE:
<221> NAME/KEY: misc_feature
<222> LOCATION: (1)..(1116)
<223> OTHER INFORMATION: Codon optimized Nucleic acid encoding SEQ ID
      NO:16 (shortened from SEQ ID NO:14 GNM 9819B)

<400> SEQUENCE: 18
gcaccgctgc cgttaggccg cttggcaccg accgaagatt actttgccca acaggcgaaa      60
```

-continued

| | |
|---|---|
| caagccgtca ccccggatgt tatggcccag ctggcgtaca tgaattacat cgacttcatt | 120 |
| agcccgtttt acagccgtgg ttgcagcttc gaggcgtggg agttgaaaca cacgccgcag | 180 |
| cgtgtcatca agtatagcat tgcgttctat gcgtacggcc tggcaagcgt cgcactgatc | 240 |
| gacccgaatc tgcgtgctct ggcgggtcat gacctggata tcgcggtcag caagatgaaa | 300 |
| tgtaagcgcg tgtggggtga ttgggaagaa gatggctttg gtgatgaccc gattgagaaa | 360 |
| gaaaacatta tgtataaggg ccacctgaac ctcatgtacg gtctgtatca actggtgacc | 420 |
| ggtagccgtc gctatgaagc ggagcatgcc cacttgaccc gtattatcca cgacgaaatc | 480 |
| ggtgcaaacc cgttcgcggg tattgtgtgc gagccggaca attactttgt gcagtgtaac | 540 |
| tctgtcgcgt acctgagcct gtgggtatat gatcgtctgc atggcaccga ctaccgtgca | 600 |
| gcgacgcgtg cctggctgga tttcatccag aaagatctga ttgacccgga gcgcggtgcg | 660 |
| ttttacctga gctatcaccc tgagtccggt gccgtgaaac cgtggattag cgcgtacact | 720 |
| acggcgtgga ccctggcgat ggtgcatggc atggatccgg cgttcagcga gcgttattac | 780 |
| ccggcgttca aaaagacctt tgttgaagtt tacgacggtg gccgcaaggc acgtgtccgt | 840 |
| gaaacggcag gcacggcaga tgccgacggt ggcgttggtc tggcgtctgc tttcaccctg | 900 |
| ctgcttgcgc gcgagatggg tgaccaaacg ctgtttgacc aattgctgaa tcacctggag | 960 |
| ccgccagcac aaccgtccat cgtgagcgct agcctgcgtt atgagcaccc gggtagcctg | 1020 |
| ctgttcgacg aactgctgtt cttggccaag gttcatgccg gctttggcgc gctgctgcag | 1080 |
| atgccgccac cggcagctaa atcgggtggc aagtaa | 1116 |

<210> SEQ ID NO 19
<211> LENGTH: 81
<212> TYPE: DNA
<213> ORGANISM: Castellaniella defragrans
<220> FEATURE:
<221> NAME/KEY: misc_feature
<222> LOCATION: (1)..(81)
<223> OTHER INFORMATION: Native Nucleic acid encoding signal sequence
      SEQ ID NO:20; from SEQ ID NO:11

<400> SEQUENCE: 19

| | |
|---|---|
| atgcgtttta ccctgaaaac accggcaatt gcaagcgcag ttgcagcact gctgattggt | 60 |
| ctgggtcagc ctgcacatgc a | 81 |

<210> SEQ ID NO 20
<211> LENGTH: 27
<212> TYPE: PRT
<213> ORGANISM: Castellaniella defragrans
<220> FEATURE:
<221> NAME/KEY: misc_feature
<222> LOCATION: (1)..(27)
<223> OTHER INFORMATION: Signal peptide from SEQ ID NO:12(GNM 9819)

<400> SEQUENCE: 20

Met Arg Phe Thr Leu Lys Thr Pro Ala Ile Ala Ser Ala Val Ala Ala
1               5                   10                  15

Leu Leu Val Gly Leu Gly Gln Pro Ala His Ala
            20                  25

<210> SEQ ID NO 21
<211> LENGTH: 1197
<212> TYPE: DNA
<213> ORGANISM: Castellaniella defragrans
<220> FEATURE:
<221> NAME/KEY: misc_feature
<222> LOCATION: (1)..(1197)

<223> OTHER INFORMATION: Nucleic acid encoding full-length variant SEQ
ID NO:22, designated 9819C; differs from wild type SEQ ID NO:13
GNM 9819A by having 11 codon substitutions

<400> SEQUENCE: 21

```
atgcgtttta ccctgaaaac accggcaatt gcaagcgcag ttgcagcact gctgattggt      60
ctgggtcagc tgcacatgc agcaccgctg ccgctgggtc gtctggcacc gaccgaagat     120
tattttgcac agcaggcaaa acaggcagtt acaccggatg ttatggcaca gctggcatat     180
atgaactata tcgatttat cagcccgttt tttagccgca gctgtagctt tgaagcatgg     240
gaactgaaac atacaccgca gcgtgttatc aaatatagca ttgccttttta tgcatatggt     300
ctggcaagcg ttgcactgat tgatccgaat ctgcgtgcac tggcaggtca tgatctggat     360
attgcagtta gcaaaatgaa atgcaaacgc gtgtggatgg attgggaaga ggatggtttt     420
ggtgatgatc cgattgagaa agaaaacatc atgtataaag gccatctgaa cctgatgtat     480
ggtctgtatc agctggttac cggtagccgt aaatatgaag cagaacatgc acatctgacc     540
cgtctgattc atgatgaaat tggtgcaaat ccgtttgccg gtatttttg tgaaccgaac     600
aactattttg tgcagtgtaa tagcgttgca tatctgagcc tgtgggttta tgatcgtctg     660
catggcaccg attatcgtgc agcaacccgt gcatggctgg attttattca gaaagatctg     720
atcgatccgg aacgtggtgc attttatctg agctatcatc cggaaagcgg tgcagttaaa     780
ccgtggatta gcgcatatac caccgcatgg accctggcaa tggttcatgg tatggatccg     840
gcatttagcg aacgttatta tcctgcattc aaaaaaacct ttgtcgaggt gtatgatggt     900
ggtcgtaaag cacgtgttcg tgaaaccgca ggcaccgcag atgcagatgg tggtgttggt     960
ctggccagtg caagcaccct gctgctggca cgtgaaatgg gtgatcagac cctgtttgat    1020
cagctgctga tcatctgga accgcctgca cagccgagca ttgttagcgc aagcctgcgt    1080
tatgaacatc cgagcagcct gttttttgat gaactgctgt tctggcaaa agtgcatgca    1140
ggttttggcg cactgctgca gatgcctccg cctgcagcaa aaagcggtgg taaataa    1197
```

<210> SEQ ID NO 22
<211> LENGTH: 398
<212> TYPE: PRT
<213> ORGANISM: Castellaniella defragrans
<220> FEATURE:
<221> NAME/KEY: misc_feature
<222> LOCATION: (1)..(398)
<223> OTHER INFORMATION: Full-length variant SEQ ID NO:12 (GNM 9819)
with 11 amino acid substitutions V19I, Y71F, G74S, G133M, R171K,
I182L, V196F, D200N, F325S, G365S, L368F; designated 9819C

<400> SEQUENCE: 22

```
Met Arg Phe Thr Leu Lys Thr Pro Ala Ile Ala Ser Ala Val Ala Ala
1               5                   10                  15

Leu Leu Ile Gly Leu Gly Gln Pro Ala His Ala Ala Pro Leu Pro Leu
            20                  25                  30

Gly Arg Leu Ala Pro Thr Glu Asp Tyr Phe Ala Gln Gln Ala Lys Gln
        35                  40                  45

Ala Val Thr Pro Asp Val Met Ala Gln Leu Ala Tyr Met Asn Tyr Ile
    50                  55                  60

Asp Phe Ile Ser Pro Phe Phe Ser Arg Ser Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Asn Leu Arg
```

```
                100             105                 110
Ala Leu Ala Gly His Asp Leu Asp Ile Ala Val Ser Lys Met Lys Cys
            115                 120             125

Lys Arg Val Trp Met Asp Trp Glu Glu Asp Gly Phe Gly Asp Asp Pro
        130                 135             140

Ile Glu Lys Glu Asn Ile Met Tyr Lys Gly His Leu Asn Leu Met Tyr
145             150                 155                 160

Gly Leu Tyr Gln Leu Val Thr Gly Ser Arg Lys Tyr Glu Ala Glu His
            165                 170             175

Ala His Leu Thr Arg Leu Ile His Asp Glu Ile Gly Ala Asn Pro Phe
        180                 185             190

Ala Gly Ile Phe Cys Glu Pro Asn Asn Tyr Phe Val Gln Cys Asn Ser
        195                 200             205

Val Ala Tyr Leu Ser Leu Trp Val Tyr Asp Arg Leu His Gly Thr Asp
        210                 215             220

Tyr Arg Ala Ala Thr Arg Ala Trp Leu Asp Phe Ile Gln Lys Asp Leu
225             230                 235             240

Ile Asp Pro Glu Arg Gly Ala Phe Tyr Leu Ser Tyr His Pro Glu Ser
            245                 250             255

Gly Ala Val Lys Pro Trp Ile Ser Ala Tyr Thr Ala Trp Thr Leu
            260                 265             270

Ala Met Val His Gly Met Asp Pro Ala Phe Ser Glu Arg Tyr Tyr Pro
            275                 280             285

Ala Phe Lys Lys Thr Phe Val Glu Val Tyr Asp Gly Gly Arg Lys Ala
        290                 295             300

Arg Val Arg Glu Thr Ala Gly Thr Ala Asp Ala Asp Gly Gly Val Gly
305             310                 315             320

Leu Ala Ser Ala Ser Thr Leu Leu Leu Ala Arg Glu Met Gly Asp Gln
            325                 330             335

Thr Leu Phe Asp Gln Leu Leu Asn His Leu Glu Pro Pro Ala Gln Pro
            340                 345             350

Ser Ile Val Ser Ala Ser Leu Arg Tyr Glu His Pro Ser Ser Leu Phe
            355                 360             365

Phe Asp Glu Leu Leu Phe Leu Ala Lys Val His Ala Gly Phe Gly Ala
        370                 375             380

Leu Leu Gln Met Pro Pro Pro Ala Ala Lys Ser Gly Gly Lys
385                 390                 395

<210> SEQ ID NO 23
<211> LENGTH: 396
<212> TYPE: PRT
<213> ORGANISM: Castellaniella defragrans
<220> FEATURE:
<221> NAME/KEY: misc_feature
<222> LOCATION: (1)..(396)
<223> OTHER INFORMATION: variant enzyme: SEQ ID NO:25 (heterologous
      signal sequence LamB ss) fused to mature form wild type linD
      from C. defragrans 65Phen, SEQ ID NO:6

<400> SEQUENCE: 23

Met Met Ile Thr Leu Arg Lys Leu Pro Leu Ala Val Ala Val Ala Ala
1               5                   10                  15

Gly Val Met Ser Ala Gln Ala Met Ala Ala Glu Leu Pro Pro Gly Arg
                20                  25                  30

Leu Ala Thr Thr Glu Asp Tyr Phe Ala Gln Gln Ala Lys Gln Ala Val
            35                  40                  45
```

```
Thr Pro Asp Val Met Ala Gln Leu Ala Tyr Met Asn Tyr Ile Asp Phe
    50                  55                  60
Ile Ser Pro Phe Tyr Ser Arg Gly Cys Ser Phe Glu Ala Trp Glu Leu
 65                  70                  75                  80
Lys His Thr Pro Gln Arg Val Ile Lys Tyr Ser Ile Ala Phe Tyr Ala
                 85                  90                  95
Tyr Gly Leu Ala Ser Val Ala Leu Ile Asp Pro Lys Leu Arg Ala Leu
            100                 105                 110
Ala Gly His Asp Leu Asp Ile Ala Val Ser Lys Met Lys Cys Lys Arg
            115                 120                 125
Val Trp Gly Asp Trp Glu Glu Asp Gly Phe Gly Thr Asp Pro Ile Glu
130                 135                 140
Lys Glu Asn Ile Met Tyr Lys Gly His Leu Asn Leu Met Tyr Gly Leu
145                 150                 155                 160
Tyr Gln Leu Val Thr Gly Ser Arg Arg Tyr Glu Ala Glu His Ala His
                165                 170                 175
Leu Thr Arg Ile Ile His Asp Glu Ile Ala Ala Asn Pro Phe Ala Gly
            180                 185                 190
Ile Val Cys Glu Pro Asp Asn Tyr Phe Val Gln Cys Asn Ser Val Ala
            195                 200                 205
Tyr Leu Ser Leu Trp Val Tyr Asp Arg Leu His Gly Thr Asp Tyr Arg
210                 215                 220
Ala Ala Thr Arg Ala Trp Leu Asp Phe Ile Gln Lys Asp Leu Ile Asp
225                 230                 235                 240
Pro Glu Arg Gly Ala Phe Tyr Leu Ser Tyr His Pro Glu Ser Gly Ala
                245                 250                 255
Val Lys Pro Trp Ile Ser Ala Tyr Thr Thr Ala Trp Thr Leu Ala Met
            260                 265                 270
Val His Gly Met Asp Pro Ala Phe Ser Glu Arg Tyr Tyr Pro Arg Phe
            275                 280                 285
Lys Gln Thr Phe Val Glu Val Tyr Asp Glu Gly Arg Lys Ala Arg Val
290                 295                 300
Arg Glu Thr Ala Gly Thr Asp Asp Ala Asp Gly Gly Val Gly Leu Ala
305                 310                 315                 320
Ser Ala Phe Thr Leu Leu Leu Ala Arg Glu Met Gly Asp Gln Gln Leu
                325                 330                 335
Phe Asp Gln Leu Leu Asn His Leu Glu Pro Pro Ala Lys Pro Ser Ile
            340                 345                 350
Val Ser Ala Ser Leu Arg Tyr Glu His Pro Gly Ser Leu Leu Phe Asp
            355                 360                 365
Glu Leu Leu Phe Leu Ala Lys Val His Ala Gly Phe Gly Ala Leu Leu
370                 375                 380
Arg Met Pro Pro Pro Ala Ala Lys Leu Ala Gly Lys
385                 390                 395

<210> SEQ ID NO 24
<211> LENGTH: 396
<212> TYPE: PRT
<213> ORGANISM: Castellaniella defragrans
<220> FEATURE:
<221> NAME/KEY: misc_feature
<222> LOCATION: (1)..(396)
<223> OTHER INFORMATION: variant enzyme: SEQ ID NO:25 (heterologous
      signal sequence LamB ss) fused to mature form wild type enzyme
      from Castellaniella defragrans 62Car, SEQ ID NO:16

<400> SEQUENCE: 24
```

```
Met Met Ile Thr Leu Arg Lys Leu Pro Leu Ala Val Ala Val Ala Ala
1               5                   10                  15

Gly Val Met Ser Ala Gln Ala Met Ala Ala Pro Leu Pro Leu Gly Arg
                20                  25                  30

Leu Ala Pro Thr Glu Asp Tyr Phe Ala Gln Ala Lys Gln Ala Val
        35                  40                  45

Thr Pro Asp Val Met Ala Gln Leu Ala Tyr Met Asn Tyr Ile Asp Phe
    50                  55                  60

Ile Ser Pro Phe Tyr Ser Arg Gly Cys Ser Phe Glu Ala Trp Glu Leu
65                  70                  75                  80

Lys His Thr Pro Gln Arg Val Ile Lys Tyr Ser Ile Ala Phe Tyr Ala
                85                  90                  95

Tyr Gly Leu Ala Ser Val Ala Leu Ile Asp Pro Asn Leu Arg Ala Leu
            100                 105                 110

Ala Gly His Asp Leu Asp Ile Ala Val Ser Lys Met Lys Cys Lys Arg
        115                 120                 125

Val Trp Gly Asp Trp Glu Glu Asp Gly Phe Gly Asp Asp Pro Ile Glu
    130                 135                 140

Lys Glu Asn Ile Met Tyr Lys Gly His Leu Asn Leu Met Tyr Gly Leu
145                 150                 155                 160

Tyr Gln Leu Val Thr Gly Ser Arg Arg Tyr Glu Ala Glu His Ala His
                165                 170                 175

Leu Thr Arg Ile Ile His Asp Glu Ile Gly Ala Asn Pro Phe Ala Gly
                180                 185                 190

Ile Val Cys Glu Pro Asp Asn Tyr Phe Val Gln Cys Asn Ser Val Ala
            195                 200                 205

Tyr Leu Ser Leu Trp Val Tyr Asp Arg Leu His Gly Thr Asp Tyr Arg
210                 215                 220

Ala Ala Thr Arg Ala Trp Leu Asp Phe Ile Gln Lys Asp Leu Ile Asp
225                 230                 235                 240

Pro Glu Arg Gly Ala Phe Tyr Leu Ser Tyr His Pro Glu Ser Gly Ala
                245                 250                 255

Val Lys Pro Trp Ile Ser Ala Tyr Thr Thr Ala Trp Thr Leu Ala Met
            260                 265                 270

Val His Gly Met Asp Pro Ala Phe Ser Glu Arg Tyr Tyr Pro Ala Phe
    275                 280                 285

Lys Lys Thr Phe Val Glu Val Tyr Asp Gly Gly Arg Lys Ala Arg Val
    290                 295                 300

Arg Glu Thr Ala Gly Thr Ala Asp Ala Asp Gly Val Gly Leu Ala
305                 310                 315                 320

Ser Ala Phe Thr Leu Leu Leu Ala Arg Glu Met Gly Asp Gln Thr Leu
                325                 330                 335

Phe Asp Gln Leu Leu Asn His Leu Glu Pro Pro Ala Gln Pro Ser Ile
            340                 345                 350

Val Ser Ala Ser Leu Arg Tyr Glu His Pro Gly Ser Leu Leu Phe Asp
            355                 360                 365

Glu Leu Leu Phe Leu Ala Lys Val His Ala Gly Phe Gly Ala Leu Leu
    370                 375                 380

Gln Met Pro Pro Pro Ala Ala Lys Ser Gly Gly Lys
385                 390                 395

<210> SEQ ID NO 25
<211> LENGTH: 25
```

```
<212> TYPE: PRT
<213> ORGANISM: Castellaniella defragrans
<220> FEATURE:
<221> NAME/KEY: misc_feature
<222> LOCATION: (1)..(25)
<223> OTHER INFORMATION: peptide: heterologous signal sequence LamBss(or
      LamB ss)

<400> SEQUENCE: 25

Met Met Ile Thr Leu Arg Lys Leu Pro Leu Ala Val Ala Val Ala Ala
1               5                   10                  15

Gly Val Met Ser Ala Gln Ala Met Ala
            20                  25

<210> SEQ ID NO 26
<211> LENGTH: 26
<212> TYPE: PRT
<213> ORGANISM: Castellaniella defragrans
<220> FEATURE:
<221> NAME/KEY: misc_feature
<222> LOCATION: (1)..(26)
<223> OTHER INFORMATION: peptide: heterologous signal sequence MalE ss

<400> SEQUENCE: 26

Met Lys Ile Lys Thr Gly Ala Arg Ile Leu Ala Leu Ser Ala Leu Thr
1               5                   10                  15

Thr Met Met Phe Ser Ala Leu Ala Leu Ala
            20                  25

<210> SEQ ID NO 27
<211> LENGTH: 23
<212> TYPE: PRT
<213> ORGANISM: Castellaniella defragrans
<220> FEATURE:
<221> NAME/KEY: misc_feature
<222> LOCATION: (1)..(23)
<223> OTHER INFORMATION: peptide: heterologous signal sequence MglBss

<400> SEQUENCE: 27

Met Asn Lys Lys Val Leu Thr Leu Ser Ala Val Met Ala Ser Met Leu
1               5                   10                  15

Phe Gly Ala Ala Ala His Ala
            20

<210> SEQ ID NO 28
<211> LENGTH: 21
<212> TYPE: PRT
<213> ORGANISM: Castellaniella defragrans
<220> FEATURE:
<221> NAME/KEY: misc_feature
<222> LOCATION: (1)..(21)
<223> OTHER INFORMATION: peptide: heterologous signal sequence OmpAss

<400> SEQUENCE: 28

Met Lys Lys Thr Ala Ile Ala Ile Ala Val Ala Leu Ala Gly Phe Ala
1               5                   10                  15

Thr Val Ala Gln Ala
            20

<210> SEQ ID NO 29
<211> LENGTH: 22
<212> TYPE: PRT
<213> ORGANISM: Castellaniella defragrans
<220> FEATURE:
<221> NAME/KEY: misc_feature
<222> LOCATION: (1)..(22)
<223> OTHER INFORMATION: peptide: heterologous signal sequence PelBss
```

```
<400> SEQUENCE: 29

Met Lys Tyr Leu Leu Pro Thr Ala Ala Ala Gly Leu Leu Leu Ala
1               5                   10                  15

Ala Gln Pro Ala Met Ala
            20

<210> SEQ ID NO 30
<211> LENGTH: 21
<212> TYPE: PRT
<213> ORGANISM: Castellaniella defragrans
<220> FEATURE:
<221> NAME/KEY: misc_feature
<222> LOCATION: (1)..(21)
<223> OTHER INFORMATION: peptide: heterologous signal sequence PhoAss

<400> SEQUENCE: 30

Met Lys Gln Ser Thr Ile Ala Leu Ala Leu Leu Pro Leu Leu Phe Thr
1               5                   10                  15

Pro Val Thr Lys Ala
            20

<210> SEQ ID NO 31
<211> LENGTH: 19
<212> TYPE: PRT
<213> ORGANISM: Castellaniella defragrans
<220> FEATURE:
<221> NAME/KEY: misc_feature
<222> LOCATION: (1)..(19)
<223> OTHER INFORMATION: peptide: heterologous signal sequence DsbAss

<400> SEQUENCE: 31

Met Lys Lys Ile Trp Leu Ala Leu Ala Gly Leu Val Leu Ala Phe Ser
1               5                   10                  15

Ala Ser Ala

<210> SEQ ID NO 32
<211> LENGTH: 23
<212> TYPE: PRT
<213> ORGANISM: Castellaniella defragrans
<220> FEATURE:
<221> NAME/KEY: misc_feature
<222> LOCATION: (1)..(23)
<223> OTHER INFORMATION: peptide: heterologous signal sequence SfmCss

<400> SEQUENCE: 32

Met Met Thr Lys Ile Lys Leu Leu Met Leu Ile Ile Phe Tyr Leu Ile
1               5                   10                  15

Ile Ser Ala Ser Ala His Ala
            20

<210> SEQ ID NO 33
<211> LENGTH: 21
<212> TYPE: PRT
<213> ORGANISM: Castellaniella defragrans
<220> FEATURE:
<221> NAME/KEY: misc_feature
<222> LOCATION: (1)..(21)
<223> OTHER INFORMATION: peptide: heterologous signal sequence TolBss

<400> SEQUENCE: 33

Met Lys Gln Ala Leu Arg Val Ala Phe Gly Phe Leu Ile Leu Trp Ala
1               5                   10                  15

Ser Val Leu His Ala
            20
```

<210> SEQ ID NO 34
<211> LENGTH: 18
<212> TYPE: PRT
<213> ORGANISM: Castellaniella defragrans
<220> FEATURE:
<221> NAME/KEY: misc_feature
<222> LOCATION: (1)..(18)
<223> OTHER INFORMATION: peptide: heterologous signal sequence TorTss

<400> SEQUENCE: 34

Met Arg Val Leu Leu Phe Leu Leu Leu Ser Leu Phe Met Leu Pro Ala
1               5                   10                  15

Phe Ser

<210> SEQ ID NO 35
<211> LENGTH: 30
<212> TYPE: PRT
<213> ORGANISM: Castellaniella defragrans
<220> FEATURE:
<221> NAME/KEY: misc_feature
<222> LOCATION: (1)..(30)
<223> OTHER INFORMATION: peptide: heterologous signal sequence FhuD ss

<400> SEQUENCE: 35

Met Asn Pro Thr Leu Ile Thr Arg Arg Leu Leu Ile Ala Met Thr
1               5                   10                  15

Leu Ser Pro Leu Leu Trp Gln Met Arg Gly Ala Gln Ala Ala
            20                  25                  30

<210> SEQ ID NO 36
<211> LENGTH: 1194
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1194)
<223> OTHER INFORMATION: Native Nucleic acid encoding SEQ ID NO:37,
      which is unprocessed and includes its signal peptide

<400> SEQUENCE: 36
atgcggttca cattgaagac gacggcgatc gtgtcggccg ccgccctgct ggccggtttc      60
gggccgccgc cccgcgcggc ggaactgccg ccggggcggc tcgccaccac cgaggactat    120
ttcgcgcagc aggcgaagca ggccgtcacc cccgacgtga tggcccagct ggcctacatg    180
aactacatcg atttcatctc gcccttctac agccggggct gctccttcga ggcctgggag    240
ctcaagcaca cgccgcagcg ggtcatcaag tattcgatcg ccttctatgc gtatggcctg    300
gccagcgtgg cgctcatcga cccgaagctg cgtgcgctcg ccggccatga cctggacatc    360
gcggtctcca agatgaagtg caagcgggtc tggggcgact gggaggaaga cgggttcggc    420
accgacccga tcgagaaaga gaacatcatg tacaagggcc acctgaacct gatgtacggc    480
ctctatcagc tggtgaccgg cagccgccgg tacgaagccg agcatgccca cctcacccgc    540
atcatccatg acgagatcgc ggccaacccc tttgccggca tcgtctgcga gccggacaat    600 tatttttgtcc agtgcaattc ggtcgcctac ctgagcctgt gggtctatga ccggctgcat    660
ggcaccgact accgggcggc caccagggcc tggctggatt tcatccagaa ggacctgatc    720
gatcccgagc ggggcgcctt ctacctgtcc tatcaccccg agtccggcgc ggtgaagccg    780
tggatctcgg cgtatacgac agcctggacg ctcgccatgg tgcacggcat ggaccccgcc    840

```
ttttccgagc gctactaccc ccggttcaag cagaccttcg tcgagctcta cgacgagggc    900
cgcaaggccc gggtgcgcga gacggccggc acggacgacg cggatggcgg ggtgggcctg    960
gcttcggcgt tcaccctgct gctggcccgc gagatgggcg accagcagct cttcgaccag   1020
ttgctgaatc acctggagcc gccggccaag cccagcatcg tttcggcctc gctgcggtac   1080
gagcatcccg gcagcctgct gttcgacgag ctgctgttcc tcgccaaggt gcatgccggt   1140
tttggcgccc tgcttcagat gccgcctccg gcggccaagc tcgcggggaa ataa         1194
```

<210> SEQ ID NO 37
<211> LENGTH: 397
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(397)
<223> OTHER INFORMATION: Native, or unprocessed, LinD enzyme, including
      signal peptide

<400> SEQUENCE: 37

```
Met Arg Phe Thr Leu Lys Thr Thr Ala Ile Val Ser Ala Ala Ala Leu
1               5                   10                  15

Leu Ala Gly Phe Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
        35                  40                  45

Val Thr Pro Asp Val Met Ala Gln Leu Ala Tyr Met Asn Tyr Ile Asp
    50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
        115                 120                 125

Arg Val Trp Gly Asp Trp Glu Glu Asp Gly Phe Gly Thr Asp Pro Ile
    130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
        195                 200                 205

Ala Tyr Leu Ser Leu Trp Val Tyr Asp Arg Leu His Gly Thr Asp Tyr
    210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
```

```
                275                 280                 285
Phe Lys Gln Thr Phe Val Glu Leu Tyr Asp Glu Gly Arg Lys Ala Arg
            290                 295                 300

Val Arg Glu Thr Ala Gly Thr Asp Asp Ala Asp Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu His Pro Gly Ser Leu Leu Phe
                355                 360                 365

Asp Glu Leu Leu Phe Leu Ala Lys Val His Ala Gly Phe Gly Ala Leu
            370                 375                 380

Leu Gln Met Pro Pro Pro Ala Ala Lys Leu Ala Gly Lys
385                 390                 395

<210> SEQ ID NO 38
<211> LENGTH: 78
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(78)
<223> OTHER INFORMATION: Nucleic acid encoding GNM 9874 signal peptide

<400> SEQUENCE: 38
atgcggttca cattgaagac gacggcgatc gtgtcggccg ccgccctgct ggccggtttc    60
gggccgccgc cccgcgcg                                                   78

<210> SEQ ID NO 39
<211> LENGTH: 26
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(26)
<223> OTHER INFORMATION: GNM 9874 signal peptide

<400> SEQUENCE: 39

Met Arg Phe Thr Leu Lys Thr Thr Ala Ile Val Ser Ala Ala Ala Leu
1               5                   10                  15

Leu Ala Gly Phe Gly Pro Pro Pro Arg Ala
            20                  25

<210> SEQ ID NO 40
<211> LENGTH: 1116
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1116)
<223> OTHER INFORMATION: Nucleic acid encoding processed GNM 9874 LinD
      enzyme, no signal peptide

<400> SEQUENCE: 40
gcggaactgc cgccggggcg gctcgccacc accgaggact atttcgcgca gcaggcgaag    60
caggccgtca ccccccgacgt gatggcccag ctggcctaca tgaactacat cgatttcatc   120
```

```
tcgcccttct acagccgggg ctgctccttc gaggcctggg agctcaagca cacgccgcag    180
cgggtcatca agtattcgat cgccttctat gcgtatggcc tggccagcgt ggcgctcatc    240
gacccgaagc tgcgtgcgct cgccggccat gacctggaca tcgcggtctc caagatgaag    300
tgcaagcggg tctggggcga ctgggaggaa acgggttcg gcaccgaccc gatcgagaaa    360
gagaacatca tgtacaaggg ccacctgaac ctgatgtacg gcctctatca gctggtgacc    420
ggcagccgcc ggtacgaagc cgagcatgcc cacctcaccc gcatcatcca tgacgagatc    480
gcggccaacc cctttgccgg catcgtctgc gagccggaca attattttgt ccagtgcaat    540
tcggtcgcct acctgagcct gtgggtctat gaccggctgc atggcaccga ctaccgggcg    600
gccaccaggg cctggctgga tttcatccag aaggacctga tcgatcccga gcggggcgcc    660
ttctacctgt cctatcaccc cgagtccggc gcggtgaagc cgtggatctc ggcgtatacg    720
acagcctgga cgctcgccat ggtgcacggc atggaccccg ccttttccga gcgctactac    780
ccccggttca gcagaccctt cgtcgagctc tacgacgagg gccgcaaggc ccgggtgcgc    840
gagacggccg gcacggacga cgcggatggc ggggtgggcc tggcttcggc gttcaccctg    900
ctgctggccc gcgagatggg cgaccagcag ctcttcgacc agttgctgaa tcacctggag    960
ccgccggcca agcccagcat cgtttcggcc tcgctgcggt acgagcatcc cggcagcctg   1020
ctgttcgacg agctgctgtt cctcgccaag gtgcatgccg gttttggcgc cctgcttcag   1080
atgccgcctc cggcggccaa gctcgcgggg aaataa                             1116
```

<210> SEQ ID NO 41
<211> LENGTH: 371
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(371)
<223> OTHER INFORMATION: Processed GNM 9874 LinD enzyme, no signal
      peptide

<400> SEQUENCE: 41

```
Ala Glu Leu Pro Pro Gly Arg Leu Ala Thr Thr Glu Asp Tyr Phe Ala
1               5                   10                  15

Gln Gln Ala Lys Gln Ala Val Thr Pro Asp Val Met Ala Gln Leu Ala
            20                  25                  30

Tyr Met Asn Tyr Ile Asp Phe Ile Ser Pro Phe Tyr Ser Arg Gly Cys
        35                  40                  45

Ser Phe Glu Ala Trp Glu Leu Lys His Thr Pro Gln Arg Val Ile Lys
    50                  55                  60

Tyr Ser Ile Ala Phe Tyr Ala Tyr Gly Leu Ala Ser Val Ala Leu Ile
65                  70                  75                  80

Asp Pro Lys Leu Arg Ala Leu Ala Gly His Asp Leu Asp Ile Ala Val
                85                  90                  95

Ser Lys Met Lys Cys Lys Arg Val Trp Gly Asp Trp Glu Glu Asp Gly
            100                 105                 110

Phe Gly Thr Asp Pro Ile Glu Lys Glu Asn Ile Met Tyr Lys Gly His
        115                 120                 125

Leu Asn Leu Met Tyr Gly Leu Tyr Gln Leu Val Thr Gly Ser Arg Arg
    130                 135                 140

Tyr Glu Ala Glu His Ala His Leu Thr Arg Ile Ile His Asp Glu Ile
145                 150                 155                 160
```

Ala Ala Asn Pro Phe Ala Gly Ile Val Cys Glu Pro Asp Asn Tyr Phe
            165                 170                 175

Val Gln Cys Asn Ser Val Ala Tyr Leu Ser Leu Trp Val Tyr Asp Arg
        180                 185                 190

Leu His Gly Thr Asp Tyr Arg Ala Ala Thr Arg Ala Trp Leu Asp Phe
    195                 200                 205

Ile Gln Lys Asp Leu Ile Asp Pro Glu Arg Gly Ala Phe Tyr Leu Ser
210                 215                 220

Tyr His Pro Glu Ser Gly Ala Val Lys Pro Trp Ile Ser Ala Tyr Thr
225                 230                 235                 240

Thr Ala Trp Thr Leu Ala Met Val His Gly Met Asp Pro Ala Phe Ser
                245                 250                 255

Glu Arg Tyr Tyr Pro Arg Phe Lys Gln Thr Phe Val Glu Leu Tyr Asp
            260                 265                 270

Glu Gly Arg Lys Ala Arg Val Arg Glu Thr Ala Gly Thr Asp Asp Ala
        275                 280                 285

Asp Gly Gly Val Gly Leu Ala Ser Ala Phe Thr Leu Leu Leu Ala Arg
    290                 295                 300

Glu Met Gly Asp Gln Gln Leu Phe Asp Gln Leu Leu Asn His Leu Glu
305                 310                 315                 320

Pro Pro Ala Lys Pro Ser Ile Val Ser Ala Ser Leu Arg Tyr Glu His
                325                 330                 335

Pro Gly Ser Leu Leu Phe Asp Glu Leu Leu Phe Leu Ala Lys Val His
            340                 345                 350

Ala Gly Phe Gly Ala Leu Leu Gln Met Pro Pro Pro Ala Ala Lys Leu
        355                 360                 365

Ala Gly Lys
    370

<210> SEQ ID NO 42
<211> LENGTH: 1203
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1203)
<223> OTHER INFORMATION: Native Nucleic acid encoding SEQ ID NO: 43,
      which is unprocessed and includes its signal peptide

<400> SEQUENCE: 42
atgataaagc cccacagacg atccgccgca cgactttccc taatcatcgc agcaaccctc      60
ggtttcggca gttccgccag tgccgaagac ctgttccccg ccgcctcgc caccaccgcg     120 gactacttcg cccaacgcga aaagcacacc gtgactcccg atgtcatggc gcacctggcc     180
ttcatgaact acacggattt catttccccc ttctacagcc ggggttgtgc cttcgacgcg     240
tgggacatca agaagacacc gcaacggatc atcaagtatt cgctggcgtt ctattcctac     300
ggcctcgcta gcgttgcgct caccgatccc aaactgcgac cacttgccgc gcatgcgatc     360
gatgtcgcca cgtcaaagat gaaatgcaag cgcgtctggg aagactggga agaagatggc     420
ttcggtagcg acccgatcga aagcaaaaac atcatgtaca agggtcacct gaacctgatg     480
tatggcctct accagctggt cagcggaaac cggcagtacg aggccgaaca caaacatctg     540
accaagatca tccacgacga gatcaaggcc aacccttttcg ctggcgcgct ctgcgagccg     600
gacaactatt ttgtccaatg caactcggtc gcctatctga gcctgtgggt gtatgaccga     660

```
ctccatggca caagctacaa ggcagccacc gaaccctggc tgaaattcct gaaaaaggat    720
ctgatcgatc cgaaaacggg cgccttctat ctatcctttc accccgaatc cggcacagtg    780
aaaccctggc tctcggcgta taccacggcg tggacgctgg ccatggtgca cggcatggac    840
ccggcctttt ccgaacgcta ctacccggcg ttcaagaaga cctttgtcga agtctatgac    900
ggcggccgaa aggcacgggt cgcgagacg accaatacgc cagacgccga cggcggggtt    960
ggcgcggcct ctgcgttcac gttgctgctt gcccgtgaga tgggcgacca gacactcttc    1020
gaccagttgc tcaaccacct tgagccccg gcgaaaccca aaatcacctc agccatcttg    1080
aactacgagg cgcccagcaa cctgctcttt gatgagttgc tgttcctctc gaaagtccat    1140
gtcggctttg gtgaactgct aaaagctacg cccccgccgg cgcgcgcaga cagtcagaaa    1200
taa                                                                 1203
```

<210> SEQ ID NO 43
<211> LENGTH: 400
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(400)
<223> OTHER INFORMATION: Native, or unprocessed, LinD enzyme, including signal peptide

<400> SEQUENCE: 43

```
Met Ile Lys Pro His Arg Arg Ser Ala Ala Arg Leu Ser Leu Ile Ile
1               5                   10                  15

Ala Ala Thr Leu Gly Phe Gly Ser Ser Ala Ser Ala Glu Asp Leu Phe
            20                  25                  30

Pro Gly Arg Leu Ala Thr Thr Ala Asp Tyr Phe Ala Gln Arg Glu Lys
        35                  40                  45

His Thr Val Thr Pro Asp Val Met Ala His Leu Ala Phe Met Asn Tyr
    50                  55                  60

Thr Asp Phe Ile Ser Pro Phe Tyr Ser Arg Gly Cys Ala Phe Asp Ala
65                  70                  75                  80

Trp Asp Ile Lys Lys Thr Pro Gln Arg Ile Ile Lys Tyr Ser Leu Ala
                85                  90                  95

Phe Tyr Ser Tyr Gly Leu Ala Ser Val Ala Leu Thr Asp Pro Lys Leu
            100                 105                 110

Arg Pro Leu Ala Ala His Ala Ile Asp Val Ala Thr Ser Lys Met Lys
        115                 120                 125

Cys Lys Arg Val Trp Glu Asp Trp Glu Glu Asp Gly Phe Gly Ser Asp
    130                 135                 140

Pro Ile Glu Lys Gln Asn Ile Met Tyr Lys Gly His Leu Asn Leu Met
145                 150                 155                 160

Tyr Gly Leu Tyr Gln Leu Val Ser Gly Asn Arg Gln Tyr Glu Ala Glu
                165                 170                 175

His Lys His Leu Thr Lys Ile Ile His Asp Glu Ile Lys Ala Asn Pro
            180                 185                 190

Phe Ala Gly Ala Leu Cys Glu Pro Asp Asn Tyr Phe Val Gln Cys Asn
        195                 200                 205

Ser Val Ala Tyr Leu Ser Leu Trp Val Tyr Asp Arg Leu His Gly Thr
    210                 215                 220

Ser Tyr Lys Ala Ala Thr Glu Pro Trp Leu Lys Phe Leu Lys Lys Asp
```

```
                225                 230                 235                 240
Leu Ile Asp Pro Lys Thr Gly Ala Phe Tyr Leu Ser Phe His Pro Glu
                245                 250                 255

Ser Gly Thr Val Lys Pro Trp Leu Ser Ala Tyr Thr Thr Ala Trp Thr
            260                 265                 270

Leu Ala Met Val His Gly Met Asp Pro Ala Phe Ser Glu Arg Tyr Tyr
        275                 280                 285

Pro Ala Phe Lys Lys Thr Phe Val Glu Val Tyr Asp Gly Gly Arg Lys
    290                 295                 300

Ala Arg Val Arg Glu Thr Thr Asn Thr Pro Asp Ala Asp Gly Gly Val
305                 310                 315                 320

Gly Ala Ala Ser Ala Phe Thr Leu Leu Leu Ala Arg Glu Met Gly Asp
                325                 330                 335

Gln Thr Leu Phe Asp Gln Leu Leu Asn His Leu Glu Pro Pro Ala Lys
            340                 345                 350

Pro Lys Ile Thr Ser Ala Ile Leu Asn Tyr Glu Ala Pro Ser Asn Leu
        355                 360                 365

Leu Phe Asp Glu Leu Leu Phe Leu Ser Lys Val His Val Gly Phe Gly
    370                 375                 380

Glu Leu Leu Lys Ala Thr Pro Pro Ala Arg Ala Asp Ser Gln Lys
385                 390                 395                 400

<210> SEQ ID NO 44
<211> LENGTH: 84
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(84)
<223> OTHER INFORMATION: Nucleic acid encoding GNM 9873 signal peptide

<400> SEQUENCE: 44
atgataaagc cccacagacg atccgccgca cgactttccc taatcatcgc agcaaccctc      60
ggtttcggca gttccgccag tgcc                                             84

<210> SEQ ID NO 45
<211> LENGTH: 28
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(28)
<223> OTHER INFORMATION: GNM 9873 signal peptide

<400> SEQUENCE: 45

Met Ile Lys Pro His Arg Arg Ser Ala Ala Arg Leu Ser Leu Ile Ile
1               5                   10                  15

Ala Ala Thr Leu Gly Phe Gly Ser Ser Ala Ser Ala
            20                  25

<210> SEQ ID NO 46
<211> LENGTH: 1119
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
```

```
<222> LOCATION: (1)..(1119)
<223> OTHER INFORMATION: Nucleic acid encoding processed GNM 9873 LinD
      enzyme, no signal peptide

<400> SEQUENCE: 46
gaagacctgt tccccggccg cctcgccacc accgcggact acttcgccca acgcgaaaag    60
cacaccgtga ctcccgatgt catggcgcac ctggccttca tgaactacac ggatttcatt   120 tccccttct acagccgggg ttgtgccttc gacgcgtggg acatcaagaa gacaccgcaa    180
cggatcatca agtattcgct ggcgttctat tcctacggcc tcgctagcgt tgcgctcacc   240
gatcccaaac tgcgaccact tgccgcgcat gcgatcgatg tcgccacgtc aaagatgaaa   300
tgcaagcgcg tctgggaaga ctgggaagaa gatggcttcg gtagcgaccc gatcgagaag   360
caaaacatca tgtacaaggg tcacctgaac ctgatgtatg ccctctacca gctggtcagc   420
ggaaaccggc agtacgaggc cgaacacaaa catctgacca agatcatcca cgacgagatc   480
aaggccaacc ctttcgctgg cgcgctctgc gagccggaca actattttgt ccaatgcaac   540
tcggtcgcct atctgagcct gtgggtgtat gaccgactcc atggcacaag ctacaaggca   600
gccaccgaac cctggctgaa attcctgaaa aaggatctga tcgatccgaa acgggcgcc    660 ttctatctat cctttcaccc cgaatccggc acagtgaaac cctggctctc ggcgtatacc   720
acggcgtgga cgctggccat ggtgcacggc atggacccgg ccttttccga acgctactac   780
ccggcgttca agaagaccctt tgtcgaagtc tatgacggcg gccgaaaggc acgggttcgc   840
gagacgacca atacgccaga cgccgacggc ggggttggcg cggcctctgc gttcacgttg    900
ctgcttgccc gtgagatggg cgaccagaca ctcttcgacc agttgctcaa ccaccttgag   960
cccccggcga aacccaaaat cacctcagcc atcttgaact acgaggcgcc cagcaacctg  1020
ctctttgatg agttgctgtt cctctcgaaa gtccatgtcg gctttggtga actgctaaaa  1080
gctacgcccc cgccggcgcg cgcagacagt cagaaataa                         1119

<210> SEQ ID NO 47
<211> LENGTH: 372
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(372)
<223> OTHER INFORMATION: Processed GNM 9873 LinD enzyme, no signal
      peptide

<400> SEQUENCE: 47

Glu Asp Leu Phe Pro Gly Arg Leu Ala Thr Thr Ala Asp Tyr Phe Ala
1               5                   10                  15

Gln Arg Glu Lys His Thr Val Thr Pro Asp Val Met Ala His Leu Ala
            20                  25                  30

Phe Met Asn Tyr Thr Asp Phe Ile Ser Pro Phe Tyr Ser Arg Gly Cys
        35                  40                  45

Ala Phe Asp Ala Trp Asp Ile Lys Lys Thr Pro Gln Arg Ile Ile Lys
    50                  55                  60

Tyr Ser Leu Ala Phe Tyr Ser Tyr Gly Leu Ala Ser Val Ala Leu Thr
65                  70                  75                  80

Asp Pro Lys Leu Arg Pro Leu Ala Ala His Ala Ile Asp Val Ala Thr
                85                  90                  95

Ser Lys Met Lys Cys Lys Arg Val Trp Glu Asp Trp Glu Glu Asp Gly
            100                 105                 110
```

Phe Gly Ser Asp Pro Ile Glu Lys Gln Asn Ile Met Tyr Lys Gly His
            115                 120                 125

Leu Asn Leu Met Tyr Gly Leu Tyr Gln Leu Val Ser Gly Asn Arg Gln
        130                 135                 140

Tyr Glu Ala Glu His Lys His Leu Thr Lys Ile Ile His Asp Glu Ile
145                 150                 155                 160

Lys Ala Asn Pro Phe Ala Gly Ala Leu Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Ser Tyr Lys Ala Ala Thr Glu Pro Trp Leu Lys Phe
        195                 200                 205

Leu Lys Lys Asp Leu Ile Asp Pro Lys Thr Gly Ala Phe Tyr Leu Ser
210                 215                 220

Phe His Pro Glu Ser Gly Thr Val Lys Pro Trp Leu Ser Ala Tyr Thr
225                 230                 235                 240

Thr Ala Trp Thr Leu Ala Met Val His Gly Met Asp Pro Ala Phe Ser
                245                 250                 255

Glu Arg Tyr Tyr Pro Ala Phe Lys Lys Thr Phe Val Glu Val Tyr Asp
            260                 265                 270

Gly Gly Arg Lys Ala Arg Val Arg Glu Thr Thr Asn Thr Pro Asp Ala
        275                 280                 285

Asp Gly Gly Val Gly Ala Ala Ser Ala Phe Thr Leu Leu Leu Ala Arg
    290                 295                 300

Glu Met Gly Asp Gln Thr Leu Phe Asp Gln Leu Leu Asn His Leu Glu
305                 310                 315                 320

Pro Pro Ala Lys Pro Lys Ile Thr Ser Ala Ile Leu Asn Tyr Glu Ala
                325                 330                 335

Pro Ser Asn Leu Leu Phe Asp Glu Leu Leu Phe Leu Ser Lys Val His
            340                 345                 350

Val Gly Phe Gly Glu Leu Leu Lys Ala Thr Pro Pro Ala Arg Ala
        355                 360                 365

Asp Ser Gln Lys
    370

<210> SEQ ID NO 48
<211> LENGTH: 1206
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1206)
<223> OTHER INFORMATION: Native Nucleic acid encoding SEQ ID NO:49,
      which is unprocessed and includes its signal peptide

<400> SEQUENCE: 48
atgaagaaca tccaaaagac ggctgccgcg ctgcccgcca tccttgccgc agtgctcgcg      60
ttcagtgcgc cggcccattc ggcggacctg ccgcccgggc gcctcgcctc gaccgaggaa     120
tatttcgccc agcgcgagaa acaggccgtc acgcccgacg tcatggccca cctcgcctac     180
atgaactaca ccgatttcgt ctcgcccttc tacagccggg gctgcgcctt cgacgcctgg     240
gcgatcaaga agacccccgca gcggatcatc aagtactcgc tcgccttcta cgcctatggc     300
ctggccagcg tcgcgctcac cgatccgcag ctgcgtccgc tcgccggaca tgcaatcgac     360

| | | |
|---|---|---|
| atcgcgaccg ccaagatgaa atgcaagcag gtctggggag actgggagga agacgggttc | 420 | |
| ggcgaggatc cgatcgagaa agagaacatc atgtacaagg ccacttgaa cctgatgtac | 480 | |
| ggcctctacc aactggtcac cggcaaccgc cggtacgaga aggagcacgc ccgcctcacg | 540 | |
| cggatcatcc acgacgagat caaggccaat ccctacgccg catcgtctg cgagccggac | 600 | |
| aactatttcg ttcagtgcaa ctcggtcgcc tacctgagcc tgtgggtcca tgaccgcctg | 660 | |
| cacggcaccg actaccgggc ggcgacggcg gaatggctga aattcatcga gcacgacctg | 720 | |
| atcgacccga aacacggcgc cttccacctg tcctaccatc cggaatccca cgcggtgaaa | 780 | |
| ccgtgggtct ccgcatacac cacggcgtgg acgctcgcca tggtgcacgg catggatccc | 840 | |
| gctttcgccg agcgctacta ccccgcttc aaggagacct tcgtcgaggt ctacgacgat | 900 | |
| ggccgcaagg cccgggtccg cgagacgacc ggcaccaccg acgccgatgg cggcgtcggc | 960 | |
| gcggcctccg cgttcaccct gctgctcgcc cgcgagatgg gcgaccggca gctcttcgac | 1020 | |
| cagttgctga accacctgga gccccggca agaccgagga tcacctcggg catcctggaa | 1080 | |
| tacgcggccc ccagcaatct gctgttcgac gagctgctgt tcctcgccaa ggtacacgtc | 1140 | |
| ggtttcggcc agttgctgca ggccgggtcg gcgccgcccc cgccgggccc cgccagggg | 1200 | |
| aaatga | 1206 | |

<210> SEQ ID NO 49
<211> LENGTH: 401
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(401)
<223> OTHER INFORMATION: Native, or unprocessed, LinD enzyme, including
      signal peptide

<400> SEQUENCE: 49

```
Met Lys Asn Ile Gln Lys Thr Ala Ala Ala Leu Pro Ala Ile Leu Ala
1               5                   10                  15

Ala Val Leu Ala Phe Ser Ala Pro Ala His Ser Ala Asp Leu Pro Pro
                20                  25                  30

Gly Arg Leu Ala Ser Thr Glu Glu Tyr Phe Ala Gln Arg Glu Lys Gln
            35                  40                  45

Ala Val Thr Pro Asp Val Met Ala His Leu Ala Tyr Met Asn Tyr Thr
        50                  55                  60

Asp Phe Val Ser Pro Phe Tyr Ser Arg Gly Cys Ala Phe Asp Ala Trp
65                  70                  75                  80

Ala Ile Lys Lys Thr Pro Gln Arg Ile Ile Lys Tyr Ser Leu Ala Phe
                85                  90                  95

Tyr Ala Tyr Gly Leu Ala Ser Val Ala Leu Thr Asp Pro Gln Leu Arg
            100                 105                 110

Pro Leu Ala Gly His Ala Ile Asp Ile Ala Thr Ala Lys Met Lys Cys
        115                 120                 125

Lys Gln Val Trp Gly Asp Trp Glu Glu Asp Gly Phe Gly Glu Asp Pro
    130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Asn Arg Arg Tyr Glu Lys Glu His
                165                 170                 175

Ala Arg Leu Thr Arg Ile Ile His Asp Glu Ile Lys Ala Asn Pro Tyr
```

```
            180                 185                 190
Ala Gly Ile Val Cys Glu Pro Asp Asn Tyr Phe Val Gln Cys Asn Ser
            195                 200                 205

Val Ala Tyr Leu Ser Leu Trp Val His Asp Arg Leu His Gly Thr Asp
        210                 215                 220

Tyr Arg Ala Ala Thr Ala Glu Trp Leu Lys Phe Ile Glu His Asp Leu
225                 230                 235                 240

Ile Asp Pro Lys His Gly Ala Phe His Leu Ser Tyr His Pro Glu Ser
                245                 250                 255

His Ala Val Lys Pro Trp Val Ser Ala Tyr Thr Thr Ala Trp Thr Leu
            260                 265                 270

Ala Met Val His Gly Met Asp Pro Ala Phe Ala Glu Arg Tyr Tyr Pro
        275                 280                 285

Arg Phe Lys Glu Thr Phe Val Glu Val Tyr Asp Asp Gly Arg Lys Ala
    290                 295                 300

Arg Val Arg Glu Thr Thr Gly Thr Thr Asp Ala Asp Gly Gly Val Gly
305                 310                 315                 320

Ala Ala Ser Ala Phe Thr Leu Leu Leu Ala Arg Glu Met Gly Asp Arg
                325                 330                 335

Gln Leu Phe Asp Gln Leu Leu Asn His Leu Glu Pro Pro Ala Arg Pro
            340                 345                 350

Arg Ile Thr Ser Gly Ile Leu Glu Tyr Ala Ala Pro Ser Asn Leu Leu
        355                 360                 365

Phe Asp Glu Leu Leu Phe Leu Ala Lys Val His Val Gly Phe Gly Gln
    370                 375                 380

Leu Leu Gln Ala Gly Ser Ala Pro Pro Pro Gly Pro Ala Arg Gly
385                 390                 395                 400

Lys

<210> SEQ ID NO 50
<211> LENGTH: 81
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(81)
<223> OTHER INFORMATION: Nucleic acid encoding GNM 9875 signal peptide

<400> SEQUENCE: 50
atgaagaaca tccaaaagac ggctgccgcg ctgcccgcca tccttgccgc agtgctcgcg      60
ttcagtgcgc cggcccattc g                                               81

<210> SEQ ID NO 51
<211> LENGTH: 27
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(27)
<223> OTHER INFORMATION: GNM 9875 signal peptide

<400> SEQUENCE: 51

Met Lys Asn Ile Gln Lys Thr Ala Ala Ala Leu Pro Ala Ile Leu Ala
1               5                   10                  15

Ala Val Leu Ala Phe Ser Ala Pro Ala His Ser
            20                  25
```

<210> SEQ ID NO 52
<211> LENGTH: 1125
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1125)
<223> OTHER INFORMATION: Nucleic acid encoding processed GNM 9875 LinD enzyme, no signal peptide

<400> SEQUENCE: 52

```
gcggacctgc cgcccgggcg cctcgcctcg accgaggaat atttcgccca gcgcgagaaa        60
caggccgtca cgcccgacgt catggcccac ctcgcctaca tgaactacac cgatttcgtc       120
tcgcccttct acagccgggg ctgcgccttc gacgcctggg cgatcaagaa gaccccgcag       180
cggatcatca gtactcgct cgccttctac gcctatggcc tggccagcgt cgcgctcacc        240
gatccgcagc tgcgtccgct cgccggacat gcaatcgaca tcgcgaccgc caagatgaaa       300
tgcaagcagg tctggggaga ctgggaggaa cacgggttcg gcgaggatcc gatcgagaaa       360
gagaacatca tgtacaaggg ccacttgaac ctgatgtacg gcctctacca actggtcacc       420
ggcaaccgcc ggtacgagaa ggagcacgcc cgcctcacgc ggatcatcca cgacgagatc       480
aaggccaatc cctacgccgg catcgtctgc gagccggaca actatttcgt tcagtgcaac       540
tcggtcgcct acctgagcct gtgggtccat gaccgcctgc acggcaccga ctaccgggcg       600
gcgacggcgg aatggctgaa attcatcgag cacgacctga tcgacccgaa acacggcgcc       660
ttccacctgt cctaccatcc ggaatcccac gcggtgaaac cgtgggtctc cgcatacacc       720
acggcgtgga cgctcgccat ggtgcacggc atggatcccg cttcgccga gcgctactac        780
ccccgcttca aggagacctt cgtcgaggtc tacgacgatg ccgcaaggc ccgggtccgc        840
gagacgaccg gcaccaccga cgccgatggc ggcgtcggcg cggcctccgc gttcaccctg       900
ctgctcgccc gcgagatggg cgaccggcag ctcttcgacc agttgctgaa ccacctggag       960
cccccggcaa gaccgaggat cacctcgggc atcctggaat acgcggcccc cagcaatctg      1020
ctgttcgacg agctgctgtt cctcgccaag gtacacgtcg gtttcggcca gttgctgcag      1080
gccgggtcgg cgccgccccc gccgggcccc gccaggggga aatga                      1125
```

<210> SEQ ID NO 53
<211> LENGTH: 374
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(374)
<223> OTHER INFORMATION: Processed GNM 9875 LinD enzyme, no signal peptide

<400> SEQUENCE: 53

```
Ala Asp Leu Pro Pro Gly Arg Leu Ala Ser Thr Glu Glu Tyr Phe Ala
1               5                   10                  15

Gln Arg Glu Lys Gln Ala Val Thr Pro Asp Val Met Ala His Leu Ala
            20                  25                  30

Tyr Met Asn Tyr Thr Asp Phe Val Ser Pro Phe Tyr Ser Arg Gly Cys
        35                  40                  45
```

-continued

```
Ala Phe Asp Ala Trp Ala Ile Lys Lys Thr Pro Gln Arg Ile Ile Lys
 50                  55                  60
Tyr Ser Leu Ala Phe Tyr Ala Tyr Gly Leu Ala Ser Val Ala Leu Thr
 65                  70                  75                  80
Asp Pro Gln Leu Arg Pro Leu Ala Gly His Ala Ile Asp Ile Ala Thr
                 85                  90                  95
Ala Lys Met Lys Cys Lys Gln Val Trp Gly Asp Trp Glu Glu Asp Gly
                100                 105                 110
Phe Gly Glu Asp Pro Ile Glu Lys Glu Asn Ile Met Tyr Lys Gly His
            115                 120                 125
Leu Asn Leu Met Tyr Gly Leu Tyr Gln Leu Val Thr Gly Asn Arg Arg
130                 135                 140
Tyr Glu Lys Glu His Ala Arg Leu Thr Arg Ile Ile His Asp Glu Ile
145                 150                 155                 160
Lys Ala Asn Pro Tyr Ala Gly Ile Val Cys Glu Pro Asp Asn Tyr Phe
                165                 170                 175
Val Gln Cys Asn Ser Val Ala Tyr Leu Ser Leu Trp Val His Asp Arg
                180                 185                 190
Leu His Gly Thr Asp Tyr Arg Ala Ala Thr Ala Glu Trp Leu Lys Phe
            195                 200                 205
Ile Glu His Asp Leu Ile Asp Pro Lys His Gly Ala Phe His Leu Ser
210                 215                 220
Tyr His Pro Glu Ser His Ala Val Lys Pro Trp Val Ser Ala Tyr Thr
225                 230                 235                 240
Thr Ala Trp Thr Leu Ala Met Val His Gly Met Asp Pro Ala Phe Ala
                245                 250                 255
Glu Arg Tyr Tyr Pro Arg Phe Lys Glu Thr Phe Val Glu Val Tyr Asp
                260                 265                 270
Asp Gly Arg Lys Ala Arg Val Arg Glu Thr Thr Gly Thr Thr Asp Ala
            275                 280                 285
Asp Gly Gly Val Gly Ala Ala Ser Ala Phe Thr Leu Leu Leu Ala Arg
290                 295                 300
Glu Met Gly Asp Arg Gln Leu Phe Asp Gln Leu Leu Asn His Leu Glu
305                 310                 315                 320
Pro Pro Ala Arg Pro Arg Ile Thr Ser Gly Ile Leu Glu Tyr Ala Ala
                325                 330                 335
Pro Ser Asn Leu Leu Phe Asp Glu Leu Leu Phe Leu Ala Lys Val His
            340                 345                 350
Val Gly Phe Gly Gln Leu Leu Gln Ala Gly Ser Ala Pro Pro Pro Pro
            355                 360                 365
Gly Pro Ala Arg Gly Lys
    370
```

<210> SEQ ID NO 54
<211> LENGTH: 1191
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1191)
<223> OTHER INFORMATION: Native Nucleic acid encoding SEQ ID NO:55,
      which is unprocessed and includes its signal peptide

<400> SEQUENCE: 54
atgaagaaca tcgccgcgc ggccgcactg gcagccgcca tcatcgccac gatgcccggg    60

```
cccggtacgc cagcccacgc ggcagagttg ctgcccggac gcctcgcctc gaccgaggcc    120
tacttcgccc agcgcgaacg gcaggccgtc accccgacg tgatggccca cctcgcctac    180
atgaactaca cggacttcgt ttccccttc tacagccggg gctgcgcctt cgatgcgtgg    240
acgatcaaga gaccccgca gcggatcatc aagtactcgc tggccttcta cgcctacggc    300
ctcgccagcg tcgcgctcat cgacccgcag ctgcgcccac tcgccggcca cgcactcgac    360
atcgccacgg ccaagatgaa atgcaagcag gtctggggag actgggagga agacggcttc    420
ggcgacgatc cgatcgagaa ggaaaacatc atgtacaagg ccacctgaa cctgatgtac    480 ggcctccacc agctggtcac cggcaaccgg cggtacgaga aggaacacgc ccgcctcacg    540
cagatcatcc gcgacgagat cgcggccaac ccctacgccg gcatcgtctg cgagcccgac    600
aactacttcg tccagtgcaa ctcggtcgcc tacctgagcc tgtgggtcta cgaccgcctg    660
cacggcacca accacagggc ggcgaccgca gcgtggctca agttcatcga ggacgacctg    720
atcgacccga gcacggcgt cttccacctc tcctaccatc cggagtccgg cgcggtgaag    780
ccctgggtct cggcatacac gacggcatgg accctcgcca tggtgcacgg catggatccc    840 gccttttgccg agcgctacta ccccgcttc aaggaaacct tcgtcgaggt ctacgacgac    900
ggccgcaagg cccgggtccg cgagacgacc ggcaccaccg atgccgatgg cggcgtcggc    960
gcggcctccg ccttcaccct gctgctcgcc cgcgagatgg cgaccagca gctcttcgac    1020 cagttgctga accacctcga gccgccggca agaccgaaga tcacctcggg catcctggac    1080
tacgaagcgc ccagcaacct gctgttcgac gaactgctgt tcctcgccaa ggtgcacgtc    1140
ggtttcggcc agctgctgca ggcccggccg gatcccgcca gggggcaatg a            1191
```

<210> SEQ ID NO 55
<211> LENGTH: 396
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(396)
<223> OTHER INFORMATION: Native, or unprocessed, LinD enzyme, including
      signal peptide

<400> SEQUENCE: 55

```
Met Lys Asn Ile Ala Arg Ala Ala Ala Leu Ala Ala Ile Ile Ala
1               5                   10                  15

Thr Met Pro Gly Pro Gly Thr Pro Ala His Ala Ala Glu Leu Leu Pro
            20                  25                  30

Gly Arg Leu Ala Ser Thr Glu Ala Tyr Phe Ala Gln Arg Glu Arg Gln
        35                  40                  45

Ala Val Thr Pro Asp Val Met Ala His Leu Ala Tyr Met Asn Tyr Thr
    50                  55                  60

Asp Phe Val Ser Pro Phe Tyr Ser Arg Gly Cys Ala Phe Asp Ala Trp
65                  70                  75                  80

Thr Ile Lys Lys Thr Pro Gln Arg Ile Ile Lys Tyr Ser Leu Ala Phe
                85                  90                  95

Tyr Ala Tyr Gly Leu Ala Ser Val Ala Leu Ile Asp Pro Gln Leu Arg
            100                 105                 110

Pro Leu Ala Gly His Ala Leu Asp Ile Ala Thr Ala Lys Met Lys Cys
        115                 120                 125

Lys Gln Val Trp Gly Asp Trp Glu Glu Asp Gly Phe Gly Asp Asp Pro
```

```
                  130                 135                 140
Ile Glu Lys Glu Asn Ile Met Tyr Lys Gly His Leu Asn Leu Met Tyr
145                 150                 155                 160

Gly Leu His Gln Leu Val Thr Gly Asn Arg Arg Tyr Glu Lys Glu His
                165                 170                 175

Ala Arg Leu Thr Gln Ile Ile Arg Asp Glu Ile Ala Ala Asn Pro Tyr
            180                 185                 190

Ala Gly Ile Val Cys Glu Pro Asp Asn Tyr Phe Val Gln Cys Asn Ser
        195                 200                 205

Val Ala Tyr Leu Ser Leu Trp Val Tyr Asp Arg Leu His Gly Thr Asn
210                 215                 220

His Arg Ala Ala Thr Ala Ala Trp Leu Lys Phe Ile Glu Asp Asp Leu
225                 230                 235                 240

Ile Asp Pro Lys His Gly Val Phe His Leu Ser Tyr His Pro Glu Ser
                245                 250                 255

Gly Ala Val Lys Pro Trp Val Ser Ala Tyr Thr Thr Ala Trp Thr Leu
            260                 265                 270

Ala Met Val His Gly Met Asp Pro Ala Phe Ala Glu Arg Tyr Tyr Pro
        275                 280                 285

Arg Phe Lys Glu Thr Phe Val Glu Val Tyr Asp Asp Gly Arg Lys Ala
290                 295                 300

Arg Val Arg Glu Thr Thr Gly Thr Thr Asp Ala Asp Gly Gly Val Gly
305                 310                 315                 320

Ala Ala Ser Ala Phe Thr Leu Leu Leu Ala Arg Glu Met Gly Asp Gln
                325                 330                 335

Gln Leu Phe Asp Gln Leu Leu Asn His Leu Glu Pro Pro Ala Arg Pro
            340                 345                 350

Lys Ile Thr Ser Gly Ile Leu Asp Tyr Glu Ala Pro Ser Asn Leu Leu
        355                 360                 365

Phe Asp Glu Leu Leu Phe Leu Ala Lys Val His Val Gly Phe Gly Gln
    370                 375                 380

Leu Leu Gln Ala Arg Pro Asp Pro Ala Arg Gly Gln
385                 390                 395

<210> SEQ ID NO 56
<211> LENGTH: 81
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(81)
<223> OTHER INFORMATION: Nucleic acid encoding GNM 9894 signal peptide

<400> SEQUENCE: 56
atgaagaaca tcgcccgcgc ggccgcactg gcagccgcca tcatcgccac gatgcccggg      60
cccggtacgc cagcccacgc g                                                81

<210> SEQ ID NO 57
<211> LENGTH: 27
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(27)
<223> OTHER INFORMATION: GNM 9894 signal peptide
```

<400> SEQUENCE: 57

Met Lys Asn Ile Ala Arg Ala Ala Ala Leu Ala Ala Ile Ile Ala
1               5                   10                  15

Thr Met Pro Gly Pro Gly Thr Pro Ala His Ala
            20                  25

<210> SEQ ID NO 58
<211> LENGTH: 1110
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1110)
<223> OTHER INFORMATION: Nucleic acid encoding processed GNM 9894 LinD
      enzyme, no signal peptide

<400> SEQUENCE: 58
gcagagttgc tgcccggacg cctcgcctcg accgaggcct acttcgccca gcgcgaacgg      60
caggccgtca cccccgacgt gatggcccac ctcgcctaca tgaactacac ggacttcgtt     120
tccccctcct acagccgggg ctgcgccttc gatgcgtgga cgatcaagaa gaccccgcag     180
cggatcatca gtactcgct ggccttctac gcctacggcc tcgccagcgt cgcgctcatc      240
gacccgcagc tgcgcccact cgccggccac gcactcgaca tcgccacggc caagatgaaa     300
tgcaagcagg tctggggaga ctgggaggaa acggcttcg gcgacgatcc gatcgagaag      360
gaaaacatca tgtacaaggg ccacctgaac ctgatgtacg cctccacca gctggtcacc      420 ggcaaccggc ggtacgagaa ggaacacgcc cgcctcacgc agatcatccg cgacgagatc     480
gcggccaacc cctacgccgg catcgtctgc gagcccgaca actacttcgt ccagtgcaac     540
tcggtcgcct acctgagcct gtgggtctac gaccgcctgc acggcaccaa ccacagggcg     600
gcgaccgcag cgtggctcaa gttcatcgag acgacctga tcgacccgaa gcacggcgtc      660
ttccacctct cctaccatcc ggagtccggc gcggtgaagc cctgggtctc ggcatacacg     720
acggcatgga ccctcgccat ggtgcacggc atggatcccg cctttgccga gcgctactac     780
ccccgcttca aggaaaacctt cgtcgaggtc tacgacgacg gccgcaaggc ccgggtccgc    840
gagacgaccg gcaccaccga tgccgatggc ggcgtcggcg cggcctccgc cttcaccctg    900
ctgctcgccc gcgagatggg cgaccagcag ctcttcgacc agttgctgaa ccacctcgag    960
ccgccggcaa gaccgaagat cacctcgggc atcctggact acgaagcgcc cagcaacctg   1020
ctgttcgacg aactgctgtt cctcgccaag gtgcacgtcg gtttcggcca gctgctgcag   1080
gcccggccgg atcccgccag ggggcaatga                                     1110

<210> SEQ ID NO 59
<211> LENGTH: 369
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(369)
<223> OTHER INFORMATION: Processed GNM 9894 LinD enzyme, no signal
      peptide

<400> SEQUENCE: 59

Ala Glu Leu Leu Pro Gly Arg Leu Ala Ser Thr Glu Ala Tyr Phe Ala
1               5                   10                  15

Gln Arg Glu Arg Gln Ala Val Thr Pro Asp Val Met Ala His Leu Ala
         20                  25                  30

Tyr Met Asn Tyr Thr Asp Phe Val Ser Pro Phe Tyr Ser Arg Gly Cys
         35                  40                  45

Ala Phe Asp Ala Trp Thr Ile Lys Lys Thr Pro Gln Arg Ile Ile Lys
 50                  55                  60

Tyr Ser Leu Ala Phe Tyr Ala Tyr Gly Leu Ala Ser Val Ala Leu Ile
 65                  70                  75                  80

Asp Pro Gln Leu Arg Pro Leu Ala Gly His Ala Leu Asp Ile Ala Thr
                 85                  90                  95

Ala Lys Met Lys Cys Lys Gln Val Trp Gly Asp Trp Glu Glu Asp Gly
        100                 105                 110

Phe Gly Asp Asp Pro Ile Glu Lys Glu Asn Ile Met Tyr Lys Gly His
        115                 120                 125

Leu Asn Leu Met Tyr Gly Leu His Gln Leu Val Thr Gly Asn Arg Arg
130                 135                 140

Tyr Glu Lys Glu His Ala Arg Leu Thr Gln Ile Ile Arg Asp Glu Ile
145                 150                 155                 160

Ala Ala Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
        180                 185                 190

Leu His Gly Thr Asn His Arg Ala Ala Thr Ala Ala Trp Leu Lys Phe
        195                 200                 205

Ile Glu Asp Asp Leu Ile Asp Pro Lys His Gly Val Phe His Leu Ser
210                 215                 220

Tyr His Pro Glu Ser Gly Ala Val Lys Pro Trp Val Ser Ala Tyr Thr
225                 230                 235                 240

Thr Ala Trp Thr Leu Ala Met Val His Gly Met Asp Pro Ala Phe Ala
                245                 250                 255

Glu Arg Tyr Tyr Pro Arg Phe Lys Glu Thr Phe Val Glu Val Tyr Asp
        260                 265                 270

Asp Gly Arg Lys Ala Arg Val Arg Glu Thr Thr Gly Thr Thr Asp Ala
        275                 280                 285

Asp Gly Gly Val Gly Ala Ala Ser Ala Phe Thr Leu Leu Leu Ala Arg
290                 295                 300

Glu Met Gly Asp Gln Gln Leu Phe Asp Gln Leu Leu Asn His Leu Glu
305                 310                 315                 320

Pro Pro Ala Arg Pro Lys Ile Thr Ser Gly Ile Leu Asp Tyr Glu Ala
                325                 330                 335

Pro Ser Asn Leu Leu Phe Asp Glu Leu Leu Phe Leu Ala Lys Val His
        340                 345                 350

Val Gly Phe Gly Gln Leu Leu Gln Ala Arg Pro Asp Pro Ala Arg Gly
        355                 360                 365

Gln

<210> SEQ ID NO 60
<211> LENGTH: 1185
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1185)

<223> OTHER INFORMATION: Native Nucleic acid encoding SEQ ID NO:61,
which is unprocessed and includes its signal peptide with no
identified signal peptide cleavage site.

<400> SEQUENCE: 60

```
atgacacaat ggttatcaac accctgcctg gcggcgattt taagtgcaat ttttattgtt      60
gtacccaaat tcgggttgac agagacatta ctgccggggc gattagccac tacgaaggcg     120
tattttcac agcaacgcaa ccaaaaactg acgccggata tggatgccca gctggcctat     180
atgtcctaca ctgattttat ttcacctttc tatagtcgag gttgcgcctt tgaggcttgg     240
gaactgaaac aggctcccca gagaattatc aaatactccc ttgcctggta ttcctacggc     300
cttgccagtg tcgctgtcat tgatcccagc ctgcaccgat atgcaggcca caatattgat     360
attgccatcg caaaaatgaa gtgcagacag gtttggggcg actgggaaga agacggcttt     420
ggctccaacc ctattgccca ccaaaatatt atgtacaaag acacttgaa tctgatgtat      480
ggcctttatc agctgttaac gggcaatact cagtatgaag aggaattcat cgatctctct     540
aatatcatct atagcgaaat caaggaaaac ccttatgcag gtattgcttg cgagccggac     600
aattactttc cgcagtgcaa ctccgtcgcc tatctcagcc tgtgggttta tgatcgtctc     660
taccacaccg actacaaagc agtcacaaaa ccctggcttg attttttaca gaaaaaactc     720
atagatcctg aaaccggcac atttcatgtt gcctatcatc aacatctca cgccgttaaa     780
ccctgggttt ccgcctacac cacggcctgg gcgctaacca tgattcatgg tctgaatccg     840
gaatttgcca aaaagtacta ccctaatttt aagcaaacct tgttgaggt ttttgacaac      900
ggcaccaaag ccagggtgcg cgaaaccgcc cacaccacgg atgttgatgg tggcgtcggc     960
gccgcctcga ttttcacgct ggtgttggca agggaaatga atgatcagga gctgtttgat    1020
caactattga attatctcga accgccagca aagcctgtga tttattcggg gattctgcga    1080
tatgaaaatc caacgagcct gctattcgat gaactgcttt tgtcgccaa ggtgcatgtg     1140
ggttttggcg aactgatcaa tctcaaacct gttgaaacag actag                    1185
```

<210> SEQ ID NO 61
<211> LENGTH: 394
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(394)
<223> OTHER INFORMATION: Native, or unprocessed, LinD enzyme, including
signal peptide with no identified signal peptide cleavage site.

<400> SEQUENCE: 61

```
Met Thr Gln Trp Leu Ser Thr Pro Cys Leu Ala Ala Ile Leu Ser Ala
1               5                   10                  15

Ile Phe Ile Val Val Pro Lys Phe Gly Leu Thr Glu Thr Leu Leu Pro
            20                  25                  30

Gly Arg Leu Ala Thr Thr Lys Ala Tyr Phe Ser Gln Gln Arg Asn Gln
        35                  40                  45

Lys Leu Thr Pro Asp Met Asp Ala Gln Leu Ala Tyr Met Ser Tyr Thr
    50                  55                  60

Asp Phe Ile Ser Pro Phe Tyr Ser Arg Gly Cys Ala Phe Glu Ala Trp
65                  70                  75                  80

Glu Leu Lys Gln Ala Pro Gln Arg Ile Ile Lys Tyr Ser Leu Ala Trp
                85                  90                  95
```

```
Tyr Ser Tyr Gly Leu Ala Ser Val Ala Val Ile Asp Pro Ser Leu His
            100                 105                 110

Arg Tyr Ala Gly His Asn Ile Asp Ile Ala Ile Ala Lys Met Lys Cys
        115                 120                 125

Arg Gln Val Trp Gly Asp Trp Glu Glu Asp Gly Phe Gly Ser Asn Pro
    130                 135                 140

Ile Ala His Gln Asn Ile Met Tyr Lys Gly His Leu Asn Leu Met Tyr
145                 150                 155                 160

Gly Leu Tyr Gln Leu Leu Thr Gly Asn Thr Gln Tyr Glu Glu Glu Phe
                165                 170                 175

Ile Asp Leu Ser Asn Ile Ile Tyr Ser Glu Ile Lys Gly Asn Pro Tyr
            180                 185                 190

Ala Gly Ile Ala Cys Glu Pro Asp Asn Tyr Phe Pro Gln Cys Asn Ser
        195                 200                 205

Val Ala Tyr Leu Ser Leu Trp Val Tyr Asp Arg Leu Tyr His Thr Asp
    210                 215                 220

Tyr Lys Ala Val Thr Lys Pro Trp Leu Asp Phe Leu Gln Lys Lys Leu
225                 230                 235                 240

Ile Asp Pro Glu Thr Gly Thr Phe His Val Ala Tyr His Pro Thr Ser
                245                 250                 255

His Ala Val Lys Pro Trp Val Ser Ala Tyr Thr Thr Ala Trp Ala Leu
            260                 265                 270

Thr Met Ile His Gly Leu Asn Pro Glu Phe Ala Lys Lys Tyr Tyr Pro
        275                 280                 285

Asn Phe Lys Gln Thr Phe Val Glu Val Phe Asp Asn Gly Thr Lys Ala
    290                 295                 300

Arg Val Arg Glu Thr Ala His Thr Thr Asp Val Asp Gly Gly Val Gly
305                 310                 315                 320

Ala Ala Ser Ile Phe Thr Leu Val Leu Ala Arg Glu Met Asn Asp Gln
                325                 330                 335

Glu Leu Phe Asp Gln Leu Leu Asn Tyr Leu Pro Pro Ala Lys Pro
            340                 345                 350

Val Ile Tyr Ser Gly Ile Leu Arg Tyr Glu Asn Pro Thr Ser Leu Leu
        355                 360                 365

Phe Asp Glu Leu Leu Phe Val Ala Lys Val His Val Gly Phe Gly Glu
    370                 375                 380

Leu Ile Asn Leu Lys Pro Val Glu Thr Asp
385                 390
```

<210> SEQ ID NO 62
<211> LENGTH: 394
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(394)
<223> OTHER INFORMATION: LinD enzyme SEQ ID NO: 61 having an A196F modification; designated 9895B.

<400> SEQUENCE: 62

```
Met Thr Gln Trp Leu Ser Thr Pro Cys Leu Ala Ala Ile Leu Ser Ala
1               5                   10                  15

Ile Phe Ile Val Val Pro Lys Phe Gly Leu Thr Glu Thr Leu Leu Pro
            20                  25                  30

Gly Arg Leu Ala Thr Thr Lys Ala Tyr Phe Ser Gln Gln Arg Asn Gln
```

```
                35                  40                  45
Lys Leu Thr Pro Asp Met Asp Ala Gln Leu Ala Tyr Met Ser Tyr Thr
 50                  55                  60

Asp Phe Ile Ser Pro Phe Tyr Ser Arg Gly Cys Ala Phe Glu Ala Trp
 65                  70                  75                  80

Glu Leu Lys Gln Ala Pro Gln Arg Ile Ile Lys Tyr Ser Leu Ala Trp
                 85                  90                  95

Tyr Ser Tyr Gly Leu Ala Ser Val Ala Val Ile Asp Pro Ser Leu His
            100                 105                 110

Arg Tyr Ala Gly His Asn Ile Asp Ile Ala Ile Ala Lys Met Lys Cys
            115                 120                 125

Arg Gln Val Trp Gly Asp Trp Glu Glu Asp Gly Phe Gly Ser Asn Pro
130                 135                 140

Ile Ala His Gln Asn Ile Met Tyr Lys Gly His Leu Asn Leu Met Tyr
145                 150                 155                 160

Gly Leu Tyr Gln Leu Leu Thr Gly Asn Thr Gln Tyr Glu Glu Glu Phe
                165                 170                 175

Ile Asp Leu Ser Asn Ile Ile Tyr Ser Glu Ile Lys Glu Asn Pro Tyr
            180                 185                 190

Ala Gly Ile Phe Cys Glu Pro Asp Asn Tyr Phe Pro Gln Cys Asn Ser
            195                 200                 205

Val Ala Tyr Leu Ser Leu Trp Val Tyr Asp Arg Leu Tyr His Thr Asp
210                 215                 220

Tyr Lys Ala Val Thr Lys Pro Trp Leu Asp Phe Leu Gln Lys Lys Leu
225                 230                 235                 240

Ile Asp Pro Glu Thr Gly Thr Phe His Val Ala Tyr His Pro Thr Ser
                245                 250                 255

His Ala Val Lys Pro Trp Val Ser Ala Tyr Thr Thr Ala Trp Ala Leu
            260                 265                 270

Thr Met Ile His Gly Leu Asn Pro Glu Phe Ala Lys Lys Tyr Tyr Pro
275                 280                 285

Asn Phe Lys Gln Thr Phe Val Glu Val Phe Asp Asn Gly Thr Lys Ala
290                 295                 300

Arg Val Arg Glu Thr Ala His Thr Thr Asp Val Asp Gly Gly Val Gly
305                 310                 315                 320

Ala Ala Ser Ile Phe Thr Leu Val Leu Ala Arg Glu Met Asn Asp Gln
                325                 330                 335

Glu Leu Phe Asp Gln Leu Leu Asn Tyr Leu Glu Pro Pro Ala Lys Pro
            340                 345                 350

Val Ile Tyr Ser Gly Ile Leu Arg Tyr Glu Asn Pro Thr Ser Leu Leu
            355                 360                 365

Phe Asp Glu Leu Leu Phe Val Ala Lys Val His Val Gly Phe Gly Glu
370                 375                 380

Leu Ile Asn Leu Lys Pro Val Glu Thr Asp
385                 390

<210> SEQ ID NO 63
<211> LENGTH: 1197
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1197)
<223> OTHER INFORMATION: Native Nucleic acid encoding SEQ ID NO: 64,
``` which is unprocessed and includes its signal peptide

<400> SEQUENCE: 63

```
atgcgctttta ctctgaaaac ccctgctatc gcttccgccg ttgctgcact gttggttggt      60
ctgggtcagc cagcgcacgc ggcaccgctg ccgttaggcc gcttggcacc gaccgaagat     120
tactttgccc aacaggcgaa acaagccgtc accccggatg ttatggccca gctggcgtac     180
atgaattaca tcgacttcat tagcccgttt tacagccgta gctgcagctt cgaggcgtgg     240
gagttgaaac acacgccgca gcgtgtcatc aagtatagca ttgcgttcta tgcgtacggc     300
ctggcaagcg tcgcactgat cgacccgaat ctgcgtgctc tggcgggtca tgacctggat     360
atcgcggtca gcaagatgaa atgtaagcgc gtgtggcaag attgggaaga agatggcttt     420
ggtgatgacc cgattgagaa agaaaaacatt atgtataagg ccacctgaa cctcatgtac     480
ggtctgtatc aactggtgac cggtagccgt aaatatgaag cggagcatgc ccacttgacc     540
cgtttgatcc acgacgaaat cggtgcaaac ccgttcgcgg tattttttg cgagccgggt     600
aattactttg tgcagtgtaa ctctgtcgcg tacctgagcc tgtgggtata tgatcgtctg     660
catggcaccg actaccgtgc agcgacgcgt gcctggctgg atttcatcca gaaagatctg     720
attgacccgg agcgcggtgc gttttacctg agctatcacc ctgagtccgg tgccgtgaaa     780
ccgtggatta gcgcgtacac tacggcgtgg accctggcga tggtgcatgg catggatccg     840
gcgttcagcg agcgttatta cccggcgttc aaaaagacct tgttgaagt ttacgacggt     900
ggccgcaagg cacgtgtccg tgaaacggca ggcacggcag atgccgacgg tggcgttggt     960
ctggcgtctg ctttcaccct gctgcttgcg cgcgagatgg gtgaccaaac gctgtttgac    1020
caattgctga atcacctgga gccgccagca caaccgtcca tcgtgagcgc tagcctgcgt    1080
tatgagcacc cgagcagcct gctgttcgac gaactgctgt tcttggccaa ggttcatgcc    1140
ggctttggcg cgctgctgca gatgccgcca ccggcagcta atcgggtgg caagtaa       1197
```

<210> SEQ ID NO 64
<211> LENGTH: 398
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(398)
<223> OTHER INFORMATION: Native, or unprocessed, engineered LinD enzyme, including signal peptide.

<400> SEQUENCE: 64

```
Met Arg Phe Thr Leu Lys Thr Pro Ala Ile Ala Ser Ala Val Ala Ala
1               5                   10                  15

Leu Leu Val Gly Leu Gly Gln Pro Ala His Ala Ala Pro Leu Pro Leu
                20                  25                  30

Gly Arg Leu Ala Pro Thr Glu Asp Tyr Phe Ala Gln Gln Ala Lys Gln
            35                  40                  45

Ala Val Thr Pro Asp Val Met Ala Gln Leu Ala Tyr Met Asn Tyr Ile
        50                  55                  60

Asp Phe Ile Ser Pro Phe Tyr Ser Arg Ser Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Asn Leu Arg
            100                 105                 110
```

Ala Leu Ala Gly His Asp Leu Asp Ile Ala Val Ser Lys Met Lys Cys
            115                 120                 125

Lys Arg Val Trp Gln Asp Trp Glu Glu Asp Gly Phe Gly Asp Asp Pro
    130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Ser Arg Lys Tyr Glu Ala Glu His
                165                 170                 175

Ala His Leu Thr Arg Leu Ile His Asp Glu Ile Gly Ala Asn Pro Phe
            180                 185                 190

Ala Gly Ile Phe Cys Glu Pro Gly Asn Tyr Phe Val Gln Cys Asn Ser
            195                 200                 205

Val Ala Tyr Leu Ser Leu Trp Val Tyr Asp Arg Leu His Gly Thr Asp
    210                 215                 220

Tyr Arg Ala Ala Thr Arg Ala Trp Leu Asp Phe Ile Gln Lys Asp Leu
225                 230                 235                 240

Ile Asp Pro Glu Arg Gly Ala Phe Tyr Leu Ser Tyr His Pro Glu Ser
                245                 250                 255

Gly Ala Val Lys Pro Trp Ile Ser Ala Tyr Thr Thr Ala Trp Thr Leu
            260                 265                 270

Ala Met Val His Gly Met Asp Pro Ala Phe Ser Glu Arg Tyr Tyr Pro
            275                 280                 285

Ala Phe Lys Lys Thr Phe Val Glu Val Tyr Asp Gly Gly Arg Lys Ala
    290                 295                 300

Arg Val Arg Glu Thr Ala Gly Thr Ala Asp Ala Asp Gly Gly Val Gly
305                 310                 315                 320

Leu Ala Ser Ala Phe Thr Leu Leu Ala Arg Glu Met Gly Asp Gln
                325                 330                 335

Thr Leu Phe Asp Gln Leu Leu Asn His Leu Glu Pro Pro Ala Gln Pro
            340                 345                 350

Ser Ile Val Ser Ala Ser Leu Arg Tyr Glu His Pro Ser Ser Leu Leu
            355                 360                 365

Phe Asp Glu Leu Leu Phe Leu Ala Lys Val His Ala Gly Phe Gly Ala
            370                 375                 380

Leu Leu Gln Met Pro Pro Ala Ala Lys Ser Gly Gly Lys
385                 390                 395

<210> SEQ ID NO 65
<211> LENGTH: 1194
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1194)
<223> OTHER INFORMATION: Native Nucleic acid encoding SEQ ID NO: 66,
      which is unprocessed and includes its signal peptide

<400> SEQUENCE: 65
atgcggttca cattgaagac gacggcgatc gcgtcggccg ccgccctgct ggtcggcctc      60
gggcagccgc cccgcgcggc ggaactgccg ccggggcggc tcgccaccac cgaggactat     120
ttcgcgcagc aggcgaagca ggccgtcacc cccgacgtga tggcccagct ggcctacatg     180
aactacatcg atttcatctc gcccttctac agcgggggct gctccttcga ggcctgggag     240
ctcaagcaca cgccgcagcg ggtcatcaag tattcgatcg ccttctatgc gtatggcctg     300

-continued

```
gccagcgtgg cgctcatcga cccgaagctg cgtgcgctcg ccggccatga cctggacatc     360
gcggtctcca agatgaagtg caagcgggtc tggggcgact gggaggaaga cgggttcggc     420
accgacccga tcgagaaaga gaacatcatg tacaagggcc acctgaacct gatgtacggc     480
ctctatcagc tggtgaccgg cagccgccgg tacgaagccg agcatgcgca cctcacccgc     540
atcatccatg acgagatcgc ggccaacccc tttgccggca tcgtctgcga gccggacaat     600
tatttcgtcc agtgcaattc ggtcgcctac ctgagcctgt gggtctatga ccggctgcat     660
ggcaccgact accgggcggc caccagggcc tggctggatt tcatccagaa ggacctgatc     720
gatcccgagc ggggcgcctt ctacctgtcc tatcaccccg agtccggcgc ggtgaagccg     780
tggatctcgg cgtatacgac ggcctggacg ctcgccatgg tgcacggcat ggaccccgcc     840
ttttccgagc gctactaccc ccggttcaag cagaccttcg tcgaggtcta cgacgagggc     900
cgcaaggccc gggtgcgcga cacggccggc acggacgacg cggatggcgg ggtgggcctg     960
gcttcggcgt tcaccctgct gctggcccgc gagatgggcg accagcagct cttcgaccag    1020
ttgctgaatc aacctggagcc gccggctaag ccgagcatcg tctcggcctc gctgcggtac    1080
gagcaacccg gcagcctgct gttcgacgag ctgctgttcc tcgccaaggt gcatgccggt    1140
tttggcgccc tgcttcggat gccgcctccg gcggccaagc tcgcggggaa ataa          1194
```

<210> SEQ ID NO 66
<211> LENGTH: 397
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(397)
<223> OTHER INFORMATION: Native, or unprocessed, LinD enzyme GNM 10038,
      including signal peptide

<400> SEQUENCE: 66

```
Met Arg Phe Thr Leu Lys Thr Thr Ala Ile Ala Ser Ala Ala Ala Leu
1               5                   10                  15

Leu Val Gly Leu Gly Gln Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
        35                  40                  45

Val Thr Pro Asp Val Met Ala Gln Leu Ala Tyr Met Asn Tyr Ile Asp
    50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr
                85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
        115                 120                 125

Arg Val Trp Gly Asp Trp Glu Glu Asp Gly Phe Gly Thr Asp Pro Ile
    130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175
```

-continued

His Leu Thr Arg Ile Ile His Asp Glu Ile Ala Ala Asn Pro Phe Ala
                180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr Asp Tyr
        210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
        275                 280                 285

Phe Lys Gln Thr Phe Val Glu Val Tyr Asp Glu Gly Arg Lys Ala Arg
    290                 295                 300

Val Arg Glu Thr Ala Gly Thr Asp Asp Ala Asp Gly Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu Gln Pro Gly Ser Leu Leu Phe
        355                 360                 365

Asp Glu Leu Leu Phe Leu Ala Lys Val His Ala Gly Phe Gly Ala Leu
    370                 375                 380

Leu Arg Met Pro Pro Ala Ala Lys Leu Ala Gly Lys
385                 390                 395

<210> SEQ ID NO 67
<211> LENGTH: 78
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(78)
<223> OTHER INFORMATION: Nucleic acid encoding GNM 10038 signal peptide

<400> SEQUENCE: 67
atgcggttca cattgaagac gacggcgatc gcgtcggccg ccgccctgct ggtcggcctc      60
gggcagccgc cccgcgcg                                                   78

<210> SEQ ID NO 68
<211> LENGTH: 26
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(26)
<223> OTHER INFORMATION: GNM 10038 signal peptide

<400> SEQUENCE: 68

Met Arg Phe Thr Leu Lys Thr Thr Ala Ile Ala Ser Ala Ala Ala Leu
1               5                   10                  15

Leu Val Gly Leu Gly Gln Pro Pro Arg Ala
            20                  25

<210> SEQ ID NO 69
<211> LENGTH: 1116
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1116)
<223> OTHER INFORMATION: Nucleic acid encoding Processed (mature) GNM 10038 LinD enzyme, no signal peptide

<400> SEQUENCE: 69

```
gcggaactgc cgccggggcg gctcgccacc accgaggact atttcgcgca gcaggcgaag      60
caggccgtca cccccgacgt gatggcccag ctggcctaca tgaactacat cgatttcatc     120
tcgcccttct acagccgggg ctgctccttc gaggcctggg agctcaagca cacgccgcag     180
cgggtcatca gtattcgat cgccttctat gcgtatggcc tggccagcgt ggcgctcatc      240
gacccgaagc tgcgtgcgct cgccggccat gacctgaca tcgcggtctc caagatgaag      300
tgcaagcggg tctgggcga ctgggaggaa gacgggttcg gcaccgaccc gatcgagaaa     360
gagaacatca tgtacaaggg ccacctgaac ctgatgtacg cctctatca gctggtgacc      420
ggcagccgcc ggtacgaagc cgagcatgcg cacctcaccc gcatcatcca tgacgagatc     480
gcggccaacc ccttgtgccgg catcgtctgc gagccggaca attatttcgt ccagtgcaat    540
tcggtcgcct acctgagcct gtgggtctat gaccggctgc atggcaccga ctaccgggcg    600
gccaccaggg cctggctgga tttcatccag aaggacctga tcgatcccga gcggggcgcc   660
ttctacctgt cctatcaccc cgagtccggc gcggtgaagc cgtggatctc ggcgtatacg   720
acggcctgga cgctcgccat ggtgcacggc atggaccccg cctttccga cgcgctactac  780
ccccggttca gcagaccctt cgtcgaggtc tacgacgagg gccgcaaggc ccgggtgcgc  840
gagacggccg gcacggacga cgcggatggc ggggtggggcc tggcttcggc gttcaccctg  900
ctgctggccc gcgagatggg cgaccagcag ctcttcgacc agttgctgaa tcacctggag  960
ccgccggcta agccgagcat cgtctcggcc tcgctgcggt acgagcaacc cggcagcctg 1020
ctgttcgacg agctgctgtt cctcgccaag gtgcatgccg gttttggcgc cctgcttcgg 1080
atgccgcctc cggcggccaa gctcgcgggg aaataa                             1116
```

<210> SEQ ID NO 70
<211> LENGTH: 371
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(371)
<223> OTHER INFORMATION: Processed (mature) GNM 10038 LinD enzyme, no signal peptide

<400> SEQUENCE: 70

```
Ala Glu Leu Pro Pro Gly Arg Leu Ala Thr Thr Glu Asp Tyr Phe Ala
1               5                  10                  15

Gln Gln Ala Lys Gln Ala Val Thr Pro Asp Val Met Ala Gln Leu Ala
            20                  25                  30

Tyr Met Asn Tyr Ile Asp Phe Ile Ser Pro Phe Tyr Ser Arg Gly Cys
        35                  40                  45

Ser Phe Glu Ala Trp Glu Leu Lys His Thr Pro Gln Arg Val Ile Lys
```

```
                    50                  55                  60
Tyr Ser Ile Ala Phe Tyr Ala Tyr Gly Leu Ala Ser Val Ala Leu Ile
 65                  70                  75                  80

Asp Pro Lys Leu Arg Ala Leu Ala Gly His Asp Leu Asp Ile Ala Val
                     85                  90                  95

Ser Lys Met Lys Cys Lys Arg Val Trp Gly Asp Trp Glu Asp Gly
                100                 105                 110

Phe Gly Thr Asp Pro Ile Glu Lys Glu Asn Ile Met Tyr Lys Gly His
                115                 120                 125

Leu Asn Leu Met Tyr Gly Leu Tyr Gln Leu Val Thr Gly Ser Arg Arg
            130                 135                 140

Tyr Glu Ala Glu His Ala His Leu Thr Arg Ile Ile His Asp Glu Ile
145                 150                 155                 160

Ala Ala Asn Pro Phe Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
                180                 185                 190

Leu His Gly Thr Asp Tyr Arg Ala Ala Thr Arg Ala Trp Leu Asp Phe
            195                 200                 205

Ile Gln Lys Asp Leu Ile Asp Pro Glu Arg Gly Ala Phe Tyr Leu Ser
210                 215                 220

Tyr His Pro Glu Ser Gly Ala Val Lys Pro Trp Ile Ser Ala Tyr Thr
225                 230                 235                 240

Thr Ala Trp Thr Leu Ala Met Val His Gly Met Asp Pro Ala Phe Ser
                245                 250                 255

Glu Arg Tyr Tyr Pro Arg Phe Lys Gln Thr Phe Val Glu Val Tyr Asp
                260                 265                 270

Glu Gly Arg Lys Ala Arg Val Arg Glu Thr Ala Gly Thr Asp Asp Ala
            275                 280                 285

Asp Gly Gly Val Gly Leu Ala Ser Ala Phe Thr Leu Leu Leu Ala Arg
            290                 295                 300

Glu Met Gly Asp Gln Gln Leu Phe Asp Gln Leu Leu Asn His Leu Glu
305                 310                 315                 320

Pro Pro Ala Lys Pro Ser Ile Val Ser Ala Ser Leu Arg Tyr Glu Gln
                325                 330                 335

Pro Gly Ser Leu Leu Phe Asp Glu Leu Leu Phe Leu Ala Lys Val His
            340                 345                 350

Ala Gly Phe Gly Ala Leu Leu Arg Met Pro Pro Ala Ala Lys Leu
            355                 360                 365

Ala Gly Lys
370
```

<210> SEQ ID NO 71
<211> LENGTH: 1185
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1185)
<223> OTHER INFORMATION: Native Nucleic acid encoding SEQ ID NO: 72, which is unprocessed and includes its signal peptide which has no identified signal peptidecleavage site.

<400> SEQUENCE: 71
atgacacaat ggttatcaac accctgcctg gcggcgattt taagtgcaat ttttattgtt    60

-continued

```
gtacccaaat tcgggttgac agagacatta ctgccggggc gattagccac tacggaggcg      120 tattttcac agcaacgcaa ccaaaaactg acgccggata tggatgccca gctggcctat      180
atgtcctaca ctgattttat ttcacctttc tatagtcgag gttgcgcctt tgaggcttgg      240
gaactgaaac aggctcccca gagaattatc aaatactccc ttgcctggta ttcctacggc      300
cttgccagtg tcgctgtcat tgatcccagc ctgcaccgat atgcaggcca caatattgat      360
attgccatcg caaaaatgaa gtgcagacag gtttggggcg actgggaaga agacggcttt      420
ggctccaacc ctattgccca ccaaaatatt atgtacaaag acacttgaa tctgatgtat      480 ggcctttatc agctgttaac gggcaatact cagtatgaag aggaattcat cgatctctct      540
aatatcatct atagcgaaat caaggaaaac ccttatgcag gtattgcttg cgagccggac      600
aattactttc gcagtgcaa ctccgtcgcc tatctcagcc tgtgggttta tgatcgtctc      660
taccacaccg actacaaagc agtcacaaaa ccctggcttg atttttaca gaaaaaactc      720 atagatcctg aaaccggcac atttcatgtt gcctatcatc aacatctca cgccgttaaa      780 ccctgggttt ccgcctacac cacggcctgg gcgctaacca tgattcatgg tctgaatccg      840
gaatttgcca aaagtacta ccctaatttt aagcaaacct tgttgaggt ttttgacaac      900 ggcaccaaag ccagggtgcg cgaaaccgcc cacaccacgg atgttgatgg tggcgtcggc      960
gccgcctcga ttttcacgct ggtgttggca agggaaatga atgatcagga gctgtttgat     1020
caactattga attatctcga accgccagca aagcctgtga tttattcggg gattctgcga     1080
tatgaaaatc caacgagcct gctattcgat gaactgcttt tgtcgccaa ggtgcatgtg     1140 ggttttggcg aactgatcaa tctcaaacct gttgaaacag actag                     1185
```

<210> SEQ ID NO 72
<211> LENGTH: 394
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(394)
<223> OTHER INFORMATION: Native, or unprocessed, LinD enzyme GNM 10039, including signal peptide which has no identified signal peptide cleavage site.

<400> SEQUENCE: 72

```
Met Thr Gln Trp Leu Ser Thr Pro Cys Leu Ala Ala Ile Leu Ser Ala
1               5                   10                  15

Ile Phe Ile Val Val Pro Lys Phe Gly Leu Thr Glu Thr Leu Leu Pro
            20                  25                  30

Gly Arg Leu Ala Thr Thr Glu Ala Tyr Phe Ser Gln Gln Arg Asn Gln
        35                  40                  45

Lys Leu Thr Pro Asp Met Asp Ala Gln Leu Ala Tyr Met Ser Tyr Thr
    50                  55                  60

Asp Phe Ile Ser Pro Phe Tyr Ser Arg Gly Cys Ala Phe Glu Ala Trp
65                  70                  75                  80

Glu Leu Lys Gln Ala Pro Gln Arg Ile Ile Lys Tyr Ser Leu Ala Trp
                85                  90                  95

Tyr Ser Tyr Gly Leu Ala Ser Val Ala Val Ile Asp Pro Ser Leu His
            100                 105                 110

Arg Tyr Ala Gly His Asn Ile Asp Ile Ala Ile Ala Lys Met Lys Cys
        115                 120                 125
```

Arg Gln Val Trp Gly Asp Trp Glu Glu Asp Gly Phe Gly Ser Asn Pro
    130                 135                 140
Ile Ala His Gln Asn Ile Met Tyr Lys Gly His Leu Asn Leu Met Tyr
145                 150                 155                 160
Gly Leu Tyr Gln Leu Leu Thr Gly Asn Thr Gln Tyr Glu Glu Phe
                165                 170                 175
Ile Asp Leu Ser Asn Ile Ile Tyr Ser Glu Ile Lys Glu Asn Pro Tyr
                180                 185                 190
Ala Gly Ile Ala Cys Glu Pro Asp Asn Tyr Phe Pro Gln Cys Asn Ser
                195                 200                 205
Val Ala Tyr Leu Ser Leu Trp Val Tyr Asp Arg Leu Tyr His Thr Asp
    210                 215                 220
Tyr Lys Ala Val Thr Lys Pro Trp Leu Asp Phe Leu Gln Lys Lys Leu
225                 230                 235                 240
Ile Asp Pro Glu Thr Gly Thr Phe His Val Ala Tyr His Pro Thr Ser
                245                 250                 255
His Ala Val Lys Pro Trp Val Ser Ala Tyr Thr Thr Ala Trp Ala Leu
                260                 265                 270
Thr Met Ile His Gly Leu Asn Pro Glu Phe Ala Lys Lys Tyr Tyr Pro
275                 280                 285
Asn Phe Lys Gln Thr Phe Val Glu Val Phe Asp Asn Gly Thr Lys Ala
    290                 295                 300
Arg Val Arg Glu Thr Ala His Thr Thr Asp Val Asp Gly Gly Val Gly
305                 310                 315                 320
Ala Ala Ser Ile Phe Thr Leu Val Leu Ala Arg Glu Met Asn Asp Gln
                325                 330                 335
Glu Leu Phe Asp Gln Leu Leu Asn Tyr Leu Glu Pro Pro Ala Lys Pro
                340                 345                 350
Val Ile Tyr Ser Gly Ile Leu Arg Tyr Glu Asn Pro Thr Ser Leu Leu
                355                 360                 365
Phe Asp Glu Leu Leu Phe Val Ala Lys Val His Val Gly Phe Gly Glu
    370                 375                 380
Leu Ile Asn Leu Lys Pro Val Glu Thr Asp
385                 390

<210> SEQ ID NO 73
<211> LENGTH: 1206
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1206)
<223> OTHER INFORMATION: Native Nucleic acid encoding SEQ ID NO: 74,
      which is unprocessed and includes its signal peptide

<400> SEQUENCE: 73
atgaagaaac ccgcccctt gaccgtcctg gccggcctgg ccagcgccgt cctgctcgcc      60
cttggcacgc cggccacggc agccgagccg atgcccggcc gcctggcctc gaccgacgac     120
tacttcgccc agagcgagaa gcacgccctg acgccggacg tgatggcgca actgcgctac     180
atgaactaca ccgatttcat ttcgccgttc tacagccggg gctgcgcctt cgacgcctgg     240
acgatgaaga agatgccgcc cgcatcatc aaatattcgc tcgcctggta cgcctacggc     300
ctggccagcg tcgccctgac cgaccgggcg atgcgcccgg tggccggtca cgcgattgac     360
atcgcgaccg ccaagatgca ttgcaagcag gtctggggcg actgggagga agacggtttc     420

```
ggcagcgacc cgatcatccg ccagaacgtc atgtacaagg ccacctgaa cctgatgtac    480 gggctctacc agttgatcac cggcgaccgc aagtacgaga aggaaaacac ccgcctgacc    540
cgcatcatgc acaaggagat gaagagcaat ccgtacgccg gcatcgtctg cgaacccgac    600
aactacttcg tccagtgcaa ctcggtcgcc tacctgagcc tgtgggttta cgaccggctg    660
cacggcaccc agtacaaggc ggcaaccagg gagtggctga aattcatcga ggacgaactg    720
atcgacccga agaccggcag cttctatctt tcctaccacc ccgaaaccgg tgccgtgaag    780
ccgtggcagt cggcctacac gaccgcctgg acgctggcca tggtgcatgg catggacccg    840
gccttcgccg aacgctatta cccgaaattc aaggaaagct cgtcgaggt ctatgacgac    900 ggccgcaagg cgcgcgtccg cgaaatgacc ggcaccaccg acaccgacgg cggcgtcggc    960
gccgcgtcgg cgttcatgct ggtcctggca cgtgaaatgg cgacaagca actgttcgac    1020 cagctgctga accacctcga accgccagcc ggaccgacga tcacttcggg catcctgcat    1080
tacgcgcagc cgagcaatct gctgttcgac gaattgctgt tcgtcggcaa ggtgcatgtc    1140
ggcttcgcca agctgctcaa tgcgccgccg gcaccggctc gcccggccct gcaaaagaag    1200
aaatga                                                               1206
```

<210> SEQ ID NO 74
<211> LENGTH: 401
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(401)
<223> OTHER INFORMATION: Native, or unprocessed, LinD enzyme GNM 10058, including signal peptide

<400> SEQUENCE: 74

```
Met Lys Lys Pro Arg Pro Leu Thr Val Leu Ala Gly Leu Ala Ser Ala
1               5                   10                  15

Val Leu Ala Leu Gly Thr Pro Ala Thr Ala Ala Glu Pro Met Pro
            20                  25                  30

Gly Arg Leu Ala Ser Thr Asp Asp Tyr Phe Ala Gln Ser Glu Lys His
        35                  40                  45

Ala Leu Thr Pro Asp Val Met Ala Gln Leu Arg Tyr Met Asn Tyr Thr
    50                  55                  60

Asp Phe Ile Ser Pro Phe Tyr Ser Arg Gly Cys Ala Phe Asp Ala Trp
65                  70                  75                  80

Thr Met Lys Lys Met Pro Pro Arg Ile Ile Lys Tyr Ser Leu Ala Trp
                85                  90                  95

Tyr Ala Tyr Gly Leu Ala Ser Val Ala Leu Thr Asp Pro Ala Met Arg
            100                 105                 110

Pro Val Ala Gly His Ala Ile Asp Ile Ala Thr Ala Lys Met His Cys
        115                 120                 125

Lys Gln Val Trp Gly Asp Trp Glu Glu Asp Gly Phe Gly Ser Asp Pro
    130                 135                 140

Ile Ile Arg Gln Asn Val Met Tyr Lys Gly His Leu Asn Leu Met Tyr
145                 150                 155                 160

Gly Leu Tyr Gln Leu Ile Thr Gly Asp Arg Lys Tyr Glu Lys Glu Asn
                165                 170                 175

Thr Arg Leu Thr Arg Ile Met His Lys Glu Met Lys Ser Asn Pro Tyr
            180                 185                 190
```

Ala Gly Ile Val Cys Glu Pro Asp Asn Tyr Phe Val Gln Cys Asn Ser
        195                 200                 205

Val Ala Tyr Leu Ser Leu Trp Val Tyr Asp Arg Leu His Gly Thr Gln
210                 215                 220

Tyr Lys Ala Ala Thr Arg Glu Trp Leu Lys Phe Ile Glu Asp Glu Leu
225                 230                 235                 240

Ile Asp Pro Lys Thr Gly Ser Phe Tyr Leu Ser Tyr His Pro Glu Thr
                245                 250                 255

Gly Ala Val Lys Pro Trp Gln Ser Ala Tyr Thr Thr Ala Trp Thr Leu
            260                 265                 270

Ala Met Val His Gly Met Asp Pro Ala Phe Ala Glu Arg Tyr Tyr Pro
        275                 280                 285

Lys Phe Lys Glu Ser Phe Val Glu Val Tyr Asp Asp Gly Arg Lys Ala
    290                 295                 300

Arg Val Arg Glu Met Thr Gly Thr Thr Asp Thr Asp Gly Gly Val Gly
305                 310                 315                 320

Ala Ala Ser Ala Phe Met Leu Val Leu Ala Arg Glu Met Gly Asp Lys
                325                 330                 335

Gln Leu Phe Asp Gln Leu Leu Asn His Leu Glu Pro Pro Ala Gly Pro
            340                 345                 350

Thr Ile Thr Ser Gly Ile Leu His Tyr Ala Gln Pro Ser Asn Leu Leu
        355                 360                 365

Phe Asp Glu Leu Leu Phe Val Gly Lys Val His Val Gly Phe Ala Lys
    370                 375                 380

Leu Leu Asn Ala Pro Pro Ala Pro Ala Arg Pro Ala Leu Gln Lys Lys
385                 390                 395                 400

Lys

<210> SEQ ID NO 75
<211> LENGTH: 81
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(81)
<223> OTHER INFORMATION: Nucleic acid encoding GNM 10058 signal peptide

<400> SEQUENCE: 75
atgaagaaac ccgcccctt gaccgtcctg gccggcctgg ccagcgccgt cctgctcgcc       60
cttggcacgc cggccacggc a                                                81

<210> SEQ ID NO 76
<211> LENGTH: 27
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(27)
<223> OTHER INFORMATION: GNM 10058 signal peptide

<400> SEQUENCE: 76

Met Lys Lys Pro Arg Pro Leu Thr Val Leu Ala Gly Leu Ala Ser Ala
1               5                   10                  15

Val Leu Leu Ala Leu Gly Thr Pro Ala Thr Ala
            20                  25

<210> SEQ ID NO 77
<211> LENGTH: 1125
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1125)
<223> OTHER INFORMATION: Nucleic acid encoding Processed (mature) GNM 10058 LinD enzyme, no signal peptide

<400> SEQUENCE: 77

```
gccgagccga tgcccggccg cctggcctcg accgacgact acttcgccca gagcgagaag      60
cacgccctga cgccggacgt gatggcgcaa ctgcgctaca tgaactacac cgatttcatt     120
tcgccgttct acagccgggg ctgcgccttc gacgcctgga cgatgaagaa gatgccgccc     180
cgcatcatca atattcgct cgcctggtac gcctacggcc tggccagcgt cgccctgacc     240
gacccggcga tgcgccccgt ggccggtcac gcgattgaca tcgcgaccgc caagatgcat     300
tgcaagcagg tctggggcga ctgggaggaa gacggtttcg gcagcgaccc gatcatccgc     360
cagaacgtca tgtacaaggg ccacctgaac ctgatgtacg gctctacca gttgatcacc     420 ggcgaccgca agtacgagaa ggaaaacacc cgcctgaccc gcatcatgca caggagatg     480 aagagcaatc cgtacgccgg catcgtctgc gaacccgaca actacttcgt ccagtgcaac     540
tcggtcgcct acctgagcct gtgggtttac gaccggctgc acggcaccca gtacaaggcg     600
gcaaccaggg agtggctgaa attcatcgag gacgaactga tcgacccgaa gaccggcagc     660
ttctatcttt cctaccaccc cgaaaccggt gccgtgaagc cgtggcagtc ggcctacacg     720
accgcctgga cgctggccat ggtgcatggc atggaccccgg ccttcgccga acgctattac     780
ccgaaattca aggaaagctt cgtcgaggtc tatgacgacg gccgcaaggc gcgcgtccgc     840
gaaatgaccg gcaccaccga caccgacggc ggcgtcggcg ccgcgtcggc gttcatgctg     900
gtcctggcac gtgaaatggg cgacaagcaa ctgttcgacc agctgctgaa ccacctcgaa     960
ccgccagccg accgacgat cacttcgggc atcctgcatt acgcgcagcc gagcaatctg    1020
ctgttcgacg aattgctgtt cgtcggcaag gtgcatgtcg gcttcgccaa gctgctcaat    1080
gcgccgccgg caccggctcg cccggcccctg caaaagaaga aatga                   1125
```

<210> SEQ ID NO 78
<211> LENGTH: 374
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(374)
<223> OTHER INFORMATION: Processed (mature) GNM 10058 LinD enzyme, no signal peptide.

<400> SEQUENCE: 78

```
Ala Glu Pro Met Pro Gly Arg Leu Ala Ser Thr Asp Asp Tyr Phe Ala
1               5                   10                  15

Gln Ser Glu Lys His Ala Leu Thr Pro Asp Val Met Ala Gln Leu Arg
            20                  25                  30

Tyr Met Asn Tyr Thr Asp Phe Ile Ser Pro Tyr Ser Arg Gly Cys
        35                  40                  45

Ala Phe Asp Ala Trp Thr Met Lys Lys Met Pro Pro Arg Ile Ile Lys
```

|    |    |    |    |    | 50  |    |    |    |    | 55  |    |    |    |    | 60  |
|----|----|----|----|----|-----|----|----|----|----|-----|----|----|----|----|-----|

Tyr Ser Leu Ala Trp Tyr Ala Tyr Gly Leu Ala Ser Val Ala Leu Thr
65                  70                  75                  80

Asp Pro Ala Met Arg Pro Val Ala Gly His Ala Ile Asp Ile Ala Thr
                    85                  90                  95

Ala Lys Met His Cys Lys Gln Val Trp Gly Asp Trp Glu Glu Asp Gly
                100                 105                 110

Phe Gly Ser Asp Pro Ile Ile Arg Gln Asn Val Met Tyr Lys Gly His
            115                 120                 125

Leu Asn Leu Met Tyr Gly Leu Tyr Gln Leu Ile Thr Gly Asp Arg Lys
130                 135                 140

Tyr Glu Lys Glu Asn Thr Arg Leu Thr Arg Ile Met His Lys Glu Met
145                 150                 155                 160

Lys Ser Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
                180                 185                 190

Leu His Gly Thr Gln Tyr Lys Ala Ala Thr Arg Glu Trp Leu Lys Phe
            195                 200                 205

Ile Glu Asp Glu Leu Ile Asp Pro Lys Thr Gly Ser Phe Tyr Leu Ser
210                 215                 220

Tyr His Pro Glu Thr Gly Ala Val Lys Pro Trp Gln Ser Ala Tyr Thr
225                 230                 235                 240

Thr Ala Trp Thr Leu Ala Met Val His Gly Met Asp Pro Ala Phe Ala
                245                 250                 255

Glu Arg Tyr Tyr Pro Lys Phe Lys Glu Ser Phe Val Glu Val Tyr Asp
                260                 265                 270

Asp Gly Arg Lys Ala Arg Val Arg Glu Met Thr Gly Thr Thr Asp Thr
            275                 280                 285

Asp Gly Gly Val Gly Ala Ala Ser Ala Phe Met Leu Val Leu Ala Arg
290                 295                 300

Glu Met Gly Asp Lys Gln Leu Phe Asp Gln Leu Leu Asn His Leu Glu
305                 310                 315                 320

Pro Pro Ala Gly Pro Thr Ile Thr Ser Gly Ile Leu His Tyr Ala Gln
                325                 330                 335

Pro Ser Asn Leu Leu Phe Asp Glu Leu Leu Phe Val Gly Lys Val His
                340                 345                 350

Val Gly Phe Ala Lys Leu Leu Asn Ala Pro Pro Ala Pro Ala Arg Pro
            355                 360                 365

Ala Leu Gln Lys Lys Lys
            370

<210> SEQ ID NO 79
<211> LENGTH: 1206
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1206)
<223> OTHER INFORMATION: Native Nucleic acid encoding SEQ ID NO: 80,
      which is unprocessed and includes its signal peptide

<400> SEQUENCE: 79
atgaaaaaaa cacgcttttc cgtcgcactg accggcctga ctgccgccac cctgatcgca      60

-continued

```
ttcggttcgc ccgccacggc cggcgaattg ccacccggcc gactggcttc gaccgacgac    120
tacttcaccc agcgtgaaaa acaggcactg acgcccgacg tcatggcgca actgcgctac    180
atgaactaca ccgatttcat ttcgccgttc tacagccggg gctgcgcctt cgatgcctgg    240
acgatgaaga agatgccgcc gcgcatcatc aagtattcgc tggccttcta cgcctacggg    300
ctggccagcg tcgcccagac cgacccgaaa atgcgtcccc tcgccggcca cgcgatcgac    360
atcgccaccg ccaagatgca ctgcaagcag gtctggggcg actgggagga agacggtttc    420
ggcaaggacc cgatcatcaa ggaaaacgtc atgtacaagg ccatctgaa cctgatgtac     480 gggctgtacc agatggtcac cggcgaccgg aaatacgaga aggaaaatac ccgcctgacc    540
caaatcatgc tcaaggagat caaggccaat ccgtatgccg catcgtctg cgagccggac     600 aactacttcg tgcaatgcaa ttcggtcgcc tacctgagcc tgtgggtcta tgaccggctg    660
cacggcacca accacaaggc cgtgaccaag gaatggctga agttcatcga ggacgagctg    720
atcgacccca gagcggcag cttctacctc tcctaccatc ccgagaccgg cgccgtgaag     780
ccctggcaat cggcctacac gtcggcctgg gcgctggcga tggtgcacgg catggacccg    840
gcgttcacgg agcgccatta cccgaagttc aaggaaacct tcgtcgaggt ttatgacgga    900
ggccacaagg cccgcgtccg cgaaatgacc ggcactccgg acgccgatgg cggggtcggc    960
ctggcctcgg ccttcacgct gctgctggcc cgcgaaatgg gtgacaagga acttttcgac   1020
cagctgttga accacctcga accgccagcc aagccgacga tcacctccgg catcctgcat   1080
tacgggcagc cgagcagcct gctgttcgac gaattgctgt tcgtcggcaa ggtgcacgtc   1140
ggcttcgcca acctgctcaa tgcgccgctg gccccgcccc gccctgccct gcaaaagaag   1200
aaatga                                                              1206
```

<210> SEQ ID NO 80
<211> LENGTH: 401
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(401)
<223> OTHER INFORMATION: Native, or unprocessed, LinD enzyme GNM 10092, including signal peptide

<400> SEQUENCE: 80

```
Met Lys Lys Thr Arg Phe Ser Val Ala Leu Thr Gly Leu Thr Ala Ala
1               5                   10                  15

Thr Leu Ile Ala Phe Gly Ser Pro Ala Thr Ala Gly Glu Leu Pro Pro
            20                  25                  30

Gly Arg Leu Ala Ser Thr Asp Asp Tyr Phe Thr Gln Arg Glu Lys Gln
        35                  40                  45

Ala Leu Thr Pro Asp Val Met Ala Gln Leu Arg Tyr Met Asn Tyr Thr
    50                  55                  60

Asp Phe Ile Ser Pro Phe Tyr Ser Arg Gly Cys Ala Phe Asp Ala Trp
65                  70                  75                  80

Thr Met Lys Lys Met Pro Pro Arg Ile Ile Lys Tyr Ser Leu Ala Phe
                85                  90                  95

Tyr Ala Tyr Gly Leu Ala Ser Val Ala Gln Thr Asp Pro Lys Met Arg
            100                 105                 110

Pro Leu Ala Gly His Ala Ile Asp Ile Ala Thr Ala Lys Met His Cys
        115                 120                 125
```

```
Lys Gln Val Trp Gly Asp Trp Glu Glu Asp Gly Phe Gly Lys Asp Pro
    130                 135                 140
Ile Ile Lys Glu Asn Val Met Tyr Lys Gly His Leu Asn Leu Met Tyr
145                 150                 155                 160
Gly Leu Tyr Gln Met Val Thr Gly Asp Arg Lys Tyr Glu Lys Glu Asn
                165                 170                 175
Thr Arg Leu Thr Gln Ile Met Leu Lys Glu Ile Lys Ala Asn Pro Tyr
            180                 185                 190
Ala Gly Ile Val Cys Glu Pro Asp Asn Tyr Phe Val Gln Cys Asn Ser
        195                 200                 205
Val Ala Tyr Leu Ser Leu Trp Val Tyr Asp Arg Leu His Gly Thr Asn
    210                 215                 220
His Lys Ala Val Thr Lys Glu Trp Leu Lys Phe Ile Glu Asp Glu Leu
225                 230                 235                 240
Ile Asp Pro Lys Ser Gly Ser Phe Tyr Leu Ser Tyr His Pro Glu Thr
                245                 250                 255
Gly Ala Val Lys Pro Trp Gln Ser Ala Tyr Thr Ser Ala Trp Ala Leu
            260                 265                 270
Ala Met Val His Gly Met Asp Pro Ala Phe Thr Glu Arg His Tyr Pro
        275                 280                 285
Lys Phe Lys Glu Thr Phe Val Glu Val Tyr Asp Gly Gly His Lys Ala
    290                 295                 300
Arg Val Arg Glu Met Thr Gly Thr Pro Asp Ala Asp Gly Gly Val Gly
305                 310                 315                 320
Leu Ala Ser Ala Phe Thr Leu Leu Ala Arg Glu Met Gly Asp Lys
                325                 330                 335
Glu Leu Phe Asp Gln Leu Leu Asn His Leu Glu Pro Pro Ala Lys Pro
            340                 345                 350
Thr Ile Thr Ser Gly Ile Leu His Tyr Gly Gln Pro Ser Ser Leu Leu
        355                 360                 365
Phe Asp Glu Leu Leu Phe Val Gly Lys Val His Val Gly Phe Ala Asn
    370                 375                 380
Leu Leu Asn Ala Pro Leu Ala Pro Pro Arg Pro Ala Leu Gln Lys Lys
385                 390                 395                 400
Lys

<210> SEQ ID NO 81
<211> LENGTH: 81
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(81)
<223> OTHER INFORMATION: Nucleic acid encoding GNM 10092 signal peptide

<400> SEQUENCE: 81
atgaaaaaaa cacgcttttc cgtcgcactg accggcctga ctgccgccac cctgatcgca        60
ttcggttcgc ccgccacggc c                                                  81

<210> SEQ ID NO 82
<211> LENGTH: 27
<212> TYPE: PRT
<213> ORGANISM: Unknown
<220> FEATURE:
<223> OTHER INFORMATION: Linalool dehydratase (LinD) from unknown origin
<220> FEATURE:
```

<220> FEATURE:
<221> NAME/KEY: misc_feature
<222> LOCATION: (1)..(27)
<223> OTHER INFORMATION: GNM 10092 signal peptide

<400> SEQUENCE: 82

Met Lys Lys Thr Arg Phe Ser Val Ala Leu Thr Gly Leu Thr Ala Ala
1               5                   10                  15

Thr Leu Ile Ala Phe Gly Ser Pro Ala Thr Ala
            20                  25

<210> SEQ ID NO 83
<211> LENGTH: 1125
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1125)
<223> OTHER INFORMATION: Nucleic acid encoding Processed (mature) GNM
      10092 LinD enzyme, no signal peptide

<400> SEQUENCE: 83

| | | | | |
|---|---|---|---|---|
| ggcgaattgc | cacccggccg | actggcttcg | accgacgact | acttcaccca gcgtgaaaaa | 60 |
| caggcactga | cgcccgacgt | catggcgcaa | ctgcgctaca | tgaactacac cgatttcatt | 120 |
| tcgccgttct | acagccgggg | ctgcgccttc | gatgcctgga | cgatgaagaa gatgccgccg | 180 |
| cgcatcatca | gtattcgct | ggccttctac | gcctacgggc | tggccagcgt cgcccagacc | 240 |
| gacccgaaaa | tgcgtcccct | cgccggccac | gcgatcgaca | tcgccaccgc caagatgcac | 300 |
| tgcaagcagg | tctgggcga | ctgggaggaa | gacggtttcg | gcaaggaccc gatcatcaag | 360 |
| gaaaacgtca | tgtacaaggg | ccatctgaac | ctgatgtacg | gctgtacca gatggtcacc | 420 |
| ggcgaccgga | aatacgagaa | ggaaaatacc | cgcctgaccc | aaatcatgct caaggagatc | 480 |
| aaggccaatc | cgtatgccgg | catcgtctgc | gagccggaca | actacttcgt gcaatgcaat | 540 |
| tcggtcgcct | acctgagcct | gtgggtctat | gaccggctgc | acggcaccaa ccacaaggcc | 600 |
| gtgaccaagg | aatggctgaa | gttcatcgag | gacgagctga | tcgacccaa gagcggcagc | 660 |
| ttctacctct | cctaccatcc | cgagaccggc | gccgtgaagc | cctggcaatc ggcctacacg | 720 |
| tcggcctggg | cgctggcgat | ggtgcacggc | atggacccgg | cgttcacgga gcgccattac | 780 |
| ccgaagttca | aggaaacctt | cgtcgaggtt | tatgacggag | ccacaaggc ccgcgtccgc | 840 |
| gaaatgaccg | gcactccgga | cgccgatggc | ggggtcggcc | tggcctcggc cttcacgctg | 900 |
| ctgctggccc | gcgaaatggg | tgacaaggaa | cttttcgacc | agctgttgaa ccacctcgaa | 960 |
| ccgccagcca | agccgacgat | cacctccggc | atcctgcatt | acgggcagcc gagcagcctg | 1020 |
| ctgttcgacg | aattgctgtt | cgtcggcaag | gtgcacgtcg | gcttcgccaa cctgctcaat | 1080 |
| gcgccgctgg | ccccgccccg | ccctgccctg | caaaagaaga | aatga | 1125 |

<210> SEQ ID NO 84
<211> LENGTH: 374
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(374)
<223> OTHER INFORMATION: Processed (mature) GNM 10092 LinD enzyme, no
      signal peptide.

<400> SEQUENCE: 84

Gly Glu Leu Pro Pro Gly Arg Leu Ala Ser Thr Asp Tyr Phe Thr
1               5                   10                  15

Gln Arg Glu Lys Gln Ala Leu Thr Pro Asp Val Met Ala Gln Leu Arg
            20                  25                  30

Tyr Met Asn Tyr Thr Asp Phe Ile Ser Pro Tyr Ser Arg Gly Cys
        35                  40                  45

Ala Phe Asp Ala Trp Thr Met Lys Lys Met Pro Pro Arg Ile Ile Lys
50                  55                  60

Tyr Ser Leu Ala Phe Tyr Ala Tyr Gly Leu Ala Ser Val Ala Gln Thr
65                  70                  75                  80

Asp Pro Lys Met Arg Pro Leu Ala Gly His Ala Ile Asp Ile Ala Thr
                85                  90                  95

Ala Lys Met His Cys Lys Gln Val Trp Gly Asp Trp Glu Glu Asp Gly
            100                 105                 110

Phe Gly Lys Asp Pro Ile Ile Lys Glu Asn Val Met Tyr Lys Gly His
            115                 120                 125

Leu Asn Leu Met Tyr Gly Leu Tyr Gln Met Val Thr Gly Asp Arg Lys
    130                 135                 140

Tyr Glu Lys Glu Asn Thr Arg Leu Thr Gln Ile Met Leu Lys Glu Ile
145                 150                 155                 160

Lys Ala Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Asn His Lys Ala Val Thr Lys Glu Trp Leu Lys Phe
            195                 200                 205

Ile Glu Asp Glu Leu Ile Asp Pro Lys Ser Gly Ser Phe Tyr Leu Ser
210                 215                 220

Tyr His Pro Glu Thr Gly Ala Val Lys Pro Trp Gln Ser Ala Tyr Thr
225                 230                 235                 240

Ser Ala Trp Ala Leu Ala Met Val His Gly Met Asp Pro Ala Phe Thr
                245                 250                 255

Glu Arg His Tyr Pro Lys Phe Lys Glu Thr Phe Val Glu Val Tyr Asp
            260                 265                 270

Gly Gly His Lys Ala Arg Val Arg Glu Met Thr Gly Thr Pro Asp Ala
            275                 280                 285

Asp Gly Gly Val Gly Leu Ala Ser Ala Phe Thr Leu Leu Leu Ala Arg
290                 295                 300

Glu Met Gly Asp Lys Glu Leu Phe Asp Gln Leu Leu Asn His Leu Glu
305                 310                 315                 320

Pro Pro Ala Lys Pro Thr Ile Thr Ser Gly Ile Leu His Tyr Gly Gln
                325                 330                 335

Pro Ser Ser Leu Leu Phe Asp Glu Leu Leu Phe Val Gly Lys Val His
            340                 345                 350

Val Gly Phe Ala Asn Leu Leu Asn Ala Pro Leu Ala Pro Pro Arg Pro
            355                 360                 365

Ala Leu Gln Lys Lys Lys
    370

<210> SEQ ID NO 85
<211> LENGTH: 1206
<212> TYPE: DNA
<213> ORGANISM: Unknown
<220> FEATURE:

```
<223> OTHER INFORMATION: Linalool dehydratase (LinD) from unknown origin
<220> FEATURE:
<221> NAME/KEY: misc_feature
<222> LOCATION: (1)..(1206)
<223> OTHER INFORMATION: Native Nucleic acid encoding SEQ ID NO: 86,
      which is unprocessed and includes its signal peptide

<400> SEQUENCE: 85
atgaagaaac ccgcccctt gaccgtcctg ccggcctgg ccagcgccgt cctgctcgcc      60
cttggcacgc cggccacggc agtcgagccg atgcccggcc gcctggcctc gaccgacgac    120
tacttcgccc agagcgagaa gcacgccctg acgcccgacg tgatggcgca actgcgctac    180
atgaactaca ccgatttcat ctcgccgttc tatagccggg gctgcgcctt cgatgcctgg    240
acgatgaaga agatgccgcc ccgcatcatc aagtattcgc tcgcctggta cgcctacggc    300
ctggccagcg tcgccctgac cgatccggcg atgcggccgg tggccggcca tgcgatcgac    360
atcgcgaccg ccaagatgca ttgcaagcag gtctggggcg actgggagga agacggcttc    420
ggcagcgacc cgatcatccg cgaaaacgtc atgtacaagg ccacctgaa cctgatgtac     480 ggtctctacc agctgatcac cggcgaccgc aagtacgaga aggaaaacac ccgcctgacc    540
cgcatcatgc acaaggagat gaagagcaat ccgtacgccg gcatcgtctg gaacccgac    600 aactacttcg tccagtgcaa ctcggtcgcc tacctgagcc tgtgggttta cgaccggctg    660
cacggcaccc agtacaaggc ggcaaccagg gagtggctga aattcatcga ggacgaactg    720
atcgacccga agaccggcag cttctatctt tcctaccatc ccgaaaccgg tgccgtgaag    780
ccgtggcagt cggcctacac gaccgcctgg acgctggcca tggtgcatgg catggacccg    840
gccttcgccg aacgctatta cccgaaattc aaggaaagct tcgtcgaggt ctatgacgac    900
ggccgcaagg cgcgcgtccg cgaaatgacc ggcaccaccg acaccgacgg cggcgtcggc    960
gccgcgtcgg cgttcatgct ggtcctggcg cgtgaaatgg gcgacaagca actgttcgac   1020
cagctgctga ccacctcga accgccagcc ggaccgacga tcacttcggg catcctgcat   1080
tacgcgcagc cgagcaatct gctgttcgac gaattgctgt tcgtcggcaa ggtgcatgtc   1140
ggcttcgcca aactgctcaa tgcgccgccg gcaccggccc gccccgccct gcaaaagaag   1200
aaatga                                                               1206

<210> SEQ ID NO 86
<211> LENGTH: 401
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(401)
<223> OTHER INFORMATION: Native, or unprocessed, LinD enzyme GNM 10093,
      including signal peptide

<400> SEQUENCE: 86

Met Lys Lys Pro Arg Pro Leu Thr Val Leu Ala Gly Leu Ala Ser Ala
1               5                   10                  15

Val Leu Leu Ala Leu Gly Thr Pro Ala Thr Ala Val Glu Pro Met Pro
            20                  25                  30

Gly Arg Leu Ala Ser Thr Asp Asp Tyr Phe Ala Gln Ser Glu Lys His
        35                  40                  45

Ala Leu Thr Pro Asp Val Met Ala Gln Leu Arg Tyr Met Asn Tyr Thr
    50                  55                  60

Asp Phe Ile Ser Pro Phe Tyr Ser Arg Gly Cys Ala Phe Asp Ala Trp
```

```
                65                  70                  75                  80
Thr Met Lys Lys Met Pro Pro Arg Ile Ile Lys Tyr Ser Leu Ala Trp
                        85                  90                  95
Tyr Ala Tyr Gly Leu Ala Ser Val Ala Leu Thr Asp Pro Ala Met Arg
                    100                 105                 110
Pro Val Ala Gly His Ala Ile Asp Ile Ala Thr Ala Lys Met His Cys
                115                 120                 125
Lys Gln Val Trp Gly Asp Trp Glu Asp Gly Phe Gly Ser Asp Pro
            130                 135                 140
Ile Ile Arg Glu Asn Val Met Tyr Lys Gly His Leu Asn Leu Met Tyr
145                 150                 155                 160
Gly Leu Tyr Gln Leu Ile Thr Gly Asp Arg Lys Tyr Glu Lys Glu Asn
                165                 170                 175
Thr Arg Leu Thr Arg Ile Met His Lys Glu Met Lys Ser Asn Pro Tyr
                180                 185                 190
Ala Gly Ile Val Cys Glu Pro Asp Asn Tyr Phe Val Gln Cys Asn Ser
            195                 200                 205
Val Ala Tyr Leu Ser Leu Trp Val Tyr Asp Arg Leu His Gly Thr Gln
210                 215                 220
Tyr Lys Ala Ala Thr Arg Glu Trp Leu Lys Phe Ile Glu Asp Glu Leu
225                 230                 235                 240
Ile Asp Pro Lys Thr Gly Ser Phe Tyr Leu Ser Tyr His Pro Glu Thr
                245                 250                 255
Gly Ala Val Lys Pro Trp Gln Ser Ala Tyr Thr Thr Ala Trp Thr Leu
                260                 265                 270
Ala Met Val His Gly Met Asp Pro Ala Phe Ala Glu Arg Tyr Tyr Pro
            275                 280                 285
Lys Phe Lys Glu Ser Phe Val Glu Val Tyr Asp Asp Gly Arg Lys Ala
            290                 295                 300
Arg Val Arg Glu Met Thr Gly Thr Thr Asp Thr Asp Gly Gly Val Gly
305                 310                 315                 320
Ala Ala Ser Ala Phe Met Leu Val Leu Ala Arg Glu Met Gly Asp Lys
                325                 330                 335
Gln Leu Phe Asp Gln Leu Leu Asn His Leu Glu Pro Pro Ala Gly Pro
            340                 345                 350
Thr Ile Thr Ser Gly Ile Leu His Tyr Ala Gln Pro Ser Asn Leu Leu
            355                 360                 365
Phe Asp Glu Leu Leu Phe Val Gly Lys Val His Val Gly Phe Ala Lys
            370                 375                 380
Leu Leu Asn Ala Pro Pro Ala Pro Ala Arg Pro Ala Leu Gln Lys Lys
385                 390                 395                 400
Lys

<210> SEQ ID NO 87
<211> LENGTH: 81
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(81)
<223> OTHER INFORMATION: Nucleic acid encoding GNM 10093 signal peptide

<400> SEQUENCE: 87
atgaagaaac ccgcccctt gaccgtcctg gccggcctgg ccagcgccgt cctgctcgcc      60
```
cttggcacgc cggccacggc a                                                   81

<210> SEQ ID NO 88
<211> LENGTH: 27
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(27)
<223> OTHER INFORMATION: GNM 10093 signal peptide

<400> SEQUENCE: 88

Met Lys Lys Pro Arg Pro Leu Thr Val Leu Ala Gly Leu Ala Ser Ala
1               5                   10                  15

Val Leu Leu Ala Leu Gly Thr Pro Ala Thr Ala
            20                  25

<210> SEQ ID NO 89
<211> LENGTH: 1125
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1125)
<223> OTHER INFORMATION: Nucleic acid encoding Processed (mature) GNM
      10093 LinD enzyme, no signal peptide

<400> SEQUENCE: 89
gtcgagccga tgcccggccg cctggcctcg accgacgact acttcgccca gagcgagaag     60
cacgccctga cgcccgacgt gatggcgcaa ctgcgctaca tgaactacac cgatttcatc    120
tcgccgttct atagccgggg ctgcgccttc gatgcctgga cgatgaagaa gatgccgccc    180
cgcatcatca gtattcgct cgcctggtac gcctacggcc tggccagcgt cgccctgacc    240
gatccggcga tgcggccggt ggccggccat gcgatcgaca tcgcgaccgc caagatgcat    300
tgcaagcagg tctggggcga ctgggaggaa gacggcttcg gcagcgaccc gatcatccgc    360
gaaaacgtca tgtacaaggg ccacctgaac ctgatgtacg gtctctacca gctgatcacc    420
ggcgaccgca gtacgagaa ggaaaacacc cgcctgaccc gcatcatgca aaggagatg     480 aagagcaatc cgtacgccgg catcgtctgc gaacccgaca actacttcgt ccagtgcaac    540
tcggtcgcct acctgagcct gtgggtttac gaccggctgc acggcaccca gtacaaggcg    600
gcaaccaggg agtggctgaa attcatcgag gacgaactga tcgacccgaa gaccggcagc    660
ttctatcttt cctaccatcc cgaaaccggt gccgtgaagc cgtggcagtc ggcctacacg    720
accgcctgga cgctggccat ggtgcatggc atggacccgg ccttcgccga acgctattac    780
ccgaaattca aggaaagctt cgtcgaggtc tatgacgacg ccgcaaggc gcgcgtccgc    840 gaaatgaccg gcaccaccga caccgacggc ggcgtcggcg ccgcgtcggc gttcatgctg    900
gtcctggcgc gtgaaatggg cgacaagcaa ctgttcgacc agctgctgaa ccacctcgaa    960
ccgccagccg gaccgacgat cacttcgggc atcctgcatt acgcgcagcc gagcaatctg   1020
ctgttcgacg aattgctgtt cgtcggcaag gtgcatgtcg gcttcgccaa actgctcaat   1080
gcgccgccgg caccggcccg ccccgcccctg caaaagaaga aatga                  1125

<210> SEQ ID NO 90
<211> LENGTH: 374

```
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(374)
<223> OTHER INFORMATION: Processed (mature) GNM 10093 LinD enzyme, no
      signal peptide.

<400> SEQUENCE: 90

Val Glu Pro Met Pro Gly Arg Leu Ala Ser Thr Asp Asp Tyr Phe Ala
1               5                   10                  15

Gln Ser Glu Lys His Ala Leu Thr Pro Asp Val Met Ala Gln Leu Arg
            20                  25                  30

Tyr Met Asn Tyr Thr Asp Phe Ile Ser Pro Phe Tyr Ser Arg Gly Cys
        35                  40                  45

Ala Phe Asp Ala Trp Thr Met Lys Lys Met Pro Pro Arg Ile Ile Lys
    50                  55                  60

Tyr Ser Leu Ala Trp Tyr Ala Tyr Gly Leu Ala Ser Val Ala Leu Thr
65                  70                  75                  80

Asp Pro Ala Met Arg Pro Val Ala Gly His Ala Ile Asp Ile Ala Thr
                85                  90                  95

Ala Lys Met His Cys Lys Gln Val Trp Gly Asp Trp Glu Glu Asp Gly
            100                 105                 110

Phe Gly Ser Asp Pro Ile Ile Arg Glu Asn Val Met Tyr Lys Gly His
        115                 120                 125

Leu Asn Leu Met Tyr Gly Leu Tyr Gln Leu Ile Thr Gly Asp Arg Lys
130                 135                 140

Tyr Glu Lys Glu Asn Thr Arg Leu Thr Arg Ile Met His Lys Glu Met
145                 150                 155                 160

Lys Ser Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr Gln Tyr Lys Ala Ala Thr Arg Glu Trp Leu Lys Phe
        195                 200                 205

Ile Glu Asp Glu Leu Ile Asp Pro Lys Thr Gly Ser Phe Tyr Leu Ser
    210                 215                 220

Tyr His Pro Glu Thr Gly Ala Val Lys Pro Trp Gln Ser Ala Tyr Thr
225                 230                 235                 240

Thr Ala Trp Thr Leu Ala Met Val His Gly Met Asp Pro Ala Phe Ala
                245                 250                 255

Glu Arg Tyr Tyr Pro Lys Phe Lys Glu Ser Phe Val Glu Val Tyr Asp
            260                 265                 270

Asp Gly Arg Lys Ala Arg Val Arg Glu Met Thr Gly Thr Thr Asp Thr
        275                 280                 285

Asp Gly Gly Val Gly Ala Ala Ser Ala Phe Met Leu Val Leu Ala Arg
    290                 295                 300

Glu Met Gly Asp Lys Gln Leu Phe Asp Gln Leu Leu Asn His Leu Glu
305                 310                 315                 320

Pro Pro Ala Gly Pro Thr Ile Thr Ser Gly Ile Leu His Tyr Ala Gln
                325                 330                 335

Pro Ser Asn Leu Leu Phe Asp Glu Leu Leu Phe Val Gly Lys Val His
            340                 345                 350

Val Gly Phe Ala Lys Leu Leu Asn Ala Pro Pro Ala Pro Ala Arg Pro
```

Ala Leu Gln Lys Lys Lys
    370

<210> SEQ ID NO 91
<211> LENGTH: 1206
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1206)
<223> OTHER INFORMATION: Native Nucleic acid encoding SEQ ID NO: 92,
      which is unprocessed and includes its signal peptide

<400> SEQUENCE: 91

```
atgaagaaca tccaaaaggc agctgccgcg ctgcccgcca tccttgccgc agtgctcgcg      60
ttcagtgcgc cggcccattc ggcggacctg ccgcccggcc gcctgcctc gaccgaggcc     120 tacttcgccc agcgcgaaag gcaggccgtc acgcccgacg tgatggccca cctcgcctac     180
atgaactaca ccgatttcgt ctcccccttc tacagccggg gctgcgcctt cgatgcatgg     240
accatcaaga agacgccgca gcggatcatc aagtactcgc tcgccttcta cgcctacggg     300
ctggccagcg tcgcgctcac cgatccgcag ctgcgtccgc tcgccggcca cgcgatcgac     360
atcgccaccc caagatgca atgcaagcag gtctggggag actgggagga agacgggttc     420
ggcgacgatc cgatcgagaa agagaacatc atgtacaagg ccacttgaa cctgatgtac     480 ggcctttacc agctggtcac cggcaaccgc cggtacgaga aggagcacgc ccgcctcacg     540
cggatcatcc acgacgagat caaggccaat ccctacgccg gcatcgtctg cgagccggac     600
aactatttcg tccagtgcaa ctcggtcgcc tacctgagcc tgtgggtcca tgaccgcctg     660
cacggcaccg actaccgggc ggcgacggcg gagtggctga aattcatcga gcacgacctg     720
atcgacccga aacacggcgc cttccacctg tcctaccatc cggaatccca cgcggtgaaa     780
ccgtgggtct ccgcatacac cacggcgtgg acgctcgcca tggtgcacgg catggatccc     840
gctttcgccg agcgctacta cccccgcttc aaggaaacct tcgtcgaggt ctacgacgat     900
ggccgcaagg cccgggtccg cgagacgacc ggcaccaccg acgccgatgg cggcgtcggc     960
gcggcctccg cgttcaccct gctgctcgcc cgtgagatgg cgaccggca gctcttcgac    1020 cagttgctga ccacctgga gccccggca agaccgcgga tcacctcggg catcctggaa    1080
tacgaggcgc ccagcaacct gctgttcgac gagttgctgt tcctcgccaa ggtgcacgtc    1140
ggtttcggcc agttgctgga ggccgggtcg gcgccacctc ggccgggccc caccggggg    1200 aaatga                                                              1206
```

<210> SEQ ID NO 92
<211> LENGTH: 401
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(401)
<223> OTHER INFORMATION: Native, or unprocessed, LinD enzyme GNM 10094,
      including signal peptide

<400> SEQUENCE: 92

Met Lys Asn Ile Gln Lys Ala Ala Ala Ala Leu Pro Ala Ile Leu Ala
1               5                   10                  15

Ala Val Leu Ala Phe Ser Ala Pro Ala His Ser Ala Asp Leu Pro Pro
            20                  25                  30

Gly Arg Leu Ala Ser Thr Glu Ala Tyr Phe Ala Gln Arg Glu Arg Gln
        35                  40                  45

Ala Val Thr Pro Asp Val Met Ala His Leu Ala Tyr Met Asn Tyr Thr
50                  55                  60

Asp Phe Val Ser Pro Phe Tyr Ser Arg Gly Cys Ala Phe Asp Ala Trp
65                  70                  75                  80

Thr Ile Lys Lys Thr Pro Gln Arg Ile Ile Lys Tyr Ser Leu Ala Phe
                85                  90                  95

Tyr Ala Tyr Gly Leu Ala Ser Val Ala Leu Thr Asp Pro Gln Leu Arg
            100                 105                 110

Pro Leu Ala Gly His Ala Ile Asp Ile Ala Thr Ala Lys Met Gln Cys
        115                 120                 125

Lys Gln Val Trp Gly Asp Trp Glu Glu Asp Gly Phe Gly Asp Asp Pro
130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Asn Arg Arg Tyr Glu Lys Glu His
                165                 170                 175

Ala Arg Leu Thr Arg Ile Ile His Asp Glu Ile Lys Ala Asn Pro Tyr
            180                 185                 190

Ala Gly Ile Val Cys Glu Pro Asp Asn Tyr Phe Val Gln Cys Asn Ser
        195                 200                 205

Val Ala Tyr Leu Ser Leu Trp Val His Asp Arg Leu His Gly Thr Asp
210                 215                 220

Tyr Arg Ala Ala Thr Ala Glu Trp Leu Lys Phe Ile Glu His Asp Leu
225                 230                 235                 240

Ile Asp Pro Lys His Gly Ala Phe His Leu Ser Tyr His Pro Glu Ser
                245                 250                 255

His Ala Val Lys Pro Trp Val Ser Ala Tyr Thr Thr Ala Trp Thr Leu
            260                 265                 270

Ala Met Val His Gly Met Asp Pro Ala Phe Ala Glu Arg Tyr Tyr Pro
        275                 280                 285

Arg Phe Lys Glu Thr Phe Val Glu Val Tyr Asp Asp Gly Arg Lys Ala
290                 295                 300

Arg Val Arg Glu Thr Thr Gly Thr Thr Asp Ala Asp Gly Val Gly
305                 310                 315                 320

Ala Ala Ser Ala Phe Thr Leu Leu Leu Ala Arg Glu Met Gly Asp Arg
            325                 330                 335

Gln Leu Phe Asp Gln Leu Leu Asn His Leu Glu Pro Pro Ala Arg Pro
        340                 345                 350

Arg Ile Thr Ser Gly Ile Leu Glu Tyr Glu Ala Pro Ser Asn Leu Leu
355                 360                 365

Phe Asp Glu Leu Leu Phe Leu Ala Lys Val His Val Gly Phe Gly Gln
370                 375                 380

Leu Leu Glu Ala Gly Ser Ala Pro Pro Arg Pro Gly Pro Thr Gly Gly
385                 390                 395                 400

Lys

<210> SEQ ID NO 93
<211> LENGTH: 81
<212> TYPE: DNA

<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(81)
<223> OTHER INFORMATION: Nucleic acid encoding GNM 10094 signal peptide

<400> SEQUENCE: 93

| | | | | | |
|---|---|---|---|---|---|
| atgaagaaca | tccaaaaggc | agctgccgcg | ctgcccgcca | tccttgccgc | agtgctcgcg | 60 |
| ttcagtgcgc | cggcccattc | g | | | | 81 |

<210> SEQ ID NO 94
<211> LENGTH: 27
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(27)
<223> OTHER INFORMATION: GNM 10094 signal peptide

<400> SEQUENCE: 94

Met Lys Asn Ile Gln Lys Ala Ala Ala Ala Leu Pro Ala Ile Leu Ala
1               5                   10                  15

Ala Val Leu Ala Phe Ser Ala Pro Ala His Ser
            20                  25

<210> SEQ ID NO 95
<211> LENGTH: 1125
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1125)
<223> OTHER INFORMATION: Nucleic acid encoding Processed (mature) GNM
      10094 LinD enzyme, no signal peptide

<400> SEQUENCE: 95

| | | | | | |
|---|---|---|---|---|---|
| gcggacctgc | cgcccggccg | cctcgcctcg | accgaggcct | acttcgccca | gcgcgaaagg | 60 |
| caggccgtca | cgcccgacgt | gatggcccac | ctcgcctaca | tgaactacac | cgatttcgtc | 120 |
| tccccttct | acagccgggg | ctgcgccttc | gatgcatgga | ccatcaagaa | gacgccgcag | 180 |
| cggatcatca | agtactcgct | cgccttctac | gcctacgggc | tggccagcgt | cgcgctcacc | 240 |
| gatccgcagc | tgcgtccgct | cgccggccac | gcgatcgaca | tcgccaccgc | caagatgcaa | 300 |
| tgcaagcagg | tctggggaga | ctgggaggaa | gacgggttcg | gcgacgatcc | gatcgagaaa | 360 |
| gagaacatca | tgtacaaggg | ccacttgaac | ctgatgtacg | gcctttacca | gctggtcacc | 420 |
| ggcaaccgcc | ggtacgagaa | ggagcacgcc | cgcctcacgc | ggatcatcca | gacgagatc | 480 |
| aaggccaatc | cctacgccgg | catcgtctgc | gagccggaca | actatttcgt | ccagtgcaac | 540 |
| tcggtcgcct | acctgagcct | gtgggtccat | gaccgcctgc | acggcaccga | ctaccgggcg | 600 |
| gcgacggcgg | agtggctgaa | attcatcgag | cacgacctga | tcgacccgaa | acacggcgcc | 660 |
| ttccacctgt | cctaccatcc | ggaatcccac | gcggtgaaac | cgtgggtctc | cgcatacacc | 720 |
| acggcgtgga | cgctcgccat | ggtgcacggc | atggatcccg | ctttcgccga | gcgctactac | 780 |
| ccccgcttca | aggaaacctt | cgtcgaggtc | tacgacgatg | ccgcaaggc | ccgggtccgc | 840 |
| gagacgaccg | gcaccaccga | cgccgatggc | ggcgtcggcg | cggcctccgc | gttcaccctg | 900 |

-continued

```
ctgctcgccc gtgagatggg cgaccggcag ctcttcgacc agttgctgaa ccacctggag      960
ccccgggcaa gaccgcggat cacctcgggc atcctggaat acgaggcgcc cagcaacctg     1020
ctgttcgacg agttgctgtt cctcgccaag gtgcacgtcg gtttcggcca gttgctggag     1080
gccgggtcgg cgccacctcg gccgggcccc accgggggga aatga                    1125
```

<210> SEQ ID NO 96
<211> LENGTH: 374
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(374)
<223> OTHER INFORMATION: Processed (mature) GNM 10094 LinD enzyme, no
      signal peptide.

<400> SEQUENCE: 96

```
Ala Asp Leu Pro Pro Gly Arg Leu Ala Ser Thr Glu Ala Tyr Phe Ala
1               5                   10                  15

Gln Arg Glu Arg Gln Ala Val Thr Pro Asp Val Met Ala His Leu Ala
            20                  25                  30

Tyr Met Asn Tyr Thr Asp Phe Val Ser Pro Phe Tyr Ser Arg Gly Cys
        35                  40                  45

Ala Phe Asp Ala Trp Thr Ile Lys Lys Thr Pro Gln Arg Ile Ile Lys
    50                  55                  60

Tyr Ser Leu Ala Phe Tyr Ala Tyr Gly Leu Ala Ser Val Ala Leu Thr
65                  70                  75                  80

Asp Pro Gln Leu Arg Pro Leu Ala Gly His Ala Ile Asp Ile Ala Thr
                85                  90                  95

Ala Lys Met Gln Cys Lys Gln Val Trp Gly Asp Trp Glu Glu Asp Gly
            100                 105                 110

Phe Gly Asp Asp Pro Ile Glu Lys Glu Asn Ile Met Tyr Lys Gly His
        115                 120                 125

Leu Asn Leu Met Tyr Gly Leu Tyr Gln Leu Val Thr Gly Asn Arg Arg
    130                 135                 140

Tyr Glu Lys Glu His Ala Arg Leu Thr Arg Ile Ile His Asp Glu Ile
145                 150                 155                 160

Lys Ala Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val His Asp Arg
            180                 185                 190

Leu His Gly Thr Asp Tyr Arg Ala Ala Thr Ala Glu Trp Leu Lys Phe
        195                 200                 205

Ile Glu His Asp Leu Ile Asp Pro Lys His Gly Ala Phe His Leu Ser
    210                 215                 220

Tyr His Pro Glu Ser His Ala Val Lys Pro Trp Val Ser Ala Tyr Thr
225                 230                 235                 240

Thr Ala Trp Thr Leu Ala Met Val His Gly Met Asp Pro Ala Phe Ala
                245                 250                 255

Glu Arg Tyr Tyr Pro Arg Phe Lys Glu Thr Phe Val Glu Val Tyr Asp
            260                 265                 270

Asp Gly Arg Lys Ala Arg Val Arg Glu Thr Thr Gly Thr Thr Asp Ala
        275                 280                 285

Asp Gly Gly Val Gly Ala Ala Ser Ala Phe Thr Leu Leu Leu Ala Arg
    290                 295                 300
```

Glu Met Gly Asp Arg Gln Leu Phe Asp Gln Leu Leu Asn His Leu Glu
305                 310                 315                 320

Pro Pro Ala Arg Pro Arg Ile Thr Ser Gly Ile Leu Glu Tyr Glu Ala
            325                 330                 335

Pro Ser Asn Leu Leu Phe Asp Glu Leu Leu Phe Leu Ala Lys Val His
        340                 345                 350

Val Gly Phe Gly Gln Leu Leu Glu Ala Gly Ser Ala Pro Pro Arg Pro
        355                 360                 365

Gly Pro Thr Gly Gly Lys
        370

```
<210> SEQ ID NO 97
<211> LENGTH: 1203
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1203)
<223> OTHER INFORMATION: Native Nucleic acid encoding SEQ ID NO: 98,
      which is unprocessed and includes its signal peptide

<400> SEQUENCE: 97
atgaaaaaat tccgcccctt cgcgccgctg gctgccgcgc tcgccggcct gatcgcctgc      60
gccacgccgg ccgctgcggc cgagctgatg cccggccgcc tggcctcgac cgaggattac     120
ttcgcccagc gcgaaaagca ggcgctgacg cccgacgtca tggcccacct gcgctacatg     180
aactacaccg atttcatttc gccgttctac agccggggct gcgccttcga tgcctgggcg     240
atgaagaaga cgcccaaccg catcatcaag tattcgctcg cctggtacgc ctacggcctg     300
gccagcgtcg cccagaccga tccggccatg cgccaggtgg ccggccacgc gatcgacatc     360
gcgaccgcca agatgcactg caagcaggtc tggggcgact gggaggaaga ccagttcggc     420
agcgacccga tcatccggga aaacgtcatg tacaagggtc acctgaacct gatgtacggg     480
ctttaccaga tggtgaccgg cgaccgcaag tacgagaagg aaaacgccag gctcaccaaa     540
atcatggcca gggagatcaa ggccaacccc tacgccggca tcgtctgcga accggacaac     600
tacttcgtgc aatgcaattc ggtcgcctac ctgagcctgt gggtctatga ccgcctgcac     660
ggcacccatt acaaggcgct gaccaaggac tggctgaagt tcatcgagga agaactgatc     720
gacccgaaga ccggcagctt ctatctctcc taccaccccg aatcgggcgc ggtgaagccg     780
tggcagtcgg cctacacgac cgcctgggcg ctggccatgg tgcacggcat ggacccggcc     840
ttctccgagc gctattaccc gaagttcaag gaaaacttcg tcgaggtcta tgacgacggc     900
cgcaaggcgc gcgtccgcga aacgaccggc acggcggata ccgacggcgg cgtcggcgca     960
gcctcggcgt tcacgctggt gctagcccgc gaaatgggcg accagaaact cttcgaccag    1020
ttgctgaacc atctcgaacc cccggccgga ccgaaaatca cctcgggcat cctgcattac    1080
gcgcagccga gcaacctgct gttcgacgaa ttgctgttcg tcggcaaagt gcatgtcggc    1140
ttcgccaatc tgctcaatgc gccgccggca ccggctcgcc cggtcctgca aagaagaaa     1200 tga                                                                  1203

<210> SEQ ID NO 98
<211> LENGTH: 400
<212> TYPE: PRT
<213> ORGANISM: Unknown
<220> FEATURE:
```

<223> OTHER INFORMATION: Linalool dehydratase (LinD) from unknown origin
<220> FEATURE:
<221> NAME/KEY: misc_feature
<222> LOCATION: (1)..(400)
<223> OTHER INFORMATION: Native, or unprocessed, LinD enzyme GNM 10097, including signal peptide

<400> SEQUENCE: 98

```
Met Lys Lys Phe Arg Pro Phe Ala Pro Leu Ala Ala Ala Leu Ala Gly
1               5                   10                  15

Leu Ile Ala Cys Ala Thr Pro Ala Ala Ala Glu Leu Met Pro Gly
            20                  25                  30

Arg Leu Ala Ser Thr Glu Asp Tyr Phe Ala Gln Arg Glu Lys Gln Ala
            35                  40                  45

Leu Thr Pro Asp Val Met Ala His Leu Arg Tyr Met Asn Tyr Thr Asp
        50                  55                  60

Phe Ile Ser Pro Phe Tyr Ser Arg Gly Cys Ala Phe Asp Ala Trp Ala
65                  70                  75                  80

Met Lys Lys Thr Pro Asn Arg Ile Ile Lys Tyr Ser Leu Ala Trp Tyr
                85                  90                  95

Ala Tyr Gly Leu Ala Ser Val Ala Gln Thr Asp Pro Ala Met Arg Gln
            100                 105                 110

Val Ala Gly His Ala Ile Asp Ile Ala Thr Ala Lys Met His Cys Lys
            115                 120                 125

Gln Val Trp Gly Asp Trp Glu Asp Gln Phe Gly Ser Asp Pro Ile
130                 135                 140

Ile Arg Glu Asn Val Met Tyr Lys Gly His Leu Asn Leu Met Tyr Gly
145                 150                 155                 160

Leu Tyr Gln Met Val Thr Gly Asp Arg Lys Tyr Glu Lys Glu Asn Ala
                165                 170                 175

Arg Leu Thr Lys Ile Met Ala Arg Glu Ile Lys Ala Asn Pro Tyr Ala
            180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr His Tyr
        210                 215                 220

Lys Ala Leu Thr Lys Asp Trp Leu Lys Phe Ile Glu Glu Leu Ile
225                 230                 235                 240

Asp Pro Lys Thr Gly Ser Phe Tyr Leu Ser Tyr His Pro Glu Ser Gly
                245                 250                 255

Ala Val Lys Pro Trp Gln Ser Ala Tyr Thr Thr Ala Trp Ala Leu Ala
            260                 265                 270

Met Val His Gly Met Asp Pro Ala Phe Ser Glu Arg Tyr Tyr Pro Lys
            275                 280                 285

Phe Lys Glu Asn Phe Val Glu Val Tyr Asp Asp Gly Arg Lys Ala Arg
        290                 295                 300

Val Arg Glu Thr Thr Gly Thr Ala Asp Thr Asp Gly Val Gly Ala
305                 310                 315                 320

Ala Ser Ala Phe Thr Leu Val Leu Ala Arg Glu Met Gly Asp Gln Lys
            325                 330                 335

Leu Phe Asp Gln Leu Leu Asn His Leu Glu Pro Ala Gly Pro Lys
            340                 345                 350

Ile Thr Ser Gly Ile Leu His Tyr Ala Gln Pro Ser Asn Leu Leu Phe
        355                 360                 365

Asp Glu Leu Leu Phe Val Gly Lys Val His Val Gly Phe Ala Asn Leu
```

Leu Asn Ala Pro Pro Ala Pro Ala Arg Pro Val Leu Gln Lys Lys Lys
          370                 375                 380
385                 390                 395                 400

<210> SEQ ID NO 99
<211> LENGTH: 78
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(78)
<223> OTHER INFORMATION: Nucleic acid encoding GNM 10097 signal peptide

<400> SEQUENCE: 99
atgaaaaaat tccgccccctt cgcgccgctg gctgccgcgc tcgccggcct gatcgcctgc    60
gccacgccgg ccgctgcg                                                   78

<210> SEQ ID NO 100
<211> LENGTH: 26
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(26)
<223> OTHER INFORMATION: GNM 10097 signal peptide

<400> SEQUENCE: 100

Met Lys Lys Phe Arg Pro Phe Ala Pro Leu Ala Ala Ala Leu Ala Gly
1               5                   10                  15

Leu Ile Ala Cys Ala Thr Pro Ala Ala Ala
            20                  25

<210> SEQ ID NO 101
<211> LENGTH: 1125
<212> TYPE: DNA
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(1125)
<223> OTHER INFORMATION: Nucleic acid encoding Processed (mature) GNM
      10097 LinD enzyme, no signal peptide

<400> SEQUENCE: 101
gccgagctga tgcccggccg cctggcctcg accgaggatt acttcgccca gcgcgaaaag    60
caggcgctga cgcccgacgt catggcccac ctgcgctaca tgaactacac cgatttcatt   120
tcgccgttct acagccgggg ctgcgccttc gatgcctggg cgatgaagaa gacgcccaac   180
cgcatcatca gtattcgcct cgcctggtac gcctacggcc tggccagcgt cgcccagacc   240
gatccggcca tgcgccaggt ggccggccac gcgatcgaca tcgcgaccgc caagatgcac   300
tgcaagcagg tctggggcga ctgggaggaa gaccagttcg gcagcgaccc gatcatccgg   360
gaaaacgtca tgtacaaggg tcacctgaac ctgatgtacg gctttacca gatggtgacc   420 ggcgaccgca agtacgagaa ggaaaacgcc aggctcacca aaatcatggc caggagatc   480 aaggccaacc cctacgccgg catcgtctgc gaaccggaca actacttcgt gcaatgcaat   540
tcggtcgcct acctgagcct gtgggtctat gaccgcctgc acggcaccca ttacaaggcg   600
ctgaccaagg actggctgaa gttcatcgag gaagaactga tcgacccgaa gaccggcagc   660

-continued

```
ttctatctct cctaccaccc cgaatcgggc gcggtgaagc cgtggcagtc ggcctacacg    720
accgcctggg cgctggccat ggtgcacggc atggacccgg ccttctccga gcgctattac    780
ccgaagttca aggaaaactt cgtcgaggtc tatgacgacg ccgcaaggc gcgcgtccgc     840 gaaacgaccg gcacggcgga taccgacggc ggcgtcggcg cagcctcggc gttcacgctg    900
gtgctagccc gcgaaatggg cgaccagaaa ctcttcgacc agttgctgaa ccatctcgaa    960
cccccggccg gaccgaaaat cacctcgggc atcctgcatt acgcgcagcc gagcaacctg   1020
ctgttcgacg aattgctgtt cgtcggcaaa gtgcatgtcg gcttcgccaa tctgctcaat   1080
gcgccgccgg caccggctcg cccggtcctg caaaagaaga aatga                  1125
```

<210> SEQ ID NO 102
<211> LENGTH: 374
<212> TYPE: PRT
<213> ORGANISM: Unknown
<220> FEATURE:
<223> OTHER INFORMATION: Linalool dehydratase (LinD) from unknown origin
<220> FEATURE:
<221> NAME/KEY: misc_feature
<222> LOCATION: (1)..(374)
<223> OTHER INFORMATION: Processed (mature) GNM 10097 LinD enzyme, no
      signal peptide.

<400> SEQUENCE: 102

```
Ala Glu Leu Met Pro Gly Arg Leu Ala Ser Thr Glu Asp Tyr Phe Ala
1               5                   10                  15

Gln Arg Glu Lys Gln Ala Leu Thr Pro Asp Val Met Ala His Leu Arg
            20                  25                  30

Tyr Met Asn Tyr Thr Asp Phe Ile Ser Pro Phe Tyr Ser Arg Gly Cys
        35                  40                  45

Ala Phe Asp Ala Trp Ala Met Lys Lys Thr Pro Asn Arg Ile Ile Lys
    50                  55                  60

Tyr Ser Leu Ala Trp Tyr Ala Tyr Gly Leu Ala Ser Val Ala Gln Thr
65                  70                  75                  80

Asp Pro Ala Met Arg Gln Val Ala Gly His Ala Ile Asp Ile Ala Thr
                85                  90                  95

Ala Lys Met His Cys Lys Gln Val Trp Gly Asp Trp Glu Glu Asp Gln
            100                 105                 110

Phe Gly Ser Asp Pro Ile Ile Arg Glu Asn Val Met Tyr Lys Gly His
        115                 120                 125

Leu Asn Leu Met Tyr Gly Leu Tyr Gln Met Val Thr Gly Asp Arg Lys
    130                 135                 140

Tyr Glu Lys Glu Asn Ala Arg Leu Thr Lys Ile Met Ala Arg Glu Ile
145                 150                 155                 160

Lys Ala Asn Pro Tyr Ala Gly Ile Val Cys Glu Pro Asp Asn Tyr Phe
                165                 170                 175

Val Gln Cys Asn Ser Val Ala Tyr Leu Ser Leu Trp Val Tyr Asp Arg
            180                 185                 190

Leu His Gly Thr His Tyr Lys Ala Leu Thr Lys Asp Trp Leu Lys Phe
        195                 200                 205

Ile Glu Glu Glu Leu Ile Asp Pro Lys Thr Gly Ser Phe Tyr Leu Ser
    210                 215                 220

Tyr His Pro Glu Ser Gly Ala Val Lys Pro Trp Gln Ser Ala Tyr Thr
225                 230                 235                 240

Thr Ala Trp Ala Leu Ala Met Val His Gly Met Asp Pro Ala Phe Ser
                245                 250                 255
```

```
Glu Arg Tyr Tyr Pro Lys Phe Lys Glu Asn Phe Val Glu Val Tyr Asp
            260                 265                 270

Asp Gly Arg Lys Ala Arg Val Arg Glu Thr Thr Gly Thr Ala Asp Thr
            275                 280                 285

Asp Gly Gly Val Gly Ala Ala Ser Ala Phe Thr Leu Val Leu Ala Arg
            290                 295                 300

Glu Met Gly Asp Gln Lys Leu Phe Asp Gln Leu Leu Asn His Leu Glu
305                 310                 315                 320

Pro Pro Ala Gly Pro Lys Ile Thr Ser Gly Ile Leu His Tyr Ala Gln
                325                 330                 335

Pro Ser Asn Leu Leu Phe Asp Glu Leu Leu Phe Val Gly Lys Val His
            340                 345                 350

Val Gly Phe Ala Asn Leu Leu Asn Ala Pro Ala Pro Ala Arg Pro
            355                 360                 365

Val Leu Gln Lys Lys Lys
    370

<210> SEQ ID NO 103
<211> LENGTH: 398
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(398)
<223> OTHER INFORMATION: a provisoed out cdLD-Botes protein  (which is
      SEQ ID NO:1 of USPN 9,220,742)

<400> SEQUENCE: 103

Met Met Arg Phe Thr Leu Lys Thr Thr Ala Ile Val Ser Ala Ala Ala
1               5                   10                  15

Leu Leu Ala Gly Phe Gly Pro Pro Arg Ala Ala Glu Leu Pro Pro
            20                  25                  30

Gly Arg Leu Ala Thr Thr Glu Asp Tyr Phe Ala Gln Gln Ala Lys Gln
            35                  40                  45

Ala Val Thr Pro Asp Val Met Ala Gln Leu Ala Tyr Met Asn Tyr Ile
    50                  55                  60

Asp Phe Ile Ser Pro Phe Tyr Ser Arg Gly Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Lys Leu Arg
            100                 105                 110

Ala Leu Ala Gly His Asp Leu Asp Ile Ala Val Ser Lys Met Lys Cys
            115                 120                 125

Lys Arg Val Trp Gly Asp Trp Glu Glu Asp Gly Phe Gly Thr Asp Pro
            130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Ser Arg Arg Tyr Glu Ala Glu His
                165                 170                 175

Ala His Leu Thr Arg Ile Ile His Asp Glu Ile Ala Ala Asn Pro Phe
            180                 185                 190

Ala Gly Ile Val Cys Glu Pro Asp Asn Tyr Phe Val Gln Cys Asn Ser
            195                 200                 205
```

```
Val Ala Tyr Leu Ser Leu Trp Val Tyr Asp Arg Leu His Gly Thr Asp
    210                 215                 220

Tyr Arg Ala Ala Thr Arg Ala Trp Leu Asp Phe Ile Gln Lys Asp Leu
225                 230                 235                 240

Ile Asp Pro Glu Arg Gly Ala Phe Tyr Leu Ser Tyr His Pro Glu Ser
                245                 250                 255

Gly Ala Val Lys Pro Trp Ile Ser Ala Tyr Thr Thr Ala Trp Thr Leu
                260                 265                 270

Ala Met Val His Gly Met Asp Pro Ala Phe Ser Glu Arg Tyr Tyr Pro
                275                 280                 285

Arg Phe Lys Gln Thr Phe Val Glu Val Tyr Asp Glu Gly Arg Lys Ala
290                 295                 300

Arg Val Arg Glu Thr Ala Gly Thr Asp Asp Ala Asp Gly Gly Val Gly
305                 310                 315                 320

Leu Ala Ser Ala Phe Thr Leu Leu Ala Arg Glu Met Gly Asp Gln
                325                 330                 335

Gln Leu Phe Asp Gln Leu Leu Asn His Leu Glu Pro Pro Ala Lys Pro
                340                 345                 350

Ser Ile Val Ser Ala Ser Leu Arg Tyr Glu His Pro Gly Ser Leu Leu
                355                 360                 365

Phe Asp Glu Leu Leu Phe Leu Ala Lys Val His Ala Gly Phe Gly Ala
370                 375                 380

Leu Leu Arg Met Pro Pro Ala Ala Lys Leu Ala Gly Lys
385                 390                 395
```

<210> SEQ ID NO 104
<211> LENGTH: 408
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(408)
<223> OTHER INFORMATION: a provisoed out cdLD-Botes protein (which is
      SEQ ID NO:4 of USPN 9,220,742)

<400> SEQUENCE: 104

```
Met Met Arg Phe Thr Leu Lys Thr Thr Ala Ile Val Ser Ala Ala Ala
1               5                   10                  15

Leu Leu Ala Gly Phe Gly Pro Pro Arg Ala Ala Glu Leu Pro Pro
                20                  25                  30

Gly Arg Leu Ala Thr Thr Glu Asp Tyr Phe Ala Gln Gln Ala Lys Gln
                35                  40                  45

Ala Val Thr Pro Asp Val Met Ala Gln Leu Ala Tyr Met Asn Tyr Ile
            50                  55                  60

Asp Phe Ile Ser Pro Phe Tyr Ser Arg Gly Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Lys Leu Arg
                100                 105                 110

Ala Leu Ala Gly His Asp Leu Asp Ile Ala Val Ser Lys Met Lys Cys
                115                 120                 125

Lys Arg Val Trp Gly Asp Trp Glu Glu Asp Gly Phe Gly Thr Asp Pro
130                 135                 140

Ile Glu Lys Glu Asn Ile Met Tyr Lys Gly His Leu Asn Leu Met Tyr
```

```
                145                 150                 155                 160
Gly Leu Tyr Gln Leu Val Thr Gly Ser Arg Arg Tyr Glu Ala Glu His
                165                 170                 175

Ala His Leu Thr Arg Ile Ile His Asp Glu Ile Ala Ala Asn Pro Phe
                180                 185                 190

Ala Gly Ile Val Cys Glu Pro Asp Asn Tyr Phe Val Gln Cys Asn Ser
                195                 200                 205

Val Ala Tyr Leu Ser Leu Trp Val Tyr Asp Arg Leu His Gly Thr Asp
            210                 215                 220

Tyr Arg Ala Ala Thr Arg Ala Trp Leu Asp Phe Ile Gln Lys Asp Leu
225                 230                 235                 240

Ile Asp Pro Glu Arg Gly Ala Phe Tyr Leu Ser Tyr His Pro Glu Ser
                245                 250                 255

Gly Ala Val Lys Pro Trp Ile Ser Ala Tyr Thr Thr Ala Trp Thr Leu
                260                 265                 270

Ala Met Val His Gly Met Asp Pro Ala Phe Ser Glu Arg Tyr Tyr Pro
            275                 280                 285

Arg Phe Lys Gln Thr Phe Val Glu Val Tyr Asp Glu Gly Arg Lys Ala
        290                 295                 300

Arg Val Arg Glu Thr Ala Gly Thr Asp Asp Ala Asp Gly Gly Val Gly
305                 310                 315                 320

Leu Ala Ser Ala Phe Thr Leu Leu Leu Ala Arg Glu Met Gly Asp Gln
                325                 330                 335

Gln Leu Phe Asp Gln Leu Leu Asn His Leu Glu Pro Pro Ala Lys Pro
                340                 345                 350

Ser Ile Val Ser Ala Ser Leu Arg Tyr Glu His Pro Gly Ser Leu Leu
            355                 360                 365

Phe Asp Glu Leu Leu Phe Leu Ala Lys Val His Ala Gly Phe Gly Ala
        370                 375                 380

Leu Leu Arg Met Pro Pro Ala Ala Lys Leu Ala Gly Lys Gly Ser
385                 390                 395                 400

Leu Glu His His His His His His
            405

<210> SEQ ID NO 105
<211> LENGTH: 382
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(382)
<223> OTHER INFORMATION: a provisoed out cdLD-Botes protein (which is
      SEQ ID NO:5 of USPN 9,220,742)

<400> SEQUENCE: 105

Met Ala Glu Leu Pro Pro Gly Arg Leu Ala Thr Thr Glu Asp Tyr Phe
1               5                   10                  15

Ala Gln Gln Ala Lys Gln Ala Val Thr Pro Asp Val Met Ala Gln Leu
                20                  25                  30

Ala Tyr Met Asn Tyr Ile Asp Phe Ile Ser Pro Phe Tyr Ser Arg Gly
            35                  40                  45

Cys Ser Phe Glu Ala Trp Glu Leu Lys His Thr Pro Gln Arg Val Ile
        50                  55                  60

Lys Tyr Ser Ile Ala Phe Tyr Ala Tyr Gly Leu Ala Ser Val Ala Leu
65                  70                  75                  80
```

Ile Asp Pro Lys Leu Arg Ala Leu Ala Gly His Asp Leu Asp Ile Ala
                85                  90                  95

Val Ser Lys Met Lys Cys Lys Arg Val Trp Gly Asp Trp Glu Glu Asp
            100                 105                 110

Gly Phe Gly Thr Asp Pro Ile Glu Lys Glu Asn Ile Met Tyr Lys Gly
        115                 120                 125

His Leu Asn Leu Met Tyr Gly Leu Tyr Gln Leu Val Thr Gly Ser Arg
    130                 135                 140

Arg Tyr Glu Ala Glu His Ala His Leu Thr Arg Ile Ile His Asp Glu
145                 150                 155                 160

Ile Ala Ala Asn Pro Phe Ala Gly Ile Val Cys Glu Pro Asp Asn Tyr
                165                 170                 175

Phe Val Gln Cys Asn Ser Val Ala Tyr Leu Ser Leu Trp Val Tyr Asp
            180                 185                 190

Arg Leu His Gly Thr Asp Tyr Arg Ala Ala Thr Arg Ala Trp Leu Asp
        195                 200                 205

Phe Ile Gln Lys Asp Leu Ile Asp Pro Glu Arg Gly Ala Phe Tyr Leu
    210                 215                 220

Ser Tyr His Pro Glu Ser Gly Ala Val Lys Pro Trp Ile Ser Ala Tyr
225                 230                 235                 240

Thr Thr Ala Trp Thr Leu Ala Met Val His Gly Met Asp Pro Ala Phe
                245                 250                 255

Ser Glu Arg Tyr Tyr Pro Arg Phe Lys Gln Thr Phe Val Glu Val Tyr
            260                 265                 270

Asp Glu Gly Arg Lys Ala Arg Val Arg Glu Thr Ala Gly Thr Asp Asp
        275                 280                 285

Ala Asp Gly Gly Val Gly Leu Ala Ser Ala Phe Thr Leu Leu Leu Ala
    290                 295                 300

Arg Glu Met Gly Asp Gln Gln Leu Phe Asp Gln Leu Leu Asn His Leu
305                 310                 315                 320

Glu Pro Pro Ala Lys Pro Ser Ile Val Ser Ala Ser Leu Arg Tyr Glu
                325                 330                 335

His Pro Gly Ser Leu Leu Phe Asp Glu Leu Leu Phe Leu Ala Lys Val
            340                 345                 350

His Ala Gly Phe Gly Ala Leu Leu Arg Met Pro Pro Ala Ala Lys
        355                 360                 365

Leu Ala Gly Lys Gly Ser Leu Glu His His His His His His
    370                 375                 380

<210> SEQ ID NO 106
<211> LENGTH: 397
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(397)
<223> OTHER INFORMATION: a provisoed out cdLD-Botes protein (which is
      SEQ ID NO:7 of USPN 9,220,742)

<400> SEQUENCE: 106

Met Arg Phe Thr Leu Lys Thr Thr Ala Ile Val Ser Ala Ala Leu
1               5                   10                  15

Leu Ala Gly Phe Gly Pro Pro Arg Ala Ala Glu Leu Pro Pro Gly
            20                  25                  30

```
Arg Leu Ala Thr Thr Glu Asp Tyr Phe Ala Gln Gln Ala Lys Gln Ala
             35                  40                  45

Val Thr Pro Asp Val Met Ala Gln Leu Ala Tyr Met Asn Tyr Ile Asp
 50                  55                  60

Phe Ile Ser Pro Phe Tyr Ser Arg Gly Cys Ser Phe Glu Ala Trp Glu
 65                  70                  75                  80

Leu Lys His Thr Pro Gln Arg Val Ile Lys Tyr Ser Ile Ala Phe Tyr
                 85                  90                  95

Ala Tyr Gly Leu Ala Ser Val Ala Leu Ile Asp Pro Lys Leu Arg Ala
                100                 105                 110

Leu Ala Gly His Asp Leu Asp Ile Ala Val Ser Lys Met Lys Cys Lys
            115                 120                 125

Arg Val Trp Gly Asp Trp Glu Asp Gly Phe Gly Thr Asp Pro Ile
            130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr Asp Tyr
            210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
            275                 280                 285

Phe Lys Gln Thr Phe Val Glu Val Tyr Asp Glu Gly Arg Lys Ala Arg
290                 295                 300

Val Arg Glu Thr Ala Gly Thr Asp Asp Ala Asp Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Lys Pro Ser
            340                 345                 350

Ile Val Ser Ala Ser Leu Arg Tyr Glu His Pro Gly Ser Leu Leu Phe
            355                 360                 365

Asp Glu Leu Leu Phe Leu Ala Lys Val His Ala Gly Phe Gly Ala Leu
370                 375                 380

Leu Arg Met Pro Pro Pro Ala Ala Lys Leu Ala Gly Lys
385                 390                 395

<210> SEQ ID NO 107
<211> LENGTH: 376
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(376)
```

<223> OTHER INFORMATION: a provisoed out cdLD-Botes protein (which is
      SEQ ID NO:8 of USPN 9,220,742)

<400> SEQUENCE: 107

Met Ala Glu Leu Pro Pro Gly Arg Leu Ala Thr Thr Glu Asp Tyr Phe
1               5                   10                  15

Ala Gln Gln Ala Lys Gln Ala Val Thr Pro Asp Val Met Ala Gln Leu
            20                  25                  30

Ala Tyr Met Asn Tyr Ile Asp Phe Ile Ser Pro Phe Tyr Ser Arg Gly
        35                  40                  45

Cys Ser Phe Glu Ala Trp Glu Leu Lys His Thr Pro Gln Arg Val Ile
    50                  55                  60

Lys Tyr Ser Ile Ala Phe Tyr Ala Tyr Gly Leu Ala Ser Val Ala Leu
65                  70                  75                  80

Ile Asp Pro Lys Leu Arg Ala Leu Ala Gly His Asp Leu Asp Ile Ala
                85                  90                  95

Val Ser Lys Met Lys Cys Lys Arg Val Trp Gly Asp Trp Glu Glu Asp
            100                 105                 110

Gly Phe Gly Thr Asp Pro Ile Glu Lys Glu Asn Ile Met Tyr Lys Gly
        115                 120                 125

His Leu Asn Leu Met Tyr Gly Leu Tyr Gln Leu Val Thr Gly Ser Arg
    130                 135                 140

Arg Tyr Glu Ala Glu His Ala His Leu Thr Arg Ile Ile His Asp Glu
145                 150                 155                 160

Ile Ala Ala Asn Pro Phe Ala Gly Ile Val Cys Glu Pro Asp Asn Tyr
                165                 170                 175

Phe Val Gln Cys Asn Ser Val Ala Tyr Leu Ser Leu Trp Val Tyr Asp
            180                 185                 190

Arg Leu His Gly Thr Asp Tyr Arg Ala Ala Thr Arg Ala Trp Leu Asp
        195                 200                 205

Phe Ile Gln Lys Asp Leu Ile Asp Pro Glu Arg Gly Ala Phe Tyr Leu
    210                 215                 220

Ser Tyr His Pro Glu Ser Gly Ala Val Lys Pro Trp Ile Ser Ala Tyr
225                 230                 235                 240

Thr Thr Ala Trp Thr Leu Ala Met Val His Gly Met Asp Pro Ala Phe
                245                 250                 255

Ser Glu Arg Tyr Tyr Pro Arg Phe Lys Gln Thr Phe Val Glu Val Tyr
            260                 265                 270

Asp Glu Gly Arg Lys Ala Arg Val Arg Glu Thr Ala Gly Thr Asp Asp
        275                 280                 285

Ala Asp Gly Gly Val Gly Leu Ala Ser Ala Phe Thr Leu Leu Leu Ala
    290                 295                 300

Arg Glu Met Gly Asp Gln Gln Leu Phe Asp Gln Leu Leu Asn His Leu
305                 310                 315                 320

Glu Pro Pro Ala Lys Pro Ser Ile Val Ser Ala Ser Leu Arg Tyr Glu
                325                 330                 335

His Pro Gly Ser Leu Leu Phe Asp Glu Leu Leu Phe Leu Ala Lys Val
            340                 345                 350

His Ala Gly Phe Gly Ala Leu Leu Arg Met Pro Pro Ala Ala Lys
        355                 360                 365

Leu Ala Gly Lys Gly Ser Leu Glu
    370                 375

<210> SEQ ID NO 108

```
<211> LENGTH: 398
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(398)
<223> OTHER INFORMATION: All Xaa are any amino acid consistent with the
      consensus sequence shown in figures 4 and 11

<400> SEQUENCE: 108
```

| | | | | | | | | | | | | | | | |
|---|---|---|---|---|---|---|---|---|---|---|---|---|---|---|---|
| Met | Arg | Phe | Thr | Leu | Lys | Thr | Xaa | Ala | Ile | Xaa | Ser | Xaa | Xaa | Ala | Ala |
| 1 | | | | 5 | | | | | 10 | | | | | 15 | |
| Leu | Leu | Xaa | Gly | Xaa | Gly | Xaa | Pro | Xaa | Xaa | Ala | Ala | Xaa | Leu | Pro | Xaa |
| | | | 20 | | | | | 25 | | | | | 30 | | |
| Gly | Arg | Leu | Ala | Xaa | Thr | Glu | Asp | Tyr | Phe | Ala | Gln | Gln | Ala | Lys | Gln |
| | | | 35 | | | | | 40 | | | | | 45 | | |
| Ala | Val | Thr | Pro | Asp | Val | Met | Ala | Gln | Leu | Ala | Tyr | Met | Asn | Tyr | Ile |
| | 50 | | | | | 55 | | | | | 60 | | | | |
| Asp | Phe | Ile | Ser | Pro | Phe | Tyr | Ser | Arg | Gly | Cys | Ser | Phe | Glu | Ala | Trp |
| 65 | | | | | 70 | | | | | 75 | | | | | 80 |
| Glu | Leu | Lys | His | Thr | Pro | Gln | Arg | Val | Ile | Lys | Tyr | Ser | Ile | Ala | Phe |
| | | | | 85 | | | | | 90 | | | | | 95 | |
| Tyr | Ala | Tyr | Gly | Leu | Ala | Ser | Val | Ala | Leu | Ile | Asp | Pro | Xaa | Leu | Arg |
| | | | 100 | | | | | 105 | | | | | 110 | | |
| Ala | Leu | Ala | Gly | His | Asp | Leu | Asp | Ile | Ala | Val | Ser | Lys | Met | Lys | Cys |
| | | | 115 | | | | | 120 | | | | | 125 | | |
| Lys | Arg | Val | Trp | Gly | Asp | Trp | Glu | Glu | Asp | Gly | Phe | Gly | Xaa | Asp | Pro |
| 130 | | | | | 135 | | | | | 140 | | | | | |
| Ile | Glu | Lys | Glu | Asn | Ile | Met | Tyr | Lys | Gly | His | Leu | Asn | Leu | Met | Tyr |
| 145 | | | | | 150 | | | | | 155 | | | | | 160 |
| Gly | Leu | Tyr | Gln | Leu | Val | Thr | Gly | Ser | Arg | Arg | Tyr | Glu | Ala | Glu | His |
| | | | | 165 | | | | | 170 | | | | | 175 | |
| Ala | His | Leu | Thr | Arg | Ile | Ile | His | Asp | Glu | Ile | Xaa | Ala | Asn | Pro | Phe |
| | | | 180 | | | | | 185 | | | | | 190 | | |
| Ala | Gly | Ile | Val | Cys | Glu | Pro | Asp | Asn | Tyr | Phe | Val | Gln | Cys | Asn | Ser |
| | | | 195 | | | | | 200 | | | | | 205 | | |
| Val | Ala | Tyr | Leu | Ser | Leu | Trp | Val | Tyr | Asp | Arg | Leu | His | Gly | Thr | Asp |
| | 210 | | | | | 215 | | | | | 220 | | | | |
| Tyr | Arg | Ala | Ala | Thr | Arg | Ala | Trp | Leu | Asp | Phe | Ile | Gln | Lys | Asp | Leu |
| 225 | | | | | 230 | | | | | 235 | | | | | 240 |
| Ile | Asp | Pro | Glu | Arg | Gly | Ala | Phe | Tyr | Leu | Ser | Tyr | His | Pro | Glu | Ser |
| | | | | 245 | | | | | 250 | | | | | 255 | |
| Gly | Ala | Val | Lys | Pro | Trp | Ile | Ser | Ala | Tyr | Thr | Thr | Ala | Trp | Thr | Leu |
| | | | 260 | | | | | 265 | | | | | 270 | | |
| Ala | Met | Val | His | Gly | Met | Asp | Pro | Ala | Phe | Ser | Glu | Arg | Tyr | Tyr | Pro |
| | | | 275 | | | | | 280 | | | | | 285 | | |
| Xaa | Phe | Lys | Xaa | Thr | Phe | Val | Glu | Val | Tyr | Asp | Xaa | Gly | Arg | Lys | Ala |
| | 290 | | | | | 295 | | | | | 300 | | | | |
| Arg | Val | Arg | Glu | Thr | Ala | Gly | Thr | Xaa | Asp | Ala | Asp | Gly | Gly | Val | Gly |
| 305 | | | | | 310 | | | | | 315 | | | | | 320 |
| Leu | Ala | Ser | Ala | Phe | Thr | Leu | Leu | Leu | Ala | Arg | Glu | Met | Gly | Asp | Gln |
| | | | | 325 | | | | | 330 | | | | | 335 | |
| Xaa | Leu | Phe | Asp | Gln | Leu | Leu | Asn | His | Leu | Glu | Pro | Pro | Ala | Xaa | Pro |
| | | | 340 | | | | | 345 | | | | | 350 | | |

```
Ser Ile Val Ser Ala Ser Leu Arg Tyr Glu His Pro Gly Ser Leu Leu
            355                 360                 365

Phe Asp Glu Leu Leu Phe Leu Ala Lys Val His Ala Gly Phe Gly Ala
        370                 375                 380

Leu Leu Xaa Met Pro Pro Ala Ala Lys Xaa Xaa Gly Lys
385             390                 395

<210> SEQ ID NO 109
<211> LENGTH: 398
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(398)
<223> OTHER INFORMATION: All Xaa are any amino acid consistent with the
      consensus sequence shown in Figure 5

<400> SEQUENCE: 109

Met Arg Phe Thr Leu Lys Thr Pro Ala Ile Ala Ser Ala Val Ala Ala
1               5                   10                  15

Leu Leu Xaa Gly Leu Gly Gln Pro Ala His Ala Ala Pro Leu Pro Leu
            20                  25                  30

Gly Arg Leu Ala Pro Thr Glu Asp Tyr Phe Ala Gln Gln Ala Lys Gln
        35                  40                  45

Ala Val Thr Pro Asp Val Met Ala Gln Leu Ala Tyr Met Asn Tyr Ile
    50                  55                  60

Asp Phe Ile Ser Pro Phe Xaa Ser Arg Xaa Cys Ser Phe Glu Ala Trp
65                  70                  75                  80

Glu Leu Lys His Thr Pro Gln Arg Val Ile Lys Tyr Ser Ile Ala Phe
                85                  90                  95

Tyr Ala Tyr Gly Leu Ala Ser Val Ala Leu Ile Asp Pro Asn Leu Arg
            100                 105                 110

Ala Leu Ala Gly His Asp Leu Asp Ile Ala Val Ser Lys Met Lys Cys
        115                 120                 125

Lys Arg Val Trp Xaa Asp Trp Glu Glu Asp Gly Phe Gly Asp Asp Pro
130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Ser Arg Xaa Tyr Glu Ala Glu His
                165                 170                 175

Ala His Leu Thr Arg Xaa Ile His Asp Glu Ile Gly Ala Asn Pro Phe
            180                 185                 190

Ala Gly Ile Xaa Cys Glu Pro Xaa Asn Tyr Phe Val Gln Cys Asn Ser
        195                 200                 205

Val Ala Tyr Leu Ser Leu Trp Val Tyr Asp Arg Leu His Gly Thr Asp
    210                 215                 220

Tyr Arg Ala Ala Thr Arg Ala Trp Leu Asp Phe Ile Gln Lys Asp Leu
225                 230                 235                 240

Ile Asp Pro Glu Arg Gly Ala Phe Tyr Leu Ser Tyr His Pro Glu Ser
                245                 250                 255

Gly Ala Val Lys Pro Trp Ile Ser Ala Tyr Thr Thr Ala Trp Thr Leu
            260                 265                 270

Ala Met Val His Gly Met Asp Pro Ala Phe Ser Glu Arg Tyr Tyr Pro
        275                 280                 285

Ala Phe Lys Lys Thr Phe Val Glu Val Tyr Asp Gly Gly Arg Lys Ala
```

-continued

```
                290                 295                 300
Arg Val Arg Glu Thr Ala Gly Thr Ala Asp Ala Asp Gly Gly Val Gly
305                 310                 315                 320

Leu Ala Ser Ala Xaa Thr Leu Leu Leu Ala Arg Glu Met Gly Asp Gln
                325                 330                 335

Thr Leu Phe Asp Gln Leu Leu Asn His Leu Glu Pro Pro Ala Gln Pro
                340                 345                 350

Ser Ile Val Ser Ala Ser Leu Arg Tyr Glu His Pro Xaa Ser Leu Xaa
                355                 360                 365

Phe Asp Glu Leu Leu Phe Leu Ala Lys Val His Ala Gly Phe Gly Ala
                370                 375                 380

Leu Leu Gln Met Pro Pro Ala Ala Lys Ser Gly Gly Lys
385                 390                 395

<210> SEQ ID NO 110
<211> LENGTH: 400
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(400)
<223> OTHER INFORMATION: All Xaa, except for those designated as being
      Leucine or Isoleucine, are any amino acid consistent with the
      consensus sequence shown in Fig. 12
<220> FEATURE:
<221> NAME/KEY: misc_feature
<222> LOCATION: (83)..(83)
<223> OTHER INFORMATION: Xaa is Leucine or Isoleucine
<220> FEATURE:
<221> NAME/KEY: misc_feature
<222> LOCATION: (95)..(95)
<223> OTHER INFORMATION: Xaa is Leucine or Isoleucine
<220> FEATURE:
<221> NAME/KEY: misc_feature
<222> LOCATION: (120)..(120)
<223> OTHER INFORMATION: Xaa is Leucine or Isoleucine
<220> FEATURE:
<221> NAME/KEY: misc_feature
<222> LOCATION: (237)..(237)
<223> OTHER INFORMATION: Xaa is Leucine or Isoleucine
<220> FEATURE:
<221> NAME/KEY: misc_feature
<222> LOCATION: (264)..(264)
<223> OTHER INFORMATION: Xaa is Leucine or Isoleucine

<400> SEQUENCE: 110

Met Xaa Xaa Xaa Xaa Xaa Xaa Xaa Ala Xaa Xaa Ser Xaa Xaa Xaa
1               5                   10                  15

Ala Xaa Xaa Xaa Gly Phe Gly Xaa Xaa Xaa Ala Xaa Xaa Leu Xaa
                20                  25                  30

Pro Gly Arg Leu Ala Thr Thr Xaa Asp Tyr Phe Ala Gln Xaa Xaa Lys
                35                  40                  45

Xaa Xaa Val Thr Pro Asp Val Met Ala Xaa Leu Ala Xaa Met Asn Tyr
                50                  55                  60

Xaa Asp Phe Ile Ser Pro Phe Tyr Ser Arg Gly Cys Xaa Phe Xaa Ala
65                  70                  75                  80

Trp Xaa Xaa Lys Xaa Thr Pro Gln Arg Xaa Ile Lys Tyr Ser Xaa Ala
                85                  90                  95

Phe Tyr Xaa Tyr Gly Leu Ala Ser Val Ala Leu Xaa Asp Pro Lys Leu
                100                 105                 110

Arg Xaa Leu Ala Xaa His Xaa Xaa Asp Xaa Ala Xaa Ser Lys Met Lys
                115                 120                 125
```

```
Cys Lys Arg Val Trp Xaa Asp Trp Glu Glu Asp Gly Phe Gly Xaa Asp
        130                 135                 140

Pro Ile Glu Lys Glx Asn Ile Met Tyr Lys Gly His Leu Asn Leu Met
145                 150                 155                 160

Tyr Gly Leu Tyr Gln Leu Val Xaa Gly Xaa Arg Xaa Tyr Glu Ala Glu
                165                 170                 175

His Xaa His Leu Thr Xaa Ile Ile His Asp Glu Ile Xaa Ala Asn Pro
            180                 185                 190

Phe Ala Gly Xaa Xaa Cys Glu Pro Asp Asn Tyr Phe Val Gln Cys Asn
        195                 200                 205

Ser Val Ala Tyr Leu Ser Leu Trp Val Tyr Asp Arg Leu His Gly Thr
    210                 215                 220

Xaa Tyr Xaa Ala Ala Thr Xaa Xaa Trp Leu Xaa Phe Xaa Xaa Lys Asp
225                 230                 235                 240

Leu Ile Asp Pro Xaa Xaa Gly Ala Phe Tyr Leu Ser Xaa His Pro Glu
                245                 250                 255

Ser Gly Xaa Val Lys Pro Trp Xaa Ser Ala Tyr Thr Ala Trp Thr
            260                 265                 270

Leu Ala Met Val His Gly Met Asp Pro Ala Phe Ser Glu Arg Tyr Tyr
            275                 280                 285

Pro Xaa Phe Lys Xaa Thr Phe Val Glu Val Tyr Asp Xaa Gly Arg Lys
    290                 295                 300

Ala Arg Val Arg Glu Thr Xaa Xaa Thr Xaa Asp Ala Asp Gly Gly Val
305                 310                 315                 320

Gly Xaa Ala Ser Ala Phe Thr Leu Leu Leu Ala Arg Glu Met Gly Asp
                325                 330                 335

Gln Xaa Leu Phe Asp Gln Leu Leu Asn His Leu Glu Pro Pro Ala Lys
                340                 345                 350

Pro Xaa Ile Xaa Ser Ala Xaa Leu Xaa Tyr Glu Xaa Pro Xaa Xaa Leu
    355                 360                 365

Leu Phe Asp Glu Leu Leu Phe Leu Xaa Lys Val His Xaa Gly Phe Gly
    370                 375                 380

Xaa Leu Leu Xaa Xaa Xaa Pro Pro Xaa Ala Xaa Xaa Xaa Xaa Xaa Lys
385                 390                 395                 400

<210> SEQ ID NO 111
<211> LENGTH: 397
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(397)
<223> OTHER INFORMATION: All Xaa are any amino acid consistent with the
      consensus sequence shown in Figure 13

<400> SEQUENCE: 111

Met Arg Phe Thr Leu Lys Thr Thr Ala Ile Val Ser Ala Ala Ala Leu
1               5                   10                  15

Leu Ala Gly Phe Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
        35                  40                  45

Val Thr Pro Asp Val Met Ala Gln Leu Ala Tyr Met Asn Tyr Ile Asp
    50                  55                  60
```

```
Phe Ile Ser Pro Phe Tyr Ser Arg Gly Cys Ser Phe Glu Ala Trp Glu
 65                  70                  75                  80

Leu Lys His Thr Pro Gln Arg Val Ile Lys Tyr Ser Ile Ala Phe Tyr
                 85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
        115                 120                 125

Arg Val Trp Gly Asp Trp Glu Asp Gly Phe Gly Thr Asp Pro Ile
    130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
                165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
        195                 200                 205

Ala Tyr Leu Ser Leu Trp Val Tyr Asp Arg Leu His Gly Thr Asp Tyr
    210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
                245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
        275                 280                 285

Phe Lys Gln Thr Phe Val Glu Xaa Tyr Asp Glu Gly Arg Lys Ala Arg
    290                 295                 300

Val Arg Glu Thr Ala Gly Thr Asp Asp Ala Asp Gly Gly Val Gly Leu
305                 310                 315                 320

Ala Ser Ala Phe Thr Leu Leu Leu Ala Arg Glu Met Gly Asp Gln Gln
                325                 330                 335

Leu Phe Asp Gln Leu Leu Asn His Leu Glu Pro Pro Ala Lys Pro Ser
            340                 345                 350

Ile Val Ser Ala Ser Leu Arg Tyr Glu His Pro Gly Ser Leu Leu Phe
        355                 360                 365

Asp Glu Leu Leu Phe Leu Ala Lys Val His Ala Gly Phe Gly Ala Leu
    370                 375                 380

Leu Xaa Met Pro Pro Ala Ala Lys Leu Ala Gly Lys
385                 390                 395

<210> SEQ ID NO 112
<211> LENGTH: 401
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(401)
<223> OTHER INFORMATION: All Xaa, except for those designated as being
      Leucine or Isoleucine, are any amino acid consistent with the
      consensus sequence shown in Fig. 14
<220> FEATURE:
<221> NAME/KEY: misc_feature
<222> LOCATION: (82)..(82)
```

```
<223> OTHER INFORMATION: Xaa is Leucine or Isoleucine
<220> FEATURE:
<221> NAME/KEY: misc_feature
<222> LOCATION: (94)..(94)
<223> OTHER INFORMATION: Xaa is Leucine or Isoleucine
<220> FEATURE:
<221> NAME/KEY: misc_feature
<222> LOCATION: (119)..(119)
<223> OTHER INFORMATION: Xaa is Leucine or Isoleucine

<400> SEQUENCE: 112

Met Xaa Xaa Xaa Xaa Lys Thr Xaa Ala Xaa Xaa Ala Xaa Xaa Ala
1               5                   10                  15

Xaa Xaa Xaa Xaa Phe Xaa Xaa Pro Xaa Xaa Xaa Ala Xaa Leu Pro Pro
            20                  25                  30

Gly Arg Leu Ala Xaa Thr Glu Xaa Tyr Phe Ala Gln Xaa Xaa Lys Gln
            35                  40                  45

Ala Val Thr Pro Asp Val Met Ala Xaa Leu Ala Tyr Met Asn Tyr Xaa
        50                  55                  60

Asp Phe Xaa Ser Pro Phe Tyr Ser Arg Gly Cys Xaa Phe Xaa Ala Trp
65                  70                  75                  80

Xaa Xaa Lys Xaa Thr Pro Gln Arg Xaa Ile Lys Tyr Ser Xaa Ala Phe
                85                  90                  95

Tyr Ala Tyr Gly Leu Ala Ser Val Ala Leu Xaa Asp Pro Xaa Leu Arg
            100                 105                 110

Xaa Leu Ala Gly His Xaa Xaa Asp Ile Ala Xaa Xaa Lys Met Lys Cys
            115                 120                 125

Lys Xaa Val Trp Gly Asp Trp Glu Glu Asp Gly Phe Gly Xaa Asp Pro
        130                 135                 140

Ile Glu Lys Glu Asn Ile Met Tyr Lys Gly His Leu Asn Leu Met Tyr
145                 150                 155                 160

Gly Leu Tyr Gln Leu Val Thr Gly Xaa Arg Arg Tyr Glu Xaa Glu His
                165                 170                 175

Ala Xaa Leu Thr Arg Ile Ile His Asp Glu Ile Xaa Ala Asn Pro Xaa
            180                 185                 190

Ala Gly Ile Val Cys Glu Pro Asp Asn Tyr Phe Val Gln Cys Asn Ser
            195                 200                 205

Val Ala Tyr Leu Ser Leu Trp Val Xaa Asp Arg Leu His Gly Thr Asp
        210                 215                 220

Tyr Arg Ala Ala Thr Xaa Xaa Trp Leu Xaa Phe Ile Glx Xaa Asp Leu
225                 230                 235                 240

Ile Asp Pro Xaa Xaa Gly Ala Phe Xaa Leu Ser Tyr His Pro Glu Ser
                245                 250                 255

Xaa Ala Val Lys Pro Trp Xaa Ser Ala Tyr Thr Thr Ala Trp Thr Leu
            260                 265                 270

Ala Met Val His Gly Met Asp Pro Ala Phe Xaa Glu Arg Tyr Tyr Pro
        275                 280                 285

Arg Phe Lys Glx Thr Phe Val Glu Val Tyr Asp Xaa Gly Arg Lys Ala
            290                 295                 300

Arg Val Arg Glu Thr Xaa Gly Thr Xaa Asp Ala Asp Gly Gly Val Gly
305                 310                 315                 320

Xaa Ala Ser Ala Phe Thr Leu Leu Leu Ala Arg Glu Met Gly Asp Xaa
                325                 330                 335

Gln Leu Phe Asp Gln Leu Leu Asn His Leu Glu Pro Pro Ala Xaa Pro
            340                 345                 350

Xaa Ile Xaa Ser Xaa Xaa Leu Xaa Tyr Xaa Xaa Pro Xaa Xaa Leu Leu
```

```
                355                 360                 365
Phe Asp Glu Leu Leu Phe Leu Ala Lys Val His Xaa Gly Phe Gly Xaa
    370                 375                 380

Leu Leu Xaa Xaa Xaa Xaa Pro Pro Pro Xaa Xaa Xaa Xaa Xaa Gly
385                 390                 395                 400

Lys

<210> SEQ ID NO 113
<211> LENGTH: 398
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(398)
<223> OTHER INFORMATION: All Xaa, except for those designated as being
      Leucine or Isoleucine, are any amino acid consistent with the
      consensus sequence shown in Figure 15
<220> FEATURE:
<221> NAME/KEY: misc_feature
<222> LOCATION: (10)..(10)
<223> OTHER INFORMATION: Xaa is Leucine or Isoleucine
<220> FEATURE:
<221> NAME/KEY: misc_feature
<222> LOCATION: (82)..(82)
<223> OTHER INFORMATION: Xaa is Leucine or Isoleucine
<220> FEATURE:
<221> NAME/KEY: misc_feature
<222> LOCATION: (94)..(94)
<223> OTHER INFORMATION: Xaa is Leucine or Isoleucine

<400> SEQUENCE: 113

Met Xaa Xaa Xaa Xaa Xaa Xaa Ala Xaa Xaa Xaa Ala Xaa Xaa Ala
1               5                   10                  15

Xaa Xaa Xaa Gly Xaa Gly Xaa Pro Xaa Xaa Ala Ala Glu Leu Xaa Pro
                20                  25                  30

Gly Arg Leu Ala Xaa Thr Glu Xaa Tyr Phe Ala Gln Xaa Xaa Xaa Gln
            35                  40                  45

Ala Val Thr Pro Asp Val Met Ala Xaa Leu Ala Tyr Met Asn Tyr Xaa
50                  55                  60

Asp Phe Xaa Ser Pro Phe Tyr Ser Arg Gly Cys Xaa Phe Xaa Ala Trp
65                  70                  75                  80

Xaa Xaa Lys Xaa Thr Pro Gln Arg Xaa Ile Lys Tyr Ser Xaa Ala Phe
                85                  90                  95

Tyr Ala Tyr Gly Leu Ala Ser Val Ala Leu Ile Asp Pro Xaa Leu Arg
            100                 105                 110

Xaa Leu Ala Gly His Xaa Leu Asp Ile Ala Xaa Xaa Lys Met Lys Cys
            115                 120                 125

Lys Xaa Val Trp Gly Asp Trp Glu Glu Asp Gly Phe Gly Xaa Asp Pro
    130                 135                 140

Ile Glu Lys Glu Asn Ile Met Tyr Lys Gly His Leu Asn Leu Met Tyr
145                 150                 155                 160

Gly Leu Xaa Gln Leu Val Thr Gly Xaa Arg Arg Tyr Glu Xaa Glu His
            165                 170                 175

Ala Xaa Leu Thr Xaa Ile Ile Xaa Asp Glu Ile Ala Ala Asn Pro Xaa
            180                 185                 190

Ala Gly Ile Val Cys Glu Pro Asp Asn Tyr Phe Val Gln Cys Asn Ser
        195                 200                 205

Val Ala Tyr Leu Ser Leu Trp Val Tyr Asp Arg Leu His Gly Thr Asx
        210                 215                 220
```

```
Xaa Arg Ala Ala Thr Xaa Ala Trp Leu Xaa Phe Ile Glx Xaa Asp Leu
225                 230                 235                 240

Ile Asp Pro Xaa Xaa Gly Xaa Phe Xaa Leu Ser Tyr His Pro Glu Ser
            245                 250                 255

Gly Ala Val Lys Pro Trp Xaa Ser Ala Tyr Thr Thr Ala Trp Thr Leu
                260                 265                 270

Ala Met Val His Gly Met Asp Pro Ala Phe Xaa Glu Arg Tyr Tyr Pro
        275                 280                 285

Arg Phe Lys Glx Thr Phe Val Glu Val Tyr Asp Xaa Gly Arg Lys Ala
        290                 295                 300

Arg Val Arg Glu Thr Xaa Gly Thr Xaa Asp Ala Asp Gly Gly Val Gly
305                 310                 315                 320

Xaa Ala Ser Ala Phe Thr Leu Leu Ala Arg Glu Met Gly Asp Gln
                325                 330                 335

Gln Leu Phe Asp Gln Leu Leu Asn His Leu Glu Pro Pro Ala Xaa Pro
                340                 345                 350

Xaa Ile Xaa Ser Xaa Xaa Leu Xaa Tyr Glu Xaa Pro Xaa Xaa Leu Leu
            355                 360                 365

Phe Asp Glu Leu Leu Phe Leu Ala Lys Val His Xaa Gly Phe Gly Xaa
        370                 375                 380

Leu Leu Xaa Xaa Xaa Pro Xaa Xaa Ala Xaa Xaa Xaa Xaa Lys
385                 390                 395

<210> SEQ ID NO 114
<211> LENGTH: 398
<212> TYPE: PRT
<213> ORGANISM: Artificial Sequence
<220> FEATURE:
<223> OTHER INFORMATION: Synthetic: consensus sequence
<220> FEATURE:
<221> NAME/KEY: misc_feature
<222> LOCATION: (1)..(398)
<223> OTHER INFORMATION: All Xaa, except for those designated as being
      Leucine or Isoleucine, are any amino acid consistent with the
      consensus sequence shown in Figure 16
<220> FEATURE:
<221> NAME/KEY: misc_feature
<222> LOCATION: (10)..(10)
<223> OTHER INFORMATION: Xaa is Leucine or Isoleucine
<220> FEATURE:
<221> NAME/KEY: misc_feature
<222> LOCATION: (17)..(17)
<223> OTHER INFORMATION: Xaa is Leucine or Isoleucine
<220> FEATURE:
<221> NAME/KEY: misc_feature
<222> LOCATION: (94)..(94)
<223> OTHER INFORMATION: Xaa is Leucine or Isoleucine
<220> FEATURE:
<221> NAME/KEY: misc_feature
<222> LOCATION: (119)..(119)
<223> OTHER INFORMATION: Xaa is Leucine or Isoleucine
<220> FEATURE:
<221> NAME/KEY: misc_feature
<222> LOCATION: (236)..(236)
<223> OTHER INFORMATION: Xaa is Leucine or Isoleucine
<220> FEATURE:
<221> NAME/KEY: misc_feature
<222> LOCATION: (386)..(386)
<223> OTHER INFORMATION: Xaa is Leucine or Isoleucine

<400> SEQUENCE: 114

Met Xaa Xaa Xaa Leu Xaa Thr Xaa Xaa Xaa Xaa Xaa Xaa Xaa Xaa Xaa
1               5                   10                  15

Xaa Xaa Xaa Xaa Pro Xaa Xaa Xaa Xaa Xaa Xaa Xaa Leu Xaa Pro
            20                  25                  30
```

```
Gly Arg Leu Ala Thr Thr Xaa Xaa Tyr Phe Xaa Gln Gln Xaa Xaa Gln
             35                  40                  45

Xaa Xaa Thr Pro Asp Xaa Xaa Ala Gln Leu Ala Tyr Met Xaa Tyr Xaa
 50                  55                  60

Asp Phe Ile Ser Pro Phe Tyr Ser Arg Gly Cys Xaa Phe Glu Ala Trp
 65                  70                  75                  80

Glu Leu Lys Xaa Xaa Pro Gln Arg Xaa Ile Lys Tyr Ser Xaa Ala Xaa
                 85                  90                  95

Tyr Xaa Tyr Gly Leu Ala Ser Val Ala Xaa Ile Asp Pro Xaa Leu Xaa
             100                 105                 110

Xaa Xaa Ala Gly His Asx Xaa Asp Ile Ala Xaa Xaa Lys Met Lys Cys
             115                 120                 125

Xaa Xaa Val Trp Gly Asp Trp Glu Glu Asp Gly Phe Gly Xaa Asx Pro
             130                 135                 140

Ile Xaa Xaa Glx Asn Ile Met Tyr Lys Gly His Leu Asn Leu Met Tyr
145                 150                 155                 160

Gly Leu Tyr Gln Leu Xaa Thr Gly Xaa Xaa Xaa Tyr Glu Xaa Glu Xaa
                 165                 170                 175

Xaa Xaa Leu Xaa Xaa Ile Ile Xaa Xaa Glu Ile Xaa Xaa Asn Pro Xaa
             180                 185                 190

Ala Gly Ile Xaa Cys Glu Pro Asp Asn Tyr Phe Xaa Gln Cys Asn Ser
             195                 200                 205

Val Ala Tyr Leu Ser Leu Trp Val Tyr Asp Arg Leu Xaa Xaa Thr Asp
             210                 215                 220

Tyr Xaa Ala Xaa Thr Xaa Xaa Trp Leu Asp Phe Xaa Gln Lys Xaa Leu
225                 230                 235                 240

Ile Asp Pro Glu Xaa Gly Xaa Phe Xaa Xaa Xaa Tyr His Pro Xaa Ser
                 245                 250                 255

Xaa Ala Val Lys Pro Trp Xaa Ser Ala Tyr Thr Thr Ala Trp Xaa Leu
             260                 265                 270

Xaa Met Xaa His Gly Xaa Asx Pro Xaa Phe Xaa Xaa Xaa Tyr Tyr Pro
             275                 280                 285

Xaa Phe Lys Gln Thr Phe Val Glu Val Xaa Asp Xaa Gly Xaa Lys Ala
             290                 295                 300

Arg Val Arg Glu Thr Ala Xaa Thr Xaa Asp Xaa Asp Gly Gly Val Gly
305                 310                 315                 320

Xaa Ala Ser Xaa Phe Thr Leu Xaa Leu Ala Arg Glu Met Xaa Asp Gln
             325                 330                 335

Glx Leu Phe Asp Gln Leu Leu Asn Xaa Leu Glu Pro Pro Ala Lys Pro
             340                 345                 350

Xaa Ile Xaa Ser Xaa Xaa Leu Arg Tyr Glu Xaa Pro Xaa Ser Leu Leu
             355                 360                 365

Phe Asp Glu Leu Leu Phe Xaa Ala Lys Val His Xaa Gly Phe Gly Xaa
             370                 375                 380

Leu Xaa Xaa Xaa Xaa Pro Xaa Xaa Xaa Xaa Ala Gly Lys
385                 390                 395
```

VINYLISOMERASE-DEHYDRATASES, ALKENOL DEHYDRATASES, LINALOOL DEHYDRATASES AND CROTYL ALCOHOL DEHYDRATASES AND METHODS FOR MAKING AND USING THEM

RELATED APPLICATIONS

This application is a national phase application claiming benefit of priority under 35 U.S.C. § 371 to International (PCT) Patent Application serial number PCT/US2016/034488, filed May 26, 2016, which claims the benefit of priority to U.S. Provisional Patent Application Ser. No. 62/168,787, filed May 30, 2015; U.S. Ser. No. 62/236,662, filed Oct. 2, 2015; and U.S. Ser. No. 62/314,531, filed Mar. 29, 2016. The aforementioned applications are expressly incorporated herein by reference in their entirety and for all purposes.

INCORPORATION BY REFERENCE OF SEQUENCE LISTING PROVIDED ELECTRONICALLY

This application is being filed electronically via EFS-Web and includes an electronically submitted sequence listing in .txt format. The .txt file contains a sequence listing entitled "2013-05-04 BIO-005 ST25.txt" created on May 4, 2013 and is 92,335 bytes in size. The sequence listing contained in this .txt file is part of the specification and is hereby incorporated by reference herein in its entirety.

TECHNICAL FIELD

This invention generally relates to enzymology and biosynthetic processes for the production of organic chemicals. Provided are non-natural or genetically engineered vinylisomerase-dehydratase enzymes, including alkenol dehydratases, linalool dehydratases and crotyl alcohol dehydratases, which may be bifunctional in that an enzyme as provided herein has both isomerase and dehydratase activity, but not necessary at the same level. Also provided are genetically engineered microbes containing such enzymes and their use in sustainable production of alkenols and alkenes.

BACKGROUND

Over 25 billion pounds of butadiene (BD, BDE), including 1,3-butadiene, are produced annually and are applied in the manufacture of polymers such as synthetic rubbers and ABS resins, and chemicals such as hexamethylenediamine and 1,4-butanediol. Butadiene is typically produced as a by-product of the steam cracking process for conversion of petroleum feedstocks such as naphtha, liquefied petroleum gas, ethane or natural gas to ethylene and other olefins. The ability to manufacture butadiene from alternative and/or renewable feedstocks represents a major advance in the quest for more sustainable chemical production processes. Butadiene can be produced renewably by fermentation of sugars or other feedstocks to produce diols, such as 1,4-butanediol or 1,3-butanediol, which are separated, purified, and then dehydrated to butadiene in a second step involving metal-based catalysis.

However, direct fermentative production of butadiene (or other dialkene) from renewable feedstocks obviates the need for chemical dehydration steps since butadiene gas (boiling point, or bp, is −4.4° C.) could be continuously emitted from the fermenter and readily collected, e.g. by condensation. The direct fermentative production process eliminates the need for fossil-based butadiene (or other dialkene) and would allow substantial savings in cost, energy, and harmful waste and emissions relative to petrochemically-derived butadiene.

Improved enzymes, microbial organisms and methods for effectively producing butadiene or a dialkene from cheap renewable feedstocks such as dextrose, molasses, sugar cane juice, and sugars derived from biomass sources, including agricultural and wood waste, as well as C1 feedstocks such as syngas, methanol and carbon dioxide, are needed.

SUMMARY

In alternative embodiments, provided are isolated, synthetic or recombinant nucleic acids (polynucleotides) comprising (a) a nucleic acid sequence having at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a nucleic acid sequence consisting of SEQ ID NO: 11, 13, 14, 21, 36, 42, 48, 54, 60, 63, 65, 71, 73, 79, 85, 91 or 97 (encoding full length enzyme) or SEQ ID NO: 15, 17, 18, 40, 46, 52, 58, 69, 77, 83, 89, 95 or 101 (encoding processed mature enzyme),
or its complementary sequence,
with the proviso that the nucleic acid sequence does not encode a "LDRV" or a "cdLD-Botes" protein with or without its signal peptide, or any periplasmic sequence, or a polypeptide having a sequence as set forth in SEQ ID NO:2, SEQ ID NO:6 or SEQ ID NO:10 with or without its signal peptide, or
a nucleic acid sequence having at least 95%, 96%, 97%, 98%, 99% or 100% sequence identity to a nucleic acid sequence consisting of SEQ ID NO: 11, 13, 14, 21, 36, 42, 48, 54, 60, 63, 65, 71, 73, 79, 85, 91 or 97 (encoding full length enzyme) or SEQ ID NO: 15, 17, 18, 40, 46, 52, 58, 69, 77, 83, 89, 95 or 101 (encoding processed mature enzyme),
or its complementary sequence;
(b) a nucleic acid (polynucleotide) sequence that hybridizes under stringent conditions to a nucleic acid comprising SEQ ID NO: 11, 13, 14, 21, 36, 42, 48, 54, 60, 63, 65, 71, 73, 79, 85, 91 or 97 (encoding full length enzyme) or SEQ ID NO: 15, 17, 18, 40, 46, 52, 58, 69, 77, 83, 89, 95 or 101 (encoding processed mature enzyme), and the stringent conditions comprise a wash step comprising a wash in 0.2×SSC at a temperature of about 65° C. for about 15 minutes,
or its complementary sequence,
with the proviso that the nucleic acid sequence does not encode a "LDRV" or a "cdLD-Botes" protein or a polypeptide having a sequence as set forth in SEQ ID NO:2, SEQ ID NO:6 or SEQ ID NO:10 with or without its signal peptide;
(c) a nucleic that encodes a polypeptide having a sequence as set forth in SEQ ID NO: 12, 22, 37, 43, 49, 55, 61, 62, 64, 66, 72, 74, 80, 86, 92 or 98 (ful length enzyme) or SEQ ID NO: 16, 41, 47, 53, 59, 70, 78, 84, 90, 96 or 102 (processed mature enzyme), or an enzymatically active fragment thereof, or a complementary sequence of the encoding nucleic acid;

(d) the nucleic acid of (c), encoding a polypeptide having at least one conservative amino acid substitution, or a complementary sequence of the encoding nucleic acid;

(e) a nucleic that encodes a polypeptide having a sequence as set forth in SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102, or an enzymatically active fragment thereof, that has at least one, two, 3, 4, 5, 6, 7, 8, 9, 10, 11 or 12 amino acid substitutions selected from the group consisting of: V19I, L21L, Y71F, G74S, G133M, R171K, I182L, V196F, D200N, F325S, G365S and L368F (numbering with reference to SEQ ID NO:12) or the same substitution at a corresponding position identified by alignment to SEQ ID NO:12;

(f) the nucleic acid of (e), encoding a polypeptide having at least one conservative amino acid substitution, or a complementary sequence of the encoding nucleic acid;

(g) a nucleic that encodes a polypeptide having a sequence as set forth in SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102, or an enzymatically active fragment thereof, that has at least one, two, 3, 4, 5, 6, 7, 8, 9, 10, 11 or 12 amino acid substitutions selected from the group consisting of: an amino acid substitution made to SEQ ID NO:2 as found in an "LDRV" protein (numbering with reference to SEQ ID NO:2) or the same substitution at a corresponding position identified by alignment to SEQ ID NO:2, (h) the nucleic acid of (g), encoding a polypeptide having at least one conservative amino acid substitution, or a complementary sequence of the encoding nucleic acid or (i) a nucleic that encodes a polypeptide capable of generating an antibody that binds specifically to a polypeptide having the sequence of SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102, or its complementary sequence;

wherein the nucleic acid of any of (a) to (i) encodes a polypeptide:
(1) having a linalool dehydratase-isomerase (LinD) activity,
(2) having a vinylisomerase activity,
(3) having a dehydratase activity, optionally an alkenol dehydratase activity,
(4) able to enzymatically catalyze the conversion of a crotyl alcohol (but-2-en-1-ol) to a 3-buten-2-ol,
(5) able to enzymatically catalyze the conversion of a 3-buten-2-ol to a butadiene or a 1,3 butadiene,
(6) able to enzymatically catalyze the conversion of a crotyl alcohol (but-2-en-1-ol) to a butadiene or a 1,3 butadiene,
(7) able to enzymatically catalyze the conversion of a 2,3-dimethyl-but-2-en-1-ol into dimethyl-butadiene,
(8) catalyzing the conversion of a compound corresponding to the general formula $C_nH_{2n}O$ into $C_nH_{2n-2}+H_2O$ with $3<n<7$,
wherein optionally the compound corresponding to the general formula $CnH_{2n}O$ with $3<n<7$ is a crotyl alcohol, a but-3-en-2-ol or a but-3-en-1-ol, and/or the compound corresponding to the general formula $C_nH_{2n-2}$ with $3<n<7$ is a 1,3 butadiene; and optionally the compound corresponding to the general formula $C_nH_{2n}O$ with $3<n<7$ is a 2,3-dimethyl-but-2-en-1-ol, a 2,3-dimethyl-but-3-en-2-ol or a 2,3-dimethyl-but-3-en-1-ol, and/or the compound corresponding to the general formula $C_nH_{2n-2}$ with $3<n<7$ is a dimethylbutadiene; or (9) any combination of (1) to (8).

In alternative embodiments, nucleic acids provided herein (a) further comprise a nucleic acid sequence encoding a polypeptide or peptide comprising (or having) or consisting of: a signal sequence, a periplasmic targeting sequence (PTS) or periplasmic signal sequence (PSS) or a polypeptide or peptide having a PTS or PSS activity; or, a eukaryotic signal sequence; or (b) comprises nucleic acid sequence SEQ ID NO: 11, 13, 14, 21, 36, 42, 48, 54, 60, 63, 65, 71, 73, 79, 85, 91 or 97 or SEQ ID NO: 15, 17, 18, 40, 46, 52, 58, 69, 77, 83, 89, 95 or 101.

In alternative embodiments, nucleic acids provided herein further comprise a coding sequence (or a codon) encoding an N-terminal methionine.

In alternative embodiments, for nucleic acids provided herein:
(a) the nucleic acid sequence has at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a nucleic acid sequence consisting of SEQ ID NO: 11, 13, 14, 21, 36, 42, 48, 54, 60, 63, 65, 71, 73, 79, 85, 91 or 97,
or its complementary sequence,
with the proviso that the nucleic acid sequence does not encode a "LDRV" or a "cdLD-Botes" protein or a polypeptide having a sequence as set forth in SEQ ID NO:2, SEQ ID NO:6 or SEQ ID NO:10 with or without its signal peptide, or
a nucleic acid sequence having at least 95%, 96%, 97%, 98%, 99% or 100% sequence identity to a nucleic acid sequence consisting of SEQ ID NO: 11, 13, 14, 21, 36, 42, 48, 54, 60, 63, 65, 71, 73, 79, 85, 91 or 97;
or its complementary sequence;
(b) a nucleic acid (polynucleotide) sequence that hybridizes under stringent conditions to a nucleic acid comprising SEQ ID NO: 11, 13, 14, 21, 36, 42, 48, 54, 60, 63, 65, 71, 73, 79, 85, 91 or 97, and the stringent conditions comprise a wash step comprising a wash in 0.2×SSC at a temperature of about 65° C. for about 15 minutes,
or its complementary sequence,
with the proviso that the nucleic acid sequence does not encode a "LDRV" or a "cdLD-Botes" protein or a polypeptide, including a protein having a sequence as set forth in SEQ ID NO:2, SEQ ID NO:6 or SEQ ID NO:10 with or without its signal peptide.

In alternative embodiments, the periplasmic targeting sequence (PTS) or periplasmic signal sequence (PSS) is: a post-translational SecB-targeting pathway PTS or PSS; a co-translational signal recognition particle (SRP)-targeting pathway PTS or PSS; or, a twin-arginine translocation (TAT) Sec independent system PTS or PSS. In alternative embodiments, the periplasmic targeting sequence (PTS) or periplasmic signal sequence (PSS) comprises or consists of:
(a) an amino acid sequence as set forth in SEQ ID NO:8;
(b) an amino acid sequence as set forth in SEQ ID NO: 20, 39, 45, 51, 57, 68, 76, 82, 88, 94 or 100;
(c) SEQ ID NO:25 [Lam B signal sequence, or LamBss], and optionally the encoded polypeptide comprises SEQ ID NO:24;
(d) SEQ ID NO:26 [MalE signal sequence, or MalEss];
(e) SEQ ID NO:36 [FhuD signal sequence, or FhuDss];

(f) SEQ ID NO:27, SEQ ID NO:28, SEQ ID NO:29, SEQ ID NO:30, SEQ ID NO:31, SEQ ID NO:32, SEQ ID NO:33, or SEQ ID NO:34;
(g) an LamB ss, a MalE ss, a Mg1B ss, an OmpA ss, a PelB ss, a PhoA ss, a DsbA ss, an SfmC ss, a TolB ss, a TorT ss, a FhuD ss, a PelB ss, a YcdO ss, an MdoD ss, a Tor Ass or a YcdO ss; or
(h) a peptide encoded by a nucleic acid having about 90%, 91%, 92%, 93%, 94%, 95%, 96%, 97%, 98%, 99% or 100% sequence identity to SEQ ID NO: 7, or SEQ ID NO: 19, 38, 44, 50, 56, 67, 75, 81, 87, 93 or 99;
and optionally the polypeptide or peptide comprising or having the periplasmic targeting sequence (PTS), periplasmic signal sequence (PSS) or having a PTS or PSS activity is operably linked on the amino terminal of the polypeptide encoded by the isolated, synthetic or recombinant nucleic acid (polynucleotide) of claim 1, and optionally an amino terminal methionine is placed amino terminal to the polypeptide or peptide comprising or having the periplasmic targeting sequence (PTS), periplasmic signal sequence (PSS) or having a PTS or PSS activity. The eukaryotic signal sequence can be a yeast or a fungal signal sequence.

In alternative embodiments, a nucleic acid as provided herein further comprises: a nucleic acid encoding a polypeptide comprising a heterologous amino acid sequence, or a heterologous nucleotide sequence, and optionally the heterologous amino acid sequence comprises or functions as a tag or an epitope, and optionally the heterologous amino acid sequence comprises or functions as an N-terminal and/or C-terminal extension for targeting to an endoplasmic reticulum (ER) or endomembrane, or acting as a periplasmic targeting sequence periplasmic signal sequence or having a PTS or PSS activity.

In alternative embodiments, provided herein are expression cassettes, vectors or cloning vehicles comprising or having contained therein: (a) a nucleic acid sequence as provided herein; (b) the expression cassette, vector or cloning vehicle of (a) comprising, or inserted into, a viral vector, a plasmid, a phage, a phagemid, a cosmid, a fosmid, a bacteriophage or an artificial chromosome; (c) the expression cassette, vector or cloning vehicle of (b), wherein the viral vector comprises or is an adenovirus vector, a retroviral vector or an adeno-associated viral vector; or (d) the expression cassette, vector or cloning vehicle of (a), (b) or (c), comprising, or inserted into, a bacterial artificial chromosome (BAC), a plasmid, a bacteriophage P1-derived vector (PAC), a yeast artificial chromosome (YAC), or a mammalian artificial chromosome (MAC).

In alternative embodiments, provided herein are transformed or transduced cells (e.g., non-natural or engineered cells):
(a) comprising a nucleic acid as provided herein;
(b) comprising the expression cassette, a vector or a cloning vehicle as provided herein;
(c) the transformed or transduced cell of (a) or (b), wherein the cell is a bacterial cell, a mammalian cell, a fungal cell, a yeast cell, an insect cell or a plant cell;
(d) the transformed or transduced cell of (c), wherein wherein the cell is a methylotroph or a methanotroph, and optionally any species within the genera *Bacillus, Methylobacterium, Methyloversatilis, Methylococcus, Methylocystis* or *Hyphomicrobium*, optionally a *Bacillus methanolicus*, a *Methylobacterium extorquens* or a *Methylococcus capsulatis*;
(e) the transformed or transduced cell of (c), wherein the bacterial cell or fungal cell is any species within the genera *Aspergillus, Saccharomyces, Escherichia, Streptomyces, Salmonella, Pseudomonas, Castellaniella, Bacillus*, Cornyebacteria, or *Staphylococcus*;
(f) the transformed or transduced cell of (c), wherein the bacterial cell or fungal cell is an *Escherichia coli, Lactococcus lactis, Bacillus subtilis, Bacillus cereus, Bacillus licheniformis, Bacillus clausii, Castellaniella Defragrans, Salmonella typhimurium, Pseudomonas fluorescens, Klebsiella oxytoca, Anaerobiospirillum succiniciproducens, Actinobacillus succinogenes, Mannheimia succiniciproducens, Rhizobium etli, Corynebacterium glutamicum, Gluconobacter oxydans, Zymomonas mobilis, Lactococcus lactis, Lactobacillus plantarum, Streptomyces coelicolor, Clostridium acetobutylicum, Pseudomonas fluorescens*, a *Pseudomonas putida, Aspergillus niger, Aspergillus oryzae, Aspergillus nidulans*, or a *Saccharomyces cerevisiae*;
(g) the transformed or transduced cell of (c), wherein the yeast cell or fungal cell is any species selected from or within the:
genera Saccharomycetales, or the family Saccaromycetaceae, or the genera *Saccharomyces, Kluyveromyces, Pichia, Schizosaccharomyces, Schizochytrium, Rhodotorula, Thraustochytrium, Aspergillus, Kluyveromyces, Issatchenkia, Yarrowia*, Ogataea, Kuraishia, *Hansenula, Candida*, Ogataea, Kuraishia or Komagataella;
order Saccharomycetales, or the family Dipodascaceae, or the genus *Yarrowia*;
order Schizosaccharomycetales, or the family Schizosaccaromycetaceae, or the genus *Schizosaccharomyces*;
order Eurotiales, or the family Trichocomaceae, or the genus *Aspergillus*;
order Mucorales, or the family Mucoraceae, or the genus *Rhizopus*;
(h) the transformed or transduced cell of (c), wherein the yeast cell or fungal cell is any species selected from: *Saccharomyces cerevisiae, Schizosaccharomyces pombe, Kluyveromyces lactis, Kluyveromyces marxianus, Aspergillus terreus, Aspergillus niger, Pichia pastoris, Rhizopus arrhizus, Rhizopus oryzae, Yarrowia lipolytica, Issatchenkia orientalis, Hansenula polymorpha, Candida boidinii* or *Pichia methanolica*; or
(i) the transformed or transduced cell of (c), wherein the bacterial cell or fungal cell is any species selected from or within the:
order Enterobacteriales, or the family Enterobacteriaceae, or the genera *Escherichia* and *Klebsiella*;
order Aeromonadales, or the family Succinivibrionaceae, or the genus *Anaerobiospirillum*;
order Pasteurellales, or the family Pasteurellaceae, or the genera *Actinobacillus* and Mannheimia;
order Rhizobiales, or the family Bradyrhizobiaceae, or the genus *Rhizobium*;
order Bacillales, or the family Bacillaceae, or the genus *Bacillus*;
order Actinomycetales, or the families Corynebacteriaceae and Streptomycetaceae, or the genus *Corynebacterium* and the genus *Streptomyces*, respectively;
order Rhodospirillales, or the family Acetobacteraceae, or the genus *Gluconobacter*;
order Sphingomonadales, or the family Sphingomonadaceae, or the genus *Zymomonas*;

order Lactobacillales, or the families Lactobacillaceae and Streptococcaceae, or the genus *Lactobacillus* and the genus *Lactococcus*, respectively;

order Clostridiales, or the family Clostridiaceae, or the genus *Clostridium*; or order Pseudomonadales, or the family Pseudomonadaceae, or the genus *Pseudomonas*.

In alternative embodiments of the non-natural, engineered, transformed or transduced cells provided herein:

(a) the cell comprises a homologous or further comprises a heterologous crotyl alcohol dehydratase (CAD);

(b) the cell comprises a homologous or further comprises a heterologous CAD and a crotonaldehyde reductase (CAR) and/or a crotonyl-CoA reductase—alcohol forming (CCR—OH);

(c) the cell comprises a homologous or further comprises a heterologous CAD, CAR and/or a crotonyl-CoA reductase—aldehyde forming (CCR-ALD) and/or an a crotonate reductase (CTR);

(d) the cell comprises a homologous or further comprises a heterologous CAD, CAR, CCR and/or CTR, and a crotonyl-CoA hydrolase (CCH), crotonyl-CoA transferase (CCT) or crotonyl-CoA synthetase (CCS);

(e) the cell comprises a homologous or further comprises a heterologous CCR—OH and a CAD;

(f) the cell comprises a homologous or further comprises a heterologous 3-hydroxybutyryl-CoA dehydratase (HCD) or enoyl-CoA hydratase (ECH) and any combination of (a) to (e);

(g) the cell comprises a homologous or further comprises a heterologous acetoacetyl-CoA reductase ketone reducing (ACR-KET) and any combination of (a) to (f);

(h) the cell comprises a homologous or further comprises a heterologous acetyl-CoA carboxylase (AC-CAR), an acetoacetyl-CoA synthase (ACS) (optionally an ACS FhsA) and/or an acetyl-CoA:acetyl-CoA acyltransferase (ACAC-AT) (or an acetoacetyl-CoA thiolase or acetyl-CoA acetyltransferase), and any combination of (a) to (g);

(i) the cell comprises a homologous or further comprises a heterologous 3-oxoacyl-CoA synthase (OCS), and any combination of (a) to (h);

(j) the cell comprises a homologous or further comprises an enzyme for catalyzing the conversion of a 3-hydroxybutyryl-CoA to a crotonyl-CoA, or a 3-Hydroxybutyryl-CoA Dehydratase, a hydrolyase or a enoyl-CoA hydratase;

(k) the cell comprises a homologous or further comprises a heterologous oxidoreductase, an acyl-CoA reductase or an acylating aldehyde dehydrogenase to reduce an acyl-CoA to its corresponding aldehyde, or a fatty acyl-CoA reductase, a succinyl-CoA reductase, a butyryl-CoA reductase or a propionyl-CoA reductase; or (l) the cell comprises or further comprises one or more enzymes of FIG. 1 or FIG. 6;

and optionally produces an a di-alkene, where optionally the di-alkene is butadiene.

In alternative embodiments, provided are transgenic plants, plant cells or seeds: (a) comprising a sequence as provided herein, or the expression cassette, a vector or a cloning vehicle as provided herein, or a transformed cell as provided herein, wherein optionally the plant is a corn plant, a sorghum plant, a potato plant, a tomato plant, a wheat plant, an oilseed plant, a rapeseed plant, a soybean plant, a rice plant, a barley plant, a grass, a tobacco plant; or a forage and/or feed plant for an animal, or a ruminants, and optionally the forage or feed plant is hay, corn, millet, soy, wheat, buckwheat, barley, alfalfa, rye, an annual grass, sorghum, sudangrass, veldt grass or buffel grass, wherein optionally the plant cell or seed is a corn seed, a wheat kernel, an oilseed, a rapeseed, a soybean seed, a palm kernel, a sunflower seed, a sesame seed, a rice, a barley, a peanut or a tobacco plant seed; or a seed from any forage and/or feed plant for an animal or a ruminant, and optionally the forage or feed plant is hay, corn, millet, soy, wheat, buckwheat, barley, alfalfa, rye, an annual grass, sorghum, sudangrass, veldt grass or buffel grass.

In alternative embodiments, provided are isolated, synthetic or recombinant polypeptides encoded by a nucleic acid as provided herein.

In alternative embodiments, provided are isolated, synthetic or recombinant polypeptides:

(a) having an amino acid sequence at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102, with the proviso that polypeptide is not a "LDRV" or a "cdLD-Botes" protein or a polypeptide, or a protein having a sequence as set forth in SEQ ID NO:2, SEQ ID NO:6 or SEQ ID NO:10 with or without its signal peptide, or having an amino acid sequence at least 95%, 96%, 97%, 98%, 99% or 100% sequence identity to a polypeptide consisting of SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102;

(b) a polypeptide having a sequence as set forth in SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102, or an enzymatically active fragment thereof;

(c) the polypeptide of (b), having at least one conservative amino acid substitution;

(d) a polypeptide having a sequence as set forth in SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102, or an enzymatically active fragment thereof, that has at least one, two, 3, 4, 5, 6, 7, 8, 9, 10, 11 or 12 amino acid substitutions selected from the group consisting of: V19I, L21L, Y71F, G74S, G133M, R171K, I182L, V196F, D200N, F325S, G365S and L368F (numbering with reference to SEQ ID NO:12) or the same substitution at a corresponding position identified by alignment to SEQ ID NO:12;

(e) the polypeptide of (d), having at least one conservative amino acid substitution; or (f) a polypeptide having a sequence as set forth in SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102, or an enzymatically active fragment thereof, that has at least one, two, 3, 4, 5, 6, 7, 8, 9, 10, 11 or 12 amino acid substitutions selected from the group consisting of: an amino acid substitution made to SEQ ID NO:2 as found in an "LDRV" protein (numbering with reference to SEQ ID NO:2) or the same substitution at a corresponding position identified by alignment to SEQ ID NO:2;

(g) the polypeptide of (f), having at least one conservative amino acid substitution;

(h) a polypeptide capable of generating an antibody that binds specifically to a polypeptide having the sequence of SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102;

wherein the polypeptide of any of (a) to (h) comprises an activity:

(1) having a linalool dehydratase-isomerase (LinD) activity, (2) having a vinylisomerase activity, (3) having a dehydratase activity, optionally an alkenol dehydratase activity, (4) able to enzymatically catalyze the conversion of a crotyl alcohol (but-2-en-1-ol) to a 3-buten-2-ol, (5) able to enzymatically catalyze the conversion of a 3-buten-2-ol to a butadiene or a 1,3 butadiene, (6) able to enzymatically catalyze the conversion of a crotyl alcohol (but-2-en-1-ol) to a butadiene or a 1,3 butadiene, (7) able to enzymatically catalyze the conversion of a 2,3-dimethyl-but-2-en-1-ol into dimethyl-butadiene, (8) catalyzing the conversion of a compound corresponding to the general formula $C_nH_{2n}O$ into $C_nH_{2n-2}+H_2O$ with $3<n<7$, wherein optionally the compound corresponding to the general formula $C_nH_{2n}O$ with $3<n<7$ is a crotyl alcohol, a but-3-en-2-ol or a but-3-en-1-ol, and/or the compound corresponding to the general formula $C_nH_{2n-2}$ with $3<n<7$ is a 1,3 butadiene;

and optionally the compound corresponding to the general formula $C_nH_{2n}O$ with $3<n<7$ is a 2,3-dimethyl-but-2-en-1-ol, a 2,3-dimethyl-but-3-en-2-ol or a 2,3-dimethyl-but-3-en-1-ol, and/or the compound corresponding to the general formula $C_nH_{2n-2}$ with $3<n<7$ is a dimethylbutadiene; or (9) any combination of (1) to (8).

In alternative embodiments, a polypeptide provided herein: (a) further comprises or consists of: a signal peptide, a periplasmic targeting sequence (PTS) or periplasmic signal sequence (PSS) or a polypeptide or peptide having a PTS or PSS activity; or, a eukaryotic signal sequence; or (b) comprises or consists of SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102.

In alternative embodiments, a polypeptide provided herein further comprises or consists of an N-terminal methionine.

In alternative embodiments, for a polypeptide provided herein:

(a) the polypeptide has at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a polypeptide having a sequence consisting of SEQ ID NO: 12, 22, 37, 43, 49, 55, 61, 62, 64, 66, 72, 74, 80, 86, 92 or 98, with the proviso that the polypeptide is not a "LDRV" protein or a polypeptide having a sequence as set forth in SEQ ID NO:2, SEQ ID NO:6 or SEQ ID NO:10 with or without its signal peptide, or a polypeptide having at least 95%, 96%, 97%, 98%, 99% or 100% sequence identity to a polypeptide having a sequence consisting of SEQ ID NO: 12, 22, 37, 43, 49, 55, 61, 62, 64, 66, 72, 74, 80, 86, 92 or 98.

In alternative embodiments, the periplasmic targeting sequence (PTS) or periplasmic signal sequence (PSS) is: a post-translational SecB-targeting pathway PTS or PSS; a co-translational signal recognition particle (SRP)-targeting pathway PTS or PSS; or, a twin-arginine translocation (TAT) Sec independent system PTS or PSS. In alternative embodiments, the periplasmic targeting sequence (PTS) or periplasmic signal sequence (PSS) comprises or consists of:

(a) an amino acid sequence as set forth in SEQ ID NO:8;

(b) SEQ ID NO: 20, 39, 45, 51, 57, 68, 76, 82, 88, 94 or 100;

(c) SEQ ID NO:25 [Lam B signal sequence, or LamBss], and optionally the encoded polypeptide comprises SEQ ID NO:24;

(d) SEQ ID NO:26 [MalE signal sequence, or MalEss];

(e) SEQ ID NO:36 [FhuD signal sequence, or FhuDss];

(f) SEQ ID NO:27, SEQ ID NO:28, SEQ ID NO:29, SEQ ID NO:30, SEQ ID NO:31, SEQ ID NO:32, SEQ ID NO:33, or SEQ ID NO:34;

(g) an LamB ss, a MalE ss, a Mg1B ss, an OmpA ss, a PelB ss, a PhoA ss, a DsbA ss, an SfmC ss, a TolB ss, a TorT ss, a FhuD ss, a PelB ss, a YcdO ss, an MdoD ss, a Tor Ass or a YcdO ss; or (h) a peptide encoded by a nucleic acid having about 90%, 91%, 92%, 93%, 94%, 95%, 96%, 97%, 98%, 99% or 100% sequence identity to SEQ ID NO: 7, or SEQ ID NO: 19, 44, 38, 50, 56, 67, 75, 81, 87, 93 or 99;

and optionally the polypeptide or peptide comprising or having the periplasmic targeting sequence (PTS), periplasmic signal sequence (PSS) or having a PTS or PSS activity is operably linked on the amino terminal of the polypeptide of claim 13 or claim 14, and optionally an amino terminal methionine is placed amino terminal to the polypeptide or peptide comprising or having the periplasmic targeting sequence (PTS), periplasmic signal sequence (PSS) or having a PTS or PSS activity. In alternative embodiments, the eukaryotic signal sequence is a yeast or fungal signal sequence.

In alternative embodiments, for a polypeptide provided herein: the polypeptide further comprises: a heterologous amino acid sequence, and optionally the heterologous amino acid sequence comprises or functions as a tag or an epitope, and optionally the heterologous amino acid sequence comprises or functions as an N-terminal and/or C-terminal extension for targeting to an endoplasmic reticulum (ER) or endomembrane, or acting as a periplasmic targeting sequence or periplasmic signal sequence or having a PTS or PSS activity.

In alternative embodiments, for a polypeptide provided herein: (a) the conservative amino acid substitution comprises replacement of an aliphatic amino acid with another aliphatic amino acid; replacement of a Serine with a Threonine or vice versa; replacement of an acidic residue with another acidic residue; replacement of a residue bearing an amide group with another residue bearing an amide group; exchange of a basic residue with another basic residue; or, replacement of an aromatic residue with another aromatic residue, or a combination thereof; or, (b) the isolated, synthetic or recombinant polypeptide of (a), wherein the aliphatic residue comprises Alanine, Valine, Leucine, Isoleucine or a synthetic equivalent thereof, or the acidic residue comprises Aspartic acid, Glutamic acid or a synthetic equivalent thereof, or the residue comprising an amide group comprises Aspartic acid, Glutamic acid or a synthetic equivalent thereof, or the basic residue comprises Lysine, Arginine or a synthetic equivalent thereof, or the aromatic residue comprises Phenylalanine, Tyrosine or a synthetic equivalent thereof.

In alternative embodiments, provided are compositions comprising a polypeptide as provided herein, wherein optionally the composition further comprises a substrate for the polypeptide, and optionally the substrate comprises an alkenol, a crotyl alcohol, a but-3-en-2-ol or a but-3-en-1-ol, a compound corresponding to the general formula $C_nH_{2n}O$ with $3<n<7$, or a combination thereof, wherein optionally the composition comprises or is formulated as a liquid, a solid or a gel.

In alternative embodiments, a polypeptide as provided herein further comprises an epitope or a tag, and optionally the tag is an affinity tag.

In alternative embodiments, provided are isolated, synthetic or recombinant antibodies: (a) that specifically binds to a polypeptide of any of claims 13 to 22; or (b) the antibody of (a), wherein the antibody is a monoclonal or a polyclonal antibody.

In alternative embodiments, provided are hybridomas comprising an antibody that specifically binds to the polypeptide as provided herein, or a hybridoma producing an antibody as provided herein.

In alternative embodiments, provided are methods of isolating or identifying a polypeptide with an enzymatic activity comprising the steps of:
  (a) providing an antibody as provided herein;
  (b) providing a sample comprising one or a plurality of polypeptides; and
  (c) contacting the sample of step (b) with the antibody of step (a) under conditions wherein the antibody can specifically bind to the polypeptide,
  wherein optionally the enzymatic activity comprises a linalool dehydratase-isomerase (LinD) activity, a vinylisomerase activity, or a dehydratase activity,
  thereby isolating or identifying a polypeptide having the enzymatic activity.

In alternative embodiments, provided are methods of producing a recombinant polypeptide comprising
  (i) (a) providing a nucleic acid operably linked to a promoter, wherein the nucleic acid comprises a nucleic acid as provided herein; and (b) expressing the nucleic acid of step (a) under conditions that allow expression of the polypeptide, thereby producing a recombinant polypeptide; or
  (ii) the method of (i), further comprising transforming a host cell with the nucleic acid of step (i) (a) followed by expressing the nucleic acid of step (a), thereby producing a recombinant polypeptide in a transformed cell.

In alternative embodiments, provided are methods for producing a compound corresponding to the general formula $C_nH_{2n-2}$ with $3<n<7$ from a compound corresponding to, or comprising, the general formula $C_nH_{2n}O$, with $3<n<7$, comprising:
  (a) culturing the non-natural, engineered, transformed or transduced cell as provided herein, or a plant cell as provided herein, in a suitable medium comprising a carbon source or a substrate for a polypeptide as provided herein, and culturing the cell under conditions suitable to produce an enzymatic product comprising the compound; or
  (b) expressing a nucleic acid as provided herein, under conditions wherein a polypeptide as provided herein is produced, and contacting the polypeptide with a substrate for a polypeptide as provided herein, under conditions suitable to produce an enzymatic product comprising the compound,
  wherein optionally the method further comprises recovering the produced compound corresponding to the general formula $C_nH_{2n-2}$ with $3<n<7$,
  and/or optionally the compound is a butadiene (BD), or a 1,3-butadiene,
  and/or optionally the compound corresponding to the general formula $C_nH_{2n}O$ with $3<n<7$ is a crotyl alcohol, a but-3-en-2-ol or a but-3-en-1-ol, and/or the compound corresponding to the general formula $C_nH_{2n-2}$ with $3<n<7$ is a 1,3-butadiene,
  and/or optionally the compound corresponding to the general formula $C_nH_{2n}O$ with $3<n<7$ is a 2,3-dimethyl-but-2-en-1-ol, a 2,3-dimethyl-but-3-en-2-ol or a 2,3-dimethyl-but-3-en-1-ol, and/or the compound corresponding to the general formula $C_nH_{2n-2}$ with $3<n<7$ is a dimethylbutadiene, and/or
  optionally the conditions comprise in vitro expression of the nucleic acid.

In alternative embodiments, provided are methods of enzymatically catalyzing the conversion of a crotyl alcohol to a 3-buten-2-ol, comprising contacting a polypeptide as provided herein with the crotyl alcohol under conditions wherein the crotyl alcohol is enzymatically converted to the 3-buten-2-ol.

In alternative embodiments, provided are methods of enzymatically catalyzing the conversion of a 3-buten-2-ol to a butadiene, comprising contacting a polypeptide as provided herein with the 3-buten-2-ol under conditions wherein the 3-buten-2-ol is enzymatically converted to the butadiene.

In alternative embodiments, provided are methods of enzymatically catalyzing the conversion of a crotyl alcohol to a butadiene, comprising contacting a polypeptide as provided herein with the crotyl alcohol under conditions wherein the crotyl alcohol is enzymatically converted to the butadiene.

In alternative embodiments, provided are peptides or polypeptides having a bacterial periplasmic targeting activity comprising or consisting of an amino acid sequence as set forth in SEQ ID NO: 20, 39, 45, 51, 57, 68, 76, 82, 88, 94 or 100, or a sequence as set forth in SEQ ID NO: 20, 39, 45, 51, 57, 68, 76, 82, 88, 94 or 100 and having at least one conservative amino acid substitution, or having no more than one, two, three, four or five amino acid substitutions.

In alternative embodiments, provided are isolated, synthetic or recombinant polypeptides: (a) having at least 95%, 96%, 97%, 98%, 99% or 100% sequence identity to an amino acid sequence as set forth in: (i) SEQ ID NO:2; (ii) SEQ ID NO:6; or (iii) SEQ ID NO:10, or (b) comprising an enzymatically active fragment of (a), and further comprising or consisting of a periplasmic targeting sequence (PTS) or periplasmic signal sequence (PSS) or a polypeptide or peptide having a PTS or PSS activity; or, a eukaryotic signal sequence. The polypeptide can further comprise an N-terminal methionine. The polypeptide can further comprise a periplasmic targeting sequence (PTS) or a periplasmic signal sequence (PSS), which can be: a post-translational SecB-targeting pathway PTS or PSS; a co-translational signal recognition particle (SRP)-targeting pathway PTS or PSS; or, a twin-arginine translocation (TAT) Sec independent system PTS or PSS. In alternative embodiments the periplasmic targeting sequence (PTS) or periplasmic signal sequence (PSS) comprises or consists of:

(a) an amino acid sequence as set forth in SEQ ID NO:8;
(b) SEQ ID NO: 20, 39, 45, 51, 57, 68, 76, 82, 88, 94 or 100;
(c) SEQ ID NO:25 [Lam B signal sequence, or LamBss], and optionally the encoded polypeptide comprises SEQ ID NO:24;
(d) SEQ ID NO:26 [MalE signal sequence, or MalEss];
(e) SEQ ID NO:36 [FhuD signal sequence, or FhuDss];
(f) SEQ ID NO:27, SEQ ID NO:28, SEQ ID NO:29, SEQ ID NO:30, SEQ ID NO:31, SEQ ID NO:32, SEQ ID NO:33, or SEQ ID NO:34;
(g) an LamB ss, a MalE ss, a MglB ss, an OmpA ss, a PelB ss, a PhoA ss, a DsbA ss, an SfmC ss, a TolB ss, a TorT ss, a FhuD ss, a PelB ss, a YcdO ss, an MdoD ss, a Tor Ass or a YcdO ss; or
(h) a peptide encoded by a nucleic acid having about 90%, 91%, 92%, 93%, 94%, 95%, 96%, 97%, 98%, 99% or 100% sequence identity to SEQ ID NO: 7, or SEQ ID NO: 19, 44, 38, 50, 56, 67, 75, 81, 87, 93 or 99;

and optionally the polypeptide or peptide comprising or having the periplasmic targeting sequence (PTS), periplasmic signal sequence (ss) or having a PTS activity is operably linked on the amino terminal of the polypeptide of claim 34, and optionally an amino terminal methionine is placed amino terminal to the polypeptide or peptide comprising or having the periplasmic targeting sequence (PTS), periplasmic signal sequence (ss) or having a PTS or PSS activity. In alternative embodiments, the eukaryotic signal sequence is a yeast or fungal signal sequence.

In alternative embodiments, provided are uses of or a method of using a polypeptide encoded by a nucleic acid as provided herein, or a polypeptide as provided herein, or a transformed or transduced cell as provided herein, or a plant cell as provided herein, for the conversion of a compound corresponding to the general formula $C_nH_{2n}O$ into $C_nH_{2n-2}+H_2O$, with $3<n<7$. In alternative embodiments of the uses or methods:
(a) the compound corresponding to the general formula $C_nH_{2n}O$ with $3<n<7$ is a crotyl alcohol, a but-3-en-2-ol or a but-3-en-1-ol, and/or the compound corresponding to the general formula $C_nH_{2n-2}$ with $3<n<7$ is a 1,3 butadiene; or
(b) the compound corresponding to the general formula $C_nH_{2n}O$ with $3<n<7$ is a 2,3-dimethyl-but-2-en-1-ol, a 2,3-dimethyl-but-3-en-2-ol or a 2,3-dimethyl-but-3-en-1-ol, and/or the compound corresponding to the general formula $C_nH_{2n-2}$ with $3<n<7$ is a dimethylbutadiene.

In alternative embodiments, the conversion, or production of the $C_nH_{2n-2}$ with $3<n<7$, takes place in a cell in vivo or in vitro.

In alternative embodiments, provided are methods of producing or making a dialkene, a butadiene, a dimethylbutadiene, a 3-buten-2-ol, or a compound corresponding to the general formula $C_nH_{2n-2}$ with $3<n<7$ from a compound corresponding to, or comprising, the general formula $C_nH_{2n}O$, with $3<n<7$, such as a crotyl alcohol or 2,3-dimethyl-but-2-en-1-ol, comprising:
(a) culturing a transformed or transduced cell as provided herein, or a plant cell as provided herein, in a suitable medium comprising a carbon source or a substrate for a polypeptide as provided herein, and culturing the cell under conditions suitable to produce (to catalyze generation of) an enzymatic product comprising the compound; or
(b) expressing a nucleic acid as provided herein, or expressing a nucleic acid from an expression construct or vector as provided herein, under conditions wherein a polypeptide as provided herein is produced, and contacting the polypeptide with a substrate for the polypeptide under conditions suitable to produce an enzymatic product comprising the compound, wherein optionally the substrate of (a) or (b) comprises: a compound corresponding to the general formula $C_nH_{2n}O$ into $C_nH_{2n-2}+H_2O$ with $3<n<7$, a crotyl alcohol (but-2-en-1-ol), a 3-buten-2-ol, a 2,3-dimethyl-but-2-en-1-ol, or any combination thereof, wherein optionally the method further comprises recovering or isolating the produced compound, which optionally comprises or corresponds to the general formula $C_nH_{2n-2}$ with $3<n<7$, and/or optionally the produced compound comprises or is: a 3-buten-2-ol, a dimethyl-butadiene, a butadiene (BD), or a 1,3-butadiene, and/or optionally the substrate compound corresponding to the general formula $C_nH_{2n}O$ with $3<n<7$, comprises or is: a crotyl alcohol, a but-3-en-2-ol or a but-3-en-1-ol, and/or the product compound corresponding to the general formula $C—H_{2n-2}$ with $3<n<7$, comprises or is a 1,3-butadiene, and/or optionally the substrate compound corresponding to the general formula $C_nH_{2n}O$ with $3<n<7$ is or comprises a 2,3-dimethyl-but-2-en-1-ol, a 2,3-dimethyl-but-3-en-2-ol or a 2,3-dimethyl-but-3-en-1-ol, and/or the product compound corresponding to the general formula $C_nH_{2n-2}$ with $3<n<7$ is or comprises a dimethylbutadiene, and/or optionally the conditions comprise in vitro expression of the nucleic acid.

In alternative embodiments, the method further comprises one, several or all of the following steps:
(a) obtaining a fermenter off-gas comprising the conjugated diolefin, e.g. butadiene, a volatile impurity, a bio-byproduct impurity and water vapor;
(b) compressing the fermenter off-gas in a multistage compression system to produce a compressed stream;
(c) feeding the compressed stream into a first distillation zone for the removal of bio-byproduct impurity and water vapor, the first distillation zone having an upper reflux stage, middle distillation stages and a lower reboiler stage;
(d) contacting an overhead vapor stream produced from the bio-byproduct impurity and water removal distillation zone with an adsorbent to produce a dried overhead stream;
(e) feeding the dried overhead stream into a second distillation zone for the removal of volatile impurity by the top, with the second distillation zone having an upper reflux stage, middle distillation stages and a lower reboiler stage; and
(f) collecting at the bottom of the distillation zone for the removal of volatile impurity the resulting purified liquid conjugated diolefin, e.g butadiene.

In alternative embodiments, provided are methods of producing an a polymer, resin or article of manufacture comprising reacting the di-alkene, optionally butadiene, to create a polymer or resin, and further optionally forming the polymer or resin into the article of manufacture, where the di-alkene, optionally butadiene, is produced by a method as provided herein, or a use as provided herein, or optionally, produced using a composition as provided herein. In alternative embodiments, the polymer, resin or article of manufacture comprises or is a butadiene-containing polymer, polybutadiene, adiponitrile, a copolymer, acrylonitrile-butadiene-styrene (ABS), acrylonitrile-butadiene rubber (ABR), styrene-butadiene rubber (SBR) copolymers, styrene-1,3-butadiene latex, or the article of manufacture is a tire, a pipe, an automobile part, a boat part, a food container or a carpet backing.

In alternative embodiments, provided are variations of the exemplary SEQ ID NO:12 based on particular corresponding amino acid residue differences in SEQ ID NO:2; where in alternative embodiments, one more more amino acids from SEQ ID NO:2, the fill-length polypeptide WT *C. defragrans* 65Phen linD, are imported into the corresponding position of exemplary SEQ ID NO:12, as indicated in the comparison table, below. In alternative embodiments, the position changes can modify the activity of SEQ ID NO:12, or a variant thereof as provided herein, for the catalytic conversion of either crotyl alcohol to butadiene, or but-3-en-2-ol to butadiene, as indicated below.

| Corresponding positions in exemplary SEQ ID NO: 12 | Positions in SEQ ID NO: 2 for improvement for crotyl alcohol to butadiene | Positions in SEQ ID NO: 2 for improvement for but-3-en-2-ol to butadiene |
|---|---|---|
| 10 | 10 | 10 |
| 12 | 12 | 12 |
| 13 | | |
| 19 | 18 | 18 |
| 21 | 20 | 20 |
| 40 | 39 | 39 |
| 51 | 50 | |
| 69 | 68 | |
| 71 | 70 | 70 |
| 72 | | |
| 73 | 72 | 72 |
| 74 | 73 | 73 |
| 76 | 75 | 75 |
| 77 | 76 | 76 |
| 78 | 77 | 77 |
| 79 | | |
| 80 | | |
| 81 | 80 | |
| 84 | | |
| 85 | 84 | 84 |
| 96 | 95 | 95 |
| 99 | 98 | |
| 103 | | 102 |
| 107 | 106 | 106 |
| 109 | 108 | |
| 115 | 114 | 114 |
| 116 | 115 | 115 |
| 117 | 116 | |
| 119 | | |
| 120 | 119 | 119 |
| 121 | | |
| 123 | 122 | 122 |
| 124 | 123 | 123 |
| 125 | | |
| 127 | 126 | 126 |
| 129 | | |
| 130 | | |
| 131 | | |
| 132 | | |
| 133 | 132 | 132 |
| 136 | | |
| 139 | | |
| 141 | 140 | 140 |
| 142 | | |
| 144 | | |
| 145 | 144 | 144 |
| 146 | | |
| 149 | | |
| 152 | 151 | 151 |
| 153 | | |
| 156 | | |
| 157 | 156 | 156 |
| 158 | 157 | 157 |
| 159 | 158 | 158 |
| 160 | 159 | 159 |
| 167 | | 166 |
| 169 | 168 | 168 |
| 170 | 169 | 169 |
| 171 | 170 | 170 |
| 174 | 173 | 173 |
| 176 | 175 | 175 |
| 182 | 181 | 181 |
| 187 | 186 | 186 |
| 193 | 192 | |
| 195 | 194 | |
| 196 | 195 | 195 |
| 200 | 199 | 199 |
| 208 | 207 | 207 |
| 211 | 210 | |
| 228 | 227 | 227 |
| 231 | 230 | 230 |
| 235 | 234 | 234 |
| 246 | 245 | 245 |
| 248 | 247 | 247 |
| 249 | 248 | 248 |
| 252 | 251 | 251 |
| 255 | | 254 |
| 256 | 255 | 255 |
| 270 | 269 | 269 |
| 282 | 281 | 281 |
| 286 | 285 | 285 |
| 311 | 310 | 310 |
| 319 | 318 | 318 |
| 325 | 324 | 324 |
| 358 | 357 | 357 |
| 365 | 364 | 364 |
| 368 | 367 | 367 |
| 374 | | 373 |
| 383 | 382 | 382 |
| 387 | 386 | 386 |
| 390 | 389 | 389 |
| 391 | 390 | 390 |

In alternative embodiments, the invention provides a composition or method according to any embodiment of the invention, substantially as hereinbefore described, or described herein, with reference to any one of the examples.

The details of one or more embodiments of the invention are set forth in the accompanying drawings and the description below. Other features, objects, and advantages of the invention will be apparent from the description and drawings, and from the claims.

All publications, patents and patent applications cited herein are hereby expressly incorporated by reference for all purposes.

The embodiments of the description described herein are not intended to be exhaustive or to limit the disclosure to the precise forms disclosed in the following drawings or detailed description. Rather, the embodiments are chosen and described so that others skilled in the art can appreciate and understand the principles and practices of the description.

BRIEF DESCRIPTION OF THE DRAWINGS

The drawings set forth herein are illustrative of embodiments of the invention and are not meant to limit the scope of the invention as encompassed by the claims.

FIG. 3A and FIG. 3B illustrate the effect of heterologous signal peptides fused to mature LinD from *C. defragrans* 65 Phen (SEQ ID NO:6). The wild-type (WT) PTS (SEQ ID NO:8) from WT type LinD from *C. defragrans* 65 Phen (SEQ ID NO:2) was substituted with PTss from *E. coli* periplasmic proteins as indicated, expressed in *E. coli* and assayed for butadiene activity as described below.

FIG. 4 illustrates a sequence alignment (SEQ ID NO: 108): SEQ ID NO:2 (wild type) vs SEQ ID NO:12 (wild type); differences are highlighted.

FIG. 5 illustrates a sequence alignment (SEQ ID NO: 109): Alignment SEQ ID NO:12 (wild type) vs SEQ ID NO:22 (variant having 11 substitutions); Substitutions in SEQ ID NO:12: V19I, Y71F, G74S, G133M, R171K, I182L, V196F, D200N, F325S, G365S, L368F. SEQ ID NO:12 had no detectable activity on crotyl alcohol.

FIG. 11 depicts an alignment (SEQ ID NO: 108) of full-length amino acid sequences of known wild-type protein (2753) (SEQ ID NO: 2) and a polypeptide first identified herein (9819) (SEQ ID NO: 12), to show corresponding positions; signal peptide is underlined.

FIG. 12 depicts an alignment of full-length amino acid sequences of known wild-type protein (2753) and a polypeptide first identified herein (9873), to show corresponding positions; signal peptide is underlined.

FIG. 13 depicts an alignment (SEQ ID NO: 111) of full-length amino acid sequences of known wild-type protein (2753) (SEQ ID NO: 2) and a polypeptide first identified herein (9874) (SEQ ID NO: 37), to show corresponding positions; signal peptide is underlined.

FIG. 14 depicts an alignment (SEQ ID NO: 112) of full-length amino acid sequences of known wild-type protein (2753) (SEQ ID NO: 2) and a polypeptide first identified herein (9875) (SEQ ID NO: 49), to show corresponding positions; signal peptide is underlined.

FIG. 15 depicts an alignment (SEQ ID NO: 113) of full-length amino acid sequences of known wild-type protein (2753) (SEQ ID NO: 2) and a polypeptide first identified herein (9894) (SEQ ID NO: 55), to show corresponding positions; signal peptide is underlined.

FIG. 16 depicts an alignment of full-length amino acid sequences of known wild-type protein (2753) and a polypeptide first identified herein (9895), to show corresponding positions; signal peptide is underlined.

FIG. 17 presents demonstrated enzymatic activity of exemplary enzymes of the invention. "CrOH" is crotyl alcohol; "MVC" is methyl vinyl carbinol or 3-buten-2-ol; "Prenol" is prenol or 3-methyl-2-buten-1-ol.

FIG. 18A and FIG. 18B provide pairwise percent identity ("% ID") between the novel polypeptides provided herein and known wild type enzyme as well as amongst the novel polypeptides provided herein. FIG. 18A provides pairwise amino acid sequence percent identity for full length (unprocessed) protein and FIG. 18B for "mature" or processed protein.

Like reference symbols in the various drawings indicate like elements, unless otherwise stated.

Figure 1:
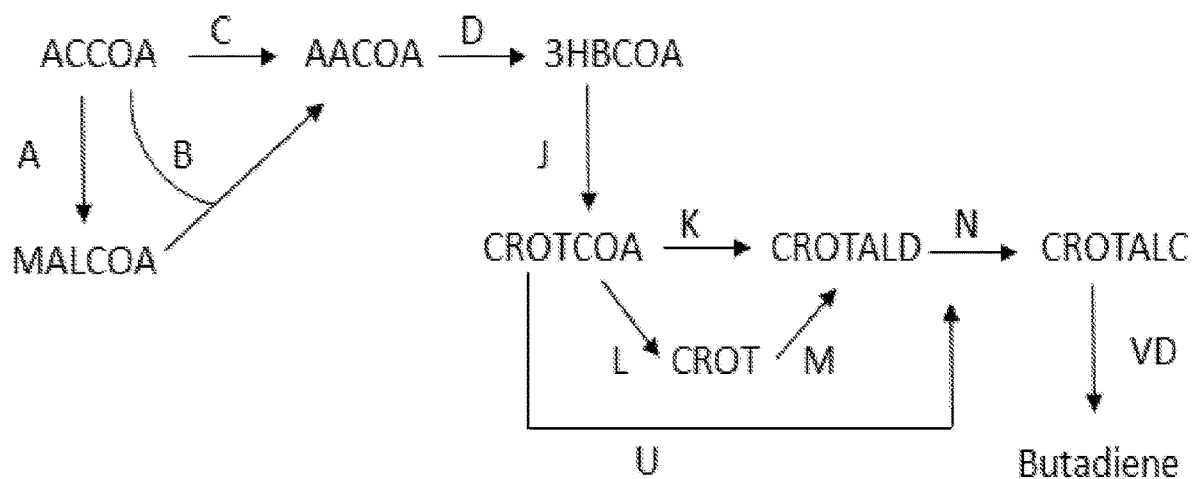
FIG. 1 schematically illustrates alternative exemplary metabolic pathways for producing crotyl alcohol and butadiene, as discussed in detail, below.

Reference will now be made in detail to various exemplary embodiments of the invention, examples of which are illustrated in the accompanying drawings. The following detailed description is provided to give the reader a better understanding of certain details of aspects and embodiments of the invention, and should not be interpreted as a limitation on the scope of the invention.

DETAILED DESCRIPTION

In alternative embodiments, provided are non-natural or genetically engineered vinylisomerase-dehydratase enzymes, including alkenol dehydratases, linalool dehydratases and crotyl alcohol dehydratases. In alternative embodiments, provided are polypeptides having an activity comprising, for example, a vinylisomerase-dehydratase, an alkenol dehydratase, a linalool dehydratase and/or a crotyl alcohol dehydratase activity, or a combination thereof. In alternative embodiments, provided are non-natural or genetically engineered enzymes that can catalyze the isomerization of a crotyl alcohol to a methyl vinyl carbinol, and optionally, are also are able to dehydrate a methyl vinyl carbinol to a butadiene, e.g., a 1,3-butadiene. In alternative embodiments, provided are non-natural or genetically engineered enzymes that can catalyze the dehydration of a methyl vinyl carbinol to a butadiene, e.g., a 1,3-butadiene.

In alternative embodiments, provided are non-natural or genetically engineered peptides having a signal sequence (SS) activity, a periplasmic targeting sequence (PTS) activity and/or a periplasmic signal sequence (PSS) activity. In one embodiment, peptides having SS, PTS or PSS activity are operatively linked to polypeptide as provided herein, or to any polypeptide, e.g., enzyme, for proper folding and/or insertion of the polypeptide in a bacteria periplasm or periplasmic space, or to direct the polypeptide into a periplasm, or to translocate the polypeptide across a bacterial inner membrane into a periplasm.

In alternative embodiments, also provided are non-natural or genetically engineered nucleic acids that encode a polypeptide (e.g., enzyme) or peptide (e.g., having SS, PTS or PSS activity) as described herein. In alternative embodiments, provided are expression systems or vehicles, e.g., recombinant vectors or viruses, cloning vectors and the like, comprising or having contained therein nucleic acid as described herein.

In alternative embodiments, also provided are non-natural or genetically engineered cells, e.g., transfected or transduced cells, comprising or having contained therein a nucleic acid as described herein and/or an expression system or vehicle, e.g., a recombinant vector or a virus, cloning vector and the like as provided herein. In alternative embodiments, the cells are bacterial, Archaeal, yeast, fungal, eukaryotic or plant cells.

In alternative embodiments, provided are non-natural or genetically engineered non-human organisms, or plants, comprising or having contained therein a nucleic acid as described herein and/or an expression system or vehicle, e.g., a recombinant vector or a virus, cloning vector and the like as provided herein.

In alternative embodiments, non-natural or genetically engineered cells or organisms as provided herein further comprise additional enzyme(s) in a metabolic pathway to produce a desired product, e.g., butadiene or 1,3-butadiene. In alternative embodiments, the additional enzyme(s) can involved in the production of a substrate of an enzyme as provided herein (e.g., a crotyl alcohol, a but-3-en-2-ol or a but-3-en-1-ol, a 2-methyl-but-3-en-1-ol, a 2-methyl-but-2-en-1-ol, a 3-methyl-but-3-en-2-ol or a 2-methyl-but-3-en-2-ol), or the additional enzyme(s) can involved in modification of a product of an enzyme as provided herein to an additional product.

In alternative embodiments, provided are cell culture systems, including bioreactors, comprising non-natural or genetically engineered cells or organisms as provided herein for the production of a desired product, e.g., to methyl vinyl carbinol and/or butadiene.

LDRV Protein Sequences

In alternative embodiments, provided are a genus of nucleic acids having at least between 50% and 99% or 100% sequence identity to a nucleic acid sequence consisting of SEQ ID NO: 11, 13, 14, 21, 36, 42, 48, 54, 60, 63, 65, 71, 73, 79, 85, 91 or 97 or SEQ ID NO: 15, 17, 18, 40, 46, 52, 58, 69, 77, 83, 89, 95 or 101, with the proviso that no nucleic acid in this genus encodes a so-called "LDRV" protein. In alternative embodiments, provided are a genus of polypeptides having at least between 50% and 99% or 100% sequence identity to a nucleic acid sequence consisting of SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102, with the proviso that no polypeptide in this genus is a so-called "LDRV" protein.

The proviso'ed out, or excluded, "LDRV" proteins comprise specific reported variants of the wild-type linalool dehydratase SEQ ID NO:2, e.g., as expressly listed in International patent application published as WO2014184345A1, including those sequences summarized below. Each of the specific variants described therein are collectively and individually referred to as "LDRV" proteins (or sequences).

For example, the proviso'ed out, or excluded, LDRV proteins include each of the variants expressly listed at pages 17 to 45 of WO2014184345A1, for example variant "V195F A18I F20L G73S G132M R170K I181L D199N W269A L367F" on page 17 to variant "V195F G73S Y70F E77I G132A" on page 45, and also including the sequence on page 82 (of WO2014184345A1), e.g. variant "V195F T84I G132R", to page 99, e.g. variant "V195F G132A W269A".

The proviso'ed out, or excluded, LDRV proteins also include each of variants expressly listed in FIG. 2 to FIG. 28 of WO2014184345A1. The LDRV proteins also include each variant expressly listed in the tables therein, which include those variants in the following tables excerpted from WO2014184345A1. Example variants include "V195F G73S R170K I181L F324S" and "V195F G132A G73S E77I" which are variants of 5 and of 4 amino acid substitutions in the wild-type linalool dehydratase SEQ ID NO:2 sequence, respectively.

The proviso'ed out, or excluded, LDRV proteins also include each of the mature protein sequences of the sequences expressly listed in WO2014184345A1, since the wild-type linalool dehydratase SEQ ID NO:2 has a signal peptide ensuring transport into the periplasmic space, where it is removed.

The proviso'ed out, or excluded, LDRV proteins also include the variants described in International patent publication WO2014033129A1, where the signal peptide is disrupted by insertion of a his-tag (6 histidines) after the initiation methionine.

Also proviso'ed out, or excluded, are LDRV nucleic acid sequences which encompasse those nucleic acid sequences that encode a proviso'ed out, or excluded, LDRV protein, and includes their degenerate nucleic acid sequence variants.

For example the following tables excerpted from WO2014184345A1 indicate specific substitution variants which are proviso'ed out, or excluded, as proteins and nucleic acids provided herein. Enzyme activities expressed are those as reported in WO2014184345A1 using specific assays and substrates reported therein.

Also proviso'ed out, or excluded, are sequences as listed in Table 1 of WO2014184345A1, which lists single amino acid change variants of wild-type linalool dehydratase from C. defragrans (referred to as Sequence 1 in WO2014184345A1 but designated herein as SEQ ID NO:2). For example V195F in the following table means the variant of that specific sequence in which V at 195 is replaced with F.

| Mutation | Fold |
|----------|------|
| V195F | 8.0 |
| H116K | 4.3 |
| E80P | 4.3 |
| V195Y | 3.5 |
| I106N | 3.4 |
| D119G | 3.3 |
| S357N | 3.1 |
| S75M | 3.1 |
| E80W | 3.0 |
| G73W | 2.8 |
| D199N | 2.7 |
| G132T | 2.6 |
| G132L | 2.6 |
| S123H | 2.6 |
| S75V | 2.6 |
| G132I | 2.58 |
| G132D | 2.5 |
| P68L | 2.3 |
| G132W | 2.3 |

-continued

| Mutation | Fold |
|---|---|
| G132S | 2.3 |
| K126Y | 2.2 |
| Y159I | 2.2 |
| A227I | 2.2 |
| L367F | 2.1 |
| F234W | 2.1 |
| S123W | 2.1 |
| G132Q | 2.0 |
| A192L | 2.0 |
| G132V | 2.0 |
| G132N | 2.0 |
| L157M | 2.0 |
| R169T | 2.0 |
| S75A | 2.0 |
| K126 | 1.9 |
| I181N | 1.9 |
| I181L | 1.9 |
|  | 1.9 |
| N156S | 1.9 |
| G132 | 1.8 |
| S75T | 1.8 |
| R169N | 1.8 |
| G132R | 1.8 |
| G132M | 1.8 |
| V122L | 1.8 |
| A192 | 1.8 |
| Y159M | 1.7 |
| G132 | 1.7 |
| Y159 | 1.7 |
| S123Y | 1.7 |
| T84Q | 1.7 |
| V318 | 1.7 |
| S123D | 1.7 |
| G132F | 1.7 |
| P389S | 1.7 |
| G115 | 1.7 |
| F76L | 1.7 |
| S75G | 1.7 |
| S123R | 1.6 |
| P390D | 1.6 |
| S75N | 1.6 |
| S75I | 1.6 |
| S255T | 1.6 |
| Y251M | 1.6 |
| S123I | 1.5 |
| F247V | 1.5 |
| S123E | 1.5 |
| T50R | 1.5 |
| G132K | 1.5 |
| Y251L | 1.5 |
| M158I | 1.4 |
| S75Y | 1.4 |
| F324S | 1.4 |
| F281Y | 1.4 |
| S123K | 1.4 |
| E77L | 1.4 |
| Y285M | 1.4 |
| A192T | 1.4 |
| Y98M | 1.4 |
| I186V | 1.3 |
| F95M | 1.3 |
| S123F | 1.3 |
| G132C | 1.2 |
| S123L | 1.2 |
| Y248K | 1.2 |
| R72S | 1.2 |
| S123T | 1.2 |
| H175S | 1.2 |
| S123V | 1.2 |
| G132Y | 1.2 |
| S123Q | 1.2 |
| S123M | 1.2 |
| H175N | 1.1 |
| I186L | 1.1 |

Also proviso'ed out, or excluded, are sequences as listed in Table 2 of WO2014184345A1, which lists two-amino acid change variants of wild-type linalool dehydratase from *C. defragrans* (referred to as Sequence 1 in WO2014184345A1 but designated herein as SEQ ID NO:2). For example G132R V195F in the following table means the variant of that specific sequence in which G at position 132 is replaced with R and V at position 195 is replaced with F.

| Mutation | Fold Increase |
|---|---|
| G132R V195F | 24.0 |
| G132L V195F | 20.0 |
| G132Q V195F | 20.0 |
| G132K V195F | 20.0 |
| G132V V195F | 16.0 |
| G132M V195F | 16.0 |
| G132I V195F | 16.0 |
| F324S V195F | 16.0 |
| G132A V195F | 15.2 |
| D119G V195F | 14.4 |
| G132S V195F | 13.6 |
| V195F D199N | 12.8 |
| G132T V195F | 12.0 |
| G132N V195F | 11.2 |
| G132F V195F | 10.4 |
| G132C V195F | 10.4 |
| A173K I181S | 1.8 |
| A173S I181A | 1.6 |
| G132R V310I | 1.4 |
| G132V G140S | 1.2 |

Also proviso'ed out, or excluded, are sequences as listed in Table 3 of WO2014184345A1, which lists amino acid change variants of wild-type linalool dehydratase from *C. defragrans* (referred to as Sequence 1 in WO2014184345A1 but designated herein as SEQ ID NO:2). For example V195F means that V at position 195 in the wild-type Sequence 1 of WO2014184345A1 is replaced with F.

| Mutation | Fold increase |
|---|---|
| F324S | 2.4 |
| V195F | 2.0 |
| F247V | 2.0 |
| G132A | 2.0 |
| G132D | 1.9 |
| I106N | 1.9 |
| G132T | 1.8 |
| R169T | 1.8 |
| S123R | 1.7 |
| G132H | 1.7 |
| N156S | 1.7 |
| S123K | 1.7 |
| Y159M | 1.6 |
| G132I | 1.6 |
| E254G | 1.6 |
| G132W | 1.6 |
| Y251M | 1.6 |
| G245A | 1.5 |
| I186L | 1.5 |
| F281Y | 1.5 |
| F76L | 1.5 |
| L157M | 1.5 |
| S123E | 1.5 |
| S75A | 1.5 |
| G132S | 1.5 |
| P390D | 1.5 |
| S75G | 1.4 |
| Y248K | 1.4 |
| F95M | 1.4 |
| Y251L | 1.4 |
| G132F | 1.4 |
| S123I | 1.4 |
| I181L | 1.4 |
| E77L | 1.4 |
| G115A | 1.3 |

-continued

| Mutation | Fold increase |
|---|---|
| R169N | 1.3 |
| F234W | 1.3 |
| F373L | 1.3 |
| K126A | 1.3 |
| I181N | 1.3 |
| G132L | 1.3 |
| G132Y | 1.3 |
| S123Q | 1.3 |
| G132N | 1.3 |
| G132R | 1.3 |
| R72S | 1.2 |
| V195Y | 1.2 |
| Y285M | 1.2 |
| A227I | 1.2 |
| Y159I | 1.2 |
| G132V | 1.2 |
| S123L | 1.2 |
| S255T | 1.2 |
| S123H | 1.2 |
| S123W | 1.2 |
| V122L | 1.2 |
| T84Q | 1.2 |
| I181S | 1.2 |
| Y159V | 1.2 |
| S357N | 1.2 |
| I186V | 1.2 |
| H175S | 1.2 |
| D119G | 1.1 |
| H175N | 1.1 |
| G132M | 1.1 |

Also proviso'ed out, or excluded, are sequences as listed in Table 4 of WO2014184345A1, which lists amino acid change variants of wild-type linalool dehydratase from *C. defragrans* (referred to as Sequence 1 in WO2014184345A1 but designated herein as SEQ ID NO:2. For example G132R V195F in the following table means the variant of that specific sequence in which G at position 132 is replaced with R and V at position 195 is replaced with F.

| Mutation | Fold increase |
|---|---|
| G132Q V195F | 3.0 |
| F324S V195F | 2.8 |
| D199N V195F | 2.7 |
| G132T V195F | 2.5 |
| G132A V195F | 2.4 |
| G132N V195F | 2.4 |
| G132L V195F | 2.3 |
| D119G V195F | 2.2 |
| G132R V195F | 2.0 |
| G132K V195F | 2.0 |
| G132V V195F | 2.0 |
| G132M V195F | 2.0 |
| G132I V195F | 2.0 |
| G132S V195F | 2.0 |
| V310I G132R | 1.6 |
| V195F G132F | 1.5 |
| G132V G140S | 1.3 |
| S102M T166S | 1.3 |

Also proviso'ed out, or excluded, are sequences as listed in Table 5 of WO2014184345A1, which lists amino acid change variants of wild-type linalool dehydratase from *C. defragrans* (referred to as Sequence 1 in WO2014184345A1 but designated herein as SEQ ID NO:2). For example G132R V195F in the following table means the variant of that specific sequence in which G at position 132 is replaced with R and V at position 195 is replaced with F.

| Mutations | Relative activity vs wild type | |
|---|---|---|
| | Conversion of crotyl alcohol into 1,3 Butadiene | Conversion of but-3-en-2-ol into 1,3 Butadiene |
| V195FA18IF20LY70FG73SG132MR170KI181LD199NF324SG364SL367F | 345.6 | |
| V195FA18IF20LG73SG132MR170KI181LD199NF324SL367F | 216 | |
| V195FG73SE77IG132AG364S | 138.00 | 7.60 |
| V195FF20LG132VR170KA173RI181LD199NF324S | 108.00 | 10.00 |
| V195FA18IF20LG73SG132MR170KI181LD199NW269AL367F | 102.08 | 5.29 |
| V195FL367FG382D | 100.00 | 4.56 |
| V195FI10AG132VR170KA173RI181LD199NF324S | 100.00 | 8.00 |
| V195FG73SR170KI181LF324S | 88.07 | 5.55 |
| V195FG73SG132GR170KI181LF324S | 86.00 | 6.00 |
| V195FG73SE77IT84IG132A | 86.00 | 7.70 |
| V195FF20LG73SG132GR170KI181LF324S | 86.00 | 7.60 |
| V195FL367FG382D | 85.18 | 4.14 |
| V195FA18IG73SR170KD199NF324SL367F | 78.90 | 4.41 |
| V195FA18IF20LD39AG132VR170KI181LF324SL367F | 75.79 | 4.14 |
| V195FG132AG73SE77I | 72.00 | 4.00 |
| V195FG73SI181LF324SL367F | 71.82 | 3.40 |
| V195FA18VF20LD39AG73SI144TR170KI181LD199NF324SL367F | 70.34 | 3.73 |
| V195FA18VG73SS123EG132SR170KI181LD199NW269A | 66.31 | 3.92 |
| V195FA18VD39AR170KI181LD199NF324SL367F | 65.33 | 3.97 |
| V195FG73SG132QR170KI181SW269A | 63.17 | 3.52 |
| V195FA18VF20LD39AG132KR170KI181LW269A | 60.17 | 3.29 |
| V195FG132VR170KA173RI181LD199NF324S | 57.6 | |
| V195FA18VG132MW269A | 53.90 | 3.46 |
| V195FG132VR170KA173RI181LF324S | 47.72 | 3.63 |
| V195FG132AG73SE77L | 47.51 | 0.00 |
| V195FA18VG73SR170KA173RP389L | 46.98 | 3.51 |
| V195FS168NR170KF324SL367F | 46.85 | 3.43 |
| V195FD39AG73SE77IG132QR170KD199NL367FG382D | 46.68 | 3.13 |
| V195FA18VG73SE77IR386S | 46.54 | 3.20 |
| V195FG73SY70FE77IG132A | 42.00 | 3.00 |
| V195FD39AG73SR170KI181LD199NF324S | 36.89 | 2.92 |
| V195FF324SL367L | 36.82 | 2.93 |

-continued

| | Relative activity vs wild type | |
|---|---|---|
| Mutations | Conversion of crotyl alcohol into 1,3 Butadiene | Conversion of but-3-en-2-ol into 1,3 Butadiene |
| G132AV195FG73S-E77L | 32.20 | 5.7 |
| V195FG132VF324S | 31.79 | 5.39 |
| V195FD199NF324S | 31.30 | 5.49 |
| V195FR170KA173RF324S | 30.82 | 2.77 |
| V195FG132MI181LF324S | 29.00 | 2.90 |
| V195FG132QF324S | 27.00 | 3.78 |
| V195FG132MF324S | 26.92 | 3.67 |
| V195FG132LF324S | 25.70 | 3.59 |
| V195FD119GS123EL365F | 25.63 | 2.11 |
| V195FS12L | 25.44 | 3.38 |
| V195FG132AD199N | 24.69 | 4.20 |
| V195FD119GS123E | 24.38 | 4.22 |
| V195FD119GG132A | 22.96 | 3.03 |
| G132AV195FR170K | 22.8 | 3.38 |
| V195FG132RF324S | 22.80 | 3.94 |
| V195FG132TD199N | 22.47 | 3.93 |
| V195FG132AD199NF324S | 22.02 | 4.85 |
| V195FG132AA173R | 22.00 | 2.97 |
| V195FG132AR170K | 21.99 | 3.49 |
| V195FG132ED199NF324S | 21.49 | 4.87 |
| G132AV195FF20L | 21.4 | 2.9 |
| V195FG132AW269A | 21 | 1.78 |
| V195FG132SD199N | 20.95 | 4.08 |
| V195FG132ND199N | 20.30 | 3.27 |
| V195FG132QD199NF324S | 20.23 | 5.68 |
| G132AV195FW269A | 20.1 | 3.4 |
| V195FG132KD199N | 20.03 | 3.40 |
| G132AV195FD39A | 20.0 | 1.64 |
| G132AV195FA18I | 19.9 | 5.2 |
| G132AV195FD119G | 19.8 | 1.42 |
| G132AV195FA173R | 19.8 | 2.4 |
| V195FG132QI181SD199N | 19.71 | 7.82 |
| V195FG132RD199NF324S | 19.67 | 5.03 |
| V195FG132KI181LD199N | 19.22 | 3.53 |
| G132RF324S | 19.22 | 3.32 |
| V195FD119GG132K | 19.19 | 2.62 |
| V195FG132AF20L | 19.18 | 2.89 |
| V195FD119GV122L | 19.2 | 7.3 |
| V195FG132TD199NF324S | 18.68 | 4.70 |
| V195FD119GS123EF324S | 18.64 | 3.58 |
| V195FD119GY151M | 18.29 | 3.12 |
| V195FA230Q | 18.24 | 2.3 |
| G132AV195FA18V | 18.2 | 3.96 |
| V195FG132AA18I | 17.98 | 2.27 |
| V195FV122LG132Q | 17.7 | 3.5 |
| V195FG132KF324S | 17.54 | 3.00 |
| V195FD119GY251M | 17.22 | 3.16 |
| V195FG132AA18V | 17.03 | 2.70 |
| V195FG132VD199NF324S | 17 | 1.74 |
| V195FG132LD199N | 16.87 | 5.57 |
| V195FG132MD199NF324S | 16.70 | 4.06 |
| V195FK126AG132AD199N | 16.7 | 2.6 |
| V195FD119GG132T | 16.66 | 2.61 |
| V195FG132AD39A | 16.65 | 2.14 |
| V195FG132AD119G | 16.56 | 2.26 |
| G132AI194RS207A | 16.25 | |
| V195FG132AY285L | 16.20 | 3.43 |
| V195FG132RD199N | 16.02 | 2.70 |
| V195FG132KP389S | 16.0 | 2.6 |
| V195FG132QV318A | 16.0 | 2.7 |
| V195FG132QY159M | 15.9 | 3.2 |
| V195FG132ND199NQ204Q | 15.8 | 2.5 |
| V195FD119GS123Q | 15.72 | 3.31 |
| V195FG132QD199NA314A | 15.5 | 3.1 |
| V195FG132AA114SV122I | 15.39 | 2.8 |
| V195FD199NL367F | 15.38 | 2.33 |
| V195FD119GG132S | 15.00 | 2.50 |
| V195FG132KL367F | 15.00 | 2.35 |
| V195FD119GS123H | 14.9 | 3.0 |
| V195FG132KR169ND199N | 14.80 | 3.05 |
| V195FG132DD199N | 14.79 | 3.76 |
| V195FG132TD199N/D119G | 14.7 | 2.8 |

|  | Relative activity vs wild type | |
|---|---|---|
| Mutations | Conversion of crotyl alcohol into 1,3 Butadiene | Conversion of but-3-en-2-ol into 1,3 Butadiene |
| V195FV122IG132L | 14.7 | 3.9 |
| V195FD199NV318A | 14.7 | 2.8 |
| V195FD119GG132N | 14.7 | 2.5 |
| V195FD119GS123EL367F | 14.57 | 2.16 |
| V195FG132KD119G | 14.5 | 2.3 |
| V195FL100LD119GGF324S | 14.30 | 2.92 |
| V195FI107ND119GS123EG132M | 14.22 | 2.08 |
| V195FG132HD199N | 14.2 | 2.9 |
| V195FG132QI181L | 14.2 | 2.6 |
| V195FM158IF324S | 14.0 | 2.7 |
| V195FS123TF324S | 13.82 | 2.75 |
| V195FV122LG132V | 13.6 | 3.4 |
| V195FD199N/Y251L | 13.21 | 3.37 |
| V195FD119GS123R | 13.12 | 2.70 |
| V195FD119GS123D | 13.10 | 2.62 |
| V195FG132TF195Y | 13.1 | 2.1 |
| V195FG132VA227I | 13.1 | 2.8 |
| V195FD119GG132KY251M | 13.00 | 3.33 |
| V195FG132KM158ID199N | 12.9 | 2.6 |
| V195FS123ED199N | 12.9 | 3.1 |
| V195FG132KR169TD199N | 12.7 | 3.0 |
| V195FD119GG132EY251M | 12.69 | 2.96 |
| V195FD119GG132AY251M | 12.61 | 3.38 |
| V195FG115AD119G | 12.5 | 2.0 |
| V195FS123RG132K | 12.4 | 3.1 |
| V195FD119GS123K | 12.4 | 3.0 |
| V195FD119GL367F | 12.32 | 1.53 |
| V195FI106ND119GS123E | 12.27 | 1.90 |
| V195FI107ND119GS123EG132Q | 12.15 | 2.73 |
| V195FG132TR169T | 12.1 | 2.2 |
| V195FG132K/G132TD199N | 12.0 | 2.2 |
| V195FG132AD119L | 11.82 | 1.2 |
| V195FG132TG140G | 11.8 | 2.5 |
| V195FG132TS357N | 11.7 | 2.2 |
| V195FD119GG132SY251M | 11.68 | 2.63 |
| V195FS123QG132S | 11.6 | 2.6 |
| V195FF76LD199N | 11.51 | 3.89 |
| V195FI107ND119GS123E | 11.20 | 3.40 |
| V195FH175N | 11.20 | 1.94 |
| V195FT84IG132R | 11.01 | 2.24 |
| V195FR169TD199N | 10.9 | 2.5 |
| V195FG132AS207C | 10.76 | 1.2 |
| V195FT84I | 10.54 | 2.10 |
| V195FA227S | 10.30 | 2.04 |
| V195FS75N | 10.13 | 3.56 |
| V195FE77L | 10.10 | 2.46 |
| V195FF76L | 9.25 | 2.07 |
| V195FG132AP108I | 8.51 | 1 |
| V195FG132AY210L | 8.28 | ND |
| V195FG132AY70A | 8.24 | ND |
| S102MT166S | 0.90 | 1.30 |

Also proviso'ed out, or excluded, are sequences as listed in Table 10 of WO2014184345A1 that lists amino acid change variants of wild-type linalool dehydratase from *C. defragrans* (referred to as Sequence 1 in WO2014184345A1 but designated herein as SEQ ID NO:2). For example at position 18 of wild-type sequence the A is substituted with I or V, creating two variants.

| Position (aa) | wild type aa | Substitution 1 aa | Substitution 2 aa | Substitution 3 aa | Substitution 4 aa | Substitution 5 aa | Substitution 6 aa | Substitution 7 aa | Substitution 8 aa | Substitution 9 aa |
|---|---|---|---|---|---|---|---|---|---|---|
| 18 | A | I | V | | | | | | | |
| 20 | F | L | | | | | | | | |
| 39 | D | A | | | | | | | | |
| 73 | G | S | | | | | | | | |

-continued

| Position (aa) | wild type aa | Substitution 1 aa | Substitution 2 aa | Substitution 3 aa | Substitution 4 aa | Substitution 5 aa | Substitution 6 aa | Substitution 7 aa | Substitution 8 aa | Substitution 9 aa |
|---|---|---|---|---|---|---|---|---|---|---|
| 77 | E | I | | | | | | | | |
| 119 | D | G | | | | | | | | |
| 123 | S | E | | | | | | | | |
| 132 | G | K | L | M | N | Q | R | S | T | V |
| 170 | R | K | | | | | | | | |
| 173 | A | R | | | | | | | | |
| 181 | I | L | S | | | | | | | |
| 199 | D | N | | | | | | | | |
| 269 | W | A | | | | | | | | |
| 324 | F | S | | | | | | | | |
| 365 | L | F | | | | | | | | |

Also proviso'ed out, or excluded, are sequences as listed in Table 13 of WO2014184345A1 that lists amino acid change variants of wild-type linalool dehydratase from *C. defragrans* (referred to as Sequence 1 in WO2014184345A1 but designated herein as SEQ ID NO:2). For example G132R V195F in the following table means the variant of that specific sequence in which G at position 132 is replaced with R and V at position 195 is replaced with F.

| Mutations | Relative activity compared to V195F variant |
|---|---|
| V195FT84IG132R | 1.21 |
| V195FA18VG73SE77IR386S | 1.16 |
| V195FD119GG132KY251M | 1.14 |
| V195FG132AG73SE77IT84I | 1.12 |
| V195FG132AG73SE77L | 1.11 |
| V195FG132AG73SE77IT141S | 1.10 |
| V195FG132AG73SE77IT141S | 1.10 |
| V195FT84I | 1.10 |
| V195FD119GS123E | 1.10 |
| V195FG132AG73SE77I | 1.09 |
| V195FG132AG73SE77IG364S | 1.09 |
| V195FG132AG73SE77I | 1.07 |
| V195FG132AG73SE77L | 1.04 |
| V195FD119GY151M | 1.04 |
| V195FG132AG73SE77ID312E | 1.04 |
| V195FD119GY251M | 1.03 |
| V195FG132QV318A | 1.03 |
| V195FG132Q | 1.02 |
| V195FG132AG73SE77IS168D | 1.00 |
| V195FG132AG73SE77IG19T | 1.00 |
| V195FG132AG73SE77IT8L | 1.00 |
| V195F | 1.00 |

Also proviso'ed out, or excluded, are sequences as listed in Table 14 of WO2014184345A1 that lists amino acid change variants of wild-type linalool dehydratase from *C. defragrans* (referred to as Sequence 1 in WO2014184345A1 but designated herein as SEQ ID NO:2). For example G132R V195F in the following table means the variant of that specific sequence in which G at position 132 is replaced with R and V at position 195 is replaced with F.

| Mutations | Relative activity compared to V195F variant |
|---|---|
| V195FA18IF20LD39AG73SD119GG132R | 2.54 |
| V195FA18IF20LG73SG132MR170KI181LD199NW269AL36 | 2.18 |
| V195FG132AG73SE77IG364S | 2.16 |
| V195FA18VD39AD119GR170KF324S | 2.15 |
| V195FD119GG132S | 2.15 |
| V195FT84IG132R | 2.10 |
| V195FG132VF324S | 2.08 |
| V195FL367F | 1.98 |
| V195FG132AG73SE77IA13I | 1.98 |
| V195FV122LG132V | 1.97 |
| V195FG132AG73SE77IA18C | 1.91 |
| V195FA18VD39AR170KI181LD199NF324SL367F | 1.85 |
| V195FA18VG73SR170KA173RP389L | 1.83 |
| V195FI181LF324S | 1.76 |
| V195FA18VD39AE77IR170KA173RD199NW269AF324S | 1.75 |
| V195FR170KA173RF324S | 1.71 |
| V195FA18ID39AG73SW269A | 1.63 |
| V195FA18VG73SD119GS123EI181LD199N | 1.57 |
| V195FA18IG73SR170KD199NF324SL367F | 1.56 |
| V195FA18VF20LD39AG73SL118LI144TR170KI181LD199NF324SL36 | 1.55 |
| V195FD119GG132KY251M | 1.52 |
| V195FV122LG132Q | 1.52 |
| V195FG132AG73SE77IS12A | 1.51 |
| V195FG132AG73SE77IT8L | 1.48 |
| V195FA18VD39AD119GI181L | 1.47 |
| V195FD119GY251M | 1.47 |

| Mutations | Relative activity compared to V195F variant |
|---|---|
| V195FA18ID39AR170KI181SW269A | 1.46 |
| V195FD39AG73SE77IG132QR170KD199NL367FG382D | 1.46 |
| V195FG132RD199NF324S | 1.44 |
| V195FG132AG73SE77IG19T | 1.44 |
| V195FG132Q | 1.44 |
| V195FA18IF20LD39AG132VR170KI181LF324SL367F | 1.43 |
| V195FL367FG382D | 1.41 |
| V195FD39AG73SR170KI181LD199NF324S | 1.37 |
| V195FA18IVD39AG73SE77ID119GR170K | 1.37 |
| V195FA18IVD119GG132SR170KA173RI181LD199NW269 | 1.36 |
| V195FG132QV318A | 1.32 |
| V195FG132AG73SE77IE145E | 1.29 |
| V195FF324S | 1.27 |
| V195FG73SG132GR170KI181LF324S | 1.20 |
| V195FD39AG132AR170KD199NW269A | 1.20 |
| V195FD39AG73SR170KI181LD199N | 1.19 |
| V195FD119GS123R | 1.19 |
| V195FG73SG132GR170KI181L | 1.17 |
| V195FT84I | 1.17 |
| V195FA18IVG73SE77IR386S | 1.17 |
| V195FG73SV122IS123EG132AD199NW269A | 1.14 |
| V195FA18IG73SR170KI181SL367F | 1.08 |
| V195FG132AG73SE77IT141S | 1.07 |
| V195FD39AG73SR170KI181LD199NL367F | 1.05 |
| V195FA18IVF20LD39AG132KR170KI181LW269A | 1.03 |
| V195FA18IG132KR170KW269AF324S | 1.03 |
| V195FG132AG73SE77I | 1.03 |
| V195FF324S | 1.02 |
| V195FG132AW269A | 1.02 |
| V195F | 1.00 |

Also proviso'ed out, or excluded, are sequences as listed in Table 16 of WO2014184345A1 that lists amino acid change variants of wild-type linalool dehydratase from *C. defragrans* (referred to as Sequence 1 in WO2014184345A1 but designated herein as SEQ ID NO:2). For example G132R V195F in the following table means the variant of that specific sequence in which G at position 132 is replaced with R and V at position 195 is replaced with F.

| ID | Mutations |
|---|---|
| Wild type enzyme | No mutations |
| Clone ID48 | V195F |
| C1246 | V195F G132A |
| C3027 | V195F G73S E77I G132A |
| C6207 | V195F A18I F20L G73S G132M R170K I181L D199N W269A |

Also proviso'ed out, or excluded, are sequences as listed in Table 17 of WO2014184345A1 that lists amino acid change variants of wild-type linalool dehydratase from *C. defragrans* (referred to as Sequence 1 in WO2014184345A1 but designated herein as SEQ ID NO:2). For example G132A V195F in the following table means the variant of that specific sequence in which G at position 132 is replaced with A and V at position 195 is replaced with F.

V195F G132A G73S E77I
G73S G132G R170K I181L V195F F324S
G132V R170K A173R I181L V195F D199N F324S
A18I F20L G73S G132M R170K I181L V195F D199N F324S L367F

-continued

A18I F20L Y70F G73S G132M R170K I181L V195F D199N F324S G364S L367F

Also proviso'ed out, or excluded, are sequences as listed in Table 19 of WO2014184345A1 that lists amino acid change variants of wild-type linalool dehydratase from *C. defragrans* (referred to as Sequence 1 in WO2014184345A1 but designated herein as SEQ ID NO:2). For example F20T in the following table means the variant of that specific sequence in which F at position 20 is replaced with T.

| Mutation(s) | Relative activity vs. wt |
|---|---|
| F20T | 1.55 |
| S71A | 5.27 |
| S71D | 4.16 |
| S71T | 2.02 |
| R72L | 3.11 |
| R72P | 4.47 |
| R72R | 2.60 |
| G73A | 3.49 |
| G73S | 3.42 |
| S75A | 4.53 |
| S75D | 2.86 |
| S75F | 2.33 |
| S75I | 3.68 |
| S75L | 2.62 |
| S75M | 3.03 |
| S75T | 4.29 |
| S75V | 3.88 |
| F76I | 1.46 |
| F76L | 2.65 |
| A78G | 1.35 |
| W79Y | 1.18 |
| T84H | 1.68 |
| G115A | 2.28 |
| G115D | 2.03 |

| Mutation(s) | Relative activity vs. wt |
|---|---|
| H116K | 3.60 |
| H116R | 2.49 |
| D119H | 2.44 |
| D119Q | 3.08 |
| D119R | 3.42 |
| I120R | 3.22 |
| I120V | 1.98 |
| V122M | 2.56 |
| S123D | 2.50 |
| S123E | 3.01 |
| S123R | 2.96 |
| S123W | 3.59 |
| K124L | 1.29 |
| K126A | 2.70 |
| K126D | 2.39 |
| K128D | 1.45 |
| K128N | 1.41 |
| V130I | 1.64 |
| W131F | 2.02 |
| G132D | 2.50 |
| G132N | 2.14 |
| G132Q | 1.88 |
| G132S | 2.10 |
| G132T | 2.36 |
| E135P | 2.29 |
| P143Y | 1.39 |
| E145P | 1.52 |
| N148D | 3.95 |
| Y151F | 2.16 |
| K152R | 3.30 |
| L155I | 1.23 |
| A192L | 2.15 |
| G193A | 5.00 |
| V195F | 6.40 |
| V195Y | 3.22 |
| D199A | 3.91 |
| D199E | 6.25 |
| D199L | 3.19 |
| D199M | 3.42 |
| D199N | 4.41 |
| D199Q | 4.78 |
| D199S | 4.46 |
| Y251M | 3.81 |
| H252D | 1.70 |
| P253H | 3.41 |
| E254G | 2.65 |
| E254H | 3.51 |
| E254P | 3.48 |
| S255G | 3.70 |
| S255H | 2.58 |
| S255L | 3.32 |
| S255Q | 2.52 |
| S255Y | 2.56 |
| V318A | 2.04 |
| V318G | 1.53 |
| G319R | 1.80 |
| E361T | 1.72 |
| L366V | 2.45 |
| L367F | 3.10 |
| A383Y | 1.52 |
| L384M | 1.49 |
| L384Y | 1.49 |
| M387D | 1.80 |
| M387N | 1.78 |
| P390D | 1.67 |

Also proviso'ed out, or excluded, are sequences as listed in Table 20 of WO2014184345A1 that lists amino acid change variants of wild-type linalool dehydratase from *C. defragrans* (referred to as Sequence 1 in WO2014184345A1 but designated herein as SEQ ID NO:2). For example S75V in the following table means the variant of that specific sequence in which S at position 75 is replaced with V.

| Mutations | Relative activity vs. wt |
|---|---|
| S75V H83M | 4.30 |
| R129L L367F | 2.91 |
| S75A H83W | 2.81 |
| S75N G138Q | 2.71 |
| F76V E77L | 2.67 |
| F76L T84I | 2.59 |
| F76L A314T | 2.30 |
| K126F G364M | 2.20 |
| S75M H83T | 2.15 |
| L239M F247V | 2.01 |
| G319R G382Q | 1.51 |

Also proviso'ed out, or excluded, are sequences as listed in Table 21 of WO2014184345A1 that lists amino acid change variants of wild-type linalool dehydratase from *C. defragrans* (referred to as Sequence 1 in WO2014184345A1 but designated herein as SEQ ID NO:2). For example A18I in the following table means the variant of that specific sequence in which A at position 18 is replaced with I.

| Mutation(s) | Relative activity on prenol vs. wt | Relative activity on crotyl alcohol vs. |
|---|---|---|
| V195F G132A | 7.10 | 15.2 |
| V195F | 6.40 | 8 |
| G73S E77I G132A V195F | 6.30 | 72 |
| G73S G132G R170K I181L V195F F324S | 5.50 | 86 |
| V195F F324S | 5.03 | 16 |
| R170K G132V A173R I181L V195F D199N | 4.12 | 57.6 |
| A18I F20L G73S G132M R170K I181L V195F D199N F324S | 3.83 | 216 |
| A18I F20L Y70F G73S G132M R170K I181L V195F D199N F324S G364S | 3.70 | 345.6 |

"cdLD-Botes" Protein Sequences

In alternative embodiments, provided are a genus of nucleic acids having at least between 50% and 99% or 100% sequence identity to a nucleic acid sequence consisting of SEQ ID NO: 11, 13, 14, 21, 36, 42, 48, 54, 60, 63, 65, 71, 73, 79, 85, 91 or 97 or SEQ ID NO: 15, 17, 18, 40, 46, 52, 58, 69, 77, 83, 89, 95 or 101, with the proviso that no nucleic acid in this genus encodes a so-called "cdLD-Botes" protein. In alternative embodiments, provided are a genus of polypeptides having at least between 50% and 99% or 100% sequence identity to a nucleic acid sequence consisting of SEQ ID NO: 12, 22, 37, 43, 49, 55, 61, 62, 64, 66, 72, 74, 80, 86, 92 or 98 or SEQ ID NO: 16, 41, 47, 53, 59, 70, 78, 84, 90, 96 or 102, with the proviso that no polypeptide in this genus is a so-called "cdLD-Botes" protein.

The proviso'ed out, or excluded, "cdLD-Botes" proteins comprise specific reported variants of the linalool dehydratase SEQ ID NO:103, e.g., as expressly listed in U.S. Pat. No. 9,220,742, including those sequences summarized below. Each of the specific variants described therein are collectively and individually referred to as "cdLD-Botes" proteins (or sequences).

In alternative embodiments, the proviso'ed out, or excluded, sequences include so-called "cdLD-Botes" nucleic acid sequences encompassing nucleic acid sequences that encode a "cdLD-Botes" protein, and includes their degenerate nucleic acid sequence variants.

The proviso'ed out, or excluded, "cdLD-Botes" proteins comprise a polypeptide (or a polynucleotide encoding it) comprising an amino acid sequence with at least 90%, or between 90% and 100%, amino acid sequence homology to SEQ ID NO:103, wherein the amino acid sequence comprises at least 1, 2, 3, 4 or 5, mutations at the following X positions of SEQ ID NO:103 (where each R is the same as the corresponding amino acid in SEQ ID NO:103)

$R_{1-95}X_{96}R_{97-98}X_{99}R_{100-122}X_{123}R_{124-185}X_{187}$
$R_{188-203}X_{204}R_{205-211}X_{212}R_{213-272}X_{273}X_{274}X_{275}$
$R_{276-323}X_{324}R_{325-327}X_{328}R_{329\text{-}R359}X_{360}$
$R_{361-365}X_{366}R_{367-381}X_{382}R_{383-398}$, wherein:

$X_{96}$ is mutated to a different amino acid selected from L and equivalent amino acids;
$X_{99}$ is mutated to a different amino acid selected from L and equivalent amino acids;
$X_{123}$ is mutated to a different amino acid selected from I and equivalent amino acids;
$X_{187}$ is mutated to a different amino acid selected from M and equivalent amino acids;
$X_{204}$ is mutated to a different amino acid selected from I and equivalent amino acids;
$X_{212}$ is mutated to a different amino acid selected from F, Y, and equivalent amino acids;
$X_{273}$ is mutated to a different amino acid selected from C and equivalent amino acids;
$X_{274}$ is mutated to a different amino acid selected from F and equivalent amino acids;
$X_{275}$ is mutated to a different amino acid selected from I and equivalent amino acids;
$X_{324}$ is mutated to a different amino acid selected from L, E, and equivalent amino acids;
$X_{328}$ is mutated to a different amino acid selected from V and equivalent amino acids;
$X_{360}$ is mutated to a different amino acid selected from Y and equivalent amino acids;
$X_{356}$ is mutated to a different amino acid selected from V, C, G, and equivalent amino acids;
$X_{382}$ is mutated to a different amino acid selected from W and equivalent amino acids.

The proviso'ed out, or excluded, "cdLD-Botes" proteins comprise a polypeptide (or a polynucleotide encoding it) comprising or consisting of (having only) the following combinations of mutations (changes) to SEQ ID NO:103:

V204I, M274F, V275I; V123I, M274F, V275I; V123I, V204I, V275I; V123I, V204I, M274F; M274F, V275I; M274F, A324L; M274F, R360Y; M274F, V275I, A324L; M274F, V275I, F382W; M274F, A324L, F382W; M274F, V275I, R360Y; F382W; V275I, A324L; V275I, F382W; V275I, A324L, R360Y; V275I, A324, F382W; R360Y, F382W; M274F; V275I; A324L; R360Y; F382W; V123I and/or V204I and any combination thereof;
V123I/V204I/M274F; M274F/M275I/F382W; V275I/A324L; V275I; V123I; and V204I;
A324L, M274F, S366V, V275I and/or F382W and any combination thereof;
V123I, V204I, M274F, V275I, and F382W;
V275I and F382W;
A324L, V275I, V123I, and V204I;
A324L and S366G;
M274F and F96L;
M274F and Y99L;
F382W and L212Y;
F382W and A273C;
F382W and L328V;
F382W, L328V, and I187M;
V204I, M274F, and V275I;
V123I, M274F, and V275I;
V123I, V204I, and V275I; V123I, V204I, and M274F;
M274F, V275I, and A324L;
M274F, V275I;
M274F, V275I, R360Y, and F382W;
V275I and A324L;
R360Y and F382W.

Additionally, "cdLD-Botes" proteins (and the nucleic acids encoding them) also include, i.e., that are also proviso'ed out, or excluded, comprise or consist of SEQ ID NO:104, SEQ ID NO:105, SEQ ID NO:106, SEQ ID NO:107.

Also proviso'ed out, or excluded, are "cdLD-Botes" proteins (and the nucleic acids encoding them) that have, or do not have: one or more N-terminal methionines, a periplasmic tag, a C-terminal tag such as a C-terminal His-tag, or any combination thereof.

Computational Approaches to Sequence Alignment and Generation of Sequence Identity In alternative embodiments, any computational approaches to sequence alignment and generation of sequence identity can be used, e.g., including global alignments and local alignments. Global alignment uses global optimization to forces alignment to span the entire length of all query sequences. Local alignments, by contrast, identify regions of similarity within long sequences that are often widely divergent overall. For understanding the identity of a target sequence to a template, a global alignment can be used. Optionally, amino terminal and/or carboxy-terminal sequences of the target sequence that share little or no identify with the template sequence can be excluded for a global alignment and generation of an identify score.

In alternative embodiments, any algorithm well known to those skilled in the art can be used, such as Align, BLAST, Clustal W and others, to compare and determine a raw sequence similarity or identity, and also determine the presence or significance of gaps in the sequence which can be assigned a weight or score. Such algorithms also are known in the art and are similarly applicable for determining nucleotide sequence similarity or identity. Parameters for sufficient similarity to determine relatedness are computed based on well known methods for calculating statistical similarity, or the chance of finding a similar match in a random polypeptide, and the significance of the match determined. A computer comparison of two or more sequences can, if desired, also be optimized visually by those skilled in the art. Related gene products or proteins can be expected to have a high similarity, for example, 45% to 100% sequence identity. Proteins that are unrelated can have an identity which is essentially the same as would be expected to occur by chance, if a database of sufficient size is scanned (about 5%).

For example, an alignment can be performed using the Needleman-Wunsch algorithm (Needleman, S. & Wunsch, C). Alternatively, a general method applicable to the search for similarities in the amino acid sequence of two proteins J. Mol. Biol, 1970, 48, 443-453, implemented through the BALIGN tool can be used. Default parameters can be used for the alignment and BLOSUM62 can be used as the scoring matrix.

In alternative embodiments, the Basic Local Alignment Search Tool (BLAST) algorithm is used to determine the sequence identity between a polypeptide sequences, or between an amino acid motif in a template sequence and a target sequence. In alternative embodiments, BLAST is used to identify or understand the identity of a shorter stretch of amino acids (e.g. a sequence motif) between a template and a target protein. In alternative embodiments BLAST finds similar sequences using a heuristic method that approximates the Smith-Waterman algorithm by locating short matches between the two sequences. The (BLAST) algorithm can identify library sequences that resemble the query sequence above a certain threshold. Exemplary parameters for determining relatedness of two or more sequences using the BLAST algorithm, for example, can be as set forth below. In alternative embodiments, amino acid sequence alignments can be performed using BLASTP version 2.0.8 (Jan. 5, 1999) and the following parameters: Matrix: 0 BLOSUM62; gap open: 11; gap extension: 1; x_dropoff: 50; expect: 10.0; wordsize: 3; filter: on. Nucleic acid sequence alignments can be performed using BLASTN version 2.0.6 (Sep. 16, 1998) and the following parameters: Match: 1; mismatch: −2; gap open: 5; gap extension: 2; x_dropoff: 50; expect: 10.0; wordsize: 11; filter: off. Those skilled in the art will know what modifications can be made to the above parameters to either increase or decrease the stringency of the comparison, for example, and determine the relatedness of two or more sequences.

Expression Systems, Engineered Cells

In alternative embodiments, expression constructs, vehicles or vectors are provided to include, or contain within, one or more nucleic acids as exemplified herein, optionally operably linked to an expression control sequence, e.g., a promoter, functional in a host organism. In alternative embodiments, expression constructs, vehicles or vectors applicable for use in the microbial host organisms provided include, for example, plasmids, phage vectors, viral vectors or recombinant viruses, episomes and artificial chromosomes, including vectors and selection sequences or markers operable for stable integration into a host chromosome. In alternative embodiments, the expression vectors also include one or more selectable marker genes and appropriate expression control sequences. Selectable marker genes also can be included that, for example, provide resistance to antibiotics or toxins, complement auxotrophic deficiencies, or supply critical nutrients not in the culture media. Expression control sequences can include constitutive and inducible promoters, transcription enhancers, transcription terminators, and the like which are well known in the art. When two or more exogenous encoding nucleic acids are to be co-expressed, both nucleic acids can be inserted, for example, into a single expression vector or in separate expression vectors. For single vector expression, the encoding nucleic acids can be operationally linked to one common expression control sequence or linked to different expression control sequences, such as one inducible promoter and one constitutive promoter.

In alternative embodiments, the transformation or transduction of a nucleic acid as provided herein into a cell, including transformation or transduction of an exogenous nucleic acid sequence involved in a metabolic or synthetic pathway, can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product. It is understood by those skilled in the art that the exogenous nucleic acid is expressed in a sufficient amount to produce the desired product, and it is further understood that expression levels can be optimized to obtain sufficient expression using methods well known in the art and as disclosed herein.

In alternative embodiments the term "exogenous" is intended to mean that the referenced molecule (e.g., a polypeptide or nucleic acid as provided herein) or the referenced (e.g., enzyme) activity is introduced into the host microbial organism. The molecule can be introduced, for example, episomally, or by introduction of a nucleic acid (e.g., a polypeptide or nucleic acid as provided herein) into a host genetic material such as by integration into a host chromosome or as non-chromosomal genetic material such as a plasmid. In alternative embodiments, the term "exogenous" is used in reference to expression of an encoding nucleic acid in an expressible form into a cell, e.g., a microbial organism. When used in reference to a biosynthetic activity, the term "exogenous" can refer to an activity that is introduced into the host reference organism. The source can be, for example, a homologous or heterologous (e.g., a polypeptide or nucleic acid as provided herein) encoding nucleic acid that expresses the referenced activity following introduction into the host microbial organism. In alternative embodiments, the term "endogenous" refers to a referenced molecule or activity that is present in the host. In alternative embodiments, the term when used in reference to expression of an encoding nucleic acid can refer to expression of an encoding nucleic acid contained within the microbial organism. In alternative embodiments the term "heterologous" can refer to a molecule or activity derived from a source other than the referenced species whereas "homologous" refers to a molecule or activity derived from the host microbial organism. In alternative embodiments, exogenous expression of an encoding nucleic acid can utilize either or both a heterologous or homologous encoding nucleic acid.

In alternative embodiments more than one exogenous nucleic acid heterologous (e.g., one or more nucleic acids as provided herein) can be introduced into the host microbial organism on separate nucleic acid molecules, on polycistronic nucleic acid molecules, or a combination thereof. In alternative embodiments, a microbial organism can be engineered to express two or more exogenous nucleic acids encoding a desired pathway enzyme or protein. In the case where two exogenous nucleic acids (e.g., where at least one is a nucleic acid as provided herein) encoding a desired activity are introduced into a host microbial organism, in alternative embodiments the two exogenous nucleic acids can be introduced as a single nucleic acid, for example, on a single plasmid, on separate plasmids, or can be integrated into the host chromosome at a single site or multiple sites. In alternative embodiments, more than two exogenous nucleic acids (e.g., where at least one is a nucleic acid as provided herein) can be introduced into a host organism in any desired combination, for example, on a single plasmid, on separate plasmids, can be integrated into the host chromosome at a single site or multiple sites.

In alternative embodiments nucleic acids provided herein can be introduced stably or transiently into a host cell using techniques well known in the art including, but not limited to, conjugation, electroporation, chemical transformation, transduction, transfection, and ultrasound transformation. Optionally, for exogenous expression in E. coli or other prokaryotic cells, some nucleic acid sequences in the genes or cDNAs of eukaryotic nucleic acids can encode targeting signals such as an N-terminal mitochondrial or other targeting signal, which can be removed before transformation into prokaryotic host cells, if desired. In alternative embodiments, removal of a mitochondrial leader sequence is done for increased expression in E. coli (Hoffmeister et al., J. Biol. Chem. 280:4329-4338 (2005)). In alternative embodiments for exogenous expression in yeast or other eukaryotic cells, genes can be expressed in the cytosol without the addition of leader sequence, or can be targeted to mitochondrion or other organelles, or targeted for secretion, by the addition of a suitable targeting sequence such as a mitochondrial targeting or secretion signal suitable for the host cells. In alternative embodiments appropriate modifications to a nucleic acid as provided herein are made, e.g., to remove or include a targeting sequence or to impart any desirable properties. In alternative embodiments, genes are be subjected to codon optimization with techniques well known in the art to achieve optimized expression of the proteins.

In alternative embodiments provided herein are "microbial cells," "microbial organisms" or "microorganisms" (e.g., containing therein a nucleic acid as provided herein to express a polypeptide as provided herein, include any organism that exists as a microscopic cell that is included within the domains of archaea, bacteria or eukarya. In alternative embodiments provided herein are prokaryotic or eukaryotic cells or organisms having a microscopic size and includes bacteria, archaea and eubacteria of all species as well as eukaryotic microorganisms such as yeast and fungi. In alternative embodiments provided herein are cell cultures of any species that can be cultured for the production of a biochemical.

In alternative embodiments provided herein are microorganisms containing therein a nucleic acid or polypeptide as provided herein; including both prokaryotic and eukaryotic organisms including, but not limited to, bacteria, including Archaea and eubacteria, and eukaryotes, including yeast, plant, insect, animal, and mammal, including in vitro human cells. Exemplary species used to practice this invention include, for example, Escherichia coli, Saccharomyces cerevisiae, Saccharomyces kluyveri, Candida boidinii, Clostridium kluyveri, Clostridium acetobutylicum, Clostridium beijerinckii, Clostridium saccharoperbutylacetonicum, Clostridium perfringens, Clostridium difficile, Clostridium botulinum, Clostridium tyrobutyricum, Clostridium tetanomorphum, Clostridium tetani, Clostridium propionicum, Clostridium aminobutyricum, Clostridium subterminale, Clostridium sticklandii, Ralstonia eutropha, Mycobacterium bovis, Mycobacterium tuberculosis, Porphyromonas gingivalis, Arabidopsis thaliana, Thermus thermophilus, Pseudomonas species, including Pseudomonas aeruginosa, Pseudomonas putida, Pseudomonas stutzeri, Pseudomonas fluorescens, Homo sapiens, Oryctolagus cuniculus, Rhodobacter spaeroides, Thermoanaerobacter brockii, Metallosphaera sedula, Leuconostoc mesenteroides, Chloroflexus aurantiacus, Roseiflexus castenholzii, Erythrobacter, Simmondsia chinensis, Acinetobacter species, including Acinetobacter calcoaceticus and Acinetobacter baylyi, Porphyromonas gingivalis, Sulfolobus tokodaii, Sulfolobus solfataricus, Sulfolobus acidocaldarius, Bacillus subtilis, Bacillus cereus, Bacillus megaterium, Bacillus brevis, Bacillus pumilus, Rattus norvegicus, Klebsiella pneumonia, Klebsiella oxytoca, Euglena gracilis, Treponema denticola, Moorella thermoacetica, Thermotoga maritima, Halobacterium salinarum, Geobacillus stearothermophilus, Aeropyrum pernix, Sus scrofa, Caenorhabditis elegans, Corynebacterium glutamicum, Acidaminococcus fermentans, Lactococcus lactis, Lactobacillus plantarum, Streptococcus thermophilus, Enterobacter aerogenes, Candida, Aspergillus terreus, Pedicoccus pentosaceus, Zymomonas mobilis, Acetobacter pasteurians, Kluyveromyces lactis, Eubacterium barkeri, Bacteroides capillosus, Anaerotruncus colihominis, Natranaerobius thermophilusm, Campylobacter jejuni, Haemophilus influenzae, Serratia marcescens, Citrobacter amalonaticus, Myxococcus xanthus, Fusobacterium nuleatum, Penicillium chrysogenum, marine gamma proteobacterium, butyrate producing bacterium, Nocardia iowensis, Nocardia farcinica, Streptomyces griseus, Schizosaccharomyces pombe, Geobacillus thermoglucosidasius, Salmonella typhimurium, Vibrio cholera, Heliobacter pylori, Nicotiana tabacum, Oryza sativa, Haloferax mediterranei, Agrobacterium tumefaciens, Achromobacter denitrificans, Fusobacterium nucleatum, Streptomyces clavuligenus, Acinetobacter baumanii, Mus musculus, Lachancea kluyveri, Trichomonas vaginalis, Trypanosoma brucei, Pseudomonas stutzeri, Bradyrhizobium japonicum, Mesorhizobium loti, Bos taurus, Nicotiana glutinosa, Vibrio vulnificus, Selenomonas ruminantium, Vibrio parahaemolyticus, Archaeoglobus fulgidus, Haloarcula marismortui, Pyrobaculum aerophilum, Mycobacterium smegmatis MC2 155, Mycobacterium avium subsp. paratuberculosis K-10, Mycobacterium marinum M Tsukamurella paurometabola DSM 20162, Cyanobium PCC7001, Dictyostelium discoideum AX4, as well as other exemplary species disclosed herein or available as source organisms for corresponding genes.

Exemplary species used to practice this invention include, for example Acinetobacter baumannii Naval-82, Acinetobacter sp. ADP1, Acinetobacter sp. strain M-1, Actinobacillus succinogenes 130Z, Allochromatium vinosum DSM 180, Amycolatopsis methanolica, Arabidopsis thaliana, Atopobium parvulum DSM 20469, Azotobacter vinelandii DJ, Bacillus alcalophilus ATCC 27647, Bacillus azotoformans LMG 9581, Bacillus coagulans 36D1, Bacillus megaterium, Bacillus methanolicus MGA3, Bacillus methanolicus PB1, Bacillus methanolicus PB-1, Bacillus selenitireducens MLS10, Bacillus smithii, Bacillus subtilis, Burkholderia cenocepacia, Burkholderia cepacia, Burkholderia multivorans, Burkholderia pyrrocinia, Burkholderia stabilis, Burkholderia thailandensis E264, Burkholderiales bacterium Joshi_001, Butyrate producing bacterium L2-50, Campylobacter jejuni, Candida albicans, Candida boidinii, Candida methylica, Carboxydothermus hydrogenoformans, Carboxydothermus hydrogenoformans Z-2901, Caulobacter sp. AP07, Chloroflexus aggregans DSM 9485, Chloroflexus aurantiacus J-10-fl, Citrobacter freundii, Citrobacter koseri ATCC BAA-895, Citrobacter youngae, Clostridium, Clostridium acetobutylicum, Clostridium acetobutylicum ATCC 824, Clostridium acidurici, Clostridium aminobutyricum, Clostridium asparagiforme DSM 15981, Clostridium beijerinckii, Clostridium beijerinckii NCIMB 8052, Clostridium bolteae ATCC BAA-613, Clostridium carboxidivorans P7, Clostridium cellulovorans 743B, Clostridium difficile, Clostridium hiranonis DSM 13275, Clostridium hylemonae DSM 15053, Clostridium kluyveri, Clostridium kluyveri DSM 555, Clostridium ljungdahli, Clostridium ljungdahlii DSM 13528, Clostridium methylpentosum DSM 5476, Clostridium pasteurianum, Clostridium pasteurianum DSM 525, Clostridium perfringens, Clostridium perfringens ATCC 13124, Clostridium perfringens str. 13, Clostridium phytofermentans ISDg, Clostridium saccharobutylicum, Clostridium saccharoperbutylacetonicum, Clostridium saccharoperbutylacetonicum N1-4, Clostridium tetani, Corynebacterium glutamicum ATCC 14067, Corynebacterium glutamicum R, Corynebacterium sp. U-96, Corynebacterium variabile, Cupriavidus necator N-1, Cyanobium PCC7001, Desulfatibacillum alkenivorans AK-01, Desulfitobacterium hafniense, Desulfitobacterium metallireducens DSM 15288, Desulfotomaculum reducens MI-1, Desulfovibrio africanus str. Walvis Bay, Desulfovibrio fructosovorans JJ, Desulfovibrio vulgaris str. Hildenborough, Desulfovibrio vulgaris str. 'Miyazaki F', Dictyostelium discoideum AX4, Escherichia coli, Escherichia coli K-12, Escherichia coli K-12 MG1655, Eubacte-

*rium hallii* DSM 3353, *Flavobacterium frigoris, Fusobacterium nucleatum* subsp. *polymorphum* ATCC 10953, *Geobacillus* sp. Y4.1MC1, *Geobacillus themodenitrificans* NG80-2, *Geobacter bemidjiensis* Bem, *Geobacter sulfurreducens, Geobacter sulfurreducens* PCA, *Geobacillus stearothermophilus* DSM 2334, *Haemophilus influenzae, Helicobacter pylori, Homo sapiens, Hydrogenobacter thermophilus, Hydrogenobacter thermophilus* TK-6, *Hyphomicrobium denitrificans* ATCC 51888, *Hyphomicrobium zavarzinii, Klebsiella pneumoniae, Klebsiella pneumoniae* subsp. *pneumoniae* MGH 78578, *Lactobacillus brevis* ATCC 367, *Leuconostoc mesenteroides, Lysinibacillus fusiformis, Lysinibacillus sphaericus, Mesorhizobium loti* MAFF303099, *Metallosphaera sedula, Methanosarcina acetivorans, Methanosarcina acetivorans* C2A, *Methanosarcina barkeri, Methanosarcina mazei* Tuc01, *Methylobacter marinus, Methylobacterium extorquens, Methylobacterium extorquens* AM1, *Methylococcus capsulatus, Methylomonas aminofaciens, Moorella thermoacetica, Mycobacter* sp. strain JC1 DSM 3803, *Mycobacterium avium* subsp. *paratuberculosis* K-10, *Mycobacterium bovis* BCG, *Mycobacterium gastri, Mycobacterium marinum* M, *Mycobacterium smegmatis, Mycobacterium smegmatis* MC2 155, *Mycobacterium tuberculosis, Nitrosopumilus salaria* BD31, *Nitrososphaera gargensis* Ga9.2, *Nocardia farcinica* IFM 10152, *Nocardia iowensis* (sp. NRRL 5646), *Nostoc* sp. PCC 7120, *Ogataea angusta, Ogataea parapolymorpha* DL-1 (*Hansenula polymorpha* DL-1), *Paenibacillus peoriae* KCTC 3763, *Paracoccus denitrificans, Penicillium chrysogenum, Photobacterium profundum* 3TCK, *Phytofermentans* ISDg, *Pichia pastoris, Picrophilus torridus* DSM9790, *Porphyromonas gingivalis, Porphyromonas gingivalis* W83, *Pseudomonas aeruginosa* PA01, *Pseudomonas denitrificans, Pseudomonas knackmussii, Pseudomonas putida, Pseudomonas* sp, *Pseudomonas syringae* pv. *syringae* B728a, *Pyrobaculum islandicum* DSM 4184, *Pyrococcus abyssi, Pyrococcus furiosus, Pyrococcus horikoshii* OT3, *Ralstonia eutropha, Ralstonia eutropha* H16, *Rhodobacter capsulatus, Rhodobacter sphaeroides, Rhodobacter sphaeroides* ATCC 17025, *Rhodopseudomonas palustris, Rhodopseudomonas palustris* CGA009, *Rhodopseudomonas palustris* DX-1, *Rhodospirillum rubrum, Rhodospirillum rubrum* ATCC 11170, *Ruminococcus obeum* ATCC 29174, *Saccharomyces cerevisiae, Saccharomyces cerevisiae* S288c, *Salmonella enterica, Salmonella enterica* subsp. *enterica* serovar *Typhimurium* str. LT2, *Salmonella enterica typhimurium, Salmonella typhimurium, Schizosaccharomyces pombe, Sebaldella termitidis* ATCC 33386, *Shewanella oneidensis* MR-1, *Sinorhizobium meliloti* 1021, *Streptomyces coelicolor, Streptomyces griseus* subsp. *griseus* NBRC 13350, *Sulfolobus acidocalarius, Sulfolobus solfataricus* P-2, *Synechocystis* str. PCC 6803, *Syntrophobacter fumaroxidans, Thauera aromatica, Thermoanaerobacter* sp. X514, *Thermococcus kodakaraensis, Thermococcus litoralis, Thermoplasma acidophilum, Thermoproteus neutrophilus, Thermotoga maritima, Thiocapsa roseopersicina, Tolumonas auensis* DSM 9187, *Trichomonas vaginalis* G3, *Trypanosoma brucei, Tsukamurella paurometabola* DSM 20162, *Vibrio cholera, Vibrio harveyi* ATCC BAA-1116, *Xanthobacter autotrophicus* Py2, *Yersinia intermedia*, or *Zea mays*.

Cell Culture Systems, Bioreactors

In alternative embodiments, provided are cell culture systems, including bioreactors, comprising non-natural or genetically engineered cells or organisms as provided herein for the production of a desired product, e.g., to methyl vinyl carbinol, butadiene. Methods for producing desired products using engineered cells as provided herein include anaerobic or aerobic fermentation, continuous or batch methods, and the like. Any culture system, reactor, bioreactor and the like known in the art can be used for practicing these methods, or using non-natural or genetically engineered cells or organisms as provided herein for the production of a desired product, e.g., as described in U.S. Pat. Nos. 9,023,642; 9,012,205; 9,005,550; 8,980,624; 8,980,623; 8,778,647; 8,709,793; 8,518,691; 8,835,159; 5,954,858; 20150104835; 20140377822; 20140187826; 20150017683; 20130005011; 20120070888.

In alternative embodiments, for using cell culture systems, any suitable carbon source can be used. For example, in one embodiment, the carbon source is methanol or formate, and either or both can be used as a carbon source in the organisms provided herein, either alone or in combination with the product pathways provided herein.

In alternative embodiments, the carbon source comprises a sugar (e.g., a glucose) or a sugar-containing biomass. For example, the carbon source can comprise methanol and/or formate and a sugar (e.g., glucose) or a sugar-containing biomass. In specific embodiments, the methanol or formate, or both, in the fermentation feed is provided as a mixture with sugar (e.g., glucose) or sugar-comprising (sugar-containing) biomass. In certain embodiments, sugar is provided for sufficient strain growth.

In alternative embodiments, non-natural or genetically engineered cells provided herein (e.g., when used for the production of a butadiene) are cultured in a medium with carbon source and other essential nutrients. In alternative embodiments it can be desirable to maintain anaerobic conditions in the fermenter to reduce the cost of the overall process. Such conditions can be obtained, for example, by first sparging the medium with nitrogen and then sealing the wells or fermenters. For strains where growth is not observed anaerobically, then microaerobic or substantially anaerobic conditions can be applied. Exemplary anaerobic conditions have been described previously and are well-known in the art. Exemplary aerobic and anaerobic conditions are described, for example, in United State publication 2009/0047719, filed Aug. 10, 2007. In alternative embodiments, fermentations can be performed in a batch, fed-batch or continuous manner.

If desired, the pH of the culture system medium can be maintained at a desired pH, in particular neutral pH, such as a pH of around 7 by addition of a base, such as NaOH or other bases, or acid, as needed to maintain the culture medium at a desirable pH. The growth rate can be determined by measuring optical density using a spectrophotometer (600 nm), and the glucose uptake rate by monitoring carbon source depletion over time.

The growth medium can include, for example, any carbohydrate source which can supply a source of carbon to the non-naturally occurring microorganism. Such sources include, for example, sugars such as glucose, xylose, arabinose, galactose, mannose, fructose, sucrose and starch. Other sources of carbohydrate include, for example, renewable feedstocks and biomass. Exemplary types of biomasses that can be used as feedstocks in the screening methods include cellulosic biomass, hemicellulosic biomass and lignin feedstocks or portions of feedstocks. Such biomass feedstocks contain, for example, carbohydrate substrates useful as carbon sources such as glucose, xylose, arabinose, galactose, mannose, fructose and starch. Given the teachings and guidance provided herein, those skilled in the art will understand that renewable feedstocks and biomass other than those exemplified above also can be used for culturing the microbial organisms provided herein, e.g., for the production of the desired compound, e.g., a butadiene.

In addition to renewable feedstocks such as those exemplified above, non-natural or genetically engineered cells provided herein also can be modified for growth on syngas as its source of carbon. In this specific embodiment, one or more proteins or enzymes are expressed in the organisms to provide a metabolic pathway for utilization of syngas or other gaseous carbon source. Synthesis gas, also known as syngas or producer gas, is the major product of gasification of coal and of carbonaceous materials such as biomass materials, including agricultural crops and residues. Syngas is a mixture primarily of $H_2$ and CO and can be obtained from the gasification of any organic feedstock, including but not limited to coal, coal oil, natural gas, biomass, and waste organic matter. Gasification is generally carried out under a high fuel to oxygen ratio. Although largely $H_2$ and CO, syngas can also include $CO_2$ and other gases in smaller quantities. Thus, synthesis gas provides a cost effective source of gaseous carbon such as CO and, additionally, $CO_2$.

In alternative embodiments, non-natural or genetically engineered cells provided herein can use the reductive (reverse) tricarboxylic acid cycle coupled with carbon monoxide dehydrogenase and/or hydrogenase activities for the conversion of CO, CO2 and/or H2 to acetyl-CoA and other products such as acetate. Organisms capable of fixing carbon via the reductive TCA pathway can utilize one or more of the following enzymes: ATP citrate-lyase, citrate lyase, aconitase, isocitrate dehydrogenase, alpha-ketoglutarate: ferredoxin oxidoreductase, succinyl-CoA synthetase, succinyl-CoA transferase, fumarate reductase, fumarase, malate dehydrogenase, NAD(P)H: ferredoxin oxidoreductase, carbon monoxide dehydrogenase, and hydrogenase. Specifically, the reducing equivalents extracted from CO and/or H2 by carbon monoxide dehydrogenase and hydrogenase are utilized to fix CO2 via the reductive TCA cycle into acetyl-CoA or acetate. Acetate can be converted to acetyl-CoA by enzymes such as acetyl-CoA transferase, acetate kinase/phosphotransacetylase, and acetyl-CoA synthetase. Acetyl-CoA can be converted to the butadiene, glyceraldehyde-3-phosphate, phosphoenolpyruvate, and pyruvate, by pyruvate: ferredoxin oxidoreductase and the enzymes of gluconeo genesis. Following the teachings and guidance provided herein for introducing a sufficient number of encoding nucleic acids to generate a desired metabolic pathway, those skilled in the art will understand that the same engineering design also can be performed with respect to introducing at least the nucleic acids encoding the reductive TCA pathway enzymes or proteins absent in the host organism. Therefore, introduction of one or more encoding nucleic acids into the microbial organisms such that the modified organism contains the complete reductive TCA pathway will confer syngas utilization ability, and libraries of such modified microbes can be screened using the apparatuses and methods described herein.

In alternative embodiments, non-natural or genetically engineered cells provided herein can initiate synthesis of a desired product, e.g., a butadiene, from an intermediate, and this intermediate can be added to the culture medium (or bioreactor) or enzymes can be added to the cell to supplement the amount of or add (de novo) to the cell the production of, for example, acetoacetyl-CoA, 3-hydroxybutyryl-CoA, crotonyl-CoA, crotonaldehyde, crotyl alcohol, 2-betenyl-phosphate, 2-butenyl-4-diphosphate, erythritol-4-phosphate, 4-(cytidine 5'-diphospho)-erythritol, 2-phospho-4-(cytidine 5'-diphospho)-erythritol, erythritol-2,4-cyclodiphosphate, 1-hydroxy-2-butenyl 4-diphosphate, butenyl 4-diphosphate, 2-butenyl 4-diphosphate, 3-oxoglutaryl-CoA, 3-hydroxyglutaryl-CoA, 3-hydroxy-5-oxopentanoate, 3,5-dihydroxy pentanoate, 3-hydroxy-5-phosphonatooxypentanoate, 3-hydroxy-5-[hydroxy (phosphonooxy) phosphoryl]oxy pentanoate, crotonate, erythrose, erythritol, 3,5-dioxopentanoate or 5-hydroxy-3-oxopentanoate.

In alternative embodiments, non-natural or genetically engineered cells provided herein are cultured under conditions that can be scaled up and/or grown continuously for manufacturing of a desired product, e.g., a butadiene. Exemplary growth procedures include, for example, fed-batch fermentation and batch separation; fed-batch fermentation and continuous separation, or continuous fermentation and continuous separation. All of these processes are well known in the art. Fermentation procedures can be useful for the biosynthetic production of commercial quantities of a desired product, e.g., a butadiene.

In alternative embodiments, as with non-continuous culture procedures, the continuous and/or near-continuous production of a desired product, e.g, a butadiene, can include culturing a non-natural or genetically engineered cell as provided herein in sufficient nutrients and medium to sustain and/or nearly sustain growth in an exponential phase. Continuous culture under such conditions can be include, for example, growth for 1 day, 2, 3, 4, 5, 6 or 7 days or more. In alternative embodiments, continuous culture can include longer time periods of 1 week, 2, 3, 4 or 5 or more weeks and up to several months. Alternatively, the microbial organisms can be cultured for hours, if suitable for a particular application. It is to be understood that the continuous and/or near-continuous culture conditions also can include all time intervals in between these exemplary periods. In alternative embodiments the time of culturing the microbial organism is for a sufficient period of time to produce a sufficient amount of product for a desired purpose.

Accordingly, provided herein are in vitro or in vivo, e.g., cell-based, methods of producing or making butadiene, a dialkene or a compound corresponding to the general formula $C_nH_{2n-2}$ with $3<n<7$ from a compound corresponding to, or comprising, the general formula $C_nH_{2n}O$, with $3<n<7$, comprising:

(a) culturing the transformed or transduced cells or plants cell of the invention described herein in a suitable medium comprising a carbon source or a substrate for a polypeptide of the invention as described herein, and culturing the cell under conditions suitable to produce an enzymatic product comprising the compound; or (b) expressing a nucleic acid of the invention under conditions wherein a polypeptide of the invention is produced, and contacting the polypeptide with a substrate for the polypeptide under conditions suitable to produce an enzymatic product comprising the compound, wherein optionally the method further comprises recovering the produced compound corresponding to the general formula $C_nH_{2n-2}$ with $3<n<7$, and/or optionally the compound is a butadiene (BD), a 1,3-butadiene, and/or optionally the compound corresponding to the general formula $C_nH_{2n}O$ with $3<n<7$ is a crotyl alcohol, a but-3-en-2-ol or a but-3-en-1-ol, and/or the compound corresponding to the general formula $C_nH_{2n-2}$ with $3<n<7$ is a 1,3-butadiene, and/or optionally the compound corresponding to the general formula $C_nH_{2n}O$ with $3<n<7$ is a 2,3-dimethyl-but-2-en-1-ol, a 2,3-dimethyl-but-3-en-2-ol or a 2,3-dimethyl-but-3-en-1-ol, and/or the compound corresponding to the general formula $C_nH_{2n-2}$ with $3<n<7$ is a dimethylbutadiene, and/or optionally the conditions comprise in vitro expression of the nucleic acid.

The fermentation can take place under aerobic, microaerobic or anaerobic conditions, preferably anaerobic where the compound, e.g. butadiene, is reactive with oxygen. Also provided is a method of producing an a polymer, resin or article of manufacture comprising reacting the compound, di-alkene, optionally butadiene, to create a polymer or resin, and further optionally forming the polymer or resin into an article of manufacture, where the compound, di-alkene, optionally butadiene, is produced by a method or use of the invention or produced using a composition, e.g. polynucleotide, enzyme, engineered microbe, alkene product composition, of the invention. Further, the polymer, resin or article of manufacture can comprise or is a butadiene-containing polymer, polybutadiene, adiponitrile, a copolymer, acrylonitrile-butadiene-styrene (ABS), acrylonitrile-butadiene rubber (ABR), styrene-butadiene rubber (SBR) copolymers, styrene-1,3-butadiene latex, or the article of manufacture is a tire, a pipe, an automobile part, a boat part, a food container or a carpet backing.

Methods for Screening for Enzyme Activity, and Recovering Products

In alternative embodiments, any method for screening for enzyme activity, e.g., production of a desired product, e.g., such as butadiene, and any method for isolating enzyme products or final products, can be used, e.g., as described in: WO2011071682A1 published 16 Jun. 2011 entitled Methods and Organisms for Converting Synthesis Gas or Other Gaseous Carbon Sources and Methanol to 1,3-Butanediol; WO2011031897A published 17 Mar. 2011 entitled Microorganisms and Methods for the Co-Production of Isopropanol with Primary Alcohols, Diols and Acids; WO2010127319A2 published 4 Nov. 2010 entitled Organisms for the Production of 1,3-Butanediol; WO2013071226A1 published 16 May 2013 entitled Eukaryotic Organisms and Methods for Increasing the Availability of Cytosolic Acetyl-CoA, and for Producing 1,3-Butanediol; WO2013028519A1 published 28 Feb. 2013 entitled Microorganisms and Methods for Producing 2,4-Pentadienoate, Butadiene, Propylene, 1,3-Butanediol and Related Alcohols; WO2013036764A1 published 14 Mar. 2013 entitled Eukaryotic Organisms and Methods for Producing 1,3-Butanediol; WO2013012975A1 published 24 Jan. 2013 entitled Methods for Increasing Product Yields; WO2012177619A2 published 27 Dec. 2012 entitled Microorganisms for Producing 1,3-Butanediol and Methods Related Thereto; and, WO/2014/106122, published Jul. 3, 2014, entitled Compositions and Methods for Bio-Butadience Production Screening.

Butadiene intermediates such as 1,4-butanediol, 1,3-butanediol, crotyl alcohol, 3-buten-2-ol (methyl vinyl carbinol) and 3-buten-1-ol, can be made by co-expressing alcohol dehydrogenases described herein with a product pathway as known in the art, e.g., as described herein. Suitable product pathways and enzymes, methods for screening and methods for isolating are found in: WO2011140171A2 published 10 Nov. 2011 entitled Microorganisms and Methods for the Biosynthesis of Butadiene; WO2012018624A2 published 9 Feb. 2012 entitled Microorganisms and Methods for the Biosynthesis of Aromatics, 2,4-Pentadienoate and 1,3-Butadiene; O2011140171A2 published 10 Nov. 2011 entitled Microorganisms and Methods for the Biosynthesis of Butadiene; WO2013040383A1 published 21 Mar. 2013 entitled Microorganisms and Methods for Producing Alkenes; WO2012177710A1 published 27 Dec. 2012 entitled Microorganisms for Producing Butadiene and Methods Related thereto; WO2012106516A1 published 9 Aug. 2012 entitled Microorganisms and Methods for the Biosynthesis of Butadiene; WO2013028519A1 published 28 Feb. 2013 entitled Microorganisms and Methods for Producing 2,4-Pentadienoate, Butadiene, Propylene, 1,3-Butanediol and Related Alcohols; and U.S. Ser. No. 61/799,255 filed 15 Mar. 2013.

The butadiene and other dialkenes made using the enzymes described herein can be separated and/or isolated from other components in the culture using a variety of methods well known in the art. In the case of a volatile dialkene such as butadiene, it can be obtained in and isolated from the fermentation off-gas. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, ultrafiltration, gas compression, extractive distillation using a solvent, solvent removal via distillation and final distillation. Further, where the dialkene, e.g. butadiene, is hazardous in the presence of sufficient oxygen, anaerobic fermentation can be used. All of the above methods are well known in the art.

For example, International patent application publication WO2014121357 entitled "Method Of Separating and Purifying a Conjugated Diolefin Produced by Fermentation under Anaerobic Conditions" provides a method for separating and purifying a fermentation under anaerobic conditions from a fermenter off-gas that includes a) obtaining a fermenter off-gas comprising the conjugated diolefin, e.g. butadiene, a volatile impurity, a bio-byproduct impurity and water vapor; b) compressing the fermenter off-gas in a multistage compression system to produce a compressed stream; c) feeding the compressed stream into a first distillation zone for the removal of bio-byproduct impurity and water vapor, the first distillation zone having an upper reflux stage, middle distillation stages and a lower reboiler stage; d) contacting an overhead vapor stream produced from the bio-byproduct impurity and water removal distillation zone with an adsorbent to produce a dried overhead stream; e) feeding the dried overhead stream into a second distillation zone for the removal of volatile impurity by the top, with the second distillation zone having an upper reflux stage, middle distillation stages and a lower reboiler stage; and f) collecting at the bottom of the distillation zone for the removal of volatile impurity the resulting purified liquid conjugated diolefin, e.g. butadiene.

The produced compound may be recovered by separating it from other components in the culture and purifying it using a variety of methods well known in the art. In the case of a volatile dialkene such as butadiene, it can be obtained in and isolated from the fermentation off-gas. Such separation methods include, for example, extraction procedures as well as methods that include continuous liquid-liquid extraction, pervaporation, membrane filtration, membrane separation, reverse osmosis, electrodialysis, distillation, crystallization, centrifugation, extractive filtration, ion exchange chromatography, size exclusion chromatography, adsorption chromatography, ultrafiltration, gas compression, extractive distillation using a solvent, solvent removal via distillation and final distillation. Recovery can comprise separating the compound from other components in the culture and purifying the compound; and further the separating or purifying can comprise collecting fermentation off-gas containing the compound, and further the separating and purifying can comprise one or more of compression of the off-gas, extractive distillation using a solvent, solvent removal via distillation and distillation. In one embodiment the method for producing the compounds, e.g. butadiene, further comprises a) obtaining a fermenter off-gas comprising the conjugated diolefin, e.g. butadiene, a volatile impurity, a bio-byproduct impurity and water vapor; b) compressing the fermenter off-gas in a multistage compression system to produce a compressed stream; c) feeding the compressed stream into a first distillation zone for the removal of bio-byproduct impurity and water vapor, the first distillation zone having an upper reflux stage, middle distillation stages and a lower reboiler stage; d) contacting an overhead vapor stream produced from the bio-byproduct impurity and water removal distillation zone with an adsorbent to produce a dried overhead stream; e) feeding the dried overhead stream into a second distillation zone for the removal of volatile impurity by the top, with the second distillation zone having an upper reflux stage, middle distillation stages and a lower reboiler stage; and f) collecting at the bottom of the distillation zone for the removal of volatile impurity the resulting purified liquid conjugated diolefin, e.g. butadiene.

In alternative embodiments, provided are microbial organisms, e.g., bacteria, for producing organic compounds, e.g., a butadiene, including producing desired compounds from renewable feedstocks, e.g., cheap renewable feedstocks such as molasses, sugar cane juice, sugars derived from biomass sources, including agricultural and wood waste, as well as C1 (one carbon compounds) feedstocks such as syngas and carbon dioxide. In alternative embodiments, polypeptides provided herein catalyze the conversion of a crotyl alcohol (but-2-en-1-ol) to a butadiene or a 1,3 butadiene, and to screen for polypeptides with this activity, any method for screening for enzyme activity, including high throughput screening (HTS) of a large population of cells for butadiene production that takes advantage of butadiene's high reactivity can be used.

In alternative embodiments, any method for detecting and/or isolating a butadiene (e.g., 1,3-butadiene), including a butadiene gas, produced in a cell as a product of a biosynthetic process, e.g., as a product of a microbial organism biosynthetic process using an enzyme as provided herein. In alternative embodiments, provided are compositions and methods for making and detecting butadiene, including butadiene gas.

In alternative embodiments, compositions and methods of the invention comprise use of any method or apparatus to detect an organic volatile, e.g., BD or BD gas, or a microbially-produced organic volatile (e.g., BD gas), by e.g., employing invasive sampling of either fermentation medium or headspace followed by subjecting the sample to gas chromatography or liquid chromatography often coupled with mass spectroscopy. In alternative embodiments, any "state-of-the-art" apparatus can be used, e.g., for high throughput" screening, e.g., an Agilent 7697A HEADSPACE SAMPLER™ (Agilent Technologies, Santa Clara Calif., USA) having a 111-vial capacity (10 mL, 20 mL, or 22 mL vials) and three 36-vial racks that can be exchanged while the headspace sampler is operating, or equivalent, can be used. In addition to limited sample configurations and numbers, the apparatus when coupled with GC or GC/MS would typically require 10-30 minutes to analyze each sample.

In alternative embodiments, apparatus are designed or configured for HTS of cell, e.g., microbial, e.g., bacterial, butadiene production by detecting and/or measuring BDE either directly or indirectly, e.g., by chemical or enzymatic reaction, e.g., in its soluble form in the cell culture medium, in its gas form in the cell culture headspace, in its soluble form in a liquid which trapped the BDE gas produced by the cell culture, and/or in its gaseous form in the headspace of that liquid.

In alternative embodiments, methods are automatable and suitable for use with laboratory robotic systems, eliminating or reducing operator involvement, while proving high-throughput screening. In some embodiments the apparatus exploit the volatile nature of BDE either by its direct detection in cell culture headspace or by trapping the off-gas BD followed by its detection in the trapped state.

Any of these described methods, or any method known in the art for detecting the generation of a product of an enzyme as provided herein, can be used to determine if a polypeptide has the requisite activity to be within the scope of this claimed invention.

Engineering Metabolic Pathways

In alternative embodiments, additional enzymes or nucleic acids encoding them (in addition to use of an enzyme as provided herein) are used (e.g., inserted in the same cell) to produce, or to increase the amount of, a substrate of an enzyme as provided herein, or a substrate of a metabolic pathway leading to production of a substrate of an enzyme as provided herein; for example, as described in FIG. 1, which illustrates an exemplary pathway enabling production of a crotyl alcohol (a substrate of an enzyme as provided herein) and a butadiene (a product of an enzyme as provided herein) from acetyl-CoA (a substrate of a metabolic pathway leading to production of a substrate of an enzyme as provided herein). As illustrated in FIG. 1, the crotyl alcohol and butadiene production can be carried out by the following enzymes: A) acetyl-CoA carboxylase, B) an acetoacetyl-CoA synthase, C) an acetyl-CoA:acetyl-CoA acyltransferase, D) an acetoacetyl-CoA reductase (ketone reducing), J) a 3-hydroxybutyryl-CoA dehydratase (HCD), K) a crotonyl-CoA reductase (aldehyde forming) (CCR-ALD), L) a crotonyl-CoA hydrolase (CCH), transferase (CCT) or synthetase (CCS), M) a crotonate reductase (CTR), N) a crotonaldehyde reductase (CAR), U) a crotonyl-CoA reductase (alcohol forming) (CCR—OH), and S) chemical dehydration or VD) a crotyl alcohol dehydratase (CAD) as described herein.

Figure 6:
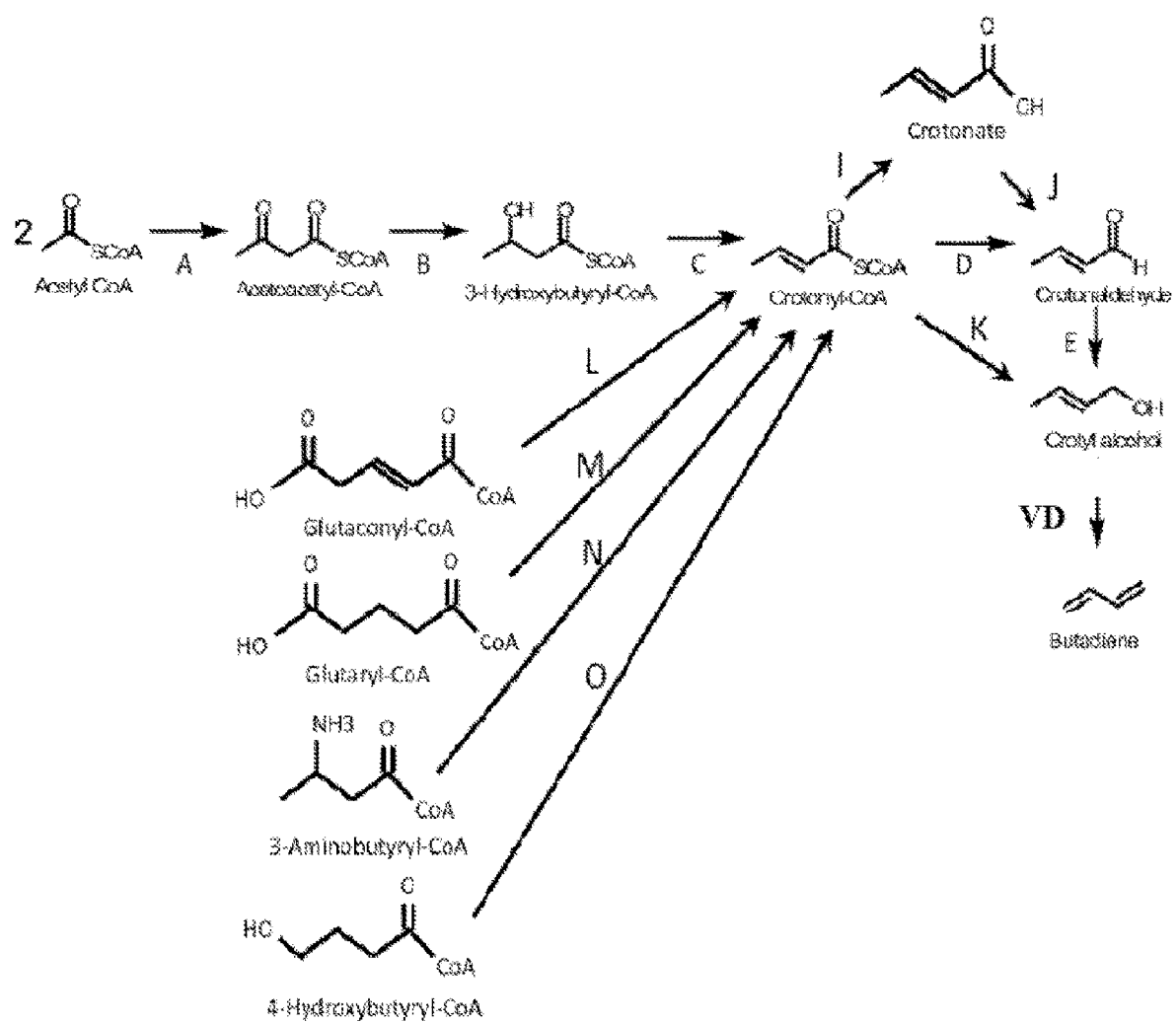
FIG. 6 schematically illustrates alternative pathways for the production of crotyl alcohol, a substrate for exemplary enzymatically active polypeptides provided herein; and also illustrates exemplary pathways for production of butadiene from acetyl-CoA, glutaconyl-CoA, glutaryl-CoA, 3-aminobutyryl-CoA or 4-hydroxybutyryl-CoA via crotyl alcohol (wherein in alternative embodiments, one, several or all of these compounds can be added to a cell, a cell culture system or a bioreactor as provided herein); also illustrated are exemplary enzymes for transformation of the identified substrates to products, and the enzymes include: A. acetyl-CoA:acetyl-CoA acyltransferase, B. acetoacetyl-CoA reductase, C. 3-hydroxybutyryl-CoA dehydratase, D. crotonyl-CoA reductase (aldehyde forming), E. crotonaldehyde reductase (alcohol forming), I. crotonyl-CoA hydrolase, synthetase, transferase, J. crotonate reductase, K. crotonyl-CoA reductase (alcohol forming), L. glutaconyl-CoA decarboxylase, M., glutaryl-CoA dehydrogenase, N. 3-aminobutyryl-CoA deaminase, O. 4-hydroxybutyryl-CoA dehydratase, and VD) a crotyl alcohol dehydratase (CAD) (wherein in alternative embodiments, one several or all of the enzymes of A through O are expressed, e.g., recombinantly expressed, in an engineered cell as provided herein). A crotyl alcohol dehydratase (CAD) is an alternative name for the enzymes of the present invention that recognizes crotyl alcohol as substrate for conversion to butadiene.
Figure 7:
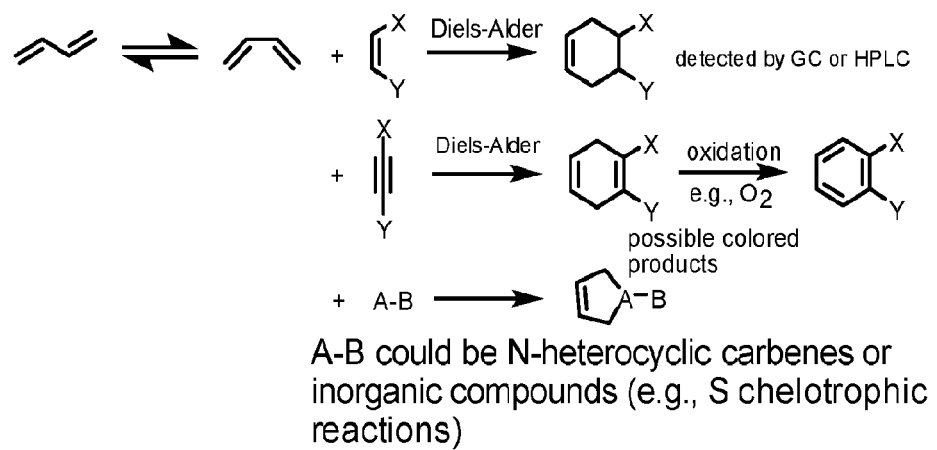
FIG. 7, illustrates exemplary reactions for detection of butadiene, e.g., in high through-put screening (HTS), as described herein.
Figure 8A:
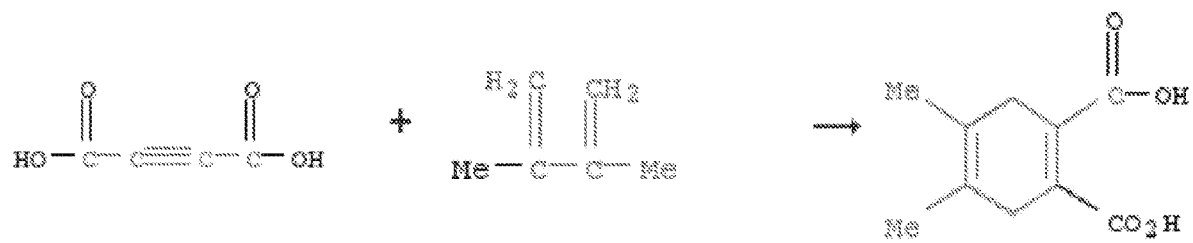
FIGS. 8A, 8B and 8C: illustrate exemplary reactions for detection of butadiene, e.g., as described herein.
Figure 8B:
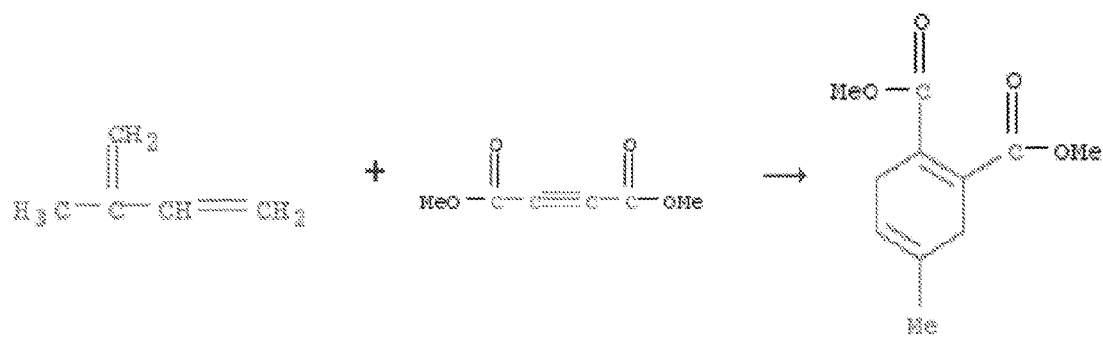
Figure 8C:
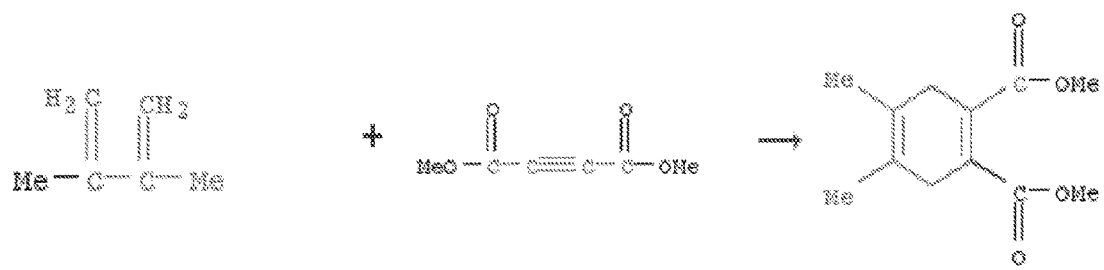
Figure 9:
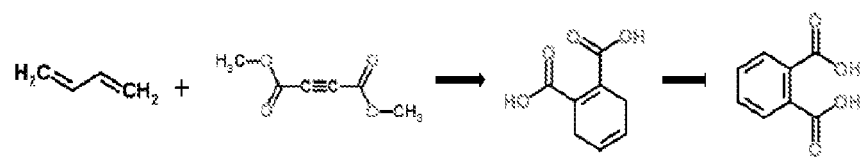
FIG. 9 illustrates exemplary reactions for detection of butadiene, e.g., as described herein.
Figure 10:
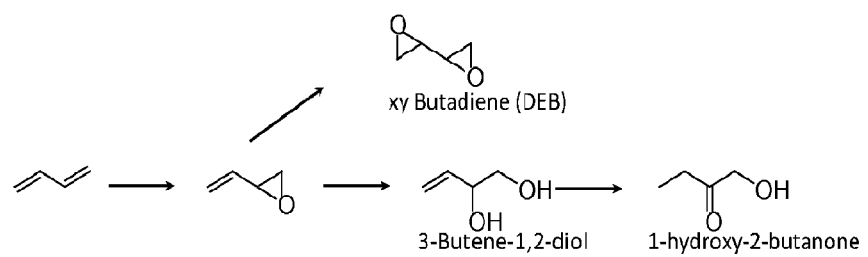
FIG. 10 illustrates exemplary enzyme pathways for use in the detection of butadiene, e.g., as described herein. Exemplary enzyme reactions for converting butadiene to 3-butene-1,2-diol or 1-hydroxy-2-butanone are shown. Enzymes are: A. butadiene monooxygenase, B. butadiene monoxide hydrolase, C. 3-butene-1,2-diol dehydrogenase, D. butadiene monoxide monooxygenase.

Any microbe producing a substrate or engineered to produce a substrate for the enzymes described herein are suitable hosts and can be used to practice this invention. For example, exemplary microbes can be engineered to produce crotyl alcohol, e.g., as described in International patent application publications WO2011140171, WO2012106516 and WO2013090915A1, the latter also disclosing use of a linalool dehydratase for enzymatic conversion of crotyl alcohol to butadiene. FIG. 1 also illustrates exemplary enzymatic steps to crotyl alcohol from acetyl-CoA (as described e.g., in WO2011140171 and WO2012106516) and its conversion to butadiene via a vinylisomerase-dehydratase (FIG. 1, step VD), which are the enzymes described herein. FIG. 6 provides illustrates alternative pathways for the production of crotyl alcohol, and in alternative embodiments, enzymes provided herein can: enzymatically catalyze the conversion of a crotyl alcohol (but-2-en-1-ol) to a 3-buten-2-ol; enzymatically catalyze the conversion of a 3-buten-2-ol to a butadiene or a 1,3 butadiene; and/or enzymatically catalyze the conversion of a crotyl alcohol (but-2-en-1-ol) to a butadiene or a 1,3 butadiene; and any one, several or all of the intermediate or precursor compounds and/or the enzymes that make them can be added to an engineered cell. The following provides details of exemplary host microbes and useful enzymes for producing crotyl alcohol for use with the enzymes described herein.

Exemplary Crotyl Alcohol and Butadiene Synthesis Enzymes

Provided are exemplary genes and enzymes that can be used for conversion of acetyl-CoA to crotyl alcohol and to butadiene as depicted in the pathways of FIG. 1 and FIG. 6; for example, in alternative embodiments, engineered cells as provided herein comprises one or several of these exemplary genes and/or enzymes in additional to a nucleic acid or enzyme as provided herein.

FIG. 1 Step A. Acetyl-CoA Carboxylase

Acetyl-CoA carboxylase (EC 6.4.1.2) catalyzes the ATP-dependent carboxylation of acetyl-CoA to malonyl-CoA. This enzyme is biotin dependent and is the first reaction of fatty acid biosynthesis initiation in several organisms. Exemplary enzymes are encoded by accABCD of *E. coli* (Davis et al, *J Biol Chem* 275:28593-8 (2000)), ACC1 of *Saccharomyces cerevisiae* and homologs (Sumper et al, *Methods Enzym* 71:34-7 (1981)).

| Protein | GenBank ID | GI Number | Organism |
|---|---|---|---|
| ACC1 | CAA96294.1 | 1302498 | *Saccharomyces* |
| KLLA0F06072g | XP_455355.1 | 50310667 | *Kluyveromyces lactis* |
| ACC1 | XP_718624.1 | 68474502 | *Candida albicans* |
| YALI0C11407p | XP_501721.1 | 50548503 | *Yarrowia lipolytica* |
| ANI_1_1724104 | XP_001395476.1 | 145246454 | *Aspergillus niger* |
| accA | AAC73296.1 | 1786382 | *Escherichia coli* |
| accB | AAC76287.1 | 1789653 | *Escherichia coli* |
| accC | AAC76288.1 | 1789654 | *Escherichia coli* |
| accD | AAC75376.1 | 1788655 | *Escherichia coli* |

FIG. 1: Step B: Acetoacetyl-CoA Synthase

The conversion of malonyl-CoA and acetyl-CoA substrates to acetoacetyl-CoA can be catalyzed by a CoA synthetase in the 2.3.1 family of enzymes. Several enzymes catalyzing the CoA synthetase activities have been described in the literature and represent suitable candidates.

3-Oxoacyl-CoA products such as acetoacetyl-CoA, 3-oxopentanoyl-CoA, 3-oxo-5-hydroxypentanoyl-CoA can be synthesized from acyl-CoA and malonyl-CoA substrates by 3-oxoacyl-CoA synthases. As enzymes in this class catalyze an essentially irreversible reaction, they are particularly useful for metabolic engineering applications for overproducing metabolites, fuels or chemicals derived from 3-oxoacyl-CoA intermediates such as acetoacetyl-CoA. Acetoacetyl-CoA synthase, for example, has been heterologously expressed in organisms that biosynthesize butanol (Lan et al, PNAS USA (2012)) and poly-(3-hydroxybutyrate) (Matsumoto et al, *Biosci Biotech Biochem*, 75:364-366 (2011). An acetoacetyl-CoA synthase (EC 2.3.1.194) enzyme (FhsA) has been characterized in the soil bacterium *Streptomyces* sp. CL190 where it participates in mevalonate biosynthesis (Okamura et al, PNAS USA 107:11265-70 (2010)). Other acetoacetyl-CoA synthase genes can be identified by sequence homology to fhsA.

| Protein | GenBank ID | GI | Organism |
|---|---|---|---|
| fhsA | BAJ83474.1 | 32530222 | *Streptomyces* sp CL 190 |
| AB183750.1:11991 . . . 1297 | BAD86806.1 | 57753876 | *Streptomyces* sp. KO-3988 |
| epzT | ADQ43379.1 | 31219095 | *Streptomyces* |
| ppzT | CAX48662.1 | 23862352 | *Streptomyces anulatus* |
| O3I_22085 | ZP_09840373. | 37881744 | *Nocardia brasiliensis* |

FIG. 1: Step C: Acetyl-CoA:acetyl-CoA Acyltransferase (Acetoacetyl-CoA thiolase)

Acetoacetyl-CoA thiolase (also known as acetyl-CoA acetyltransferase) converts two molecules of acetyl-CoA into one molecule each of acetoacetyl-CoA and CoA. Exemplary acetoacetyl-CoA thiolase enzymes include the gene products of atoB from *E. coli* (Martin et al., *Nat. Biotechnol* 21:796-802 (2003)), thlA and thlB from *C. acetobutylicum* (Hanai et al., *Appl Environ Microbiol* 73:7814-7818 (2007); Winzer et al., *J. Mol. Microbiol Biotechnol* 2:531-541 (2000), and ERG10 from *S. cerevisiae* Hiser et al., *J. Biol. Chem.* 269:31383-31389 (1994)). The acetoacetyl-CoA thiolase from *Zoogloea ramigera* is irreversible in the biosynthetic direction and a crystal structure is available (Merilainen et al, *Biochem* 48: 11011-25 (2009)). These genes/proteins are identified in the Table below.

| Gene | GenBank ID | GI Number | Organism |
|---|---|---|---|
| AtoB | NP_416728 | 16130161 | *Escherichia coli* |
| ThlA | NP_349476.1 | 15896127 | *Clostridium* |
| ThlB | NP_149242.1 | 15004782 | *Clostridium* |
| ERG10 | NP_015297 | 6325229 | *Saccharomyces* |
| phbA | P07097.4 | 135759 | *Zoogloea ramigera* |

FIG. 1: Step D: Acetoacetyl-CoA Reductase.

A suitable enzyme activity is 1.1.1.a Oxidoreductase (oxo to alcohol). See herein. In addition, Acetoacetyl-CoA reductase (EC 1.1.1.36) catalyzes the reduction of acetoacetyl-CoA to 3-hydroxybutyryl-CoA. This enzyme participates in the acetyl-CoA fermentation pathway to butyrate in several species of Clostridia and has been studied in detail (Jones et al., *Microbiol Rev.* 50:484-524 (1986)). Acetoacetyl-CoA reductase also participates in polyhydroxybutyrate biosynthesis in many organisms, and has also been used in metabolic engineering applications for overproducing PHB and 3-hydroxyisobutyrate (Liu et al., *Appl. Microbiol. Biotechnol.* 76:811-818 (2007); Qui et al., *Appl. Microbiol. Biotechnol.* 69:537-542 (2006)). The enzyme from *Clostridium acetobutylicum*, encoded by hbd, has been cloned and functionally expressed in *E. coli* (Youngleson et al., *J Bacteriol.* 171:6800-6807 (1989)). Additional gene candidates include phbB from *Zoogloea ramigera* (Ploux et al., *Eur. J Biochem.* 174:177-182 (1988)) and phaB from *Rhodobacter sphaeroides* (Alber et al., *Mol. Microbiol* 61:297-309 (2006)). The *Z. ramigera* gene is NADPH-dependent and the gene has been expressed in *E. coli* (Peoples et al., *Mol. Microbiol* 3:349-357 (1989)). Substrate specificity studies on the gene led to the conclusion that it could accept 3-oxopropionyl-CoA as a substrate besides acetoacetyl-CoA (Ploux et al., *Eur. J Biochem.* 174:177-182 (1988)). Additional genes include phaB in *Paracoccus denitrificans*, Hbd1 (C-terminal domain) and Hbd2 (N-terminal domain) in *Clostridium kluyveri* (Hillmer and Gottschalk, *Biochim. Biophys. Acta* 3334:12-23 (1974)) and HSD17B10 in *Bos taurus* (Wakil et al., *J Biol. Chem.* 207:631-638 (1954)). The enzyme from *Paracoccus denitrificans* has been functionally expressed and characterized in *E. coli*

(Yabutani et al., *FEMS Microbiol Lett.* 133:85-90 (1995)). A number of similar enzymes have been found in other species of Clostridia and in *Metallosphaera sedula* (Berg et al., Science. 318:1782-1786 (2007)). The enzyme from *Candida tropicalis* is a component of the peroxisomal fatty acid beta-oxidation multifunctional enzyme type 2 (MFE-2). The dehydrogenase B domain of this protein is catalytically active on acetoacetyl-CoA. The domain has been functionally expressed in *E. coli*, a crystal structure is available, and the catalytic mechanism is well-understood (Ylianttila et al., *Biochem Biophys Res Commun* 324:25-30 (2004); Ylianttila et al., *J Mol Biol* 358:1286-1295 (2006)).

| Protein | Genbank ID | GI Number | Organism |
| --- | --- | --- | --- |
| fadB | P21177.2 | 119811 | *Escherichia coli* |
| fadJ | P77399.1 | 3334437 | *Escherichia coli* |
| paaH | NP_415913.1 | 16129356 | *Escherichia coli* |
| Hbd2 | EDK34807.1 | 146348271 | *Clostridium kluyveri* |
| Hbd1 | EDK32512.1 | 146345976 | *Clostridium kluyveri* |
| phaC | NP_745425.1 | 26990000 | *Pseudomonas putida* |
| paaC | ABF82235.1 | 106636095 | *Pseudomonas fluorescens* |
| HSD17B10 | O02691.3 | 3183024 | *Bos taurus* |
| phbB | P23238.1 | 130017 | *Zoogloea ramigera* |
| phaB | YP_353825.1 | 77464321 | *Rhodobacter sphaeroides* |
| phaB | BAA08358 | 675524 | *Paracoccus denitrificans* |
| Hbd | NP_349314.1 | 15895965 | *Clostridium acetobutylicum* |
| Hbd | AAM14586.1 | 20162442 | *Clostridium beijerinckii* |
| Msed_1423 | YP_001191505 | 146304189 | *Metallosphaera sedula* |
| Msed_0399 | YP_001190500 | 146303184 | *Metallosphaera sedula* |
| Msed_0389 | YP_001190490 | 146303174 | *Metallosphaera sedula* |
| Msed_1993 | YP_001192057 | 146304741 | *Metallosphaera sedula* |
| Fox2 | Q02207 | 399508 | *Candida tropicalis* |

FIG. 1: Step J: 3-Hydroxybutyryl-CoA Dehydratase

An EC 4.2.1. Hydro-lyase provides suitable enzyme activity, and are described below and herein. The enoyl-CoA hydratase of *Pseudomonas putida*, encoded by ech, catalyzes the conversion of 3-hydroxybutyryl-CoA to crotonyl-CoA (Roberts et al., *Arch. Microbiol* 117:99-108 (1978)). This transformation is also catalyzed by the crt gene product of *Clostridium acetobutylicum*, the crt1 gene product of *C. kluyveri*, and other clostridial organisms Atsumi et al., *Metab Eng* 10:305-311 (2008); Boynton et al., *J Bacteriol*. 178:3015-3024 (1996); Hillmer et al., *FEBS Lett*. 21:351-354 (1972)). Additional enoyl-CoA hydratase candidates are phaA and phaB, of *P. putida*, and paaA and paaB from *P. fluorescens* (Olivera et al., *Proc. Natl. Acad. Sci USA*. 95:6419-6424 (1998)). The gene product of pimF in *Rhodopseudomonas palustris* is predicted to encode an enoyl-CoA hydratase that participates in pimeloyl-CoA degradation (Harrison et al., *Microbiology* 151:727-736 (2005)). Lastly, a number of *Escherichia coli* genes have been shown to demonstrate enoyl-CoA hydratase functionality including maoC (Park et al., *J Bacteriol*. 185:5391-5397 (2003)), paaF (Ismail et al., *Eur. J Biochem*. 270:3047-3054 (2003); Park et al., *Appl. Biochem. Biotechnol* 113-116:335-346 (2004); Park et al., *Biotechnol Bioeng* 86:681-686 (2004)) and paaG (Ismail et al., *Eur. J Biochem*. 270:3047-3054 (2003); Park and Lee, *Appl. Biochem. Biotechnol* 113-116:335-346 (2004); Park and Yup, *Biotechnol Bioeng* 86:681-686 (2004)).

| Protein | GenBank No. | GI No. | Organism |
| --- | --- | --- | --- |
| ech | NP_745498.1 | 26990073 | *Pseudomonas putida* |
| crt | NP_349318.1 | 15895969 | *Clostridium acetobutylicum* |
| crt1 | YP_001393856 | 153953091 | *Clostridium kluyveri* |
| phaA | ABF82233.1 | 26990002 | *Pseudomonas putida* |
| phaB | ABF82234.1 | 26990001 | *Pseudomonas putida* |
| paaA | NP_745427.1 | 106636093 | *Pseudomonas fluorescens* |
| paaB | NP_745426.1 | 106636094 | *Pseudomonas fluorescens* |
| maoC | NP_415905.1 | 16129348 | *Escherichia coli* |
| paaF | NP_415911.1 | 16129354 | *Escherichia coli* |
| paaG | NP_415912.1 | 16129355 | *Escherichia coli* |

FIG. 1: Step K: Crotonyl-CoA Reductase (Aldehyde Forming)

An EC 1.2.1.b Oxidoreductase (acyl-CoA to aldehyde) provides suitable enzyme activity. Acyl-CoA reductases in the 1.2.1 family reduce an acyl-CoA to its corresponding aldehyde. Several acyl-CoA reductase enzymes have been described in the open literature and represent suitable candidates for this step. Acyl-CoA reductases or acylating aldehyde dehydrogenases reduce an acyl-CoA to its corresponding aldehyde. Exemplary enzymes include fatty acyl-CoA reductase, succinyl-CoA reductase (EC 1.2.1.76), acetyl-CoA reductase, butyryl-CoA reductase, propionyl-CoA reductase (EC 1.2.1.3) and others shown in the table below.

| EC Number | Enzyme name |
| --- | --- |
| 1.2.1.10 | Acetaldehyde dehydrogenase (acetylating) |
| 1.2.1.42 | (Fatty) acyl-CoA reductase |
| 1.2.1.44 | Cinnamoyl-CoA reductase |
| 1.2.1.50 | Long chain fatty acyl-CoA reductase |
| 1.2.1.57 | Butanal dehydrogenase |
| 1.2.1.75 | Malonate semialdehyde dehydrogenase |
| 1.2.1.76 | Succinate semialdehyde dehydrogenase |
| 1.2.1.81 | Sulfoacetaldehyde dehydrogenase |
| 1.2.1.- | Propanal dehydrogenase |
| 1.2.1.- | Hexanal dehydrogenase |
| 1.2.1.- | 4-Hydroxybutyraldehyde dehydrogenase |

Exemplary fatty acyl-CoA reductases enzymes are encoded by acr1 of *Acinetobacter calcoaceticus* (Reiser, Journal of Bacteriology 179:2969-2975 (1997)) and *Acinetobacter* sp. M-1 (Ishige et al., Appl. Environ. Microbiol. 68:1192-1195 (2002)). Enzymes with succinyl-CoA reductase activity are encoded by sucD of *Clostridium kluyveri* (Sohling, J. Bacteriol. 178:871-880 (1996)) and sucD of *P. gingivalis* (Takahashi, J. Bacteriol 182:4704-4710 (2000)). Additional succinyl-CoA reductase enzymes participate in the 3-hydroxypropionate/4-hydroxybutyrate cycle of thermophilic archaea including *Metallosphaera sedula* (Berg et al., Science 318:1782-1786 (2007)) and *Thermoproteus neutrophilus* (Ramos-Vera et al., *J Bacteriol.*, 191:4286-4297 (2009)). The *M. sedula* enzyme, encoded by Msed_0709, is strictly NADPH-dependent and also has malonyl-CoA reductase activity. The *T. neutrophilus* enzyme is active with both NADPH and NADH. The enzyme acylating acetaldehyde dehydrogenase in *Pseudomonas* sp, encoded by bphG, is yet another as it has been demonstrated to oxidize and acylate acetaldehyde, propionaldehyde, butyraldehyde, isobutyraldehyde and formaldehyde (Powlowski, J. Bacteriol. 175:377-385 (1993)). In addition to reducing acetyl-CoA to ethanol, the enzyme encoded by adhE in *Leuconostoc mesenteroides* has been shown to oxidize the branched chain compound isobutyraldehyde to isobutyryl-CoA (Kazahaya, J. Gen. Appl. Microbiol. 18:43-55 (1972); and Koo et al., Biotechnol Lett.

27:505-510 (2005)). Butyraldehyde dehydrogenase catalyzes a similar reaction, conversion of butyryl-CoA to butyraldehyde, in solventogenic organisms such as *Clostridium saccharoperbutylacetonicum* (Kosaka et al., Biosci Biotechnol Biochem., 71:58-68 (2007)). Exemplary propionyl-CoA reductase enzymes include pduP of *Salmonella typhimurium* LT2 (Leal, Arch. Microbiol. 180:353-361 (2003)) and eutE from *E. coli* (Skraly, WO Patent No. 2004/024876). The propionyl-CoA reductase of *Salmonella typhimurium* LT2, which naturally converts propionyl-CoA to propionaldehyde, also catalyzes the reduction of 5-hydroxyvaleryl-CoA to 5-hydroxypentanal (WO 2010/068953A2).

aspartyl-4-phosphate to aspartate semialdehyde. Additional gene candidates can be found by sequence homology to proteins in other organisms including *Sulfolobus solfataricus* and *Sulfolobus acidocaldarius* and have been listed below. Yet another candidate for CoA-acylating aldehyde dehydrogenase is the ald gene from *Clostridium beijerinckii* (Toth, Appl. Environ. Microbiol. 65:4973-4980 (1999). This enzyme has been reported to reduce acetyl-CoA and butyryl-CoA to their corresponding aldehydes. This gene is very similar to eutE that encodes acetaldehyde dehydrogenase of *Salmonella typhimurium* and *E. coli* (Toth, Appl. Environ. Microbiol. 65:4973-4980 (1999).

| Protein | GenBank ID | GI Number | Organism |
|---|---|---|---|
| Acr1 | YP_047869.1 | 50086359 | *Acinetobacter calcoaceticus* |
| Acr1 | AAC45217 | 1684886 | *Acinetobacter baylyi* |
| Acr1 | BAB85476.1 | 18857901 | *Acinetobacter* sp. Strain M-1 |
| MSED_0709 | YP_001190808.1 | 146303492 | *Metallosphaera sedula* |
| Tneu_0421 | ACB39369.1 | 170934108 | *Thermoproteus neutrophilus* |
| sucD | P38947.1 | 172046062 | *Clostridium kluyveri* |
| sucD | NP_904963.1 | 34540484 | *Porphyromonas gingivalis* |
| bphG | BAA03892.1 | 425213 | *Pseudomonas* sp |
| adhE | AAV66076.1 | 55818563 | *Leuconostoc mesenteroides* |
| bld | AAP42563.1 | 31075383 | *Clostridium saccharoperbutylacetonicum* |
| pduP | NP_460996 | 16765381 | *Salmonella typhimurium* LT2 |
| eutE | NP_416950 | 16130380 | *Escherichia coli* |

An additional enzyme that converts an acyl-CoA to its corresponding aldehyde is malonyl-CoA reductase which transforms malonyl-CoA to malonic semialdehyde. Malonyl-CoA reductase is a key enzyme in autotrophic carbon fixation via the 3-hydroxypropionate cycle in thermoacidophilic archaeal bacteria (Berg, Science 318:1782-1786 (2007); and Thauer, Science 318:1732-1733 (2007)). The enzyme utilizes NADPH as a cofactor and has been characterized in *Metallosphaera* and *Sulfolobus* sp. (Alber et al., J. Bacteriol. 188:8551-8559 (2006); and Hugler, J. Bacteriol. 184:2404-2410 (2002)). The enzyme is encoded by Msed_0709 in *Metallosphaera sedula* (Alber et al., J. Bacteriol. 188:8551-8559 (2006); and Berg, Science 318:1782-1786 (2007)). A gene encoding a malonyl-CoA reductase from *Sulfolobus tokodaii* was cloned and heterologously expressed in *E. coli* (Alber et al., J. Bacteriol 188:8551-8559 (2006). This enzyme has also been shown to catalyze the conversion of methylmalonyl-CoA to its corresponding aldehyde (WO2007141208 (2007)). Although the aldehyde dehydrogenase functionality of these enzymes is similar to the bifunctional dehydrogenase from *Chloroflexus aurantiacus*, there is little sequence similarity. Both malonyl-CoA reductase enzyme candidates have high sequence similarity to aspartate-semialdehyde dehydrogenase, an enzyme catalyzing the reduction and concurrent dephosphorylation of

| Protein | GenBank ID | GI Number | Organism |
|---|---|---|---|
| Msed_0709 | YP_001190808.1 | 146303492 | *Metallosphaera sedula* |
| Mcr | NP_378167.1 | 15922498 | *Sulfolobus tokodaii* |
| asd-2 | NP_343563.1 | 15898958 | *Sulfolobus solfataricus* |
| Saci_2370 | YP_256941.1 | 70608071 | *Sulfolobus acidocaldarius* |
| Ald | AAT66436 | 49473535 | *Clostridium beijerinckii* |
| eutE | AAA80209 | 687645 | *Salmonella typhimurium* |

4-Hydroxybutyryl-CoA reductase catalyzes the reduction of 4-hydroxybutyryl-CoA to its corresponding aldehyde. Several acyl-CoA dehydrogenases are capable of catalyzing this activity. The succinate semialdehyde dehydrogenases (SucD) of *Clostridium kluyveri* and *P. gingivalis* were shown in ref. (WO/2008/115840) to convert 4-hydroxybutyryl-CoA to 4-hydroxybutanal as part of a pathway to produce 1,4-butanediol. Many butyraldehyde dehydrogenases are also active on 4-hydroxybutyraldehyde, including bld of *Clostridium saccharoperbutylacetonicum* and bphG of *Pseudomonas* sp (Powlowski et al., J. Bacteriol. 175:377-385 (1993)). Yet another candidate is the ald gene from *Clostridium beijerinckii* (Toth, Appl. Environ. Microbiol. 65:4973-4980 (1999). This gene is very similar to eutE that encodes acetaldehyde dehydrogenase of *Salmonella typhimurium* and *E. coli* (Toth, Appl. Environ. Microbiol. 65:4973-4980 (1999). These and additional proteins with 4-hydroxybutyryl-CoA reductase activity are identified below.

| Protein | GenBank ID | GI Number | Organism |
|---|---|---|---|
| bphG | BAA03892.1 | 425213 | *Pseudomonas* sp |
| ald | YP_001310903.1 | 150018649 | *Clostridium beijerinckii* NCIMB 8052 |
| Ald | ZP_03778292.1 | 225569267 | *Clostridium hylemonae* DSM 15053 |
| Ald | ZP_03705305.1 | 225016072 | *Clostridium methylpentosum* DSM 5476 |
| Ald | ZP_03715465.1 | 225026273 | *Eubacterium hallii* DSM 3353 |
| Ald | ZP_01962381.1 | 153809713 | *Ruminococcus obeum* ATCC 29174 |
| Ald | YP_003701164.1 | 297585384 | *Bacillus selenitireducens* MLS 10 |
| Ald | AAP42563.1 | 31075383 | *Clostridium saccharoperbutylacetonicum* N1-4 |

| Protein | GenBank ID | GI Number | Organism |
|---|---|---|---|
| Ald | YP_795711.1 | 116334184 | *Lactobacillus brevis* ATCC 367 |
| Ald | YP_002434126.1 | 218782808 | *Desulfatibacillum alkenivorans* AK-01 |
| Ald | YP_001558295.1 | 160879327 | *Clostridium phytofermentans* ISDg |
| Ald | ZP_02089671.1 | 160942363 | *Clostridium bolteae* ATCC BAA-613 |
| Ald | ZP_01222600.1 | 90414628 | *Photobacterium profundum* 3TCK |
| Ald | YP_001452373.1 | 157145054 | *Citrobacter koseri* ATCC BAA-895 |
| Ald | NP_460996.1 | 16765381 | *Salmonella enterica typhimurium* |
| Ald | YP_003307836.1 | 269119659 | *Sebaldella termitidis* ATCC 33386 |
| Ald | ZP_04969437.1 | 254302079 | *Fusobacterium nucleatum* subsp. *polymorphum* ATCC 10953 |
| Ald | YP_002892893.1 | 237808453 | *Tolumonas auensis* DSM 9187 |
| Ald | YP_426002.1 | 83592250 | *Rhodospirillum rubrum* ATCC 11170 |

FIG. 1: Step L: Crotonyl-CoA Hydrolase, Transferase or Synthetase

An EC 3.1.2.a CoA hydrolase, EC 2.8.3.a CoA transferase, and/or an EC 6.2.1.a CoA synthetase provide suitable enzyme activity, and are described herein and in the following sections.

EC 3.1.2.a CoA Hydrolase. Enzymes in the 3.1.2 family hydrolyze acyl-CoA molecules to their corresponding acids. Several such enzymes have been described in the literature and represent suitable candidates for these steps.

For example, the enzyme encoded by acot12 from *Rattus norvegicus* brain (Robinson et al., *Biochem. Biophys. Res. Commun.* 71:959-965 (1976)) can react with butyryl-CoA, hexanoyl-CoA and malonyl-CoA. The human dicarboxylic acid thioesterase, encoded by acot8, exhibits activity on glutaryl-CoA, adipyl-CoA, suberyl-CoA, sebacyl-CoA, and dodecanedioyl-CoA (Westin et al., *J. Biol. Chem.* 280: 38125-38132 (2005)). The closest *E. coli* homolog to this enzyme, tesB, can also hydrolyze a range of CoA thiolesters (Naggert et al., *J Biol Chem* 266:11044-11050 (1991)). A similar enzyme has also been characterized in the rat liver (Deana R., *Biochem Int* 26:767-773 (1992)). Additional enzymes with hydrolase activity in *E. coli* include ybgC, paaI, and ybdB (Kuznetsova, et al., *FEMS Microbiol Rev*, 2005, 29(2):263-279; Song et al., *J Biol Chem*, 2006, 281(16):11028-38). Though its sequence has not been reported, the enzyme from the mitochondrion of the pea leaf has a broad substrate specificity, with demonstrated activity on acetyl-CoA, propionyl-CoA, butyryl-CoA, palmitoyl-CoA, oleoyl-CoA, succinyl-CoA, and crotonyl-CoA (Zeiher et al., *Plant. Physiol.* 94:20-27 (1990)) The acetyl-CoA hydrolase, ACH1, from *S. cerevisiae* represents another candidate hydrolase (Buu et al., *J. Biol. Chem.* 278:17203-17209 (2003)).

| Protein | GenBank Accession No. | GI Number | Organism |
|---|---|---|---|
| Acot12 | NP_570103.1 | 18543355 | *Rattus norvegicus* |
| tesB | NP_414986 | 16128437 | *Escherichia coli* |
| acot8 | CAA15502 | 3191970 | *Homo sapiens* |
| acot8 | NP_570112 | 51036669 | *Rattus norvegicus* |
| tesA | NP_415027 | 16128478 | *Escherichia coli* |
| ybgC | NP_415264 | 16128711 | *Escherichia coli* |
| paaI | NP_415914 | 16129357 | *Escherichia coli* |
| ybdB | NP_415129 | 16128580 | *Escherichia coli* |
| ACH1 | NP_009538 | 6319456 | *Saccharomyces cerevisiae* |

Additional hydrolase enzymes include 3-hydroxyisobutyryl-CoA hydrolase which has been described to efficiently catalyze the conversion of 3-hydroxyisobutyryl-CoA to 3-hydroxyisobutyrate during valine degradation (Shimomura et al., *J Biol Chem.* 269:14248-14253 (1994)). Genes encoding this enzyme include hibch of *Rattus norvegicus* (Shimomura et al., *Methods Enzymol.* 324:229-240 (2000)) and *Homo sapiens* (Shimomura et al., supra). Similar gene candidates can also be identified by sequence homology, including hibch of *Saccharomyces cerevisiae* and BC_2292 of *Bacillus cereus*.

| Protein | GenBank No. | GI Number | Organism |
|---|---|---|---|
| hibch | Q5XIE6.2 | 146324906 | *Rattus norvegicus* |
| hibch | Q6NVY1.2 | 146324905 | *Homo sapiens* |
| hibch | P28817.2 | 2506374 | *Saccharomyces cerevisiae* |
| BC_2292 | AP09256 | 29895975 | *Bacillus cereus* |

EC 2.8.3.a CoA transferase. Enzymes in the 2.8.3 family catalyze the reversible transfer of a CoA moiety from one molecule to another. Several CoA transferase enzymes have been described in the open literature and represent suitable candidates for these steps. These are described below.

Many transferases have broad specificity and thus can utilize CoA acceptors as diverse as acetate, succinate, propionate, butyrate, 2-methylacetoacetate, 3-ketohexanoate, 3-ketopentanoate, valerate, crotonate, 3-mercaptopropionate, propionate, vinylacetate, butyrate, among others. For example, an enzyme from *Roseburia* sp. A2-183 was shown to have butyryl-CoA:acetate:CoA transferase and propionyl-CoA:acetate:CoA transferase activity (Charrier et al., Microbiology 152, 179-185 (2006)). Close homologs can be found in, for example, *Roseburia intestinalis* L1-82, *Roseburia inulinivorans* DSM 16841, *Eubacterium rectale* ATCC 33656. Another enzyme with propionyl-CoA transferase activity can be found in *Clostridium propionicum* (Selmer et al., *Eur J Biochem* 269, 372-380 (2002)). This enzyme can use acetate, (R)-lactate, (S)-lactate, acrylate, and butyrate as the CoA acceptor (Selmer et al., *Eur J Biochem* 269, 372-380 (2002); Schweiger and Buckel, *FEBS Letters*, 171 (1) 79-84 (1984)). Close homologs can be found in, for example, *Clostridium novyi* NT, *Clostridium beijerinckii* NCIMB 8052, and *Clostridium botulinum* C str. Eklund. YgfH encodes a propionyl CoA:succinate CoA transferase in *E. coli* (Haller et al., *Biochemistry*, 39(16) 4622-4629). Close homologs can be found in, for example, *Citrobacter youngae* ATCC 29220, *Salmonella enterica* subsp. *arizonae serovar*, and *Yersinia intermedia* ATCC 29909.

| Protein | GenBankID | GI Number | Organism |
| --- | --- | --- | --- |
| Ach1 | AAX19660.1 | 60396828 | Roseburia sp. A2-183 |
| ROSINTL182_07121 | ZP_04743841.2 | 257413684 | Roseburia intestinalis L1-82 |
| ROSEINA2194_03642 | ZP_03755203.1 | 225377982 | Roseburia inulinivorans |
| EUBREC_3075 | YP_002938937.1 | 238925420 | Eubacterium rectale ATCC 33656 |
| Pct | CAB77207.1 | 7242549 | Clostridium propionicum |
| NT01CX_2372 | YP_878445.1 | 118444712 | Clostridium novyi NT |
| Cbei_4543 | YP_001311608.1 | 150019354 | Clostridium beijerinckii |
| CBC_A0889 | ZP_02621218.1 | 168186583 | Clostridium botulinum C str. Eklund |
| ygfH | NP_417395.1 | 16130821 | Escherichia coli |
| CIT292_04485 | ZP_03838384.1 | 227334728 | Citrobacter youngae ATCC 29220 |
| SARI_04582 | YP_001573497.1 | 161506385 | Salmonella enterica subsp. arizonae serovar |
| yinte0001_14430 | ZP_04635364.1 | 238791727 | Yersinia intermedia ATCC 29909 |

An additional candidate enzyme is the two-unit enzyme encoded by pcaI and pcaJ in *Pseudomonas*, which has been shown to have 3-oxoadipyl-CoA/succinate transferase activity (Kaschabek et al., supra). Similar enzymes based on homology exist in *Acinetobacter* sp. ADP1 (Kowalchuk et al., *Gene* 146:23-30 (1994)) and *Streptomyces coelicolor*. Additional exemplary succinyl-CoA:3:oxoacid-CoA transferases are present in *Helicobacter pylori* (Corthesy-Theulaz et al., *J. Biol. Chem.* 272:25659-25667 (1997)) and *Bacillus subtilis* (Stols et al., *Protein. Expr. Purif.* 53:396-403 (2007)). These proteins are identified below.

| Protein | GenBank ID | GI Number | Organism |
| --- | --- | --- | --- |
| pcaI | AAN69545.1 | 24985644 | Pseudomonas putida |
| pcaJ | NP_746082.1 | 26990657 | Pseudomonas putida |
| pcaI | YP_046368.1 | 50084858 | Acinetobacter sp. ADP1 |
| pcaJ | AAC37147.1 | 141776 | Acinetobacter sp. ADP1 |
| pcaI | NP_630776.1 | 21224997 | Streptomyces coelicolor |
| pcaJ | NP_63 0775.1 | 21224996 | Streptomyces coelicolor |
| HPAG1_0676 | YP_627417 | 108563101 | Helicobacter pylori |
| HPAG1_0677 | YP_627418 | 108563102 | Helicobacter pylori |
| ScoA | NP_391778 | 16080950 | Bacillus subtilis |
| ScoB | NP_391777 | 16080949 | Bacillus subtilis |

A CoA transferase that can utilize acetate as the CoA acceptor is acetoacetyl-CoA transferase, encoded by the *E. coli* atoA (alpha subunit) and atoD (beta subunit) genes (Vanderwinkel et al., *Biochem. Biophys. Res Commun.* 33:902-908 (1968); Korolev et al., *Acta Crystallogr. D Biol Crystallogr.* 58:2116-2121 (2002)). This enzyme has also been shown to transfer the CoA moiety to acetate from a variety of branched and linear acyl-CoA substrates, including isobutyrate (Matthies et al., *Appl Environ Microbiol* 58:1435-1439 (1992)), valerate (Vanderwinkel et al., supra) and butanoate (Vanderwinkel et al., supra). Similar enzymes exist in *Corynebacterium glutamicum* ATCC 13032 (Duncan et al., *Appl Environ Microbiol* 68:5186-5190 (2002)), *Clostridium acetobutylicum* (Cary et al., *Appl Environ Microbiol* 56:1576-1583 (1990)), and *Clostridium saccharoperbutylacetonicum* (Kosaka et al., *Biosci. Biotechnol Biochem.* 71:58-68 (2007)). These proteins are identified below.

| Protein | GenBank ID | GI | Organism |
| --- | --- | --- | --- |
| atoA | P76459.1 | 2492994 | Escherichia coli K12 |
| atoD | P76458.1 | 2492990 | Escherichia coli K12 |
| actA | YP_226809.1 | 62391407 | Corynebacterium glutamicum ATCC |
| cg0592 | YP_224801.1 | 62389399 | Corynebacterium glutamicum ATCC |

-continued

| Protein | GenBank ID | GI | Organism |
| --- | --- | --- | --- |
| ctfA | NP_149326.1 | 15004866 | Clostridium acetobutylicum |
| ctfB | NP_149327.1 | 15004867 | Clostridium acetobutylicum |
| ctfA | AAP42564.1 | 31075384 | Clostridium |
| ctfB | AAP42565.1 | 31075385 | Clostridium |

Additional exemplary transferase candidates are catalyzed by the gene products of cat1, cat2, and cat3 of *Clostridium kluyveri* which have been shown to exhibit succinyl-CoA, 4-hydroxybutyryl-CoA, and butyryl-CoA transferase activity, respectively (Seedorf et al., supra; Sohling et al., *Eur. J Biochem.* 212:121-127 (1993); Sohling et al., *J Bacteriol.* 178:871-880 (1996)). Similar CoA transferase activities are also present in *Trichomonas vaginalis* (van Grinsven et al., *J. Biol. Chem.* 283:1411-1418 (2008)) and *Trypanosoma brucei* (Riviere et al., *J. Biol. Chem.* 279:45337-45346 (2004)). These proteins are identified below.

| Protein | GenBank ID | GI Number | Organism |
| --- | --- | --- | --- |
| cat1 | P38946.1 | 729048 | Clostridium kluyveri |
| cat2 | P38942.2 | 172046066 | Clostridium kluyveri |
| cat3 | EDK35586.1 | 146349050 | Clostridium kluyveri |
| TVAG_395550 | XP_001330176 | 123975034 | Trichomonas |
| Tb11.02.0290 | XP_828352 | 71754875 | Trypanosoma brucei |

The glutaconate-CoA-transferase (EC 2.8.3.12) enzyme from anaerobic bacterium *Acidaminococcus fermentans* reacts with diacid glutaconyl-CoA and 3-butenoyl-CoA (Mack et al., *FEBS Lett.* 405:209-212 (1997)). The genes encoding this enzyme are gctA and gctB. This enzyme has reduced but detectable activity with other CoA derivatives including glutaryl-CoA, 2-hydroxyglutaryl-CoA, adipyl-CoA and acrylyl-CoA (Buckel et al., *Eur. J. Biochem.* 118:315-321 (1981)). The enzyme has been cloned and expressed in *E. coli* (Mack et al., *Eur. J. Biochem.* 226:41-51 (1994)). These proteins are identified below.

| Protein | GenBank ID | GI Number | Organism |
| --- | --- | --- | --- |
| gctA | CAA57199.1 | 559392 | Acidaminococcus fermentans |
| gctB | CAA57200.1 | 559393 | Acidaminococcus fermentans |

EC 6.2.1.a CoA synthase (Acid-thiol ligase). The conversion of acyl-CoA substrates to their acid products can be catalyzed by a CoA acid-thiol ligase or CoA synthetase in the 6.2.1 family of enzymes, several of which are reversible. Several enzymes catalyzing CoA acid-thiol ligase or CoA synthetase activities have been described in the literature and represent suitable candidates for these steps.

For example, ADP-forming acetyl-CoA synthetase (ACD, EC 6.2.1.13) is an enzyme that couples the conversion of acyl-CoA esters to their corresponding acids with the concomitant synthesis of ATP. ACD I from *Archaeoglobus fulgidus*, encoded by AF1211, was shown to operate on a variety of linear and branched-chain substrates including isobutyrate, isopentanoate, and fumarate (Musfeldt et al., J Bacteriol. 184:636-644 (2002)). A second reversible ACD in *Archaeoglobus fulgidus*, encoded by AF1983, was also shown to have a broad substrate range with high activity on cyclic compounds phenylacetate and indoleacetate (Musfeldt and Schonheit, J Bacteriol. 184:636-644 (2002)). The enzyme from Haloarcula *marismortui* (annotated as a succinyl-CoA synthetase) accepts propionate, butyrate, and branched-chain acids (isovalerate and isobutyrate) as substrates, and was shown to operate in the forward and reverse directions (Brasen et al., *Arch Microbiol* 182:277-287 (2004)). The ACD encoded by PAE3250 from hyperthermophilic crenarchaeon *Pyrobaculum aerophilum* showed the broadest substrate range of all characterized ACDs, reacting with acetyl-CoA, isobutyryl-CoA (preferred substrate) and phenylacetyl-CoA (Brasen et al, supra). Directed evolution or engineering can be used to modify this enzyme to operate at the physiological temperature of the host organism. The enzymes from *A. fulgidus, H. marismortui* and *P. aerophilum* have all been cloned, functionally expressed, and characterized in *E. coli* (Brasen and Schonheit, supra; Musfeldt and Schonheit, *J Bacteriol.* 184:636-644 (2002)). An additional candidate is succinyl-CoA synthetase, encoded by sucCD of *E. coli* and LSC1 and LSC2 genes of *Saccharomyces cerevisiae*. These enzymes catalyze the formation of succinyl-CoA from succinate with the concomitant consumption of one ATP in a reaction which is reversible in vivo (Buck et al., *Biochemistry* 24:6245-6252 (1985)). The acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Appl. Environ. Microbiol.* 59:1149-1154 (1993)). A related enzyme, malonyl CoA synthetase (6.3.4.9) from *Rhizobium leguminosarum* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)).

| Protein | GenBank ID | GI Number | Organism |
| --- | --- | --- | --- |
| AF1211 | NP_070039.1 | 11498810 | Archaeoglobus fulgidus |
| AF1983 | NP_070807.1 | 11499565 | Archaeoglobus fulgidus |
| Scs | YP_135572.1 | 55377722 | Haloarcula marismortui |
| PAE3250 | NP_560604.1 | 18313937 | Pyrobaculum aerophilum |
| sucC | NP_415256.1 | 16128703 | Escherichia coli |
| sucD | AAC73823.1 | 1786949 | Escherichia coli |
| LSC1 | NP_014785 | 6324716 | Saccharomyces cerevisiae |
| LSC2 | NP_011760 | 6321683 | Saccharomyces cerevisiae |
| paaF | AAC24333.2 | 22711873 | Pseudomonas putida |
| matB | AAC83455.1 | 3982573 | Rhizobium leguminosarum |

Another candidate enzyme for these steps is 6-carboxyhexanoate-CoA ligase, also known as pimeloyl-CoA ligase (EC 6.2.1.14), which naturally activates pimelate to pimeloyl-CoA during biotin biosynthesis in gram-positive bacteria. The enzyme from *Pseudomonas mendocina*, cloned into *E. coli*, was shown to accept the alternate substrates hexanedioate and nonanedioate (Binieda et al., *Biochem. J* 340 (Pt 3):793-801 (1999)). Other candidates are found in *Bacillus subtilis* (Bower et al., *J Bacteriol.* 178: 4122-4130 (1996)) and Lysinibacillus *sphaericus* (formerly *Bacillus sphaericus*) (Ploux et al., *Biochem. J* 287 (Pt 3):685-690 (1992)).

| Protein | GenBank ID | GI Number | Organism |
| --- | --- | --- | --- |
| bioW | NP_390902.2 | 50812281 | Bacillus subtilis |
| bioW | CAA10043.1 | 3850837 | Pseudomonas mendocina |
| bioW | P22822.1 | 115012 | Bacillus sphaericus |

Additional CoA-ligases include the rat dicarboxylate-CoA ligase for which the sequence is yet uncharacterized (Vamecq et al., *Biochem. J* 230:683-693 (1985)), either of the two characterized phenylacetate-CoA ligases from *P. chrysogenum* (Lamas-Maceiras et al., *Biochem. J* 395:147-155 (2006); Wang et al., 360:453-458 (2007)), the phenylacetate-CoA ligase from *Pseudomonas putida* (Martinez-Blanco et al., *J Biol Chem* 265:7084-7090 (1990)) and the 6-carboxyhexanoate-CoA ligase from *Bacillus subtilis* (Bower et al. J Bacteriol 178(14):4122-4130 (1996)). Acetoacetyl-CoA synthetases from *Mus musculus* (Hasegawa et al., *Biochim Biophys Acta* 1779:414-419 (2008)) and *Homo sapiens* (Ohgami et al., *Biochem. Pharmacol.* 65:989-994 (2003)) naturally catalyze the ATP-dependent conversion of acetoacetate into acetoacetyl-CoA.

| Protein | Accession No. | GI No. | Organism |
| --- | --- | --- | --- |
| phl | CAJ15517.1 | 77019264 | Penicillium chrysogenum |
| phlB | ABS19624.1 | 152002983 | Penicillium chrysogenum |
| paaF | AAC24333.2 | 22711873 | Pseudomonas putida |
| bioW | NP_390902.2 | 50812281 | Bacillus subtilis |
| AACS | NP_084486.1 | 21313520 | Mus musculus |
| AACS | NP_076417.2 | 31982927 | Homo sapiens |

Like enzymes in other classes, certain enzymes in the EC class 6.2.1 have been determined to have broad substrate specificity. The acyl CoA ligase from *Pseudomonas putida* has been demonstrated to work on several aliphatic substrates including acetic, propionic, butyric, valeric, hexanoic, heptanoic, and octanoic acids and on aromatic compounds such as phenylacetic and phenoxyacetic acids (Fernandez-Valverde et al., *Applied and Environmental Microbiology* 59:1149-1154 (1993)). A related enzyme, malonyl CoA synthetase (6.3.4.9) from *Rhizobium trifolii* could convert several diacids, namely, ethyl-, propyl-, allyl-, isopropyl-, dimethyl-, cyclopropyl-, cyclopropylmethylene-, cyclobutyl-, and benzyl-malonate into their corresponding monothioesters (Pohl et al., *J. Am. Chem. Soc.* 123:5822-5823 (2001)).

FIG. 1: Step M: Crotonate Reductase:

A suitable enzyme activity is an 1.2.1.e Oxidoreductase (acid to aldehyde), which include the following.

The conversion of an acid to an aldehyde is thermodynamically unfavorable and typically requires energy-rich cofactors and multiple enzymatic steps. Direct conversion of the acid to aldehyde by a single enzyme is catalyzed by an acid reductase enzyme in the 1.2.1 family. Exemplary acid reductase enzymes include carboxylic acid reductase, alpha-aminoadipate reductase and retinoic acid reductase. Carboxylic acid reductase (CAR), found in *Nocardia iowensis*, catalyzes the magnesium, ATP and NADPH-dependent reduction of carboxylic acids to their corresponding aldehydes (Venkitasubramanian et al., *J. Biol. Chem.* 282:478-485 (2007)). The natural substrate of this enzyme is benzoate and the enzyme exhibits broad acceptance of aromatic substrates including p-toluate (Venkitasubramanian et al., Biocatalysis in Pharmaceutical and Biotechnology Industries. CRC press (2006)). The enzyme from *Nocardia iowensis*, encoded by car, was cloned and functionally expressed in *E. coli* (Venkitasubramanian et al., *J Biol. Chem.* 282:478-485 (2007)). CAR requires post-translational activation by a phosphopantetheine transferase (PPTase) that converts the inactive apo-enzyme to the active holo-enzyme (Hansen et al., *Appl. Environ. Microbiol* 75:2765-2774 (2009)). Expression of the npt gene, encoding a specific PPTase, product improved activity of the enzyme. An additional enzyme candidate found in *Streptomyces griseus* is encoded by the griC and griD genes. This enzyme is believed to convert 3-amino-4-hydroxybenzoic acid to 3-amino-4-hydroxybenzaldehyde as deletion of either griC or griD led to accumulation of extracellular 3-acetylamino-4-hydroxybenzoic acid, a shunt product of 3-amino-4-hydroxybenzoic acid metabolism (Suzuki, et al., *J. Antibiot.* 60(6):380-387 (2007)). Co-expression of griC and griD with SGR_665, an enzyme similar in sequence to the *Nocardia iowensis* npt, can be beneficial.

| Gene | GenBank Accession | GI No. | Organism |
|---|---|---|---|
| car | AAR91681.1 | 40796035 | *Nocardia iowensis* |
| npt | ABI83656.1 | 114848891 | *Nocardia iowensis* |
| griC | YP_001825755.1 | 182438036 | *Streptomyces griseus* |
| griD | YP_001825756.1 | 182438037 | *Streptomyces griseus* |

Additional car and npt genes can be identified based on sequence homology.

An enzyme with similar characteristics, alpha-aminoadipate reductase (AAR, EC 1.2.1.31), participates in lysine biosynthesis pathways in some fungal species. This enzyme naturally reduces alpha-aminoadipate to alpha-aminoadipate semialdehyde. The carboxyl group is first activated through the ATP-dependent formation of an adenylate that is then reduced by NAD(P)H to yield the aldehyde and AMP. Like CAR, this enzyme utilizes magnesium and requires activation by a PPTase. Enzyme candidates for AAR and its corresponding PPTase are found in *Saccharomyces cerevisiae* (Morris et al., *Gene* 98:141-145 (1991)), *Candida albicans* (Guo et al., *Mol. Genet. Genomics* 269:271-279 (2003)), and *Schizosaccharomyces pombe* (Ford et al., *Curr. Genet.* 28:131-137 (1995)). The AAR from *S. pombe* exhibited significant activity when expressed in *E. coli* (Guo et al., *Yeast* 21:1279-1288 (2004)). The AAR from *Penicillium chrysogenum* accepts S-carboxymethyl-L-cysteine as an alternate substrate, but did not react with adipate, L-glutamate or diaminopimelate (Hijarrubia et al., *J Biol. Chem.* 278:8250-8256 (2003)). The gene encoding the *P. chrysogenum* PPTase has not been identified to date and no high-confidence hits were identified by sequence comparison homology searching.

| Gene | GenBank Accession | GI No. | Organism |
|---|---|---|---|
| LYS2 | AAA34747.1 | 171867 | *Saccharomyces cerevisiae* |
| LYS5 | P50113.1 | 1708896 | *Saccharomyces cerevisiae* |
| LYS2 | AAC02241.1 | 2853226 | *Candida albicans* |
| LYS5 | AAO26020.1 | 28136195 | *Candida albicans* |
| Lys1p | P40976.3 | 13124791 | *Schizosaccharomyces pombe* |
| Lys7p | Q10474.1 | 1723561 | *Schizosaccharomyces pombe* |
| Lys2 | CAA74300.1 | 3282044 | *Penicillium chrysogenum* |

FIG. 1: Step N: Crotonaldehyde Reductase. A suitable enzyme activity is provided by an EC 1.1.1.a Oxidoreductase (oxo to alcohol). EC 1.1.1.a Oxidoreductase (oxo to alcohol) includes the following:

The reduction of glutarate semialdehyde to 5-hydroxyvalerate by glutarate semialdehyde reductase entails reduction of an aldehyde to its corresponding alcohol. Enzymes with glutarate semialdehyde reductase activity include the ATEG_00539 gene product of *Aspergillus terreus* and 4-hydroxybutyrate dehydrogenase of *Arabidopsis thaliana*, encoded by 4hbd (WO 2010/068953A2). The *A. thaliana* enzyme was cloned and characterized in yeast (Breitkreuz et al., *J. Biol. Chem.* 278:41552-41556 (2003)).

| Gene name | GI No. | GenBank Accession No. | Organism |
|---|---|---|---|
| fadD9 | 121638475 | YP_978699.1 | *Mycobacterium bovis* BCG |
| BCG_2812c | 121638674 | YP_978898.1 | *Mycobacterium bovis* BCG |
| nfa20150 | 54023983 | YP_118225.1 | *Nocardia farcinica* IFM 10152 |
| nfa40540 | 54026024 | YP_120266.1 | *Nocardia farcinica* IFM 10152 |
| SGR_6790 | 182440583 | YP_001828302.1 | *Streptomyces griseus* subsp. *griseus* NBRC 13350 |
| SGR_665 | 182434458 | YP_001822177.1 | *Streptomyces griseus* subsp. *griseus* NBRC 13350 |
| MSMEG_2956 | YP_887275.1 | YP_887275.1 | *Mycobacterium smegmatis* MC2 155 |
| MSMEG_5739 | YP_889972.1 | 118469671 | *Mycobacterium smegmatis* MC2 155 |
| MSMEG_2648 | YP_886985.1 | 118471293 | *Mycobacterium smegmatis* MC2 155 |
| MAP1040c | NP_959974.1 | 41407138 | *Mycobacterium avium* subsp. *paratuberculosis* K-10 |
| MAP2899c | NP_961833.1 | 41408997 | *Mycobacterium avium* subsp. *paratuberculosis* K-10 |
| MMAR_2117 | YP_001850422.1 | 183982131 | *Mycobacterium marinum* M |
| MMAR_2936 | YP_001851230.1 | 183982939 | *Mycobacterium marinum* M |
| MMAR_1916 | YP_001850220.1 | 183981929 | *Mycobacterium marinum* M |
| TpauDRAFT_33060 | ZP_04027864.1 | 227980601 | *Tsukamurella paurometabola* DSM 20162 |
| TpauDRAFT_20920 | ZP_04026660.1 | ZP_04026660.1 | *Tsukamurella paurometabola* DSM 20162 |
| CPCC7001_1320 | ZP_05045132.1 | 254431429 | *Cyanobium* PCC7001 |
| DDBDRAFT_0187729 | XP_636931.1 | 66806417 | *Dictyostelium discoideum* AX4 |

| PROTEIN | GENBANK ID | GI NUMBER | ORGANISM |
|---|---|---|---|
| ATEG_00539 | XP_001210625.1 | 115491995 | *Aspergillus terreus* NIH2624 |
| 4hbd | AAK94781.1 | 15375068 | *Arabidopsis thaliana* |

Additional genes encoding enzymes that catalyze the reduction of an aldehyde to alcohol (i.e., alcohol dehydrogenase or equivalently aldehyde reductase) include alrA encoding a medium-chain alcohol dehydrogenase for C2-C14 (Tani et al., *Appl. Environ. Microbiol.* 66:5231-5235 (2000)), yqhD and fucO from *E. coli* (Sulzenbacher et al., 342:489-502 (2004)), and bdh I and bdh II from *C. acetobutylicum* which converts butyraldehyde into butanol (Walter et al., 174:7149-7158 (1992)). YqhD catalyzes the reduction of a wide range of aldehydes using NADPH as the cofactor, with a preference for chain lengths longer than C(3) (Sulzenbacher et al., 342:489-502 (2004); Perez et al., *J Biol. Chem.* 283:7346-7353 (2008)). The adhA gene product from *Zymomonas mobilis* E has been demonstrated to have activity on a number of aldehydes including formaldehyde, acetaldehyde, propionaldehyde, butyraldehyde, and acrolein (Kinoshita et al., *Appl Microbiol Biotechnol* 22:249-254 (1985)). Additional aldehyde reductase candidates are encoded by bdh in *C. saccharoperbutylacetonicum* and Cbei_1722, Cbei_2181 and Cbei_2421 in *C. Beijerinckii*. Additional aldehyde reductase gene candidates in *Saccharomyces cerevisiae* include the aldehyde reductases GRE3, ALD2-6 and HFD1, glyoxylate reductases GOR1 and YPL113C and glycerol dehydrogenase GCY1 (WO 2011/022651A1; Atsumi et al., *Nature* 451:86-89 (2008)). The enzyme candidates described previously for catalyzing the reduction of methylglyoxal to acetol or lactaldehyde are also suitable lactaldehyde reductase enzyme candidates.

| Protein | GENBANK ID | GI | ORGANISM |
|---|---|---|---|
| alrA | BAB12273.1 | 9967138 | *Acinetobacter* sp. strain M-1 |
| ADH2 | NP_014032.1 | 6323961 | *Saccharomyces cerevisiae* |
| yqhD | NP_417484.1 | 16130909 | *Escherichia coli* |
| fucO | NP_417279.1 | 16130706 | *Escherichia coli* |
| bdh I | NP_349892.1 | 15896543 | *Clostridium acetobutylicum* |
| bdh II | NP_349891.1 | 15896542 | *Clostridium acetobutylicum* |
| adhA | YP_162971.1 | 56552132 | *Zymomonas mobilis* |
| bdh | BAF45463.1 | 124221917 | *Clostridium* |
| Cbei_1722 | YP_001308850 | 150016596 | *Clostridium beijerinckii* |
| Cbei_2181 | YP_001309304 | 150017050 | *Clostridium beijerinckii* |
| Cbei_2421 | YP_001309535 | 150017281 | *Clostridium beijerinckii* |
| GRE3 | P38715.1 | 731691 | *Saccharomyces cerevisiae* |
| ALD2 | CAA89806.1 | 825575 | *Saccharomyces cerevisiae* |
| ALD3 | NP_013892.1 | 6323821 | *Saccharomyces cerevisiae* |
| ALD4 | NP_015019.1 | 6324950 | *Saccharomyces cerevisiae* |
| ALD5 | NP_010996.2 | 330443526 | *Saccharomyces cerevisiae* |
| ALD6 | ABX39192.1 | 160415767 | *Saccharomyces cerevisiae* |
| HFD1 | Q04458.1 | 2494079 | *Saccharomyces cerevisiae* |
| GOR1 | NP_014125.1 | 6324055 | *Saccharomyces cerevisiae* |
| YPL113C | AAB68248.1 | 1163100 | *Saccharomyces cerevisiae* |
| GCY1 | CAA99318.1 | 1420317 | *Saccharomyces cerevisiae* |

Enzymes exhibiting 4-hydroxybutyrate dehydrogenase activity (EC 1.1.1.61) also fall into this category. Such enzymes have been characterized in *Ralstonia eutropha* (Bravo et al., *J Forens Sci*, 49:379-387 (2004)) and *Clostridium kluyveri* (Wolff et al., *Protein Expr. Purif* 6:206-212 (1995)). Yet another gene is the alcohol dehydrogenase adhI from *Geobacillus thermoglucosidasius* (Jeon et al., *J Biotechnol* 135:127-133 (2008)).

| PROTEIN | GENBANK ID | GI NUMBER | ORGANISM |
|---|---|---|---|
| 4hbd | YP_726053.1 | 113867564 | *Ralstonia eutropha* H16 |
| 4hbd | L21902.1 | 146348486 | *Clostridium kluyveri* DSM 555 |
| adhI | AAR91477.1 | 40795502 | *Geobacillus thermoglucosidasius* |

Another exemplary aldehyde reductase is methylmalonate semialdehyde reductase, also known as 3-hydroxyisobutyrate dehydrogenase (EC 1.1.1.31). This enzyme participates in valine, leucine and isoleucine degradation and has been identified in bacteria, eukaryotes, and mammals. The enzyme encoded by P84067 from *Thermus thermophilus* HB8 has been structurally characterized (Lokanath et al., *J Mol Biol*, 352:905-17 (2005)). The reversibility of the human 3-hydroxyisobutyrate dehydrogenase was demonstrated using isotopically-labeled substrate (Manning et al., *Biochem J*, 231:481-4 (1985)). Additional genes encoding this enzyme include 3hidh in *Homo sapiens* (Hawes et al., *Methods Enzymol*, 324:218-228 (2000)) and *Oryctolagus cuniculus* (Hawes et al., supra; Chowdhury et al., *Biosci. Biotechnol Biochem.* 60:2043-2047 (1996)), mmsB in *Pseudomonas aeruginosa* and *Pseudomonas putida*, and dhat in *Pseudomonas putida* (Aberhart et al., *J Chem. Soc.* [*Perkin 1*] 6:1404-1406 (1979); Chowdhury et al., *Biosci. Biotechnol Biochem.* 60:2043-2047 (1996); Chowdhury et al., *Biosci. Biotechnol Biochem.* 67:438-441 (2003)). Several 3-hydroxyisobutyrate dehydrogenase enzymes have been characterized in the reductive direction, including mmsB from *Pseudomonas aeruginosa* (Gokarn et al., U.S. Pat. No. 739,676, (2008)) and mmsB from *Pseudomonas putida*.

| PROTEIN | GENBANK ID | GI NUMBER | ORGANISM |
|---|---|---|---|
| P84067 | P84067 | 75345323 | *Thermus thermophilus* |
| 3hidh | P31937.2 | 12643395 | *Homo sapiens* |
| 3hidh | P32185.1 | 416872 | *Oryctolagus cuniculus* |
| mmsB | NP_746775.1 | 26991350 | *Pseudomonas putida* |
| mmsB | P28811.1 | 127211 | *Pseudomonas aeruginosa* |
| dhat | Q59477.1 | 2842618 | *Pseudomonas putida* |

There exist several exemplary alcohol dehydrogenases that convert a ketone to a hydroxyl functional group. Two such enzymes from *E. coli* are encoded by malate dehydrogenase (mdh) and lactate dehydrogenase (ldhA). In addition, lactate dehydrogenase from *Ralstonia eutropha* has been shown to demonstrate high activities on 2-ketoacids of various chain lengths including lactate, 2-oxobutyrate, 2-oxopentanoate and 2-oxoglutarate (Steinbuchel et al., *Eur. J. Biochem.* 130:329-334 (1983)). Conversion of alpha-ketoadipate into alpha-hydroxyadipate can be catalyzed by 2-ketoadipate reductase, an enzyme reported to be found in rat and in human placenta (Suda et al., *Arch. Biochem. Biophys.* 176:610-620 (1976); Suda et al., *Biochem. Biophys. Res. Commun.* 77:586-591 (1977)). An additional oxidoreductase is the mitochondrial 3-hydroxybutyrate dehydrogenase (bdh) from the human heart which has been cloned and characterized (Marks et al., *J. Biol. Chem.* 267:15459-15463 (1992)). Alcohol dehydrogenase enzymes of *C. beijerinckii* (Ismaiel et al., *J. Bacteriol.* 175:5097-5105 (1993)) and *T. brockii* (Lamed et al., *Biochem. J.* 195:183-190 (1981); Peretz et al., *Biochemistry.* 28:6549-6555

(1989)) convert acetone to isopropanol. Methyl ethyl ketone reductase catalyzes the reduction of MEK to 2-butanol. Exemplary MEK reductase enzymes can be found in *Rhodococcus ruber* (Kosjek et al., *Biotechnol Bioeng.* 86:55-62 (2004)) and *Pyrococcus furiosus* (van der Oost et al., *Eur. J. Biochem.* 268:3062-3068 (2001)).

| Protein | Genbank ID | GI Number | Organism |
|---------|------------|-----------|----------|
| mdh | AAC76268.1 | 1789632 | *Escherichia coli* |
| ldhA | NP_415898.1 | 16129341 | *Escherichia coli* |
| ldh | YP_725182.1 | 113866693 | *Ralstonia eutropha* |
| bdh | AAA58352.1 | 177198 | *Homo sapiens* |
| adh | AAA23199.2 | 60592974 | *Clostridium beijerinckii* NRRL B593 |
| adh | P14941.1 | 113443 | *Thermoanaerobacter brockii* HTD4 |
| sadh | CAD36475 | 21615553 | *Rhodococcus ruber* |
| adhA | AAC25556 | 3288810 | *Pyrococcus furiosus* |

A number of organisms encode genes that catalyze the reduction of 3-oxobutanol to 1,3-butanediol, including those belonging to the genus *Bacillus, Brevibacterium, Candida,* and *Klebsiella* among others, as described by Matsuyama et al. *J Mol Cat B Enz,* 11:513-521 (2001). One of these enzymes, SADH from *Candida parapsilosis*, was cloned and characterized in *E. coli*. A mutated *Rhodococcus* phenylacetaldehyde reductase (Sar268) and a *Leifonia* alcohol dehydrogenase have also been shown to catalyze this transformation at high yields (Itoh et al., *Appl. Microbiol Biotechnol.* 75:1249-1256 (2007)).

| Protein | Genbank ID | GI Number | Organism |
|---------|------------|-----------|----------|
| sadh | BAA24528.1 | 2815409 | *Candida parapsilosis* |

FIG. 1: Step U: Crotonyl-CoA Reductase (Alcohol Forming):

The direct conversion of crotonyl-CoA substrate to its corresponding alcohol is catalyzed by bifunctional enzymes with acyl-CoA reductase (aldehyde forming) activity and aldehyde reductase or alcohol dehydrogenase activities. Exemplary bifunctional oxidoreductases that convert an acyl-CoA to alcohol are described herein. Suitable are crotonaldehyde reductase (alcohol forming) enzymes that catalyze the 2 reduction steps required to form crotyl alcohol from crotonyl-CoA. Exemplary 2-step oxidoreductases that convert an acyl-CoA to an alcohol are provided below. Such enzymes can naturally convert crotonyl-CoA to crotyl alcohol or can be engineered to do so. These enzymes include those that transform substrates such as acetyl-CoA to ethanol (e.g., adhE from *E. coli* (Kessler et al, FEBS. Lett. 281:59-63 (1991))) and butyryl-CoA to butanol (e.g. adhE2 from *C. acetobutylicum* (Fontaine et al., J. Bacteriol. 184:821-830 (2002))). The adhE2 enzyme from *C. acetobutylicum* was specifically shown in ref. (Burk et al, supra, (2008)) to produce BDO from 4-hydroxybutyryl-CoA. In addition to reducing acetyl-CoA to ethanol, the enzyme encoded by adhE in *Leuconostoc mesenteroides* has been shown to oxide the branched chain compound isobutyraldehyde to isobutyryl-CoA (Kazahaya et al, J. Gen. Appl. Microbiol. 18:43-55 (1972); Koo et al, Biotechnol. Lett. 27:505-510 (2005)).

| Protein | GenBank ID | GI Number | Organism |
|---------|------------|-----------|----------|
| adhE | NP_415757.1 | 16129202 | *Escherichia coli* |
| adhE2 | AAK09379.1 | 12958626 | *Clostridium acetobutylicum* |
| adhE | AAV66076.1 | 55818563 | *Leuconostoc mesenteroides* |

Another exemplary enzyme is one that converts malonyl-CoA to 3-HP. An NADPH-dependent enzyme with this activity has characterized in *Chloroflexus aurantiacus* where it participates in the 3-hydroxypropionate cycle (Hugler et al, supra, (2002); Strauss et al, 215:633-643 (1993)). This enzyme, with a mass of 300 kDa, is highly substrate-specific and shows little sequence similarity to other known oxidoreductases (Hugler et al, supra, (2002)). No enzymes in other organisms have been shown to catalyze this specific reaction; however there is bioinformatic evidence that other organisms can have similar pathways (Klatt et al., Environ Microbiol. 9:2067-2078 (2007)). Enzyme candidates in other organisms including *Roseiflexus castenholzii, Erythrobacter* sp. NAP1 and marine gamma proteobacterium HTCC2080 can be inferred by sequence similarity.

| Protein | GenBank ID | GI Number | Organism |
|---------|------------|-----------|----------|
| mcr | AAS20429.1 | 42561982 | *Chloroflexus aurantiacus* |
| Rcas_2929 | YP_001433009.1 | 156742880 | *Roseiflexus castenholzii* |
| NAP1_02720 | ZP_01039179.1 | 85708113 | *Erythrobacter* sp. NAP1 |
| MGP2080_00535 | ZP_01626393.1 | 119504313 | *Marine gamma proteobacterium* HTCC 20880 |

FIG. 1: Step VD: Crotyl Alcohol Dehydratase:

Converting crotyl alcohol to butadiene using a crotyl alcohol dehydratase includes the enzyme variants of linalool dehydratase described herein. Although not to be bound by theory, the linalool dehydratase enzyme has two activities, the enzymatic isomerization of crotyl alcohol to 3-buten-2-ol and dehydration of 3-buten-2-ol to butadiene. See Brodkorb et al, *J Biol Chem* 285:30436-42 (2010) for cloning, expression and study of a wild-type linalool dehydratase.

Periplasmic Targeting Sequences, Signal Peptides

In alternative embodiments, polypeptides as provided herein further comprise (or consist of) a homologous or a heterologous signal sequence or signal peptide (the terms "signal peptide" and "signal sequence" are used interchangeably and both include the various classes of targeting and signaling peptides), for example, a periplasmic targeting sequence (PTS) or periplasmic signal sequence (PSS) or a polypeptide or peptide having a PTS or PSS activity; or, a eukaryotic signal sequence. In alternative embodiments, polypeptides as provided herein can further comprise (having in place of its native signal sequence) any periplasmic targeting sequence (PTS) or periplasmic signal sequence (PSS), e.g., any post-translational SecB-targeting pathway PTS or PSS; any co-translational signal recognition particle (SRP)-targeting pathway PTS or PSS; or, any twin-arginine translocation (TAT) Sec independent system PTS or PSS.

Figure 2:
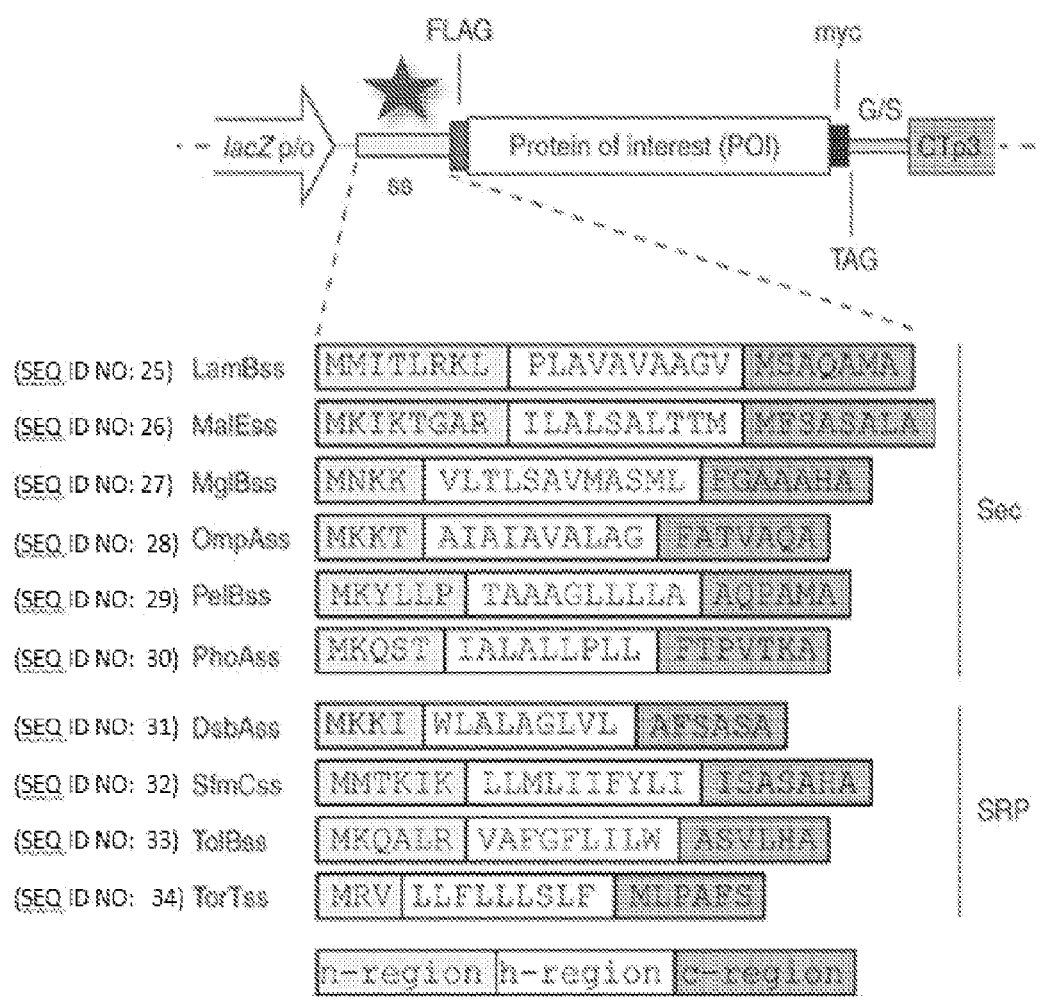
FIG. 2 illustrates periplasmic targeting sequences (PTss) which can be used to practice this invention, as described below; also as described by Steiner et al. (2006) Nature Biotechnology 24:823-831.

For example, FIG. 2 illustrates exemplary heterologous signal sequences that can be used to practice this invention, for example, on (operably linked to) an mature or processed enzyme as provided herein, e.g., the exemplary LinD polypeptide SEQ ID NO:16, which is the mature form of full-length polypeptide SEQ ID NO:12 without its native signal sequence, which is the signal peptide SEQ ID NO:20. For example, any of the signal sequences of FIG. 2, or other signal sequences, are used in place of the native signal sequence of the full length exemplary LinD enzymes SEQ ID NO:12. The exemplary LinD polypeptide SEQ ID NO:12 contains a sec-dependent periplasmic targeting sequence (PTS) as described herein (the peptide SEQ ID NO:20). In alternative embodiments, the PTS of the exemplary LinD polypeptide is replaced with each of the depicted sec-dependent and SRP-dependent PTss, as illustrated in FIG. 2, as well as TAT based sequences (not shown). Similarly, in alternative embodiments, provided herein are the exemplary full-length LinD polypeptides SEQ ID NO: 12, 22, 37, 43, 49, 55, 64, 66, 74, 80, 86, 92 or 98 with their native signal sequences (including SEQ ID NO: 20, 20, 39, 45, 51, 57, 20, 68, 76, 82, 88, 94 or 100, respectively) replaced by a signal sequence of FIG. 2, or another signal sequence.

In alternative embodiments, provided herein are novel signal sequences including SEQ ID NO: 20, 39, 45, 51, 57, 68, 76, 82, 88, 94 or 100, operatively linked to another polypeptide, e.g., another LinD polypeptide such as SEQ ID NO:2 (where a signal sequence as provided herein is substituted for SEQ ID NO:2's native signal sequence, or SEQ ID NO:8).

Heterologous signal sequences are functional, i.e., a signal sequence is functional when operatively linked to a different polypeptide from which it is derived. For example, as illustrated in FIG. 3A and FIG. 3B, wild-type (WT) PTS (SEQ ID NO:8) from WT type LinD from *C. defragrans* 65 Phen (SEQ ID NO:2) was substituted with PTss from *E. coli* periplasmic proteins, expressed in *E. coli* and assayed for butadiene activity. FIG. 3A: Sec-dependent and TAT-SEC PTss appear to have similar activity to that of the wild-type targeting sequence; FIG. 3B: signal peptides comparable to wild-type PTss are highlighted in yellow (LamB ss, MalE ss, PelB ss, FhuD) and those that significantly reduce activity are in highlighted red (MalE and YcdO).

% IDs computed using MUSCLE (MUSCLE: multiple sequence alignment with high accuracy and high throughput) alignment carried out in Geneious; Edgar (2004) Nucleic Acids Research 32(5):1792-7

Summary Exemplary Sequences:

Linalool Dehydratase (LinD) from *C. defragrans* 65Phen (Designated GMN 2753)

SEQ ID NO:1 Native nucleic acid sequence encoding wild type (WT) linalool dehydratase polypeptide SEQ ID NO:2; including signal peptide encoding sequence SEQ ID NO:2 Native full-length wild type linalool dehydratase polypeptide SEQ ID NO:3 Codon-optimized nucleic acid encoding SEQ ID NO:2

SEQ ID NO:4 Codon optimized nucleic acid encoding SEQ ID NO:2

SEQ ID NO:5 Codon Optimized nucleic acid encoding SEQ ID NO:6

SEQ ID NO:6 Mature (processed) form of SEQ ID NO:2 wild type linalool dehydratase SEQ ID NO:7 Native nucleic acid encoding signal sequence SEQ ID NO:8

SEQ ID NO:8 Signal sequence peptide from SEQ ID NO:2

SEQ ID NO:9 Nucleic acid encoding SEQ ID NO:10; differs from SEQ ID NO:4 by having 12 codon substitutions.

SEQ ID NO:10 Full-length polypeptide variant of SEQ ID NO:2; having 12 substitutions Linalool dehydratase (LinD) from *Castellaniella defragrans* 62Car; designated GNM 9819

SEQ ID NO:11 Native nucleic acid encoding SEQ ID NO:12; including signal peptide SEQ ID NO:12 Full-length wild type LinD from *C. defragrans* 62Car, with signal peptide SEQ ID NO:13 (1$^{st}$ codon optimized nucleic acid encoding full length SEQ ID NO:12; designated GNM 9819A)

SEQ ID NO:14 (2$^{nd}$ codon optimized nucleic acid encoding full-length SEQ ID NO:12; designated GNM 9819B)

SEQ ID NO:15 (Native nucleic acid encoding SEQ ID NO:16; processed (mature) form of SEQ ID NO:11 nucleic acid, GNM 9819)

SEQ ID NO:16 (Mature form of LinD polypeptide SEQ ID NO:12 (GNM 9819))

SEQ ID NO:17: (Codon optimized nucleic acid encoding SEQ ID NO:16 (shortened from SEQ ID NO:13 GNM 9819A)

SEQ ID NO:18: (Codon optimized nucleic acid encoding SEQ ID NO:16 (shortened from SEQ ID NO:14 GNM 9819B)

SEQ ID NO:19 (Native nucleic acid encoding signal sequence SEQ ID NO:20; from SEQ ID NO:11)

SEQ ID NO:20 (Signal peptide from SEQ ID NO:12 (GNM 9819))

SEQ ID NO:21 (Nucleic acid encoding full-length variant SEQ ID NO:22, designated 9819C; differs from wild type SEQ ID NO:13 GNM 9819A by having 11 codon substitutions)

SEQ ID NO:22 (Full-length variant SEQ ID NO:12 (GNM 9819) with 11 amino acid substitutions V19I, Y71F, G74S, G133M, R171K, I182L, V196F, D200N, F325S, G365S, L368F; designated 9819C)

SEQ ID NO:23 (Variant Enzyme: SEQ ID NO:25 (Heterologous Signal Sequence LamB ss) Fused to Mature Form Wild Type linD from *C. defragrans* 65Phen, SEQ ID NO:6

SEQ ID NO:24 (Variant Enzyme: SEQ ID NO:25 (Heterologous Signal Sequence LamB ss) Fused to Mature Form Wild Type Enzyme from *Castellaniella Defragrans* 62Car, SEQ ID NO:16

SEQ ID NO:25 (peptide: heterologous signal sequence (ss) LamBss (or LamB ss))

SEQ ID NO:26 (peptide: heterologous signal sequence MalE ss)

SEQ ID NO:27 (peptide: heterologous signal sequence MglBss)

SEQ ID NO:28 (peptide: heterologous signal sequence OmpAss)

SEQ ID NO:29 (peptide: heterologous signal sequence PelBss)

SEQ ID NO:30 (peptide: heterologous signal sequence PhoAss)

SEQ ID NO:31 (peptide: heterologous signal sequence DsbAss)

SEQ ID NO:32 (peptide: heterologous signal sequence SfmCss)

SEQ ID NO:33 (peptide: heterologous signal sequence TolBss)

SEQ ID NO:34 (peptide: heterologous signal sequence TorTss)

SEQ ID NO:35 (peptide: heterologous signal sequence FhuD ss)

Linalool Dehydratase (LinD) from Metagenomics on Activated Sludge from Padre Dam Enriched on Myrcene; Designated GNM 9874

SEQ ID NO:36 Native nucleic acid encoding SEQ ID NO:37, which is unprocessed and includes its signal peptide SEQ ID NO:37: Native, or unprocessed, LinD enzyme, including signal peptide SEQ ID NO:38: Nucleic acid encoding GNM 9874 signal peptide
SEQ ID NO:39: GNM 9874 signal peptide
SEQ ID NO:40: Nucleic acid encoding processed GNM 9874 LinD enzyme, no signal peptide
SEQ ID NO:41: Processed GNM 9874 LinD enzyme, no signal peptide
(Full length GNM 9874 polypeptide has 99% sequence identity to full length GNM 2753; and the mature, or processed, GNM 9874 polypeptide has 99% sequence identity to processed GNM 2753.)
(Full length GNM 9874 polypeptide has 94% sequence identity to full length GNM 9819; and the mature, or processed, GNM 9874 polypeptide has 96% sequence identity to processed GNM 9819.)
Linalool Dehydratase (LinD) from Metagenomics on Activated Sludge from Camp Pendleton Enriched on Myrcene (Secondary Enrichment); Designated GNM 9873
SEQ ID NO:42 Native nucleic acid encoding SEQ ID NO: 43, which is unprocessed and includes its signal peptide
SEQ ID NO:43: Native, or unprocessed, LinD enzyme, including signal peptide
SEQ ID NO:44: Nucleic acid encoding GNM 9873 signal peptide
SEQ ID NO:45: GNM 9873 signal peptide
SEQ ID NO:46: Nucleic acid encoding processed GNM 9873 LinD enzyme, no signal peptide
SEQ ID NO:47: Processed GNM 9873 LinD enzyme, no signal peptide
(Full length GNM 9873 polypeptide has 75% sequence identity to full length GNM 2753; and the mature, or processed, GNM 9873 polypeptide has 79% sequence identity to processed GNM 2753.)
(Full length GNM 9873 polypeptide has 75% sequence identity to full length GNM 9819; and the mature, or processed, GNM 9873 polypeptide has 79% sequence identity to processed GNM 9819.)
Linalool Dehydratase (LinD) from Metagenomics on Activated Sludge from Camp Pendleton Enriched on Myrcene (Primary Enrichment); Designated GNM 9875
SEQ ID NO:48: Native nucleic acid encoding SEQ ID NO:49, which is unprocessed and includes its signal peptide
SEQ ID NO:49: Native, or unprocessed, LinD enzyme, including signal peptide
SEQ ID NO:50: Nucleic acid encoding GNM 9875 signal peptide
SEQ ID NO:51: GNM 9875 signal peptide
SEQ ID NO:52: Nucleic acid encoding processed GNM 9875 LinD enzyme, no signal peptide
SEQ ID NO:53: Processed GNM 9875 LinD enzyme, no signal peptide
(Full length GNM 9875 polypeptide has 78% sequence identity to full length GNM 2753; and the mature, or processed, GNM 9875 polypeptide has 82% sequence identity to processed GNM 2753.)
(Full length GNM 9875 polypeptide has 78% sequence identity to full length GNM 9819; and the mature, or processed, GNM 9875 polypeptide has 81% sequence identity to processed GNM 9819.)
Linalool Dehydratase (LinD) from Metagenomics on Activated Sludge (Camp Pendleton); Designated GNM 9894
SEQ ID NO:54: Native nucleic acid encoding SEQ ID NO:55, which is unprocessed and includes its signal peptide
SEQ ID NO:55: Native, or unprocessed, LinD enzyme, including signal peptide
SEQ ID NO:56: Nucleic acid encoding GNM 9894 signal peptide
SEQ ID NO: 57: GNM 9894 signal peptide
SEQ ID NO:58: Nucleic acid encoding processed GNM 9894 LinD enzyme, no signal peptide
SEQ ID NO:59: Processed GNM 9894 LinD enzyme, no signal peptide
(Full length GNM 9894 polypeptide has 78% sequence identity to full length GNM 2753; and the mature, or processed, GNM 9894 polypeptide has 81% sequence identity to processed GNM 2753.)
(Full length GNM 9894 polypeptide has 78% sequence identity to full length GNM 9819; and the mature, or processed, GNM 9894 polypeptide has 81% sequence identity to processed GNM 9819.)
Linalool Dehydratase (LinD) from Metagenomics on Activated Sludge (Camp Pendleton); Designated GNM 9895
SEQ ID NO:60: Native nucleic acid encoding SEQ ID NO:61, which is unprocessed and includes its signal peptide with no identified signal peptide cleavage site.
SEQ ID NO:61: Native, or unprocessed, LinD enzyme, including signal peptide with no identified signal peptide cleavage site.
SEQ ID NO:62: LinD enzyme SEQ ID NO: 61 having an A196F modification; designated 9895B.
(Full length GNM 9895 polypeptide has 66% sequence identity to full length GNM 2753.
(Full length GNM 9895 polypeptide has 65% sequence identity to full length GNM 9819.
Linalool Dehydratase (LinD) (an Engineered Variant of GNM 9819 with the 7 Mutations (Amino Acid Changes): G74S, G133O, R171K, I182K, V196F, D200G, G365S); Designated GNM 9819T
SEQ ID NO: 63: Native nucleic acid encoding SEQ ID NO: 64, which is unprocessed and includes its signal peptide
SEQ ID NO: 64: Native, or unprocessed, engineered LinD enzyme, including signal peptide.
Linalool Dehydratase (LinD) from Metagenomics on Activated Sludge (Camp Pendleton); Designated GNM 10038.
SEQ ID NO: 65: Native nucleic acid encoding SEQ ID NO: 66, which is unprocessed and includes its signal peptide
SEQ ID NO: 66: Native, or unprocessed, LinD enzyme GNM 10038, including signal peptide
SEQ ID NO: 67: Nucleic acid encoding GNM 10038 signal peptide
SEQ ID NO: 68: GNM 10038 signal peptide
SEQ ID NO: 69: Nucleic acid encoding processed (mature) GNM 10038 LinD enzyme, no signal peptide
SEQ ID NO: 70: Processed (mature) GNM 10038 LinD enzyme, no signal peptide Linalool dehydratase (LinD) from Metagenomics on activated sludge (Camp Pendleton); designated GNM 10039.
SEQ ID NO: 71: Native nucleic acid encoding SEQ ID NO: 72, which is unprocessed and includes its signal peptide which has no identified signal peptidecleavage site.
SEQ ID NO: 72: Native, or unprocessed, LinD enzyme GNM 10039, including signal peptide which has no identified signal peptide cleavage site.
Linalool Dehydratase (LinD) from Metagenomics on Soil Sample (Cottonwood River); Designated GNM 10058.
SEQ ID NO: 73: Native nucleic acid encoding SEQ ID NO: 74, which is unprocessed and includes its signal peptide
SEQ ID NO: 74: Native, or unprocessed, LinD enzyme GNM 10058, including signal peptide
SEQ ID NO: 75: Nucleic acid encoding GNM 10058 signal peptide
SEQ ID NO: 76: GNM 10058 signal peptide
SEQ ID NO: 77: Nucleic acid encoding processed (mature) GNM 10058 LinD enzyme, no signal peptide SEQ ID NO: 78: Processed (mature) GNM 10058 LinD enzyme, no signal peptide.
Linalool Dehydratase (LinD) from Metagenomics on Soil Sample; Designated GNM 10092.
SEQ ID NO: 79: Native nucleic acid encoding SEQ ID NO: 80, which is unprocessed and includes its signal peptide
SEQ ID NO: 80: Native, or unprocessed, LinD enzyme GNM 10092, including signal peptide
SEQ ID NO: 81: Nucleic acid encoding GNM 10092 signal peptide
SEQ ID NO: 82: GNM 10092 signal peptide
SEQ ID NO: 83: Nucleic acid encoding processed (mature) GNM 10092 LinD enzyme, no signal peptide
SEQ ID NO: 84: Processed (mature) GNM 10092 LinD enzyme, no signal peptide.
Linalool Dehydratase (LinD) from Metagenomics on Soil Sample (Cottonwood River); Designated GNM 10093.
SEQ ID NO: 85: Native nucleic acid encoding SEQ ID NO: 86, which is unprocessed and includes its signal peptide
SEQ ID NO: 86: Native, or unprocessed, LinD enzyme GNM 10093, including signal peptide
SEQ ID NO: 87: Nucleic acid encoding GNM 10093 signal peptide
SEQ ID NO: 88: GNM 10093 signal peptide
SEQ ID NO: 89: Nucleic acid encoding processed (mature) GNM 10093 LinD enzyme, no signal peptide
SEQ ID NO: 90: Processed (mature) GNM 10093 LinD enzyme, no signal peptide.
Linalool Dehydratase (LinD) from Metagenomics on Activated Sludge (Sierra Nev.); Designated GNM 10094.
SEQ ID NO: 91: Native nucleic acid encoding SEQ ID NO: 92, which is unprocessed and includes its signal peptide
SEQ ID NO: 92: Native, or unprocessed, LinD enzyme GNM 10094, including signal peptide
SEQ ID NO: 93: Nucleic acid encoding GNM 10094 signal peptide
SEQ ID NO: 94: GNM 10094 signal peptide
SEQ ID NO: 95: Nucleic acid encoding processed (mature) GNM 10094 LinD enzyme, no signal peptide
SEQ ID NO: 96: Processed (mature) GNM 10094 LinD enzyme, no signal peptide.
Linalool Dehydratase (LinD) from Metagenomics on Soil Sample (Cottonwood River); Designated GNM 10097.
SEQ ID NO: 97: Native nucleic acid encoding SEQ ID NO: 98, which is unprocessed and includes its signal peptide
SEQ ID NO: 98: Native, or unprocessed, LinD enzyme GNM 10097, including signal peptide
SEQ ID NO: 99: Nucleic acid encoding GNM 10097 signal peptide
SEQ ID NO: 100: GNM 10097 signal peptide
SEQ ID NO: 101: Nucleic acid encoding processed (mature) GNM 10097 LinD enzyme, no signal peptide
SEQ ID NO: 102: Processed (mature) GNM 10097 LinD enzyme, no signal peptide.
Additional Exemplary Sequences of the Invention:

Additional exemplary sequences of the invention can be found in sequence comparisons of LinD amino acid residues, including the sequence comparisons of FIG. 11 to FIG. 16, as explained below:

For example, additional exemplary sequences of the invention can be found in the sequence comparisons of FIG. 12 to FIG. 16, which compare novel sequences of the invention GNM 9873 (SEQ ID NO:43) (FIG. 12); GNM 9874 (SEQ ID NO: 37) (FIG. 13); GNM 9875, (SEQ ID NO:49) (FIG. 14); GNM 9894, (SEQ ID NO:55) (FIG. 15); and GNM 9895 (SEQ ID NO:61) (FIG. 16), with known LinD polypeptide GNM 2753 (SEQ ID NO:2). Additional exemplary sequences of the invention can be found in the sequence comparison of FIG. 11, which compare the exemplary LinD enzyme GNM 9819 (SEQ ID NO:12) with the known GNM 2753 (SEQ ID NO:2).

The additional exemplary sequences of the invention are identified by the residues that differ in the sequence comparison, where each amino acid residue difference is transferred, or incorporated, to an equivalent residue of a LinD polypeptide as described herein, including the known and novel LinD sequences as described herein.

For example, the alignment of FIG. 12 shows a difference in the first amino acid (aa) residue after the signal peptide, where the first aa residue in "mature" form of full-length GNM 9873 (SEQ ID NO:43) is "E" and the first aa residue in "mature" form of full-length GNM 2753 (SEQ ID NO:2) is "A". Thus, additional exemplary sequences of the invention include LinD polypeptides where the first "mature" aa residue is either an "A" or an "E". Further additional exemplary sequences of the invention include variants of the exemplary LinD polypeptide (e.g., GNM 9819 (SEQ ID NO:12) and the known GNM 2753 (SEQ ID NO:2) where the first "mature" aa residue is either an "A" or an "E".

Another example of additional exemplary sequences of the invention from FIG. 12 can be found in the fourth aa residue of the "mature" LinD polypeptide, where the $4^{th}$ aa residue in "mature" form of full-length GNM 9873 (SEQ ID NO:43) is "F" and the $4^{th}$ aa residue in "mature" form of full-length GNM 2753 (SEQ ID NO:2) is "P". Thus, additional exemplary sequences of the invention include LinD polypeptides where the $4^{th}$ "mature" aa residue (or equivalent residue) is either an "F" or a "P". Further additional exemplary sequences of the invention include variants of the exemplary LinD polypeptides (e.g., GNM 9819 (SEQ ID NO:12) and the known GNM 2753 (SEQ ID NO:2), where the $4^{th}$ "mature" aa residue is either an "F" or a "P".

Additional exemplary sequences of the invention can be found in comparing variants of the exemplary LinD polypeptide GNM 9819 (SEQ ID NO:12) and the known GNM 2753 (SEQ ID NO:2), as in FIG. 11, and incorporating these amino acid (aa) residue differences in other novel LinD polypeptides as provided herein. For example, the $2^{nd}$ aa residue in "mature" form of full-length GNM 9819 (SEQ ID NO:12) is "P" and the 2" aa residue in "mature" form of full-length GNM 2753 (SEQ ID NO:2) is "E". Thus, additional exemplary sequences of the invention include LinD polypeptides where the $2^{nd}$ "mature" aa residue (or equivalent residue) is either an "E" or a "P"; and this includes incorporating these amino acid (aa) residue differences in the novel LinD polypeptides as provided herein, and other known LinD polypeptides (thus creating an new variant, i.e., a new novel exemplary LinD sequence provided herein).

Additional exemplary sequences of the invention are combinations of two, three, four, five, six or more of these aa residue changes as found by sequence comparisons, e.g., as provided herein. For example, an exemplary LinD polypeptide provided herein comprises two or more of: a change in its first "mature" aa residue to either an "A" or an "E"; a change in its $2^{nd}$ "mature" aa residue (or equivalent residue) to either an "E" or a "P"; a change in its $4^{th}$ "mature" aa residue (or equivalent) to either an "F" or a "P"; etc.

In alternative embodiments, practicing the invention comprises use of any conventional technique commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual," Second Edition, Cold Spring Harbor, 1989; and Ausubel et al., "Current Protocols in Molecular Biology," 1987). Unless defined otherwise herein, all technical and scientific terms used herein have the same meaning as commonly understood by one of ordinary skill in the art to which this invention pertains. For example, Singleton and Sainsbury, Dictionary of Microbiology and Molecular Biology, 2d Ed., John Wiley and Sons, N Y (1994); and Hale and Marham, The Harper Collins Dictionary of Biology, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole.

Unless defined otherwise herein, all technical and scientific terms used herein have the same meaning as commonly understood by one of ordinary skill in the art to which this invention pertains. Although any methods and materials similar or equivalent to those described herein find use in the practice of the present invention, the preferred methods and materials are described herein. Accordingly, the terms defined immediately below are more fully described by reference to the Specification as a whole.

As used herein, the singular terms "a," "an," and "the" include the plural reference unless the context clearly indicates otherwise. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

The following examples, and the figures, are intended to clarify the invention, and to demonstrate and further illustrate certain preferred embodiments and aspects without restricting the subject of the invention to the examples and figures.

EXAMPLES

Example 1. Demonstrating Linalool Dehydratase Activity

Below is a table of activity for butadiene production (in head space) of known wild type linalool dehydratase (expressed from nucleic acid designated 2753I) and its 12-amino-acid substitution variant designated 2753N expressed in *E. coli* with exogenously added crotyl alcohol; 48 hours reaction time as described herein. In the enzyme reaction, crotyl alcohol is isomerized to MVC that is dehydrated to butadiene. Butadiene is sufficiently volatile that it collects in and it measured in the head space. As reported in the literature and shown here the wild type and variant enzymes are active in vivo on crotyl alcohol.

| Crotyl alcohol substrate concentration (mM) | Butadiene (ppm) | | | | | |
|---|---|---|---|---|---|---|
| | Wild type linD of *C. defragrans* 65 Phen expressed from 2753I (test 1) | Wild type linD of *C. defragrans* 65 Phen expressed from 2753I (test 2) | Wild type linD of *C. defragrans* 65 Phen expressed from 2753I (test 3) | 12-amino acid substitution Variant of 2753 (2753N) (test 1) | 12-amino acid substitution Variant of 2753 (2753N) (test 2) | 12-amino acid substitution Variant of 2753 (2753N) (test 3) |
| 1 | 0.05 | 0.04 | 0.04 | 3.81 | 4.04 | 5.73 |
| 2.5 | 0.1 | 0.07 | 0.09 | 3.85 | 6.67 | 5.64 |
| 5 | 0.16 | 0.14 | 0.15 | 5.18 | 8.12 | 7.69 |
| 25 | 0.31 | 0.37 | 0.31 | 5.33 | 6.44 | 4.46 |

Below is a table of activity for butadiene production (in head space) of the novel alkenol dehydratase provided herein, from *C. defragrans* 62 Car, (SEQ ID NO:12), expressed from nucleic acid SEQ ID NO:11, as expressed in *E. coli* with exogenously added crotyl alcohol or its isomer methyl vinyl carbinol (MVC); 48 hours reaction time as described herein. In the enzyme reaction, crotyl alcohol is isomerized to MVC that is dehydrated to butadiene. Butadiene is sufficiently volatile that it collects in and it measured in the head space. The mature form of the novel enzyme is made by the engineered *E. coli* and is active in vivo on both crotyl alcohol and MVC as shown in the table below. The novel enzyme was also active on two C5 alkenols within the formula $C_nH_{2n}O$ where $3<n<7$. When the substitutions used in 2753N were placed simultaneously in the novel enzyme 9819, the specific 11-amino acid substation variant designated 98191, did not improve activity on crotyl alcohol but instead inactivated the protein on crotyl alcohol. Other substitution variants, including those with heterologous signal peptides or with fewer number of substitutions as described herein, were demonstrated as active or improving activity (data not shown).

| Substrate concentration (mM) | Butadiene (ppm) | | | |
|---|---|---|---|---|
| | Crotyl Alcohol (test 1) | Crotyl Alcohol (test 2) | Methyl vinyl carbinol (MVC; test 1) | Methyl vinyl carbinol (MVC; test 2) |
| 1 | 0 | 0 | 0.52 | 0.38 |
| 2.5 | 0.01 | 0 | 0.81 | 0.66 |
| 5 | 0.01 | 0.01 | 1.32 | 0.94 |
| 25 | 0.04 | 0.02 | 3.49 | 2.43 |

In Vivo 1,3-Butadiene Production Assays

*E. coli* (ATCC 8739 C variants) were transformed with the expression plasmid and selected and maintained using antibiotic selection. The day before the experiment, 1 mL overnight cultures in LB-antibiotic were inoculated and grown with a breathable seal in 24 well plate at 37° C. Overnight cultures were seeded at $OD_{600}=0.05$ into fresh 2 mL M9+4% glucose+antibiotic+IPTG+10 mM crotyl alcohol into 10 ml screw-cap bottles. Bottles were incubated for 48 hours at 37° C. and 1,3-butadiene production was validated by headspace analysis by GC-MS.

Metagenomic Sequencing

Activated sewage samples were obtained from a local wastewater treatment in California and were used as the inoculum for enrichment cultures. Metagenomic sequencing was carried out on the DNA samples extracted from the enrichment cultures using Illumina MiSeq platform. De novo assembly was performed using SPAdes assembler to generate contigs representing the metagenome. A TBLASTN search was conducted against this database of contigs using a WT *C. defragrans* 65Phen full-length polypeptide LinD to identify homologs in the metagenomic assembly; using protocols as described e.g., in Bankevich, et al., SPAdes: A New Genome Assembly Algorithm and Its Applications to Single-Cell Sequencing. Journal of Computational Biology 19(5) (2012), 455-477. doi:10.1089/cmb.2012.0021.

The table as illustrated in FIG. 18, and following table, report pairwise percent identity between the novel polypeptides provided herein and known wild type enzymes (full-length and mature forms) described herein, where percent identity (% ID) was computed using MUSCLE alignment algorithm using Geneious software (Edgar, MUSCLE: multiple sequence alignment with high accuracy and high throughput, Nucleic acids research 32 (5):1792-7 (2004)). FIG. 18's tables describe both Pairwise % ID for full length (unprocessed) protein (FIG. 18A) and Pairwise % ID for "mature" or processed protein (FIG. 18B). The tables demonstrate that the inventors have identified native enzymes with similar enzymatic function that share identical or nearly identical amino acid length and amino acid (and thus structural) identity as low as at least about 75%, and even as low as about 63% compared amongst full-length protein amino acid sequences and 67% amongst mature protein amino acid seqeunces.

Experiment also includes a repeat test of original constructs of 9895A (SEQ ID NO:61) and 9895B (which is SEQ ID NO:62 having an A196F modification).
(a ribosomal binding site (RBS) is a sequence on mRNA that is bound by the ribosome when initiating protein translation)
Experiment Design
  Host Strain(s) 8157
  Plasmids (rpt: pG_8227, pG_8228), pG_8285, pG_8286, pG_8287, pG_8288
  Genes (rpt: 9895A, 9895B, canonical RBS), 13k-9895A, 34k-9895A, 104k-9895A, 290k-9895A
  Variable RBS Strength
  Expt. Protocol Screw-cap vial cell culture in SMM5+10 mM CrOH or 10 mM MVC or 10 mM prenol
  Sampled Timepoints 72 hr cell culture headspace measurement for BDE
  Datatypes Collected BDE from CrOH and MVC by GCMS
Experimental Conditions
  2 ml LB+glucose+Kan preculture in 24-well plate, grown overnight in humidified incubator. Samples in biological duplicate.
  Used to inoculate 2 ml SMM5+Trace+Kan+IPTG+10 mM CrOH or 10 mM MVC or 10 mM prenol in 10 ml sealed glass vials. Start OD 0.1. Grown 72 hours at 35° C. Samples received 60° C., 30 min heat kill, then submitted for headspace analysis for BDE by GCMS.
  For SDS-PAGE, grew 24 hr in shake flask, SMM5+IPTG
Data (1) LinD polypeptide 9895 (SEQ ID NO:61) was demonstrated to convert methyl vinyl carbinol (MVC) at 10 mM to BDE, with as high as 0.27, 0.25 and 0.17 ppm was detected with 13, 34 and 104K RBS sequences, respectfully. Conversion of MVC to butadiene (BD, BDE) demonstrates dehydratase activity.

| GNM number | Source | Nucleotide length | Amino Acid length | Amino Acid % ID to 2753 | | Amino Acid % ID to 9819 | |
|---|---|---|---|---|---|---|---|
| | | | | Full length | Mature Protein | Full length | Mature Protein |
| 2753 | *Castellaniella defragrans* 65Phen | 1194 | 397 | 100% | 100% | 94% | 96% |
| 9819 | *Castellaniella defragrans* 62Car | 1197 | 398 | 94% | 96% | 100% | 100% |
| PD1 (9874) | Metagenomics on Activated sludge | 1194 | 397 | 99% | 99% | 94% | 96% |
| CP1 (9873) | Metagenomics on Activated sludge | 1203 | 400 | 75% | 79% | 75% | 79% |
| CP2 (9875) | Metagenomics on Activated sludge | 1206 | 401 | 78% | 82% | 78% | 81% |

Example 2. Demonstrating Linalool Dehydratase Activity

This Example provides data demonstrating the dehydratase enzyme activity, and bifunctional isomerase-dehydratase enzyme activity, of exemplary enzymes as provided herein.
Objectives/Hypothesis and Background
To test an RBS panel for the new LinD 9895A (SEQ ID NO:61, which is unprocessed and includes its signal peptide) for activity on 10 mM CrOH, MVC, and prenol.

(2) LinD polypeptide 9895 (SEQ ID NO:61) was demonstrated to convert prenol at 10 mM to isoprene, with as high as 6, 4 to 8, and 3 ppm was detected with 13, 34 and 104K RBS sequences, respectfully. Conversion of prenol to isoprene demonstrates both isomerase and dehydratase activity (wherein the isomerase activity converts the prenol to its isomer isoprenol, and the dehydratase activity converts the isoprenol to isoprene).

(3) Introduction of the mutation A196F into LinD polypeptide 9895 (designated GNM 9895B, SEQ ID NO:62) can result in a 2-fold boost in the MVC assay (to produce BDE).

In one assay, using a "canonical" RBS, the LinD polypeptide 9895 (SEQ ID NO:61) converted prenol to isoprene at a yield of 0.13 ppm, while the 9895B mutation A196F LinD (SEQ ID NO:62) converted prenol to isoprene at a yield of 0.17 ppm.

(4) LinD polypeptide 9819T (SEQ ID NO:64, which is unprocessed engineered variant and includes its signal peptide; encoded by SEQ ID NO:63) in separate runs of this assay was demonstrated to convert methyl vinyl carbinol (MVC) at 10 mM to BDE: having an average of 132 uM, the separate runs generated 7.36 ppm (or 136 uM), 7.32 ppm (135 uM), and 6.68 ppm (123 uM).

FIG. 17 in table form summarizes the demonstrated enzymatic activity of exemplary enzymes of the invention.

A number of embodiments of the invention have been described. Nevertheless, it will be understood that various modifications may be made without departing from the spirit and scope of the invention. Accordingly, other embodiments are within the scope of the following claims.

What is claimed is:

1. A method of producing or making a butadiene, a dialkene or a compound having the general formula $C_nH_{2n-2}$ with 3<n<7 from a substrate compound having the general formula $C_nH_{2n}O$, with 3<n<7, comprising:
   (a) expressing a recombinant or a synthetic nucleic acid under conditions wherein a recombinant polypeptide is produced, and
   (b) adding the substrate to a reaction mixture comprising the recombinant polypeptide under conditions suitable to produce an enzymatic product
   wherein:
   (i) the recombinant or synthetic nucleic acid comprises the nucleic acid sequence as set forth in SEQ ID NO: 63;
   or
   (ii) the recombinant or synthetic nucleic acid comprises a nucleic acid sequence that encodes a polypeptide having the sequence as set forth in SEQ ID NO:64;
   wherein the recombinant or synthetic nucleic acid encodes a polypeptide:
      (1) having a linalool dehydratase-isomerase (Lin D) activity,
      (2) having a vinylisomerase activity,
      (3) having a dehydratase activity, optionally an alkenol dehydratase activity,
      (4) able to enzymatically catalyze the conversion of a crotyl alcohol (but-2-en-1-ol) to a 3-buten-2-ol,
      (5) able to enzymatically catalyze the conversion of a 3-buten-2-ol to a butadiene or a 1,3 butadiene,
      (6) able to enzymatically catalyze the conversion of a crotyl alcohol (but-2-en-1-ol) to a butadiene or a 1,3 butadiene,
      (7) able to enzymatically catalyze the conversion of a 2,3-dimethyl-but-2-en-1-ol into dimethyl-butadiene,
      (8) catalyzing the conversion of a compound corresponding to the general formula $C_nH_{2n}O$ into $C_nH_{2n-2}+H_2O$ with 3<n<7; or
      (9) any combination of (1) to (8).

2. The method of claim 1, further comprising one, several or all of the following steps:
   (a) obtaining a fermenter off-gas comprising a conjugated diolefin, a volatile impurity, a bio-byproduct impurity and water vapor;
   (b) compressing the fermenter off-gas in a multistage compression system to produce a compressed stream;
   (c) feeding the compressed stream into a first distillation zone for the removal of bio-byproduct impurity and water vapor, the first distillation zone having an upper reflux stage, middle distillation stages and a lower reboiler stage;
   (d) contacting an overhead vapor stream produced from the bio-byproduct impurity and water removal distillation zone with an adsorbent to produce a dried overhead stream;
   (e) feeding the dried overhead stream into a second distillation zone for the removal of volatile impurity by the top, with the second distillation zone having an upper reflux stage, middle distillation stages and a lower reboiler stage; and
   (f) collecting at the bottom of the distillation zone for the removal of volatile impurity the resulting purified liquid conjugated diolefin.

3. The method of claim 1, wherein the substrate comprises: a compound corresponding to the general formula $C_nH_{2n}O$ into $C_nH_{2n-2}+H_2O$ with 3<n<7, a crotyl alcohol (but-2-en-1-ol), a 3-buten-2-ol, a 2,3-dimethyl-but-2-en-1-ol, or any combination thereof.

4. The method of claim 1, wherein the method further comprises recovering or isolating the produced compound, which optionally comprises or corresponds to the general formula $C_nH_{2n-2}$ with 3<n<7.

5. The method of claim 1, wherein the produced compound comprises or is: a 3-buten-2-ol, a dimethyl-butadiene, a butadiene (BD), or a 1,3-butadiene.

6. The method of claim 1, wherein the substrate compound corresponding to the general formula $C_nH_{2n}O$ with 3<n<7, comprises or is: a crotyl alcohol, a but-3-en-2-ol or a but-3-en-1-ol, and/or the product compound corresponding to the general formula $C_nH_{2n-2}$ with 3<n<7, comprises or is a 1,3-butadiene.

7. The method of claim 1, wherein the substrate compound corresponding to the general formula $C_nH_{2n}O$ with 3<n<7 is or comprises a 2,3-dimethyl-but-2-en-1-ol, a 2,3-dimethyl-but-3-en-2-ol or a 2,3-dimethyl-but-3-en-1-ol, and/or the product compound corresponding to the general formula $C_nH_{2n-2}$ with 3<n<7 is or comprises a dimethylbutadiene.

8. The method of claim 1, wherein the conditions wherein a recombinant polypeptide is produced, or the conditions suitable to produce an enzymatic product comprising the compound, comprise in vitro expression of the nucleic acid.

9. The method of claim 1, wherein the polypeptide comprises a heterologous protein sequence.

10. The method of claim 9, wherein the heterologous protein sequence comprises a heterologous signal sequence.

11. The method of claim 10, wherein the heterologous signal sequence comprises: SEQ ID NO:25 (a peptide heterologous signal sequence (ss) LamBss (or LamB ss)); SEQ ID NO:26 (a peptide heterologous signal sequence MalE ss); SEQ ID NO:27 (a heterologous signal sequence MglBss); SEQ ID NO:28 (a peptide heterologous signal sequence OmpAss); SEQ ID NO:29 (a peptide heterologous signal sequence PelBss); SEQ ID NO:30 (a peptide heterologous signal sequence PhoAss); SEQ ID NO:31 (a peptide heterologous signal sequence DsbAss); SEQ ID NO:32 (a peptide heterologous signal sequence SfmCss); SEQ ID NO:33 (a peptide heterologous signal sequence TolBss); SEQ ID NO:34 (a peptide heterologous signal sequence TorTss); or SEQ ID NO:35 (a peptide heterologous signal sequence FhuD ss).

12. The method of claim 1, wherein the compound corresponding to the general formula $C_nH_{2n}O$ with 3<n<7 is a crotyl alcohol, a but-3-en-2-ol or a but-3-en-1-ol, and/or the compound corresponding to the general formula $C_nH_{2n-2}$ with 3<n<7 is a 1,3 butadiene.

13. The method of claim 1, wherein the compound corresponding to the general formula $C_nH_{2n}O$ with 3<n<7 is a 2,3-dimethyl-but-2-en-1-ol, a 2,3-dimethyl-but-3-en-2-ol or a 2,3-dimethyl-but-3-en-1-ol, and/or the compound corresponding to the general formula $C_nH_{2n-2}$ with 3<n<7 is a dimethylbutadiene.

14. The method of claim 2, wherein the resulting purified liquid conjugated diolefin is butadiene.

15. The method of claim 10, wherein the heterologous signal sequence comprises a eukaryotic signal sequence.

16. The method of claim 15, wherein the eukaryotic signal sequence is a yeast or fungal signal sequence.

17. The method of claim 1, wherein the substrate comprises: a crotyl alcohol (but-2-en-1-ol) or a 3-buten-2-ol; a 2,3-dimethyl-but-2-en-1-ol.

18. The method of claim 1, wherein the enzymatic product compound comprises a butadiene or a dialkene.

* * * * *